(12) United States Patent
Zhang et al.

(10) Patent No.: US 11,472,811 B2
(45) Date of Patent: Oct. 18, 2022

(54) PYRAZOLOTRIAZOLOPYRIMIDINE DERIVATIVES AS A2A RECEPTOR ANTAGONIST

(71) Applicant: BEIGENE, LTD., Grand Cayman (KY)

(72) Inventors: Guoliang Zhang, Beijing (CN); Changyou Zhou, Princeton, NJ (US)

(73) Assignee: BEIGENE, LTD., Grand Cayman (KY)

(*) Notice: Subject to any disclaimer, the term of this patent is extended or adjusted under 35 U.S.C. 154(b) by 30 days.

(21) Appl. No.: 16/982,681

(22) PCT Filed: Apr. 8, 2019

(86) PCT No.: PCT/CN2019/081785
§ 371 (c)(1),
(2) Date: Sep. 21, 2020

(87) PCT Pub. No.: WO2019/196803
PCT Pub. Date: Oct. 17, 2019

(65) Prior Publication Data
US 2021/0198267 A1     Jul. 1, 2021

(30) Foreign Application Priority Data

Apr. 8, 2018 (WO) ................ PCT/CN2018/082140

(51) Int. Cl.
*C07D 487/14* (2006.01)

(52) U.S. Cl.
CPC .................. *C07D 487/14* (2013.01)

(58) Field of Classification Search
CPC .................................... C07D 487/14
USPC ....................................... 514/272
See application file for complete search history.

(56) References Cited

U.S. PATENT DOCUMENTS

| 2003/0139427 A1 | 7/2003 | Castelhano et al. |
| 2021/0300936 A1 | 9/2021 | Zhang et al. |

FOREIGN PATENT DOCUMENTS

| WO | WO 2001/092264 | 12/2001 |
| WO | WO 2003/030904 | 4/2003 |
| WO | WO 2005/103055 | 11/2005 |
| WO | WO 2012/038980 | 3/2012 |
| WO | WO 2012/135084 | 10/2012 |
| WO | WO 2017/136375 | 8/2017 |
| WO | WO 2019/196803 | 10/2019 |
| WO | WO 2020/020097 | 1/2020 |

OTHER PUBLICATIONS

Extended European Search Report for European Application No. 19785064.7, dated Oct. 18, 2021, 7 pages.
Harris, J. M. et al., "Potent and selective adenosine A2A receptor antagonists: [1,2,4]-triazolo[4,3-c]pyrimidin-3-ones," Bioorganic & Medicinal Chemistry Letters, vol. 21, No. 8, Feb. 2011, pp. 2497-2501.
International Search Report and Written Opinion for International Application No. PCT/CN2019/097083, dated Oct. 22, 2019, 12 pages.
International Search Report and Written Opinion for International Application No. PCT/CN2019/081785, dated Jul. 8, 2019, 9 pages.
Baraldi, P. G. et al., "Synthesis of new pyrazolo[4,3-e]1,2,4-triazolo[1,5-c] pyrimidine and 1,2,3-triazolo[4,5-e]1,2,4-triazolo[1,5-c] pyrimidine displaying potent and selective activity as A2a adenosine receptor antagonists," Bioorganic & Medicinal Chemistry Letters, vol. 4, Issue 21, Nov. 1994, pp. 2539-2533.
Muranaka, H. et al., "Photoaffinity labeling of the human A2A adenosine receptor and cross-link position analysis by mass spectrometry," ACS Medicinal Chemistry Letters, vol. 8, No. 6, Jun. 2017, pp. 660-665.
Neustadt, B. R. et al., "Potent, selective, and orally active adenosine A2A receptor antagonists: arylpiperazine derivatives of pyrazolo[4,3-e]-1,2,4-triazolo[1,5-c]pyrimidines," Bioorganic & Medicinal Chemistry Letters, Dec. 2006, 17(5):1376-1380.
Leone, R. D. et al., "A2aR antagonists: Next generation checkpoint blockade for cancer immunotherapy," Comput. Struct. Biotechnol. J., Apr. 8, 2015;13:265-72. doi: 10.1016/j.csbj.2015.03.008.
Basu, S. et al., "Discovery of potent and selective A2A antagonists with efficacy in animal models of Parkinson's Disease and depression," ACS Med. Chem. Lett, vol. 8, No. 8, Aug. 2017, pp. 835-840.

*Primary Examiner* — Taofiq A Solola
(74) *Attorney, Agent, or Firm* — Cooley LLP

(57) ABSTRACT

Disclosed herein is a pyrazolotriazolopyrimidine derivative or a stereoisomer thereof, or a pharmaceutically acceptable salt thereof useful as an A2A receptor antagonist, and a pharmaceutical composition comprising the same. Also disclosed herein is a method of treating cancer using the pyrazolotriazolopyrimidine derivative or a stereoisomer thereof, or a pharmaceutically acceptable salt thereof as an A2A receptor antagonist.

29 Claims, No Drawings

PYRAZOLOTRIAZOLOPYRIMIDINE DERIVATIVES AS A2A RECEPTOR ANTAGONIST

CROSS-REFERENCE TO RELATED APPLICATIONS

This application is a U.S. National Stage Application under 35 U.S.C. § 371 of International Application No. PCT/CN2019/081785, filed Apr. 8, 2019, which claims the benefit of International Patent Application No. PCT/CN2018/082140, filed on Apr. 8, 2018, the disclosures of which are hereby incorporated by reference in their entireties for all purposes.

FIELD OF THE INVENTION

Disclosed herein is a pyrazolotriazolopyrimidine derivative or a stereoisomer thereof, or a pharmaceutically acceptable salt thereof useful as an A2A receptor antagonist, and a pharmaceutical composition comprising the same. Also disclosed herein is a method of treating cancer using the pyrazolotriazolopyrimidine derivative or a stereoisomer thereof, or a pharmaceutically acceptable salt thereof as an A2A receptor antagonist.

BACKGROUND OF THE INVENTION

Extracellular adenosine is a key endogenous modulator of a number of physiological activities. It exerts its regulatory function by interacting with four adenosine receptors, A1, A2A, A2B and A3. All four receptors belong to G-protein-coupled receptor superfamily but have different ligand affinities, tissue distributions and effector responses. By coupling with different G proteins, they can either stimulate (A2A and A2B) or inhibit (A1 and A3) downstream adenylyl cyclase activity, and are also involved in regulating other pathways, such as phospholipase C (PLC), $Ca^{2+}$ and mitogen-activated protein kinases (MAPKs).

The immune system is not only responsible for defending its host against microbial invasion, but also can remove the changed host component from the organism, where an anti tumor immune mechanism exists. When the immune surveillance function is weakened due to the immune system per se or tumor cells, favorable conditions are provided for the development and progression of tumors. Adenosine-A2A receptor signaling emerges as a novel metabolic immune checkpoint pathway that participates in the creation of an immune-tolerant tumor microenvironment. It was demonstrated that the hypoxia in tumor tissue would induce the accumulation of higher concentrations of adenosine (~10 μM versus ~20 nM at physiological level). Hypoxia-mediated adenosine production was caused by upregulation of CD39 and CD73 ectonucleotidase in both non-hematopoietic and hematopoietic cellular subsets, which sequentially catalyzed the conversion of extracellular ATP to adenosine.

Adenosine signaling through A2A (high affinity) and A2B (low affinity) receptors-major adenosine receptors in immune cell subsets-plays an important role in protecting cancerous tissues from the attack of the immune system. Activated A2A receptors on T effector cells increase intracellular cAMP, which in turn suppresses TCR-triggered signaling and anti-tumor effector function, including reduced T cell expansion, IFN-γ releasing, and increased expression of immunosuppressive PD-1, LAG3, IL-10 and TGE-β. Increased cAMP in T cells also promotes cAMP-response element (CRE)-mediated transcription, such as FoxP3, which drives regulatory T cell phenotype. Besides, adenosine also inhibits anti-tumor immune response by disabling the cytotoxic effector function of natural killer (NK) cells, regulating immunosuppressive M2 macrophage polarization and myeloid-derived suppressor cells (MDSC) expansion. Thus, immune cells expressing A2A receptors were investigated as a potential target to disrupt adenosine-mediated immunosuppression in the tumor microenvironment. It was demonstrated that genetic deletion or pharmacological antagonism of A2AR could enhance endogenous antitumor immunity and effectively inhibited tumor growth or metastasis in established immunogenic mouse tumors.

WO0192264 disclosed the 5-amino-pyrazolo-[4,3-e]-1,2,4-triazolo[1,5-c]pyrimidine adenosine A2a receptor antagonists for the treatment of central nervous system diseases, in particular Parkinson's disease, which was proved to have a high Blood-brain Barrier Permeability.

However, there is a need for small molecule antagonists of the A2A receptor as immune modulators for anticancer therapy (Robert D. Leone, Ying-Chun Lo, Jonathan D. Powell, Mini Review, A2aR antagonists: Next generation checkpoint blockade for cancer immunotherapy. Computational and Structural Biotechnology Journal 13 (2015) 265-272).

SUMMARY OF THE INVENTION

Unexpectedly and surprisingly, the pyrazolotriazolopyrimidine derivatives disclosed herein were found to have immune modulating efficacy in anticancer therapy and have a relatively low Blood-brain Barrier Permeability which is expected to increase the therapeutic window by reducing potential CNS side effects in cancer treatment.

Disclosed herein is a compound of formula (I)

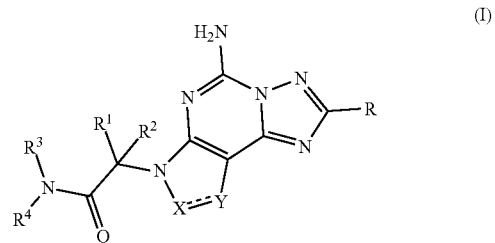

or a stereoisomer thereof, or a pharmaceutically acceptable salt thereof,
wherein:
X is N or C(=O) or $CR^a$;
Y is CH or $NR^a$;
━━━━━ is a single or double bond;
$R^a$ is independently selected from hydrogen, —$C_{1-6}$alkyl, —$C_{3-8}$cycloalkyl, heterocyclyl, aryl, or heteroaryl;
R is an aryl group or a 5 or 6-membered heteroaryl group containing 1 or 2 heteroatoms independently selected from —N=  or  =N—, —NH—, —O—, —S—, —SO—  or —$SO_2$—, and said aryl or heteroaryl group is optionally substituted with at least one substituent $R^{15}$;
$R^1$ and $R^2$, which may be the same or different, are each independently selected from hydrogen, —$C_{1-6}$alkyl, —$C_{2-6}$alkenyl, —$C_{2-6}$alkynyl, cycloalkyl, heterocyclyl, aryl, or heteroaryl, wherein said $C_{1-6}$alkyl, —$C_{2-6}$alkenyl, —$C_{2-6}$alkynyl, cycloalkyl, heterocyclyl, aryl, or heteroaryl are each independently optionally substituted with at least one substituent $R^{15}$, provided that $R^1$ and $R^2$ are not both hydrogen; or $R^1$ and $R^2$, together with the carbon atom to which they are attached, form a 3- to 12-membered saturated, partially or fully unsaturated ring comprising 0, 1 or 2 heteroatoms independently selected from —N= or =N—, —NH—, —O—, —S—, —SO— or —SO$_2$—, and said ring is optionally substituted with at least one substituent $R^{15}$;

$R^3$ is hydrogen;

$R^4$ is hydrogen, $C_{1-6}$alkyl, $C_{3-8}$cycloalkyl, aryl, heteroaryl, or heterocyclyl, wherein each of said $C_{1-6}$alkyl, $C_{3-8}$cycloalkyl, aryl, heteroaryl, or heterocyclyl is independently and optionally substituted with one or two substituents $R^5$; or two adjacent substituents $R^5$ on the $C_{3-8}$cycloalkyl, aryl, heteroaryl, or heterocyclyl ring together with the atoms they are attached form a fused ring;

$R^5$ is independently hydrogen, halogen, —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, $C_{3-8}$cycloalkyl, heterocyclyl, aryl, heteroaryl, —CN, —NO$_2$, oxo, —OR$^b$, —SO$_2$R$^b$, —COR$^b$, —CO$_2$R$^b$, —CONR$^b$R$^c$, —C(=NR$^b$)NR$^c$R$^d$, —NR$^b$R$^c$, —NR$^b$COR$^c$, —NR$^b$CONR$^c$R$^d$, —NR$^b$CO$_2$R$^c$, —NR$^b$SONR$^c$R$^d$, —NR$^b$SO$_2$NR$^c$R$^d$, or —NR$^b$SO$_2$R$^c$, wherein each of said —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, $C_{3-8}$cycloalkyl, heterocyclyl, aryl, or heteroaryl is independently and optionally substituted with one or two substituents $R^6$;

$R^6$ is independently hydrogen, halogen, —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, $C_{3-8}$cycloalkyl, heterocyclyl, aryl, heteroaryl, —CN, —NO$_2$, oxo, or —OR$^e$, wherein, as $R^6$, each of said —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, cycloalkyl, heterocyclyl, aryl, or heteroaryl is each independently and optionally substituted with one or two substituents $R^7$;

$R^7$ is, at each of its occurrences, independently hydrogen, halogen, —$C_{1-6}$alkyl, —$C_{2-6}$alkenyl, —$C_{2-6}$alkynyl, cycloalkyl, heterocyclyl, aryl, heteroaryl, —CN, —NO$_2$, oxo, —$C_{1-6}$alkoxy, —$C_{1-6}$alkoxy-$C_{1-6}$alkoxy or hydroxyl;

$R^b$, $R^c$, $R^d$, $R^e$, which may be the same or different, are each independently hydrogen, —$C_{1-6}$alkyl, $C_{1-6}$alkoxy-$C_{1-6}$alkyl-, —$C_{2-6}$alkenyl, —$C_{2-6}$alkynyl, cycloalkyl, heterocyclyl, aryl, or heteroaryl, wherein said $C_{1-6}$alkyl, —$C_{2-6}$alkenyl, —$C_{2-6}$alkynyl, cycloalkyl, heterocyclyl, aryl, or heteroaryl are each independently optionally substituted with at least one substituent $R^{15}$; and $R^{15}$ is independently hydrogen, halogen, cyano, —$C_{1-6}$alkyl, $C_{2-6}$alkenyl, —$C_{2-6}$alkynyl, halo$C_{1-6}$alkyl, halo$C_{2-6}$alkenyl, halo$C_{2-6}$alkynyl, —$C_{1-6}$alkoxy, $C_{3-8}$cycloalkyloxy, cycloalkyl, heterocyclyl, aryl, or heteroaryl.

In one embodiment, X is N and Y is CR$^a$ so that X and Y form a —N=CR$^a$— moiety. $R^a$ is defined as with formula (I); preferably $R^a$ is hydrogen or $C_{1-3}$alkyl; more preferably $R^a$ is hydrogen. In a preferred embodiment, X is N and Y is CH so that X and Y form a —N=CH— moiety.

In another embodiment, X is C(=O) and Y is NR$^a$. $R^a$ is defined as with formula (I); preferably $R^a$ is hydrogen and methyl.

In yet another embodiment, X is CR$^a$ and Y is CR$^a$ so that X and Y form a CR$^a$=CR$^a$— moiety. $R^a$ is defined as with formula (I); preferably each $R^a$ is independently selected from hydrogen or $C_{1-3}$alkyl; more preferably $R^a$ is hydrogen.

In one embodiment, R is a C-linked 5 or 6-membered heteroaryl group containing 1 or 2 heteroatoms independently selected from —N= or =N—, —NH—, —O—, or —S—, In a preferred embodiment, R is furanyl, pyrazinyl or thiazolyl; more preferably, furan-2-yl, 3-methylpyrazin-2-yl or thiazol-2-yl.

In one embodiment, $R^1$ is hydrogen and $R^2$ is phenyl; or $R^1$ is hydrogen and $R^2$ is $C_{1-6}$alkyl (preferably $C_{1-4}$alkyl, e.g., propyl or but-2-yl); or $R^1$ is $C_{1-6}$alkyl (preferably $C_{1-4}$alkyl, methyl, ethyl) and $R^2$ is phenyl; or $R^1$ is $C_{1-6}$alkyl (preferably $C_{1-4}$alkyl, e.g., methyl) and $R^2$ is pyridinyl; or $R^1$ is $C_{1-6}$alkyl (preferably $C_{1-4}$alkyl, e.g., methyl) and $R^2$ is $C_{1-6}$alkyl substituted with heterocyclyl, aryl, or heteroaryl (preferably a $C_{1-4}$alkyl substituted with a phenyl group, e.g., benzyl).

In one embodiment, $R^1$ and $R^2$, together with the carbon atom to which they are attached, form a 3- to 12-membered saturated ring comprising 0 heteroatoms. In a preferred embodiment, $R^1$ and $R^2$, together with the carbon atom to which they are attached, form a cyclopropyl, cyclobutyl, cyclopentyl, cyclohexyl, or 1,2,3,4-tetrahydronaphthalen-1-yl group.

In one embodiment, $R^4$ is $C_{1-6}$alkyl (preferably $C_{1-3}$alkyl) optionally substituted with one or two substituents $R^5$, wherein each $R^5$ is independently selected from aryl, heteroaryl, heterocyclyl, cycloalkyl, —OR$^b$ or —NR$^b$R$^c$ as defined with formula (I).

In a preferred embodiment, $R^4$ is $C_{1-6}$alkyl (preferably $C_{1-3}$alkyl) optionally substituted with an aryl group as $R^5$, said aryl group is optionally substituted with halogen, —$C_{1-6}$alkyl, halo$C_{1-6}$alkyl, or —OR$^e$, wherein $R^e$ is $C_{1-6}$alkyl optionally substituted with halogen. In a further preferred embodiment, the aryl group is phenyl or substituted phenyl (e.g., benzo[d][1,3]dioxol-5-yl). In an even further preferred embodiment, the phenyl group is optionally substituted with $C_{1-6}$alkyloxy, halo$C_{1-6}$alkoxy, F, Cl, or Br. More preferably, the phenyl group is optionally substituted with methoxy, fluoro, trifluoromethoxy, trifluoromethyl, or methyl.

Specifically, $R^4$ is phenylmethyl, 2-methoxyl)phenylmethyl, 3-methoxyl)phenylmethyl, 4-methoxyl)phenylmethyl, 2-fluorophenylmethyl, 2-(trifluoromethoxy)phenylmethyl, 4-(trifluoromethoxy)phenylmethyl, 1-phenylethyl, (S)-1-phenylethyl, (R)-1-phenylethyl, 2-phenylethyl, 3-(trifluoromethyl)phenylmethyl, 4-(trifluoromethyl)phenylmethyl, 3-methylphenylmethyl, 4-methylphenylmethyl, 4-fluorophenylmethyl, or benzo[d][1,3]dioxol-5-ylmethyl.

In a preferred embodiment, $R^4$ is $C_{1-6}$alkyl (preferably $C_{1-3}$alkyl) optionally substituted with a heterocyclyl group as $R^5$, said heterocyclyl group is optionally substituted with aryl and —OR$^e$, wherein said aryl is optionally substituted with $R^7$, and $R^e$ and $R^7$ are as defined with formula (I). In a further preferred embodiment, the heterocyclyl group is 3- to 12-membered heterocyclyl, either monocyclic or bicyclic, preferably 4-, 5-, 6-, 7-, or 8-membered monocyclic heterocyclyl ring comprising 1 or 2 or 3 heteroatoms independently selected from —NH—, —O—, —S—, —SO— or —SO$_2$—. In an even further preferred embodiment, the heterocyclyl ring is oxetanyl, piperazinyl, tetrahydrofuranyl, pyranyl, or morpholino, each of which is optionally substituted with hydroxyl.

Specifically, R⁴ is (3-hydroxyoxetan-3-yl)methyl, oxetan-3-ylmethyl, 2-(4-(4-(2-methoxyethoxy)phenyl)piperazin-1-yl)ethyl, 2-(piperazin-1-yl)ethyl, (4-methylpiperazin-yl)ethyl, (tetrahydrofuran-2-yl)methyl, ((S)-tetrahydrofuran-3-yl)methyl, ((R)-tetrahydrofuran-2-yl)methyl, ((S)-tetrahydrofuran-2-yl)methyl, ((R)-tetrahydrofuran-3-yl)methyl, 2-(tetrahydrofuran-3-yl)ethyl, (tetrahydro-2H-pyran-3-yl)methyl, 2-(tetrahydro-2H-pyran-4-yl)ethyl, (4-hydroxytetrahydro-2H-pyran-4-yl)methyl, (tetrahydro-2H-pyran-4-yl)methyl, or 2-morpholinoethyl.

In a preferred embodiment, R⁴ is $C_{1-6}$alkyl (preferably $C_{1-3}$alkyl) optionally substituted with a $C_{3-8}$cycloalkyl group as R⁵, said $C_{3-8}$cycloalkyl group is optionally substituted with hydroxyl. In a further preferred embodiment, said $C_{3-8}$cycloalkyl is cyclopropyl, cyclobutyl, cyclopentyl, cyclohexyl, cycloheptyl, or cyclooctyl; preferably cyclopropyl, cyclobutyl, or cyclohexyl. Specifically, R⁴ is (1-hydroxycyclopropyl)methyl, (1-hydroxycyclobutyl)methyl or (1-hydroxycyclohexyl)methyl.

In a preferred embodiment, R⁴ is $C_{1-6}$alkyl (preferably $C_{1-3}$alkyl) optionally substituted with a heteroaryl group as R⁵, said heteroaryl group is optionally substituted with halogen, $C_{1-6}$alkyl, $C_{3-8}$cycloalkyl, or —OR$^e$, wherein said $C_{1-6}$alkyl and $C_{3-8}$cycloalkyl is optionally substituted with hydroxy. In a further preferred embodiment, the heteroaryl group is pyridinyl including pyridin-2-yl, pyridin-3-yl or pyridin-4-yl, optionally substituted with hydroxycyclobutyl, methyl, methoxy, or halogen. Specifically, R⁴ is pyridin-2-ylmethyl, pyridin-4-ylmethyl, pyridin-3-ylmethyl, (6-(1-hydroxycyclobutyl)pyridin-2-ylmethyl, (6-methylpyridin-2-yl)methyl, (5-methylpyridin-2-yl)methyl, (4-methylpyridin-2-yl)methyl, (3-methylpyridin-2-yl)methyl, (6-methoxyl)pyridin-2-yl)methyl, (5-methoxyl)pyridin-2-yl)methyl, (4-methoxyl)pyridin-2-yl)methyl, (3-methoxyl)pyridin-2-yl)methyl, (6-fluoropyridin-2-yl)methyl, (5-fluoropyridin-2-yl)methyl, (4-fluoropyridin-2-yl)methyl, or (3-fluoropyridin-2-yl)methyl.

In a preferred embodiment, R⁴ is $C_{1-6}$alkyl (preferably $C_{1-3}$alkyl) optionally substituted with —OR$^b$ or —NR$^b$R$^c$ as R⁵, wherein R$^b$ and R$^c$ are independently hydrogen, $C_{1-6}$alkyl, or —$C_{1-6}$alkoxyC$_{1-6}$alkyl. Specifically, R⁴ is 2-methoxyethyl, 2-(dimethylamino)ethyl, 2-(2-methoxyethoxy)ethyl, 2-(methylamino)ethyl, 2-hydroxyl)propyl, (R)-2-hydroxyl)propyl, or 2-hydroxyethyl.

In another embodiment, R⁴ is $C_{3-8}$cycloalkyl optionally substituted with $C_{1-6}$alkyl, $C_{1-6}$alkoxy, or hydroxyl, said $C_{3-8}$cycloalkyl is selected from cyclopropyl, cyclobutyl, cyclopentyl, cyclohexyl, cycloheptyl, and cyclooctyl; preferably cyclopropyl, cyclobutyl, cyclopentyl, and cyclohexyl. In a further preferred embodiment, R⁴ is 4-substituted cyclohexyl wherein the substituent at position 4 and the amino group attached to position 1 are in (cis) or (trans) configurations, preferably in a (cis) configuration. In a further preferred embodiment, R⁴ is 3-substituted cyclobutyl wherein the substituent at position 3 and the amino group attached to position 1 are in (cis) or (trans) configurations, preferably in a (cis) configuration.

Specifically R⁴ is 2-hydroxycycloheptyl, 3-hydroxycycloheptyl, 4-hydroxycycloheptyl, cyclohexyl, 4-hydroxy-4-methylcyclohexyl, (trans)-4-hydroxycyclohexyl, (cis)-4-hydroxy-4-methylcyclohexyl, (cis)-4-hydroxycyclohexyl, (1S,4S)-4-hydroxy-4-methylcyclohexyl, (1S,4S)-4-hydroxycyclohexyl, (1S,2R)-2-hydroxycyclohexyl, (1S,4S)-4-hydroxy-4-methylcyclohexyl, (1S,2S)-2-hydroxycyclohexyl, (1R,2S)-2-hydroxycyclohexyl, (trans)-4-hydroxy-4-methylcyclohexyl, 3-hydroxycyclohexyl, (1R,3R)-3-hydroxycyclohexyl, (1S,3R)-3-hydroxycyclohexyl, (1R,3S)-3-hydroxycyclohexyl, (1S,3S)-3-hydroxycyclohexyl, 4-oxocyclohexyl, acetyloxycyclohexyl, cyclopentyl, 3-hydroxycyclopentyl, (1S,2R)-2-hydroxycyclopentyl, (1R,2S)-2-hydroxycyclopentyl, (I R,3R)-3-hydroxycyclopentyl, (S,3S)-3-hydroxycyclopentyl, (trans)-3-hydroxycyclobutyl, (cis)-3-hydroxycyclobutyl, (cis)-3-hydroxy-3-methylcyclobutyl, 1-(hydroxymethyl)cyclopropyl, cyclopropyl, 1,2,3,4-tetrahydronaphthalen-1-yl, or 2,3-dihydro-1H-inden-1-yl.

In another embodiment, R⁴ is aryl which is a phenyl group.

In another embodiment, R⁴ is heteroaryl which is pyridinyl. In a preferred embodiment, R⁴ is pyridin-3-yl, pyridin-4-yl, or pyridin-2-yl.

In another embodiment, R⁴ is heterocyclyl selected from pyranyl, pyrrolidinyl, tetrahydrofuranyl, chroman-4-yl, or dihydrobenzofuran-3-yl, each of which is optionally substituted as defined with formula (I). In one embodiment, the heterocyclyl is optionally substituted with aryl, oxo, or hydroxy, wherein aryl is further optionally substituted with —$C_{1-6}$alkoxy-$C_{1-6}$alkoxy. Specifically, R⁴ is tetrahydro-2H-pyran-4-yl, (S)-tetrahydro-2H-pyran-3-yl, (R)-tetrahydro-2H-pyran-3-yl, tetrahydro-2H-pyran-4-yl, (R)-chroman-4-yl, (S)-chroman-4-yl, 2,3-dihydrobenzofuran-3-yl, 1-(4-(2-methoxyethoxy)phenyl)piperidin-4-yl, (R)-piperidin-3-yl (E652), (S)-piperidin-3-yl, 4-hydroxypiperidin-1-yl, (S)-5-oxopyrrolidin-3-yl, (S)-2-oxopyrrolidin-3-yl, (3S,4R)-4-hydroxytetrahydrofuran-3-yl, (3S,4S)-4-hydroxytetrahydrofuran-3-yl, (3S,4S)-4-hydroxytetrahydrofuran-3-yl, or (3R,4R)-4-hydroxytetrahydrofuran-3-yl.

Disclosed herein is a pharmaceutical composition comprising the compound of formula (I) disclosed herein or a stereoisomer thereof, or a pharmaceutically acceptable salt thereof and a pharmaceutically acceptable excipient.

Disclosed herein is a method of treating cancer, comprising administering a subject in need thereof the compound of formula (I) disclosed herein or a stereoisomer thereof, or a pharmaceutically acceptable salt thereof. Also disclosed herein is a method of immune modulating a subject having cancer or tumor, comprising administering a subject in need thereof the compound of formula (I) disclosed herein or a stereoisomer thereof, or a pharmaceutically acceptable salt thereof.

Also disclosed herein are compounds of formulas 5 and 13

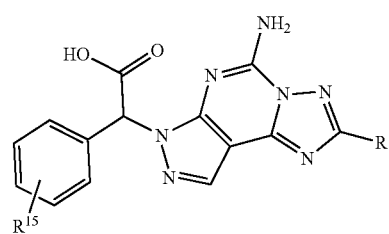

5 and

7
-continued

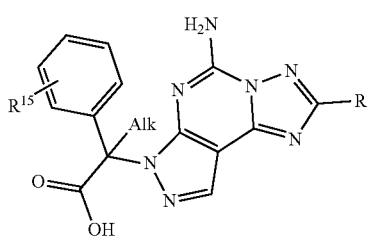
13

2. wherein R and $R^{15}$ are as defined with formula (I).

Also disclosed herein is a process of preparing the compound of formula 5, comprising hydrolyzing a compound of formula 4 into the free acid of formula 5 with a base,

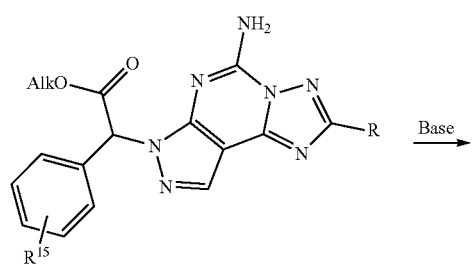
4

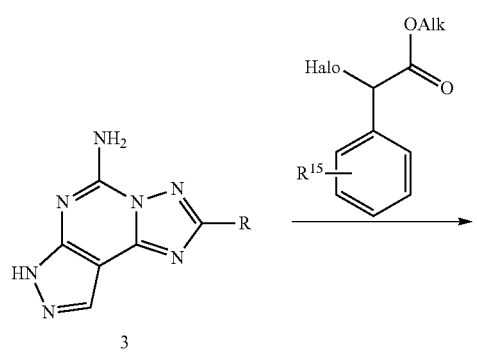
5

3. wherein Alk is an alkyl group, R and $R^{15}$ are as defined with formula (I).

In one aspect, the base is, but not limited to sodium hydroxide or potassium tert-butoxide.

In one embodiment, the process further comprises reacting formula 3 with 2-halo-2-phenylacetate ester to form formula 4

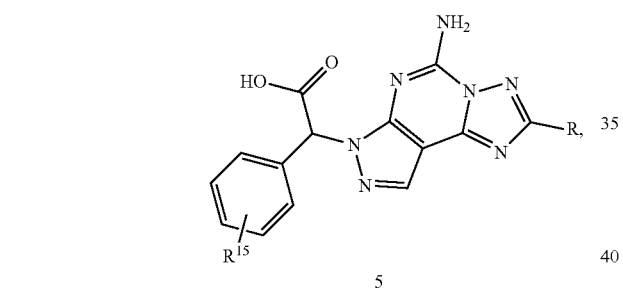

8
-continued

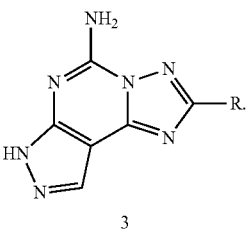
4

In one aspect, the 2-halo-2-phenylacetate ester is, but limited to, methyl 2-bromo-2-phenylacetate.

In one embodiment, the process further comprises rearranging a compound of formula 2 in the presence of acidic condition to give formula 3

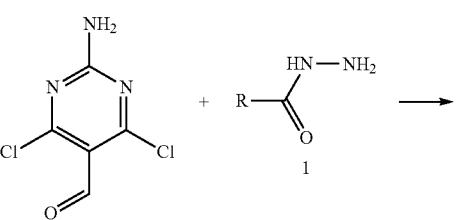
2

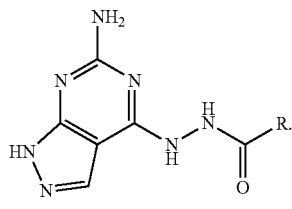
3

In one embodiment, the process further comprises reacting an aldehyde with carbohydrazide 1 to form formula 2,

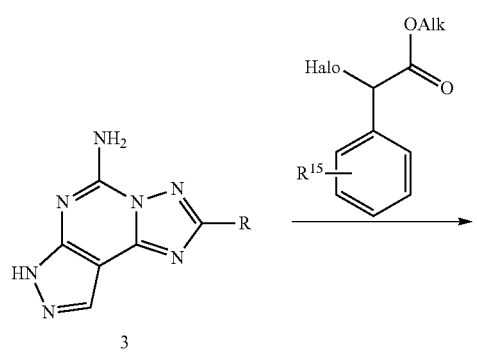

In one aspect, the carbohydrazide is, but is not limited to furan-2-carbohydrazide.

Also disclosed herein is a process of preparing the compound of formula 13, comprising hydrolyzing an ester 12 into the free acid of formula 13 by with a base,

9

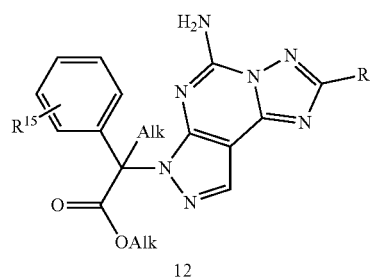

12

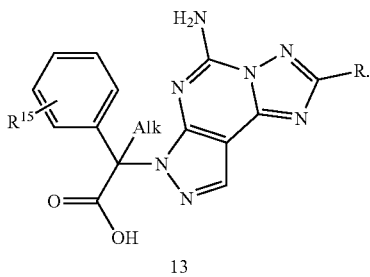

13 in one aspect, the base is, but is not limited to sodium hydroxide or potassium tert-butoxide.

In one embodiment, the process further comprises rearranging a compound 11 in the presence of acidic condition to give formula 12,

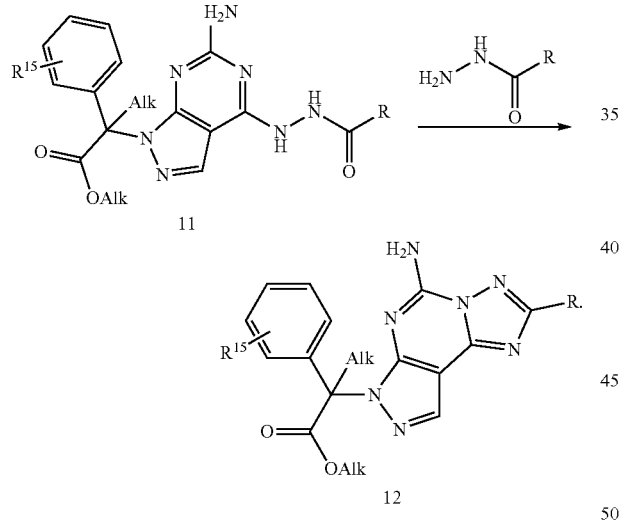

In one embodiment, the process further comprises reacting a compound of formula 10 with carbohydrazide to obtain a compound of formula 11,

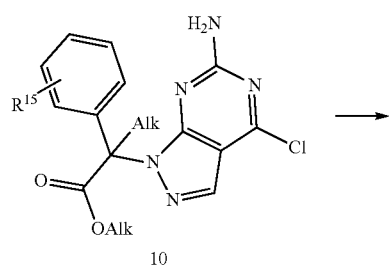

10

10

-continued

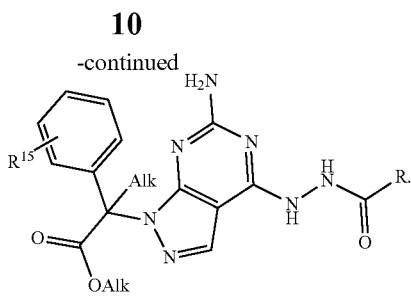

11

In one aspect, the carbohydrazide is, but not limited to furan-2-carbohydrazide.

In one embodiment, the process further comprises reacting Formula 9 with 2-amino-4,6-dichloropyrimidine-5-carbaldehyde to obtain a compound of formula 10,

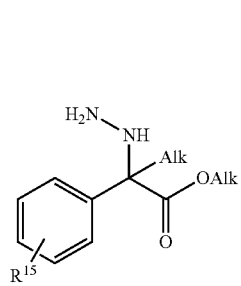 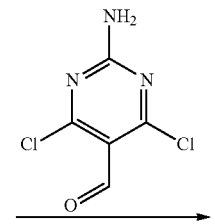

9

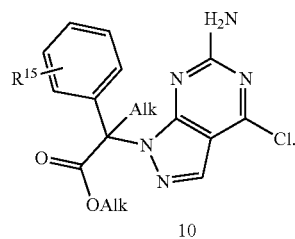

10 in one embodiment, the process further comprises reacting a compound of formula 8 with hydrazine hydrate to form formula 9,

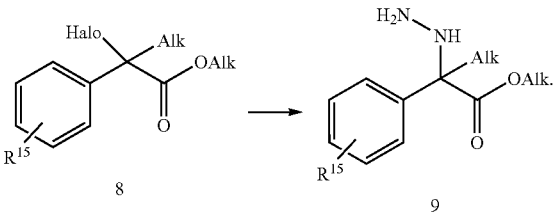

8    9

In one embodiment, the process further comprises introducing one halo atom at the alpha position of a compound of formula 7 with halogenation reagent,

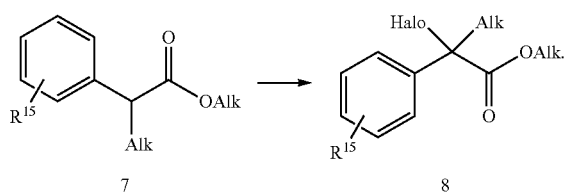

In one aspect, the halogenation reagent is, but is not limited to, N-bromosuccinimide.

In one embodiment, the process further comprises esterifying an acid, which is esterified under standard conditions known in the art to afford a compound of formula 7

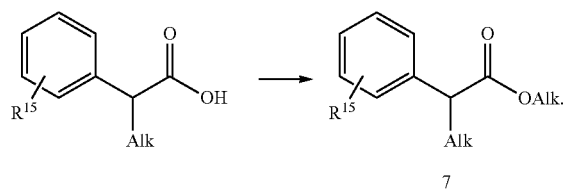

In one aspect, the acid is 2-phenylpropanoic acid.

DETAILED DESCRIPTION OF THE INVENTION

The following terms have the indicated meanings throughout the specification:

As used herein, including the appended claims, the singular forms of words such as "a", "an", and "the", include their corresponding plural references unless the context clearly dictates otherwise.

The term "or" is used to mean, and is used interchangeably with, the term "and/or" unless the context clearly dictates otherwise.

The term "alkyl" herein refers to a hydrocarbon group selected from linear and branched saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include, but not limited to, methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

The term "halogen" herein refers to fluoro (F), chloro (Cl), bromo (Br) and iodo (I).

The term "haloalkyl" herein refers to an alkyl group in which one or more hydrogen is/are replaced by one or more halogen atoms such as fluoro, chloro, bromo, and iodo. Examples of the haloalkyl include $haloC_{1-8}$alkyl, $haloC_{1-6}$alkyl or halo $C_{1-4}$alkyl, but not limited to —$CF_3$, —$CH_2Cl$, —$CH_2CF_3$, —$CCl_2$, $CF_3$, and the like.

The term "alkenyl" herein refers to a hydrocarbon group selected from linear and branched hydrocarbon groups comprising at least one C=C double bond and from 2 to 18, such as from 2 to 8, further such as from 2 to 6, carbon atoms. Examples of the alkenyl group, e.g., $C_{2-6}$ alkenyl, include, but are not limited to ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkynyl" herein refers to a hydrocarbon group selected from linear and branched hydrocarbon groups, comprising at least one C≡C triple bond and from 2 to 18, such as 2 to 8, further such as from 2 to 6, carbon atoms. Examples of the alkynyl group, e.g., $C_{2-6}$ alkynyl, include, but not limited to ethynyl, 1-propynyl, 2-propynyl (propargyl), 1-butynyl, 2-butynyl, and 3-butynyl groups.

The term "alkyloxy" or "alkoxy" herein refers to an alkyl group as defined above attached to the parent molecular moiety through an oxygen atom. Examples of an alkyloxy, e.g., $C_{1-6}$alkyloxy or $C_{1-4}$ alkyloxy includes, but not limited to, methoxy, ethoxy, isopropoxy, propoxy, n-butoxy, tert-butoxy, pentoxy and hexoxy and the like.

The term "cycloalkyl" herein refers to a hydrocarbon group selected from saturated and partially unsaturated cyclic hydrocarbon groups, comprising monocyclic and polycyclic bicyclic and tricyclic) groups. For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. In particular, examples of the saturated monocyclic cycloalkyl group, e.g., $C_{3-8}$ cycloalkyl, include, but not limited to cyclopropyl, cyclobutyl, cyclopentyl, cyclohexyl, cycloheptyl, and cyclooctyl groups. In a preferred embodiment, the cycloalkyl is a monocyclic ring comprising 3 to 6 carbon atoms (abbreviated as $C_{3-6}$ cycloalkyl), including but not limited to, cyclopropyl, cyclobutyl, cyclopentyl, and cyclohexyl. Examples of the bicyclic cycloalkyl groups include those having from 7 to 12 ring atoms arranged as a bicyclic ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. Further examples of the bicyclic cycloalkyl groups include those arranged as a bicyclic ring selected from [5,6] and [6,6] ring systems, such as

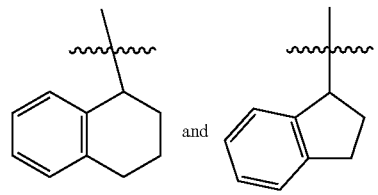 [SMILES: *C1CCCc2ccccc21 ; *C1CCc2ccccc21]

wherein the wavy lines indicate the points of attachment. The ring may be saturated or have at least one double bond (i.e. partially unsaturated), but is not fully conjugated, and is not aromatic, as aromatic is defined herein.

The term "aryl" used alone or in combination with other terms refers to a group selected from:

5- and 6-membered carbocyclic aromatic rings, e.g., phenyl;

bicyclic ring systems such as 7 to 12 membered bicyclic ring systems, wherein at least one ring is carbocyclic and aromatic, e.g., naphthyl and indanyl; and, tricyclic ring systems such as 10 to 15 membered tricyclic ring systems wherein at least one ring is carbocyclic and aromatic, e.g., fluorenyl.

The terms "aromatic hydrocarbon ring" and "aryl" are used interchangeable throughout the disclosure herein. In some embodiments, a monocyclic or bicyclic aromatic hydrocarbon ring has 5 to 10 ring-forming carbon atoms (i.e., $C_{5-10}$ aryl). Examples of a monocyclic or bicyclic aromatic hydrocarbon ring includes, but not limited to, phenyl, naphth-1-yl, naphth-2-yl, anthracenyl, phenanthrenyl, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

The term "heteroaryl" herein refers to a group selected from:
a) 5-, 6- or 7-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O), with the remaining ring atoms being carbon;
b) 8- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and
c) 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form NT-oxides. The term "C-linked heteroaryl" as used herein means that the heteroaryl group is connected to the core molecule by a bond from a C-atom of the heteroaryl ring The terms "aromatic heterocyclic ring" and "heteroaryl" are used interchangeable throughout the disclosure herein. In some embodiments, a monocyclic or bicyclic aromatic heterocyclic ring has 5-, 6-, 7-, 8-, 9- or 10-ring forming members with 1, 2, 3, or 4 heteroatom ring members independently selected from nitrogen (N), sulfur (S) and oxygen (O) and the remaining ring members being carbon. In some embodiments, the monocyclic or bicyclic aromatic heterocyclic ring is a monocyclic or bicyclic ring comprising 1 or 2 heteroatom ring members independently selected from nitrogen (N), sulfur (S) and oxygen (O). In some embodiments, the monocyclic or bicyclic aromatic heterocyclic ring is a 5- to 6-membered heteroaryl ring, which is monocyclic and which has 1 or 2 heteroatom ring members independently selected from nitrogen (N), sulfur (S) and oxygen (O). In some embodiments, the monocyclic or bicyclic aromatic heterocyclic ring is a 8- to 10-membered heteroaryl ring, which is bicyclic and which has 1 or 2 heteroatom ring members independently selected from nitrogen, sulfur and oxygen.

Examples of the heteroaryl group or the monocyclic or bicyclic aromatic heterocyclic ring include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, imidazopyridinyl, isoxazolyl, oxazolyl, thiazolyl, isothiazolyl, thiadiazolyl (such as 1,2,3-thiadiazolyl, 1,2,4-thiadiazolyl, or 1,3,4-thiadiazolyl), tetrazolyl, thienyl (such as thien-2-yl, thien-3-yl), triazinyl, benzothienyl, furyl or furanyl, benzofuryl, benzoimidazolyl, indolyl, isoindolyl, indolinyl, oxadiazolyl (such as 1,2,3-oxadiazolyl, 1,2,4-oxadiazolyl, or 1,3,4-oxadiazolyl), phthalazinyl, pyrazinyl, pyridazinyl, pyrrolyl, triazolyl (such as 1,2,3-triazolyl, 1,2,4-triazolyl, or 1,3,4-triazolyl), quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, oxa-2,3-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl (such as furazan-2-yl, furazan-3-yl), benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" herein refers to a ring selected from 3-, 4-, 5-, 6-, 7-, 8-, 9-, 10-, 11- or 12-membered monocyclic, bicyclic and tricyclic, saturated and partially unsaturated rings comprising at least one carbon atoms in addition to at least one heteroatom, such as from 1-4 heteroatoms, further such as from 1-3, or further such as 1 or 2 heteroatoms, selected from nitrogen (N), sulfur (S), oxygen (O), —SO— or —SO$_2$—.

In some embodiments, a heterocyclyl group is 4-, 5-, 6-, 7- or 8-membered monocyclic ring with at least one heteroatom selected from N, O and S. In some preferred embodiments, a heterocyclyl group is a 4-, 5-, 6-, 7- or 8-membered saturated monocytic ring comprising one nitrogen heteroatom. The exemplary heterocyclyl group is azetidinyl, pyrrolidinyl, piperidinyl, azepanyl, and azocanyl. In other embodiments, a heterocyclyl group is a 5-, 6-, 7- or 8-membered saturated monocyclic ring comprising one nitrogen atom and 1 additional heteroatom selected from —NH, —O—, —S—, —SO— or —SO$_2$—. The exemplary heterocyclyl group is a morpholino, morpholinyl or piperazinyl ring. In some embodiments, a heterocyclyl group is a 7- to 12-membered saturated bicyclic ring comprising one nitrogen atom and 0 or 1 or 2 additional heteroatoms selected from —NH, —O—, —S—, —SO— or —SO$_2$—. In some preferred embodiments, the heterocyclyl group is a bicyclic bridged or spiro-ring.

"Heterocycle" herein also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring, when the heterocyclic ring is fused with cycloalkyl. "Heterocycle" herein also refers to an aliphatic spirocyclic ring comprising at least one heteroatom selected from N, O, and S, provided that the point of attachment is at the heterocyclic ring. The ring may be saturated or have at least one double bond (i.e. partially unsaturated). The heterocycle may be substituted with oxo. The point of the attachment may be carbon or heteroatom in the heterocyclic ring. A heterocycle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, morpholinyl, morpholino, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepanyl, 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-oxidotetrahydro-2H-thiopyran-4-yl, 1-pyrrolinyl, 2-pyrrolinyl, 3-pyrrolinyl, indolinyl, 2H-pyranyl, 4H-pyranyl, 1,4-dioxanyl, dioxolanyl, pyrazolinyl, pyrazolidinyl, dithianyl, dithiolanyl, pyrazolidinyl, imidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. A substituted heterocycle also includes a ring system substituted with one or more oxo moieties, such as piperidinyl N-oxide, morpholinyl-N-oxide, 1-oxo-1-thiomorpholinyl and 1,1-dioxo-1-thiomorpholinyl.

Compounds disclosed herein may contain an asymmetric center and may thus exist as enantiomers. "Enantiomers" refer to two stereoisomers of a compound which are non-superimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds disclosed herein contain olefinic double bonds, unless specified otherwise, such double bonds are meant to include both E and Z geometric isomers.

When compounds disclosed herein contain a di-substituted cyclohexyl or cyclobutyl group, substituents found on cyclohexyl or cyclobutyl ring may adopt cis and trans formations. Cis formation means that both substituents are found on the upper side of the 2 substituent placements on the ring, while trans would mean that they were on opposing sides of the ring.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

"Diastereomers" refers to stereoisomers of a compound with two or more chiral centers but which are not mirror images of one another. Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. *Stereochemistry of Organic Compounds*: New York: John Wiley & Sons, Inc., 1994; Lochmuller, C. H., et al. *"Chromatographic resolution of enantiomers: Selective review." J. Chromatogr.*, 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. *Drug Stereochemistry: Analytical Methods and Pharmacology*. New York: Marcel Dekker, Inc., 1993.

"Pharmaceutically acceptable salts" refers to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "a pharmaceutically acceptable salt thereof" include salts of at least one compound of Formula (I), and salts of the stereoisomers of the compound of Formula (I), such as salts of enantiomers, and/or salts of diastereomers.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, rabbit) and most preferably a human.

The term "effective amount" or "therapeutically effective amount" refers to an amount of the active ingredient, such as compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer thereof, and/or at least one pharmaceutically acceptable salt thereof disclosed herein effective to "treat" as defined above, a disease or disorder in a subject. In the case of combination therapy, the "therapeutically effective amount" refers to the total amount of the combination objects for the effective treatment of a disease, a disorder or a condition.

The term "at least one substituent" disclosed herein includes, for example, from 1 to 5, such as from 1 to 4, further as 1, 2 or 3, substituents, provided that the valence allows such substitution. For example, "at least one substituent $R^{15}$" disclosed herein includes from 1 to 4, such as from 1 to 3, further as 1 or 2, substituents selected from the list of $R^{15}$ as disclosed herein.

The pharmaceutical composition comprising the compound disclosed herein can be administrated via oral, inhalation, rectal, parenteral or topical administration to a subject in need thereof. For oral administration, the pharmaceutical composition may be a regular solid formulation such as tablets, powder, granule, capsules and the like, a liquid formulation such as water or oil suspension or other liquid formulation such as syrup, solution, suspension or the like; for parenteral administration, the pharmaceutical composition may be solution, water solution, oil suspension concentrate, lyophilized powder or the like. Preferably, the formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All formulations of the pharmaceutical composition disclosed herein can be produced by the conventional methods in the pharmaceutical field. For example, the active ingredient can be mixed with one or more excipients, then to make the desired formulation. The "pharmaceutically acceptable excipient" refers to conventional pharmaceutical carriers suitable for the desired pharmaceutical formulation, for example: a diluent, a vehicle such as water, various organic solvents, etc, a filler such as starch, sucrose, etc a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye.

The term "disease" refers to any disease, discomfort, illness, symptoms or indications, and can be interchangeable with the term "disorder" or "condition".

Throughout this specification and the claims which follow, unless the context requires otherwise, the term "comprise", and variations such as "comprises" and "comprising" are intended to specify the presence of the features thereafter, but do not exclude the presence or addition of one or more other features. When used herein the term "comprising" can be substituted with the term "containing", "including" or sometimes "having".

Throughout this specification and the claims which follow, the term indicates a range which includes the endpoints, wherein n and m are integers and indicate the number of carbons. Examples include $C_{1-8}$, $C_{1-6}$, and the like.

Unless specifically defined elsewhere in this document, all other technical and scientific terms used herein have the meaning commonly understood by one of ordinary skill in the art to which this invention belongs.

General Synthesis

Compounds disclosed herein, including salts thereof, can be prepared using known organic synthesis techniques and can be synthesized according to any of numerous possible synthetic routes.

The reaction for preparing compounds disclosed herein can be carried out in suitable solvents which can be readily selected by one of skill in the art of organic synthesis. Suitable solvents can be substantially non-reactive with the starting materials, the intermediates, or products at the temperatures at which the reactions are carried out, e.g., temperatures which can range from the solvent's boiling temperature. A given reaction can be carried out in one solvent or mixture of solvents.

The selection of appropriate protecting group, can be readily determined by one skilled the art.

Reactions can be monitored according to any suitable method known in the art, such as NMR, UV, HPLC, LC-MS and TLC. Compounds can be purified by a variety of methods, including HPLC and normal phase silica chromatography.

Chiral analytic HPLC was used for the retention time analysis of different chiral examples, the conditions were divided into the methods as below according to the column, mobile phase, solvent ration used.

The compounds disclosed herein can be prepared by following Scheme I and Scheme II.

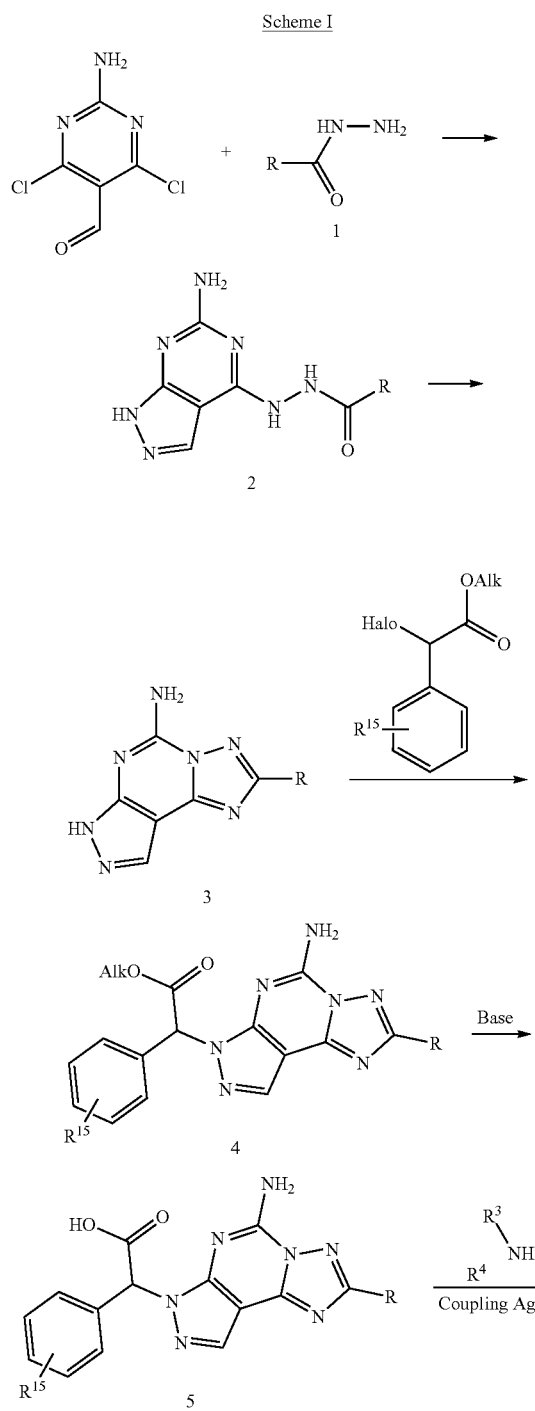

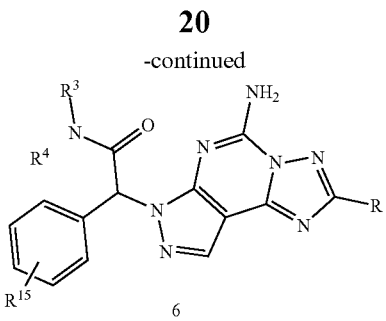

Alk = alkyl group;
Halo = halogen;

wherein R and $R^{15}$ are as defined with formula (I).

In scheme I, a commercially available aldehyde is reacted with carbohydrazide 1 (such as furan-2-carbohydrazide) to form formula 2, which is rearranged in the presence of acidic condition to give formula 3. Then formula 3 is reacted with 2-halo-2-phenylacetate ester (such as methyl 2-bromo-2-phenylacetate) to form formula 4 which subsequently is hydrolyzed into the free acid of formula 5 by using a base such as sodium hydroxide or potassium tert-butoxide. The tither coupling of the acid 5 is accomplished under standard conditions known in the art to provide a compound of Formula 6.

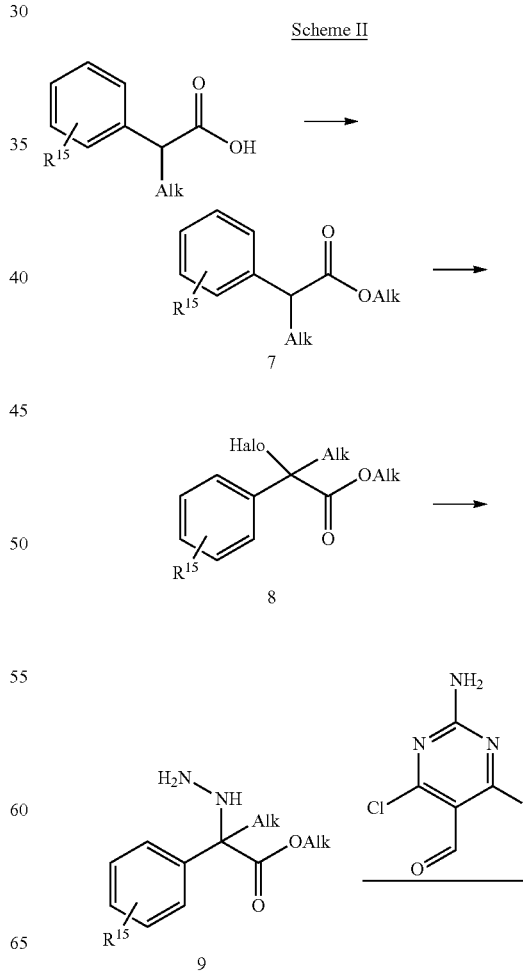

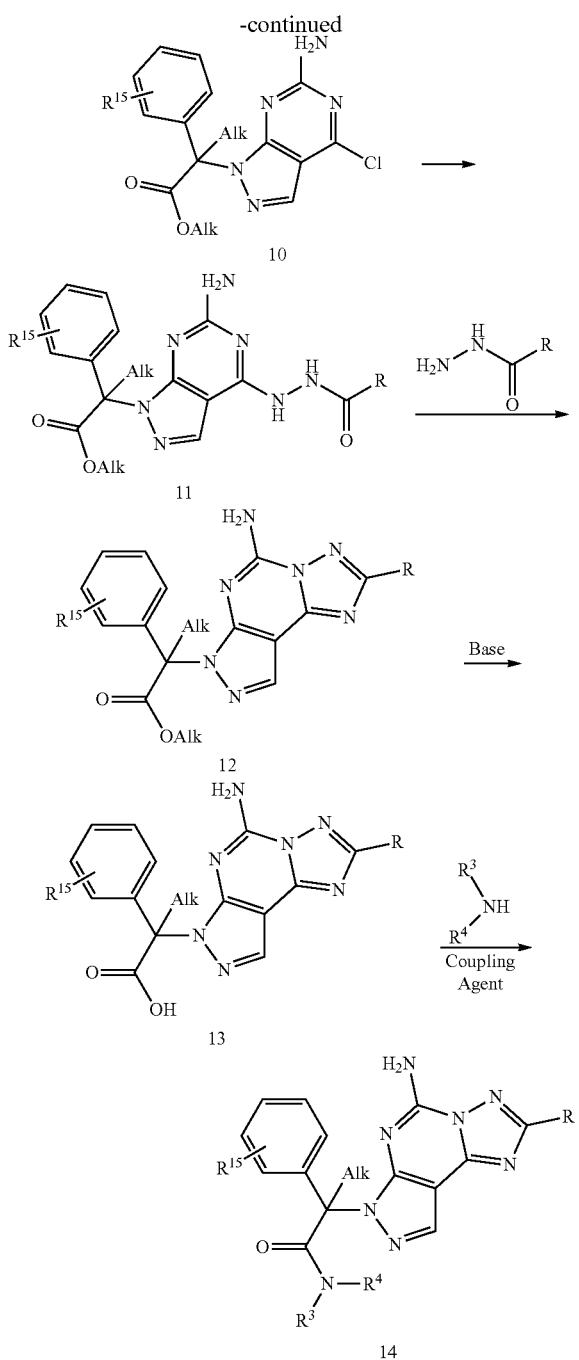

wherein R and $R^{15}$ are as defined with formula (I).

In scheme II, a commercially available acid (such as 2-phenylpropanoic acid) is esterified under standard conditions known in the art to afford one compound of formula 7 which is reacted with a halogenation reagent such as N-bromosuccinimide to introduce one halo atom at the alpha position. A compound of formula 8 is reacted with hydrazine hydrate to form formula 9. Formula 9 is reacted with a commercially available 2-amino-4,6-dichloropyrimidine-5-carbaldehyde to afford formula 10, which is reacted with carbohydrazide (such as furan-2-carbohydrazide) and further rearranged in the presence of acidic condition to give formula 12. The ester 12 subsequently is hydrolyzed into the free acid of formula 13 by using a base such as sodium hydroxide or potassium tert-butoxide. The further coupling of the acid 13 is accomplished under standard conditions known in the art to provide a compound of Formula 14.

EXAMPLES

The examples below are intended to be purely exemplary and should not be considered to be limiting in any way. Unless otherwise specified, the experimental methods in the Examples described below are conventional methods. Unless otherwise specified, the reagents and materials are all commercially available. All solvents and chemicals employed are of analytical grade or chemical purity. Solvents are all redistilled before use. Anhydrous solvents are all prepared according to standard methods or reference methods. Silica gel (100-200 meshes) for column chromatography and silica gel (GF254) for thin-layer chromatography (TLC) are commercially available from Tsingdao Haiyang Chemical Co., Ltd. or Yantai Chemical Co., Ltd. of China; all are eluted with petroleum ether (60-90° C.)/ethyl acetate (v/v), and visualized by iodine or the solution of molybdphosphoric acid in ethanol unless otherwise specified. All extraction solvents, unless otherwise specified, are dried over anhydrous $Na_2SO_4$. $^1H$ NMR spectra are recorded on Bruck-400 nuclear magnetic resonance spectrometer with TMS (tetramethylsilane) as the internal standard. LC/MS data are recorded by using Agilent1100 High Performance Liquid Chromatography-Ion Trap Mass Spectrometer (LC-MSD Trap) equipped with a diode array detector (DAD) detected at 214 nm and 254 nm, and an ion trap (ESI source) All compound names except the reagents were generated by ChemDraw® version 14.0.

In the following examples, the following abbreviations are used;

AcOH Acetic acid
ACN Acetonitrile
Aq Aqueous
Brine Saturated aqueous sodium chloride solution
Bn Benzyl
BnBr Benzyl Bromide
BPO Benzoyl peroxide
BSA NP-Bis(trimethylsilyl)acetamide
$CH_2Cl_2$ or DCM Dichloromethane
DMF N,N-Dimethylformamide
Dppf 1,1"-bis(diphenylphosphino)ferrocene
DBU 1,8-diazabicyclo[5.4.0]undec-7-ene
DIEA or DIPEA N,N-diisopropylethylamine
DMAP 4-N,N-dimethylaminopyridine
DMF N,N-dimethylfomamide
DMSO Dimethyl sulfoxide
EtOAc Ethyl acetate
EtOH Ethanol
$Et_2O$ or ether Diethyl ether
g Grams
h or hr Hour
HATU O-(7-Azabenzotriazol-1-yl)-N,N,N',N'-tetramethyluronium hexafluorophosphate
Hex Hexane
HCl Hydrochloric acid
HMDS Hexamethyldisilazane
HPLC High-performance liquid chromatography
IPA Isopropyl alcohol
i-PrOH Isopropyl alcohol
LCMS Liquid chromatography-mass spectrometry
mg milligrams
mL milliliters
mmol millimole MeCN Acetonitrile
MeOH Methanol
Min minutes
ms or MS Mass spectrum
$Na_2SO_4$ Sodium sulfate
NBS N-Bromosuccinimide
PE petroleum ether
prep preparative
Rt Retention time
RT or rt Room temperature
TBAF Tetra-butyl ammonium fluoride
TBSCl tert-Butyldimethylsilyl chloride
TFA Trifluoroacetic acid
THF tetrahydrofuran
TLC thin layer chromatography
μL microliters Example 1: 2-(5-amino-2-(furan-2-yl)-7H-pyrazolo[4,3-e][1,2,4]triazolo[1,5-c]pyrimidin-7-yl)-N-benzyl-2-phenylacetamide

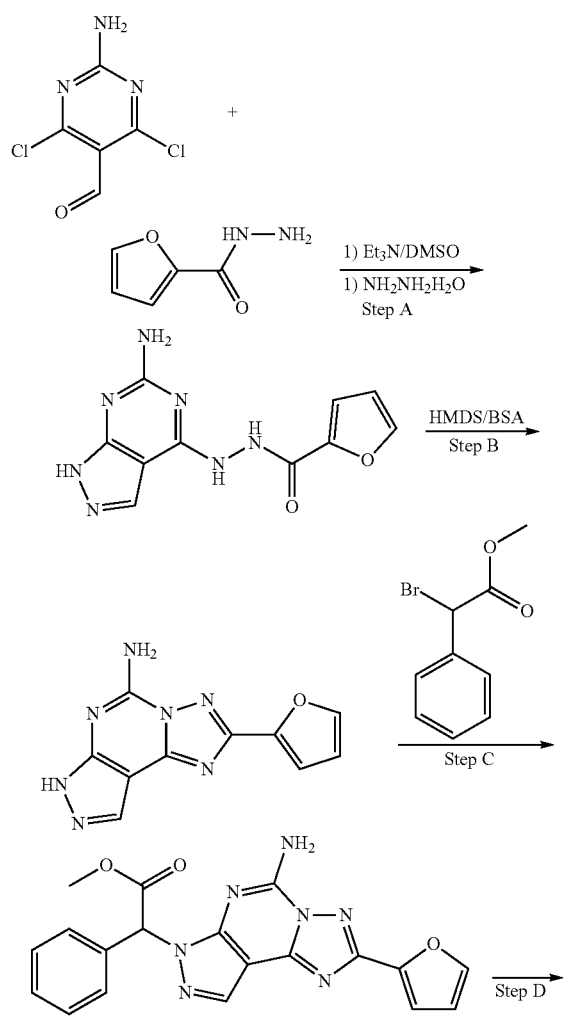

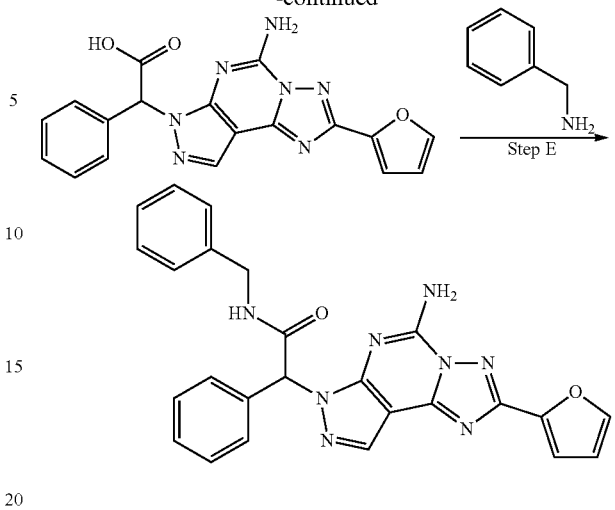

Step A: N'-(6-amino-1H-pyrazolo[3,4-d]pyrimidin-4-yl)furan-2-carbohydrazide

To a stirred solution of 2-amino-4,6-dichloropyrimidine-5-carbaldehyde (50 g, 0.26 mol) and $Et_3N$ (28.9 g, 0.28 mol) in DMSO (600 mL) was added with furan-2-carbohydrazide (32.8 g, 0.26 mol) in portionwise. Then the reaction mixture was stirred at rt overnight. LCMS showed the starting materials were converted into the intermediate. $NH_2NH_2H_2O$ (14 mL, 0.31 mol) was added and the solution was stirred at 70° C. for 3 hrs. After evaporated under reduced pressure (oil pump at 65° C.), the residue was added with water (500 mL), slurried and filtered. The cake was once more slurried with water (300 mL), filtered and dried to give the product as a yellow solid. MS: M/e 260 $(M+1)^+$.

Step B: 2-(furan-2-yl)-7H-pyrazolo[4,3-e][1,2,4]triazolo[1,5-c]pyrimidin-5-amine A solution of N'-(6-amino-1H-pyrazolo[3,4-d]pyrimidin-4-yl)furan-2-carbohydrazide (17 g, 65 mmol) in BSA (136 mL) and HMDS (160 mL) was heated at 110° C. overnight. The solution was concentrated at 60° C. under reduced pressure. The residue was added with water (200 mL) and slurried far 1 hr. The solid was filtered, washed with water and dried to obtain the desired product as a brown solid (13.1 g, 83%). MS: M/e 242 $(M+1)^+$.

Step C: methyl 2-(5-amino-2-(furan-2-yl)-7H-pyrazolo[4,3-e][1,2,4]triazolo[1,5-c]pyrimidin-7-yl)-2-phenylacetate To a stirred solution of 2-(furan-2-yl)-7H-pyrazolo[4,3-e][1,2,4]triazolo[1,5-c]pyrimidin-5-amine (1.0 g, 4.2 mmol) in DMF (50 mL) was added $K_2CO_3$ (1.3 g, 9.4 mmol) and methyl 2-bromo-2-phenylacetate (1.0 g, 4.4 mmol). After addition, the reaction mixture was stirred overnight. The reaction mixture was poured into $H_2O$ (50 mL) and extracted with EtOAc (100 mL×3). The combined organic layers were washed with brine, dried over $Na_2SO_4$, concentrated and purified by column chromatography (petroleum ether/EtOAc=2:1~1:3) to give methyl 2-(5-amino-2-(furan-2-yl)-7H-pyrazolo[4,3-e][1,2,4]triazolo[1,5-c]pyrimidin-7-yl)-2-phenylacetate (200 mg, 24.5%) as white solids. MS: M/e 390 $(M+1)^+$.

Step D: 2-(5-amino-2-(furan-2-yl)-7H-pyrazolo[4,3-e][1,2,4]triazolo[1,5-c]pyrimidin-7-yl)-2-phenylacetic acid To a stirred mixture of methyl 2-(5-amino-2-(furan-2-yl)-7H-pyrazolo[4,3-e][1,2,4]-triazolo[1,5-c]pyrimidin-7-yl)-2-phenylacetate (200 mg, 0.51 mmol) in MeOH/H2O (3 mL/1 mL) was added aq. NaOH (2.0 Ni, 2 mL). After addition, the reaction mixture was stirred overnight. Most of solvent was removed to give the aqueous layer, then acidified to pH=3~4 with aq. HCl and filtered, the cake was collected, dried to give the target compound (150 mg, 78.2%) as a white solid. MS: M/e 376 (M+1)⁺.

Step E: 2-(5-amino-2-(furan-2-yl)-7H-pyrazolo[4,3-e][1,2,4]triazolo[1,5-c]pyrimidin-7-yl)-N-benzyl-2-phenylacetamide To a mixture of phenylmethanamine (285 mg, 2.66 mmol), 2-(5-amino-2-(furan-2-yl)-7H-pyrazolo[4,3-e][1,2,4]triazolo[1,5-c]pyrimidin-7-yl)-2-phenylacetic acid (500 mg, 1.33 mmol), DIEA (1.0 g, 7.75 mmol) in DMF (15 mL) was added HATU (760 mg, 2.0 mmol) at rt and the mixture was stirred at rt for 20 hrs. 50 mL of EtOAc was added and the mixture was washed with brine (25 mL×3), dried over $Na_2SO_4$ and concentrated. The resulted residue was purified by column chromatography eluted with PE/EtOAc (3:1) to give a crude product which was added 20 mL of 2-methoxy-2-methylpropane and stirred for 20 min. The suspension was filtered and the filter cake was dried under high vacuum, lyophilized to give the title product (375 mg, yield: 61%). ¹H NMR (400 MHz, DMSO-d6) δ 8.44 (t, J=6.0 Hz, 1H), 8.20 (s, 1H), 8.15 (s, 2H), 7.94-7.87 (m, 1H), 7.43-7.36 (m, 2H), 7.36-7.29 (m, 3H), 7.29-7.22 (m, 2H), 7.22-7.14 (m, 4H), 6.70 (dd, J=3.6, 2.0 Hz, 1H), 6.44 (s, 1H), 4.29 (d, J=5.6 Hz, 2H). MS: M/e 465 (M+1)⁺.

Example 1 was separated into two enantiomeric stereoisomers, EXAMPLE 1A (earlier peak), and EXAMPLE 1B (later peak) by chiral prep-HPLC. The chiral separation conditions are shown below.

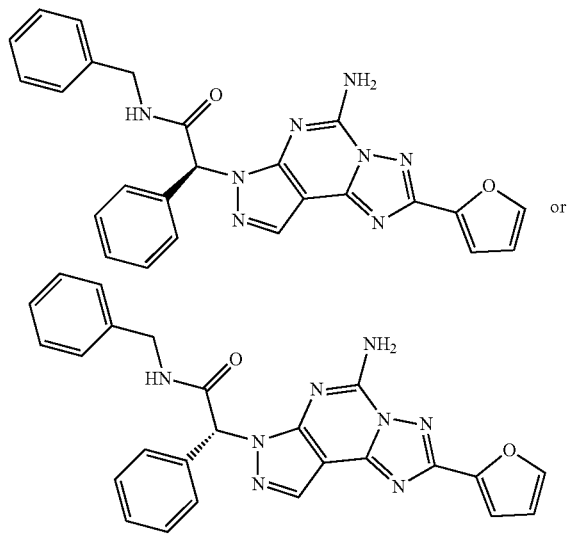

| Column | CHIRAL ART Cellulose-SB |
|---|---|
| Column size | 2 cm × 25 cm, 5 um |
| Injection | 0.8 ML |
| Mobile phase | Hex:EtOH = 70:30 |
| Flow rate | 20 ml/min |
| Wave length | UV 220 nm |
| Temperature | 25° C. |
| Sample solution | 22.9 mg/ml in DCM:EtOH = 1:3 |
| Prep-HPLC equipment | BJ-Prep-Gilson-HPLC |

Example 2: 2-(5-amino-2-(furan-2-yl)-7H-pyrazolo[4,3-e][1,2,4]triazolo[1,5-c]pyrimidin-7-yl)-N-cyclohexyl-2-phenylacetamide A mixture of 2-(5-amino-2-(furan-2-yl)-7H-pyrazolo[4,3-e][1,2,4]triazolo[1,5-c]pyrimidin-7-yl)-2-phenylacetic acid (20 mg, 0.05 mmol), cyclohexanamine (10 mg, 0.10 HART (22 mg, 0.06 mmol) and DIEA (15 mg, 0.12 mmol) in DMF (10 mL) was stirred for 4 hours at RT. The reaction mixture was poured into $H_2O$ (20 mL) and extracted with EtOAc (50 mL×3). The combined organic layers were washed with brine, dried over $Na_2SO_4$, concentrated and purified by column chromatography (petroleum ether/EtOAc=1:1~100% EtOAc) to give the target compound (10 mg, 43.8%). ¹H NMR (400 MHz, DMSO-d6) δ 8.21 (s, 1H), 8.15 (br.s, 2H), 7.95 (s, 1H), 7.90 (d, J=7.9 Hz, 1H), 7.42-7.30 (m, 5H), 7.24 (d, J=3.4 Hz, 1H), 6.77-6.71 (m, 1H), 6.38 (br.s, 1H), 3.60 (s, 1H), 1.75-1.58 (m, 5H), 1.29-1.18 (m, 5H) ppm. MS: M/e 457 (M+1)⁺.

Example 3: 2-(5-amino-2-(furan-2-yl)-7H-pyrazolo[4,3-e][1,2,4]triazolo[1,5-c]pyrimidin-7-yl)-N,2-diphenylacetamide To a mixture of aniline (12 mg, 0.13 mmol), 2-(5-amino-2-(furan-2-yl)-7H-pyrazolo[4,3-e][1,2,4]triazolo[1,5-c]pyrimidin-7-yl)-2-phenylacetic acid (30 mg, 0.08 mmol), DIEA (50 mg, 0.39 mmol) in DMF (1 mL) was added HATU (36 mg, 0.09 mmol) at it and the mixture was stirred at rt for 16 hrs. 5 mL of EtOAc was added and the mixture was washed with $NaHCO_3$ (3 mL×2), brine (3 mL×2), dried over $Na_2SO_4$ and concentrated. The resulted residue was purified by prep-TLC (PE/EtOAc=1:2) to give the title product (10.0 mg, yield: 30%). ¹H NMR (400 MHz, DMSO-d6) δ 10.31 (s, 1H), 8.20 (s, 1H), 8.15 (s, 2H), 7.95 (s, 1H), 7.58 (d, J=8.0 Hz, 2H), 7.45-7.34 (m, 5H), 7.30 (t, J=8.0 Hz, 2H), 7.25 (d, J=3.2 Hz, 1H), 7.06 (t, =7.2 Hz, 1H), 6.79-6.70 (m, 1H), 6.61 (s, 1H). MS: M/e 451 (M+1)⁺.

Example 4: 2-(5-amino-2-(furan-2-yl)-7H-pyrazolo[4,3-e][1,2,4]triazolo[1,5-c]pyrimidin-7-yl)-N-methyl-2-phenylacetamide A mixture of 2-(5-amino-2-(furan-2-yl)-7H-pyrazolo[4,3-e][1,2,4]triazolo[1,5-c]pyrimidin-7-yl)-2-phenylacetic acid (30 mg, 0.08 mmol), methanamine hydrochloride (64 mg, 0.96 mmol), HATU (35 mg, 0.09 mmol) and DIPEA (30 mg, 0.24 mmol) in DMF (5 mL) was stirred for 4 hours at RT. The reaction mixture was poured into $H_2O$ (20 mL) and extracted with EtOAc (50 mL×3). The combined organic layers were washed with brine, dried over $Na_2SO_4$, concentrated and purified by column chromatography (petroleum ether/EtOAc=1:1~100% EtOAc) to give the target compound (5 mg, 16.7%). ¹H NMR (400 MHz, DMSO-d6) δ 8.23 (s, 1H), 8.18 (br.s, 2H), 7.95 (d, J=0.8 Hz, 1H), 7.82 (d, J=4.6 Hz, 1H), 7.43-7.30 (m, 5H), 7.24 (d, J=3.3 Hz, 1H), 6.74 (dd, J=3.3, 1.8 Hz, 1H), 6.39 (br.s, 1H), 2.64 (d, J=4.5 Hz, 3H) ppm, MS: M/e 389 (M+1)$^+$.

Example 4 was separated into two enantiomeric stereoisomers, EXAMPLE 4A (earlier peak), and EXAMPLE 4B (later peak) by chiral prep-HPLC. The chiral separation conditions are shown below.

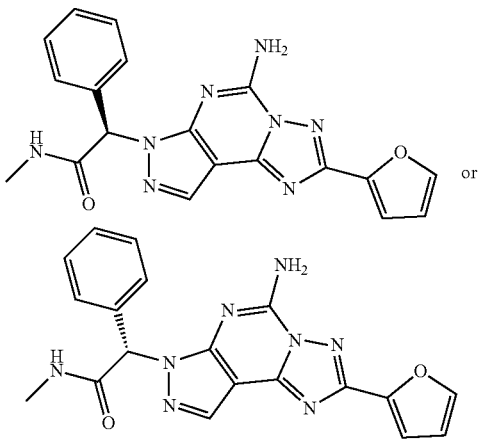

| Column | Chiralpak IA |
| --- | --- |
| Column size | 2 cm × 25 cm, 5 um |
| Injection | 1.5 ML |
| Mobile phase | Hex:EtOH = 70:30 |
| Flow rate | 20 ml/min |
| Wave length | UV 220 nm |
| Temperature | 25° C. |
| Sample solution | 16 mg/ml in EtOH:DCM |
| Prep-HPLC equipment | Prep-HPLC-04 |

Example 5: 2-(5-amino-2-(furan-2-yl)-7H-pyrazolo[4,3-e][1,2,4]triazolo[1,5-c]pyrimidin-7-yl)-N-ethyl-2-phenylacetamide A mixture of 2-(5-amino-2-(furan-2-yl)-7H-pyrazolo[4,3-e][1,2,4]triazolo[1,5-c]pyrimidin-7-yl)-2-phenylacetic acid (30 mg, 0.08 mmol), ethanamine (30%, 100 mg, 0.73 mmol), HATU (35 mg, 0.09 mmol) and DIPEA (30 mg, 0.24 mmol) in DMF (5 mL) was stirred for 4 hours at RT. The reaction mixture was poured into H$_2$O (20 mL) and extracted with EtOAc (50 mL×3). The combined organic layers were washed with brine, dried over Na$_2$SO$_4$, concentrated and purified by column chromatography (petroleum ether/EtOAc=1:1~100% EtOAc) to give the target compound (8.7 mg, 27%). $^1$H NMR (400 MHz, DMSO-d6) δ 8.20 (s, 1H), 8.16 (br.s, 2H), 7.99-7.88 (m, 2H), 7.39-7.30 (m, 5H), 7.22 (dd, J=3.4, 0.7 Hz, 1H), 6.72 (dd, J=3.4, 1.8 Hz, 1H), 6.36 (br.s, 1H), 3.15-3.08 (m, 2H), 0.99 (t, J=7.2 Hz, 3H) ppm. MS: M/e 403 (M+1)$^+$.

Example 6: 2-(5-amino-2-(furan-2-yl)-7H-pyrazolo[4,3-e][1,2,4]triazolo[1,5-c]pyrimidin-7-yl)-N-(2-triethoxybenzyl)-2-phenylacetamide To a mixture of (2-methoxyl)phenyl)methanamine (20 mg, 0.15 mmol), 2-(5-amino-2-(furan-2-yl)-7H-pyrazolo[4,3-e][1,2,4]triazolo[1,5-c]pyrimidin-7-yl)-2-phenylacetic acid (40 mg, 0.11 mmol), DIEA (150 mg, 1.16 mmol) in DMF (2 mL) was added HATU (52 mg, 0.14 mmol) at rt and the mixture was stirred at rt for 16 hrs. 20 mL of EtOAc was added and the mixture was washed with brine (10 mL×3), dried over Na$_2$SO$_4$ and concentrated. The resulted residue was purified by prep-TLC (PE/EtOAc=1:2) to give the title product (25.0 mg, yield: 49%). $^1$H NMR (400 MHz, DMSO-d6) δ 8.27 (t, J=6.0 Hz, 1H), 8.24 (s, 1H), 8.19 (s, 2H), 7.94 (s, 1H), 7.43-7.30 (m, 5H), 7.24-7.16 (m, 2H), 7.14 (d, J=7.2 Hz, 1H), 6.93 (d, J=8.0 Hz, 1H), 6.86 (t, J=7.2 Hz, 1H), 6.72 (dd, J=3.2, 1.6 Hz, 1H), 6.46 (s, 1H), 4.27 (d, J=6.0 Hz, 2H), 3.73 (s, 3H). MS: M/e 495 (M+1)$^+$.

Example 7: 2-(5-amino-2-(furan-2-yl)-7H-pyrazolo[4,3-e][1,2,4]triazolo[1,5-c]pyrimidin-7-yl)-N-(2-fluorobenzyl)-2-phenylacetamide A mixture of 2-(5-amino-2-(furan-2-yl)-7H-pyrazolo[4,3-e][1,2,4]triazolo[1,5-c]pyrimidin-7-yl)-2-phenylacetic acid (50 mg, 0.13 mmol), (2-fluorophenyl)methanamine (20 mg, 0.15 mmol), HATU (55 mg, 0.15 mmol) and DIPEA (39 mg, 0.39 mmol) in DMF (5 mL) was stirred for 4 hours at RT. The reaction mixture was poured into H$_2$O (20 mL) and extracted with EtOAc (50 mL×3). The combined organic layers were washed with brine, dried over Na$_2$SO$_4$, concentrated and purified by column chromatography (petroleum ether/EtOAc=1:1~100% EtOAc) to give the target compound (40 mg, 63.8%). $^1$H NMR (400 MHz, DMSO-d6) δ 8.48 (t, J=5.9 Hz, 1H), 8.23 (s, 1H), 8.19 (br.s, 2H), 7.93 (dd, J=1.7, 0.8 Hz, 1H), 7.42-7.24 (m, 7H), 7.23 (dd, J=3.4, 0.8 Hz, 1H), 7.17-7.10 (m, 2H), 6.72 (dd, J=3.4, 1.8 Hz, 1H), 6.47 (br.s, 1H), 4.35 (d, J=5.8 Hz, 2H) ppm. MS: M/e 483 (M+1)$^+$.

Example 8: 2-(5-amino-2-(furan-2-yl)-7H-pyrazolo[4,3-e][1,2,4]triazolo[1,5-c]pyrimidin-7-yl)-2-phenyl-N-(2-(trifluoromethoxy)benzyl)acetamide To a mixture of (2-(trifluoromethoxy)phenyl)methanamine (25 mg, 0.13 mmol), 2-(5-amino-2-(furan-2-yl)-7H-pyrazolo[4,3-e][1,2,4]triazolo[1,5-c]pyrimidin-7-yl)-2-phenylacetic acid (40 mg, 0.11 mmol), DIPEA (70 mg, 0.54 mmol) in DIME (2 mL) was added HATU (50 mg, 0.13 mmol) at it and the mixture was stirred at rt for 16 hrs. 10 mL of EtOAc EA was added and the mixture was washed with brine (5 mL×3), dried over Na$_2$SO$_4$ and concentrated. The resulted residue was purified by prep-TLC (PE/EtOAc=1:1) to give the title product (28.0 mg, yield: 48%). $^1$H NMR (400 MHz, DMSO-d6) δ 8.49 (t, J=6.0 Hz, 1H), 8.24 (s, 1H), 8.20 (s, 2H), 7.94 (dd, J=2.0, 0.8 Hz, 1H), 7.44-7.29 (m, 9H), 7.23 (dd, J=3.6, 0.8 Hz, 1H), 6.72 (dd, J=3.6, 1.6 Hz, 1H), 6.49 (s, 1H), 4.37 (d, J=6.0 Hz, 2H). MS: M/e 549 (M+1)$^+$.

Example 9: 2-(5-amino-2-(furan-2-yl)-7H-pyrazolo[4,3-e][1,2,4]triazolo[1,5-c]pyrimidin-7-yl)-2-phenyl-N—((S)-1-phenylethy)acetamide A mixture of (S)-1-phenylethan-1-amine (25.8 mg, 0.21 mmol), 2-(5-amino-2-(furan-2-yl)-7H-pyrazolo[4,3-e][1,2,4]triazolo[1,5-c]pyrimidin-7-yl)-2-phenylacetic acid (80 mg, 0.21 HATU (87.8 mg, 0.23 mmol) and DIPEA (0.3 mL, excess) in DMF (2 mL) was stirred at RT overnight. The reaction mixture was poured into water (10 mL) and extracted with EtOAc (15 mL×3). The combined organic layers were washed with brine, dried over Na$_2$SO$_4$ and concentrated under reduced pressure. The residue was purified by prep-TLC (EtOAc: 100%) to afford the title compound (60 mg, yield: 59.7%). $^1$H NMR (400 MHz, DMSO-d6) δ8.58-8.49 (m, 1H), 8.26-8.13 (m, 2H), 7.98-7.90 (m, 1H), 7.42-7.18 (m, 11H), 6.77-6.70 (m, 1H), 6.51-6.42 (m, 1H), 5.07-4.89 (m, 1H), 1.42-1.30 (m, 3H) ppm. MS: M/e 479 (M+1)$^+$.

Example 10: 2-(5-amino-2-(furan-2-yl)-7H-pyrazolo[4,3-e][1,2,4]triazolo[1,5-c]pyrimidin-7-yl)-2-phenyl-N—((R)-1-phenylethyl)acetamide A mixture of (R)-1-phenylethan-1-amine (25.8 mg, 0.2.1 mmol), 2-(5-amino-2-(furan-2-yl)-7H-pyrazolo[4,3-e][1,2,4]triazolo[1,5-c]pyrimidin-7-yl)-2-phenylacetic acid (80 mg, 0.21 mmol), HATU (87.8 mg, 0.23 mmol) and DIPEA (0.3 mL, excess) in DMF (2 mL) was stirred at RT overnight. The reaction mixture was poured into water (10 mL) and extracted with EtOAc (15 mL×3). The combined organic layers were washed with brine, dried over Na$_2$SO$_4$ and concentrated under reduced pressure. The residue was purified by prep-TLC (EtOAc: 100%) to afford the title compound (32 mg, yield: 31.8%). $^1$H NMR (400 MHz, DMSO-d6) δ 8.59-8.52 (m, 1H), 8.29-8.16 (m, 2H), 7.95 (s, 1H), 7.44-7.16 (m, 11H), 6.73 (s, 1H), 6.53-6.44 (m, 1H), 5.09-4.89 (m, 1H), 1.44-1.29 (m, 3H) ppm. MS: M/e 479 (M+1)$^+$.

Example 11: 2-(5-amino-2-(furan-2-yl)-7H-pyrazolo[4,3-e][1,2,4]triazolo[1,5-c]pyrimidin-7-yl)-2-phenyl-N-(tetrahydro-2H-pyran-4-yl)acetamide To a mixture of tetrahydro-2H-pyran-4-amine (2.0 mg, 0.2.0 mmol), 2-(5-amino-2-(furan-2-yl)-7H-pyrazolo[4,3-e][1,2,4]triazolo[1,5-c]pyrimidin-7-yl)-2-phenylacetic acid (40 mg, 0.11 mmol), DMA (70 mg, 0.54 mmol) in DMF (2 mL) was added HATU (55 mg, 0.14 mmol) at rt and the mixture was stirred at rt for 16 hrs. 10 mL of EtOAc was added and the mixture was washed with brine (5 mL×3), dried over Na$_2$SO$_4$ and concentrated. The resulted residue was purified by prep-TLC (PE/EtOAc=1:2) to give the title product (26.0 mg, yield: 52%). $^1$H NMR (400 MHz, DMSO-do) δ 8.16 (s, 1H), 8.13 (s, 1H), 8.05 (d, 7.6 Hz, 1H), 7.92 (s, 1H), 7.38-7.25 (m, 5H), 7.21 (d, J=3.6 Hz, 1H), 6.70 (dd, J=3.2, 1.6 Hz, 1H), 6.35 (s, 1H), 3.85-3.65 (m, 2H), 3.29-3.24 (m, 2H), 1.73-1.59 (m, 2H), 1.46-1.29 (m, 2H). MS: M/e 459 (M+1)$^+$.

Example 12: 2-(5-amino-2-(furan-2-yl)-7H-pyrazolo[4,3-e][1,2,4]triazolo[1,5-c]pyrimidin-7-yl)-N-cyclopentyl-2-phenylacetamide A mixture of 2-(5-amino-2-(furan-2-yl)-7H-pyrazolo[4,3-e][1,2,4]triazolo[1,5-c]pyrimidin-7-yl)-2-phenylacetic acid (50 mg, 0.13 mmol), cyclopentanamine (13 mg, 0.15 mmol), HART (55 mg, 0.15 mmol) and DIPEA (39 mg, 0.39 mmol) in DMF (10 mL) was stirred for 4 hours at RT. The reaction mixture was poured into H$_2$O (20 mL) and extracted with EtOAc (50 mL×3). The combined organic layers were washed with brine, dried over Na$_2$SO$_4$, concentrated and purified by column chromatography (petroleum ether/EtOAc=1:1~100% EtOAc) to give the target compound (24.5 mg, 42.6%). $^1$H NMR (400 MHz, DMSO-d6) δ 8.17 (s, 1H), 8.14 (br.s, 2H), 7.74 (d, J=2.9 Hz, 114), 7.48-7.30 (m, 6H), 7.26-7.21 (m, 1H), 6.64 (br.s, 1H), 6.58 (s, 1H), 4.31-4.09 (m, 1H), 2.12-1.83 (m, 2H), 1.77-1.48 (m, 5H), 1.47-1.38 (m, 1H) ppm. MS: M/e 443 (M+1)$^+$.

Example 13: 2-(5-amino-2-(furan-2-yl)-7H-pyrazolo[4,3-e][1,2,4]triazolo[1,5-c]pyrimidin-7-yl)-2-phenyl-N-(1,2,3,4-tetrahydronaphthalen-1-yl)acetamide To a mixture of 1,2,3,4-tetrahydronaphthalen-1-amine (20 mg, 0.14 mmol), 2-(5-amino-2-(furan-2-yl)-7H-pyrazolo[4,3-e][1,2,4]triazolo[1,5-c]pyrimidin-7-yl)-2-phenylacetic acid (40 mg, 0.11 mmol), DIEA (70 mg, 0.54 mmol) in DMF (2 mL) was added HART (50 mg, 0.13 mmol) at rt and the mixture was stirred at rt for 16 hrs. 10 mL of EtOAc was added and the mixture was washed with brine (5 mL×3), dried over Na$_2$SO$_4$ and concentrated. The resulted residue was purified by prep-TLC. (PE/EtOAc=1:2) to give the title product (41.0 mg, yield: 74%). $^1$H NMR (400 MHz, DMSO-d6) δ 8.39 (dd, J=8.4, 5.6 Hz, 1H), 8.29-8.10 (m, 3H), 7.95 (s, 1H), 7.46 (d, J=6.8 Hz, 1H), 7.43-7.31 (m, 4H), 7.30-7.14 (m, 2H), 7.14-7.00 (m, 3H), 6.74 (s, 1H), 6.46 (d, J=13.6 Hz, 1H), 5.10-4.95 (m, 1H), 2.77-2.60 (m, 2H), 1.97-1.57 (m, 4H). MS: M/e 505 (M+1)$^+$.

Example 14: 2-(5-amino-2-(furan-2-yl)-7H-pyrazolo[4,3-e][1,2,4]triazolo[1,5-c]pyrimidin-7-yl)-N-(2,3-dihydro-1H-inden-1-yl)-2-phenylacetamide To a mixture of 2,3-dihydro-1H-inden-1-amine (20 mg, 0.15 mmol), 2-(5-amino-2-(furan-2-yl)-7H-pyrazolo[4,3-e][1,2,4]triazolo[1,5-c]pyrimidin-7-yl)-2-phenylacetic acid (40 mg, 0.11 mmol). DIEA (70 mg, 0.54 mmol) in DMF (2 mL) was added HATU (52 mg, 0.14 mol) at rt and the mixture was stirred at rt for 16 hrs. 10 mL of EtOAc EA was added and the mixture was washed with brine (5 mL×3), dried over Na$_2$SO$_4$ and concentrated. The resulted residue was purified by prep-TLC (PE/EtOAc=1:1) to give the title product (33.0 mg, yield: 61%). $^1$H NMR (400 MHz, DMSO-d6) δ 8.43 (t, J=7.6 Hz, 1H), 8.30-8.03 (m, 3H), 7.95 (s, 1H), 7.47 (d, J=7.2 Hz, 1H), 7.44-7.31 (m, 4H), 7.29-7.06 (m, 5H), 6.81-6.68 (m, 1H), 6.46 (d, J=9.6 Hz, 1H), 5.36 (q, J=8.0 Hz, 1H), 2.91-2.75 (m, 2H), 2.43-2.31 (m, 1H), 1.89-1.71 (m, 1H). MS: M/e 491 (M+1)$^+$.

Example 15: 2-(5-amino-2-(furan-2-yl)-7H-pyrazolo[4,3-e][1,2,4]triazolo[1,5-c]pyrimidin-7-yl)-N—((R)-chroman-4-yl)-2-phenylacetamide To a mixture of (R)-chroman-4-amine hydrochloride (20 mg, 0.13 mmol), 2-(5-amino-2-(furan-2-yl)-7H-pyrazolo[4,3-e][1,2,4]triazolo[1,5-c]pyrimidin-7-yl)-2-phenylacetic acid (40 mg, 0.11 mmol), DIEA (70 mg, 0.54 mmol) in DMF (2 mL) was added HATU (50 mg, 0.13 mmol) at rt and the mixture was stirred at rt for 16 hrs. 15 mL of EtOAc was added and the mixture was washed with brine (5 mL×3), dried over Na$_2$SO$_4$ and concentrated. The resulted residue was purified by prep-TLC (PE/EtOAc=1:1) to give the title product (13.0 mg, yield: 23%). $^1$H NMR (400 MHz, DMSO-d6) δ 8.64-8.50 (m, 1H), 8.27-8.07 (m, 2H), 7.95 (s, 1H), 7.48-7.42 (m, 1H), 7.41-7.20 (m, 5H), 7.18-6.98 (m, 2H), 6.93-6.76 (m, 1H), 6.76-6.69 (m, 2H), 6.45 (d, J=14.4 Hz, 1H), 5.15-5.01 (m, 1H), 4.27-4.00 (m, 2H), 2.09-1.90 (m, 2H). MS: M/e 507 (M+1)$^+$.

Example 16: 2-(5-amino-2-(furan-2-yl)-7H-pyrazolo[4,3-e][1,2,4]triazolo[1,5-c]pyrimidin-7-yl)-N—((S)-chroman-4-yl)-2-phenylacetamide To a mixture of (S)-chroman-4-amine hydrochloride (20 mg, 0.13 mmol), 2-(5-amino-2-(furan-2-yl)-7H-pyrazolo[4,3-e][1,2,4]triazolo[1,5-c]pyrimidin-7-yl)-2-phenylacetic acid (40 mg, 0.11 mmol), DIEA (70 mg, 0.54 mmol) in DMF (2 mL) was added HATU (50 mg, 0.13 mmol) at rt and the mixture was stirred at rt for 16 hrs. 15 mL of EtOAc was added and the mixture was washed with brine (5 mL×3), dried over Na$_2$SO$_4$ and concentrated. The resulted residue was purified by prep-TLC (PE/EtOAc EA=1:1) to give the title product (25.0 mg, yield: 45%). $^1$H NMR, (400 MHz, DMSO-d6) δ 8.56 (dd, J=13.2, 8.4 Hz, 1H), 8.29-8.05 (m, 3H), 7.95 (s, 1H), 7.49-7.42 (m, 1H), 7.42-7.21 (m, 5H), 7.17-6.98 (m, 2H), 6.91-6.76 (m, 1H), 6.75-6.68 (m, 2H), 6.45 (d, J=14.4 Hz, 1H), 5.18-5.01 (m, 1H), 4.26-4.03 (m, 2H), 2.12-1.90 (m, 2H). MS: M/e 507 (M+1)+.

Example 17: 2-(5-amino-2-(furan-2-yl)-7H-pyrazolo[4,3-e][1,2,4]triazolo[1,5-c]pyrimidin-7-yl)-N-phenethyl-2-phenylacetamide To a mixture of 2-phenylethan-1-amine (160 mg, 1.32 mmol), 2-(5-amino-2-(furan-2-yl)-7H-pyrazolo[4,3-e][1,2,4]triazolo[1,5-c]pyrimidin-7-yl)-2-phenylacetic acid (450 mg, 1.2 mmol), DIEA (650 mg, 5.0 mmol) in DMF (8 mL) was added HATU (550 mg, 1.4 mmol) at rt and the mixture was stirred at rt for 16 hrs. The mixture was poured into 30 mL of H₂O. A white solid precipitated and which was filtered. The solid was washed with H₂O, dried under high vacuum and purified by column chromatograph to give the title product (385.0 mg, yield: 67%). ¹H NMR (400 MHz, DMSO-d6) δ 8.34-8.06 (m, 3H), 7.99-7.89 (m, 2H), 7.39-7.31 (m, 3H), 7.27-7.19 (m, 3H), 7.18-7.10 (m, 3H), 6.74 (dd, J=3.6, 2.0 Hz, 1H), 6.38 (s, 1H), 3.42-3.34 (m, 2H), 2.71 (t, J=7.2 Hz, 2H), MS: M/e 479 (M+1)+.

Example 17 was separated into two enantiomeric stereoisomers, EXAMPLE 17A (earlier peak), and EXAMPLE 17B (later peak) by chiral prep-HPLC. The chiral separation conditions are shown below.

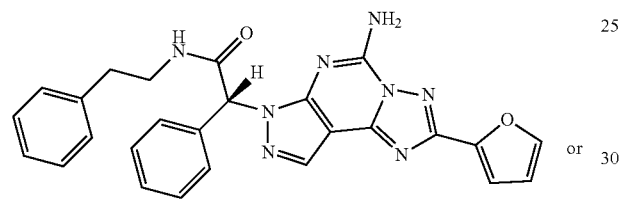 or 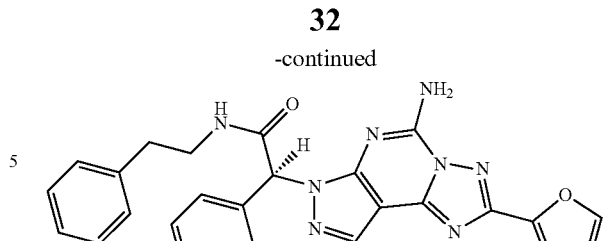

| Column | Chiralpak IF |
|---|---|
| Column size | 2 cm × 25 cm, 5 um |
| Injection | 1 ML |
| Mobile phase | Hex:EtOH = 50:50 |
| Flow rate | 15 mg/min |
| Wave length | UV 220 nm |
| Temperature | 25° C. |
| Sample solution | 38 mg/ml in EtOH:DCM = 1:1 |
| Prep-HPLC equipment | Prep-HPLC-04 |

Example 18: 2-(5-amino-2-(furan-2-yl)-7H-pyrazolo[4,3-e][1,2,4]triazolo[1,5-c]pyrimidin-7-yl)-N-((6-(1-hydroxycyclobutyl)pyridin-2-yl)methyl)-2-phenylacetamide

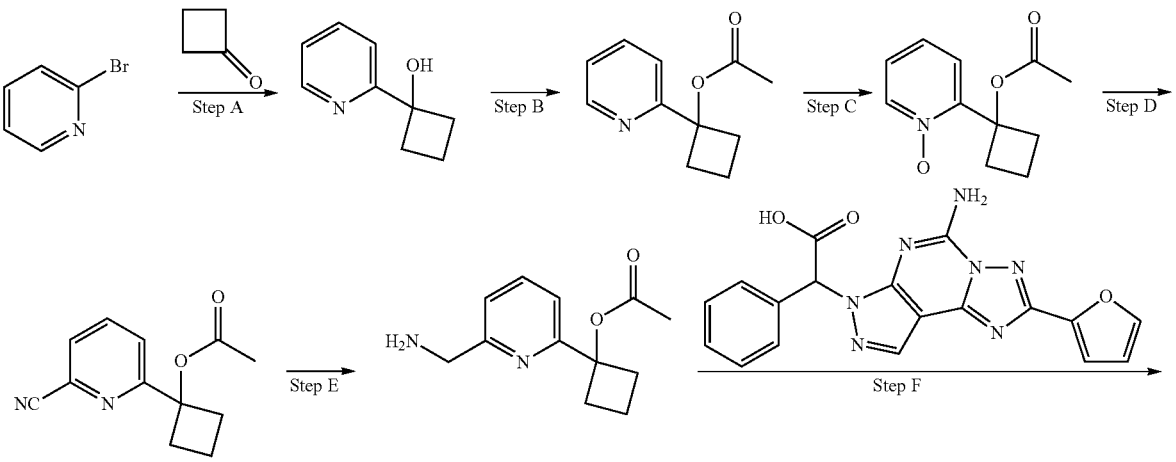

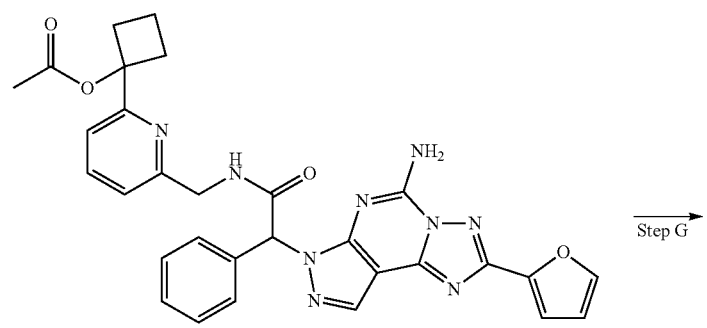

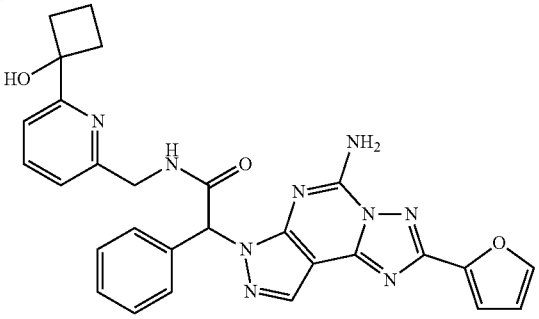

Step A: 1-(pyridin-2-yl)cyclobutan-1-ol

To a stirred solution of 2-bromopyridine (5.0 g, 31.6 mmol) in THF (60 mL) was added a solution of n-BuLi (2.4 M, 16 mL) in drops at −78° C. under $N_2$. After stirring for 20 min, a solution of cyclobutanone in THF (10 mL) was added at −78° C. After addition finished, the mixture was stirred for 30 min and slowly warmed to rt and stirred for 3 hrs. The mixture was quenched into 50 mL of an aqueous solution of $NH_4Cl$, extracted with EtOAc (50 mL×2). The combined extract was washed with brine (50 mL×3), dried over $Na_2SO_4$ and concentrated. The resulted residue was purified by column chromatography to give the title product (3.5 g, 74%) as a light yellow oil. MS: M/e 150 $(M+1)^+$.

Step B: 1-(pyridin-2-yl)cyclobutyl acetate

To a mixture of 1-(pyridin-2-yl)cyclobutan-1-ol (3.5 g, 23.5 mmol) and $Et_3N$ (6.0 g, 59.4 mmol) in $CH_2Cl_2$ (50 mL) was added DMAP (550 mg, 4.5 mmol) and followed by AcCl (2.2 g, 28.2 mmol) in drops at 0° C. The resulted mixture was stirred at rt for 16 hrs. The mixture was washed with brine (30 mL×3), dried over $Na_2SO_4$ and concentrated. The resulted residue was purified by column chromatography to give the title product (1.2 g, 27%) as a light yellow oil. MS: M/e 192 $(M+1)^+$.

Step C: 2-(1-acetoxycyclobutyl)pyridine 1-oxide

To a stirred solution of 1-(pyridin-2-yl)cyclobutyl acetate (1.2 g, 6.3 mmol) in $CH_2Cl_2$ (20 mL) was added solid m-CPBA (1.6 g, 9.3 mmol) in portions at 0° C. The resulted mixture was stirred at rt for 16 hrs. The mixture was diluted with $CH_2Cl_2$ (30 mL), washed with aqueous solution of $NaHCO_3$ (10 mL×3), brine (10 mL×2), dried over $Na_2SO_4$ and concentrated to give the title product (2.1 g, crude) as a light yellow oil. MS: M/e 208 $(M+1)^+$.

Step D: 1-(6-cyanopyridin-2-yl)cyclobutyl acetate

To a mixture of 2-(1-acetoxycyclobutyl)pyridine 1-oxide (1.7 g, 8.2 mmol) and $Et_3N$ (3.0 g, 30 mmol) in MeCN (20 mL) was added dimethylcarbamic chloride (1.7 g, 16.4 mmol) and followed by TMSCN (1.6 g, 16.4 mmol) at rt and the resulted mixture was stirred at 50° C. for 5 hrs. The mixture was diluted with EtOAc EA (50 mL) and washed with brine (30 mL×3), dried over $Na_2SO_4$ and concentrated. The resulted residue was purified by column chromatography to give the title product (420 mg, 24%) as a light yellow oil. MS: M/e 217 $(M+1)^+$.

Step E: 1-(6-(aminomethyl)pyridin-2-yl)cyclobutyl acetate

A mixture of 1-(6-(aminomethyl)pyridin-2-yl)cyclobutyl acetate (420 mg, 1.94 mmol) and Ranney Ni (500 mg) in $NH_2$/MeOH (1M, 20 mL) was stirred under $H_2$ at rt for 24 hrs. The mixture was filtered and the filtrate was concentrated to give the title product (430 mg, crude) as a light yellow oil. MS: M/e 221 $(M+1)^+$.

Step F: 1-(6-((2-(5-amino-2-(furan-2-yl)-7H-pyrazolo[4,3-e][1,2,4]triazolo[1,5-c]pyrimidin-7-yl)-2-phenylacetamido)methyl)pyridin-2-yl)cyclobutyl acetate To a mixture of 1-(6-(aminomethyl)pyridin-2-yl)cyclobutyl acetate (430 mg, 1.95 mmol), 2-(5-amino-2-(furan-2-yl)-7H-pyrazolo[4,3-e][1,2,4]triazolo[1,5-c]pyrimidin-7-yl)-2-phenylacetic acid (500 mg, 1.33 mmol), DIEA (950 mg, 7.3 mmol) in DMF (10 mL) was added HATU (600 mg, 1.58 mmol) at rt and the mixture was stirred at it for 16 hrs. The mixture was poured into 30 mL of $H_2O$ and stirred. A white solid precipitated and which was filtered. The filter cake was washed with $H_2O$ (20 mL×2), dried in air to give the title product (245 mg, yield: 32%) as a colorless oil. MS: M/e 578 $(M+1)^+$.

Step G: 2-(5-amino-2-(furan-2-yl)-7H-pyrazolo[4,3-e][1,2,4]triazolo[1,5-c]pyrimidin-7-yl)-N-((6-(1-hydroxycyclobutyl)pyridin-2-yl)methyl)-2-phenylacetamide To a stirred solution of 1-(6-((2-(5-amino-2-(furan-2-yl)-7H-pyrazolo[4,3-e][1,2,4]triazolo[1,5-c]pyrimidin-7-yl)-2-phenylacetamido)methyl)pyridin-2-yl)cyclobutyl acetate (245 mg, 0.42 mmol) in MeOH (5 mL) was added an aqueous solution of NaOH (2 M, 3 mL) at it and the resulted mixture was stirred for 5 hrs. The mixture was neutralized by HCl (1 M) to pH~7. The mixture was extracted with EtOAc (20 mL×3). The combined extracts were washed with brine (20 mL×2), dried over $Na_2SO_4$ and concentrated. The resulted residue was purified by column chromatography and prep-TLC (EtOAc, 100%) to give the title product (135 mg, 59%). $^1H$ NMR (400 MHz, DMSO-6) δ 8.45 (t, J=5.6 Hz, 1H), 8.34-8.09 (m, 3H), 7.95 (s, 1H), 7.71 (t, J=7.6 Hz, 1H), 7.53-7.44 (m, 2H), 7.44-7.31 (m, 4H), 7.25 (d, J=3.2 Hz, 1H), 7.18 (d, J=7.6 Hz, 1H), 6.77-6.69 (m, 1H), 6.53 (s, 1H), 5.66 (s, 1H), 4.56-4.40 (m, 2H), 2.47-2.35 (m, 2H), 2.21-2.06 (m, 2H), 1.86-1.60 (m, 2H). MS: M/e 536 $(M+1)^+$.

Example 18 was separated into two enantiomeric stereoisomers, EXAMPLE 18A (earlier peak), and EXAMPLE 18B (later peak) by chiral prep-HPLC. The chiral separation conditions are shown below.

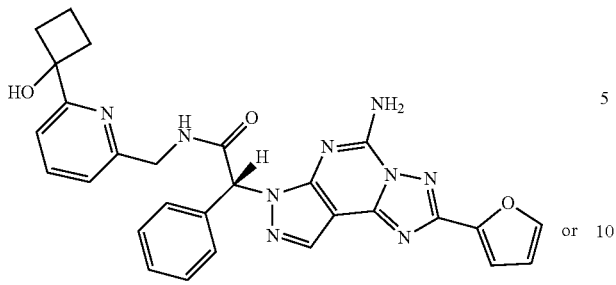

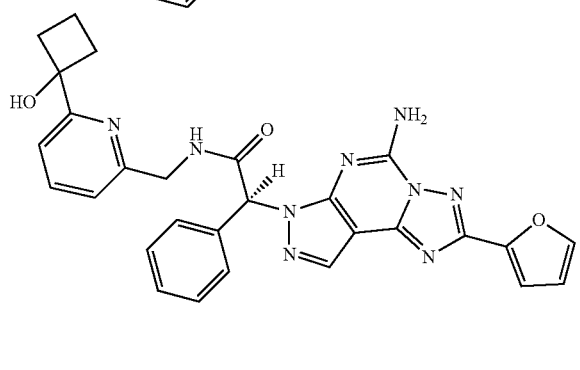

| Column | chiralpak AS-H |
|---|---|
| Column size | 2 cm × 25 cm, 5 um |
| Injection | 3.0 mL |
| Mobile phase | Hex:EtOH = 50:50 |
| Flow rate | 16 ml/min |
| Wave length | UV 220 nm |
| Temperature | 25° C. |
| Sample solution | 8.3 mg/ml in EtOH |
| Prep-HPLC equipment | BJ-Prep-Gilson-HPLC |

Example 19: 2-(5-amino-2-(furan-2-yl)-7H-pyrazolo[4,3-e][1,2,4]triazolo[1,5-c]pyrimidin-7-yl)-2-phenylacetamide A mixture of 2-(5-amino-2-(furan-2-yl)-7H-pyrazolo[4,3-e][1,2,4]triazolo[1,5-c]pyrimidin-7-yl)-2-phenylacetic acid (100 mg, 0.27 mmol), NH$_3$/MeOH (4 N, 5 mL, 20 mmol), HATU (110 mg, 0.29 mmol) and DIPEA (100 mg, 0.78 mmol) in DMF (10 mL) was stirred for 4 hours at RT. The reaction mixture was poured into H$_2$O (20 mL) and extracted with EtOAc (50 mL×3). The combined organic layers were washed with brine, dried over Na$_2$SO$_4$, concentrated and purified by column chromatography (petroleum ether/EtOAc=1:1~100% EtOAc) to give the target compound (37 mg, 36.6%), $^1$H NMR (400 MHz, DMSO-d6) δ 8.21 (s, 1H), 8.18 (br.s, 1H), 7.96 (s, 1H), 7.54 (s, 1H), 7.47-7.31 (m, 5H), 7.24 (d, =3.2 Hz, 1H), 6.74 (br.s, 2H), 6.36 (s, 1H) ppm. MS: M/e 375 (M+1)$^+$.

Example 20: 2-(5-amino-2-(furan-2-yl)-7H-pyrazolo[4,3-e][1,2,4]triazolo[1,5-c]pyrimidin-7-yl)-N-(2,3-dihydrobenzofuran-3-yl)-2-phenylacetamide To a mixture of 2,3-dihydrobenzofuran-3-amine (20 mg, 0.15 mmol), 2-(5-amino-2-(furan-2-yl)-7H-pyrazolo[4,3-e][1,2,4]triazolo[1,5-c]pyrimidin-7-yl)-2-phenylacetic acid (40 mg, 0.11 mmol), DIEA (70 mg, 0.54 mmol) in DMF (1 mL) was added HATU (50 mg, 0.13 mmol) at rt and the mixture was stirred at rt for 16 hrs. 10 mL of EtOAc was added and the mixture was washed with brine (5 mL×3), dried over Na$_2$SO$_4$ and concentrated. The resulted residue was purified by prep-TLC (PE/EtOAc=1:1) to give the title product (25.0 mg, yield: 46%). $^1$H NMR (400 MHz, DMSO-d6) δ 8.79 (dd, J=33.2, 7.2 Hz, 1H), 8.35-8.03 (m, 3H), 7.95 (s, 1H), 7.42-7.29 (m, 5H), 7.28-7.14 (m, 2H), 6.94-6.84 (m, 1H), 6.81 (d, J=8.0 Hz, 1H), 6.73 (dd, J=3.2, 2.0 Hz, 1H), 6.43 (d, J=9.2 Hz, 1H), 5.66-5.55 (m, 1H), 4.75-4.59 (m, 1H), 4.30-4.15 (m, 1H). MS: M/e 493 (M+1)$^+$.

Example 21: 2-(5-amino-2-(furan-2-yl)-7H-pyrazolo[4,3-e][1,2,4]triazolo[1,5-c]pyrimidin-7-yl)-N-(2-methoxybenzyl)pentanamide

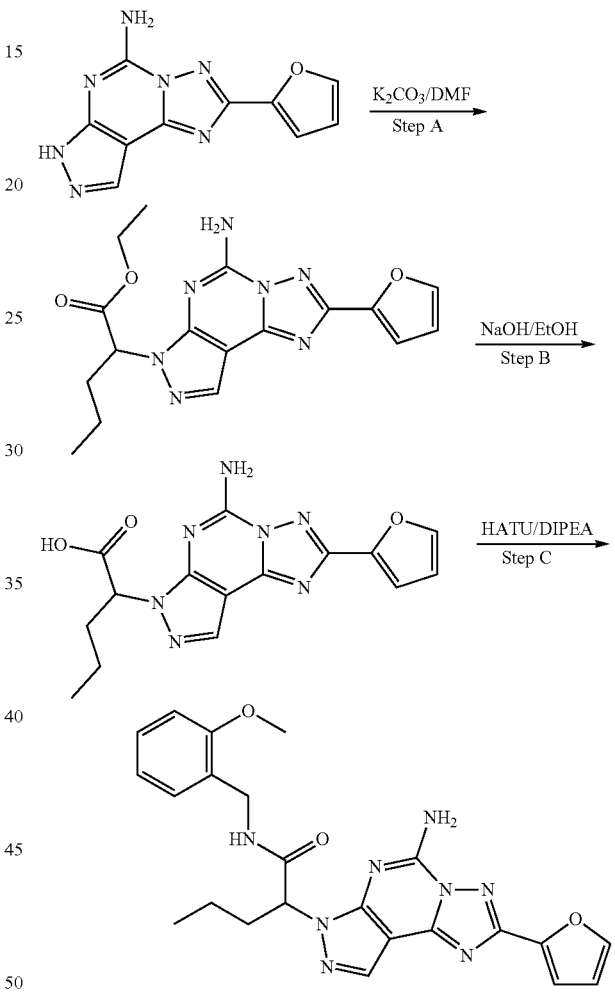

Step A: ethyl 2-(5-amino-2-(furan-2-yl)-7H-pyrazolo[4,3-e][1,2,4]triazolo[1,5-c]pyrimidin-7-yl)pentanoate A mixture of 2-(furan-2-yl)-7H-pyrazolo[4,3-e][1,2,4]triazolo[1,5-c]pyrimidin-5-amine (2 g, 8.3 mmol), ethyl 2-bromopentanoate (2.1 g, 9.9 mmol) and K$_2$CO$_3$ (2.3 g, 16.6 mmol) in DMF (50 mL) was stirred at rt overnight. The solution was added with water (30 mL), extracted with ethyl acetate (50 and washed with brine (50 mL). The organic layer was dried over Na$_2$SO$_4$, concentrated and purified by column chromatography (PE:EtOAc=4:1 to 2:1) to get ethyl 2-(5-amino-2-(furan-2-yl)-7H-pyrazolo[4,3-e][1,2,4]triazolo[1,5-c]pyrimidin-7-yl)pentanoate (600 mg, 20%). MS: M/e 370 (M+1)$^+$ Step B: 2-(5-amino-2-(furan-2-yl)-7H-pyrazolo[4,3-e][1,2,4]triazolo[1,5-c]pyrimidin-7-yl)pentanoic acid NaOH solution (324 mg, in 2 mL of water) was added to a solution of ethyl 2-(5-amino-2-(furan-2-yl)-7H-pyrazolo[4,3-e][1,2,4]triazolo[1,5-c]pyrimidin-7-yl)pentanoate (600 mg, 1.6 mmol) in ethanol (10 mL). The reaction mixture was stirred at rt for 3 hrs. The solution was concentrated, added with water (10 mL) and acidified with 1N HCl solution to pH=5. The precipitated solid was filtered and dried to get the desired product as a white solid (475 mg, 86%). MS: M/e 342 (M+1)+.

Step C: 2-(5-amino-2-(furan-2-yl)-7H-pyrazolo[4,3-e][1,2,4]triazolo[1,5-c]pyrimidin-7-yl)-N-(2-methoxybenzyl)pentanamide A mixture of 2-(5-amino-2-(furan-2-yl)-7H-pyrazolo[4,3-e][1,2,4]triazolo[1,5-c]pyrimidin-7-yl)pentanoic acid (50 mg, 0.15 mmol), (2-methoxy phenyl) methanamine (24 mg, 0.18 mmol), HATU (69 mg, 0.18 mmol) and DIEA (39 mg, 0.3 mmol) in DMF (5 mL) was stirred at rt for 2 hrs. The solution was added with water (10 mL), extracted with ethyl acetate (10 mL) and washed with brine (10 mL). The organic layer was dried, concentrated and purified by column chromatography (PE:EtOAc=1:1) to get the desired product (45 mg, 67%). $^1$H NMR (400 MHz, DMSO-d6) δ 8.30 (s, 1H), 8.15 (br.s, 2H), 7.95 (s, 1H), 7.88 (t, J=4.0 Hz, 1H), 7.25-7.10 (m, 3H), 6.95-6.74 (m, 3H), 5.25 (dd, J=12.0 Hz, 4.0 Hz, 1H), 4.28-4.15 (m, 2H), 3.75 (s, 3H), 2.35-2.14 (m, 2H), 1.19-1.11 (m, 2H), 0.86 (t, J=8.0 Hz, 3H) ppm. MS: M/e 461 (M+1)+.

Example 22: 2-(5-amino-2-(furan-2-yl)-7H-pyrazolo[4,3-e][1,2,4]triazolo[1,5-c]pyrimidin-7-yl)-2-phenyl-N-(3-(trifluoromethyl)benzyl)acetamide A mixture of 2-(5-amino-2-(furan-2-yl)-7H-pyrazolo[4,3-e][1,2,4]triazolo[1,5-c]pyrimidin-7-yl)-2-phenylacetic acid (50 mg, 0.13 mmol), (3-(trifluoromethyl)phenyl)methanamine (25.5 mg, 0.13 mmol), HATU (56 mg, 0.14 mmol) and DIEA (0.5 mL) in DMF (10 mL) was stirred at RT overnight. The reaction mixture was poured into water (20 mL) and the solid was precipitated from the system. The solid was filtered and purified by prep-TLC to afford the title compound (15 mg, yield: 21.7%). $^1$H NMR (400 MHz, DMSO-d6) δ8.65-8.52 (m, 1H), 8.24 (s, 1H), 8.19 (br.s, 1H), 7.98-7.88 (m, 1H), 7.64-7.50 (m, 4H), 7.46-7.33 (m, 5H), 7.25 (d, J=4 Hz, 1H), 6.78-6.71 (m, 1H), 6.50 (s, 1H), 4.43 (d, J=8.0 Hz, 2H) ppm. MS: M/e 533 (M+1)+.

Example 23: 2-(5-amino-2-(furan-2-yl)-7H-pyrazolo[4,3-e][1,2,4]triazolo[1,5-c]pyrimidin-7-yl)-N-(3-methylbenzyl)-2-phenylacetamide A mixture of 2-(5-amino-2-(furan-2-yl)-7H-pyrazolo[4,3-e][1,2,4]triazolo[1,5-c]pyrimidin-7-yl)-2-phenylacetic acid (50 mg, 0.13 mmol), m-tolylmethanamine (16 mg, 0.13 mmol), HATU (56 mg, 0.14 mmol) and DIEA (0.5 mL) in DMF (10 mL) was stirred at RT overnight. The reaction mixture was poured into water (20 mL) and the solid was precipitated from the system. The solid was filtered and purified by prep-TLC to afford the title compound (5 mg, yield: 8%). $^1$H NMR (400 MHz, DMSO-d6) δ8.51-8.40 (m, 1H), 8.24 (s, 1H), 8.18 (br.s, 2H), 7.98-7.91 (m, 1H), 7.48-7.41 (m, 2H), 7.41-7.32 (m, 3H), 7.27-7.23 (m, 1H), 7.21-0.14 (m, 1H), 7.07-6.98 (m, 3H), 6.77-6.71 (m, 1H), 6.48 (s, 1H), 4.30 (t, J=5.2 Hz, 2H), 2.25 (s, 3H) ppm. MS: M/e 479 (M+1)+.

Example 24: 2-(5-amino-2-(furan-2-yl)-7H-pyrazolo[4,3-e][1,2,4]triazolo[1,5-c]pyrimidin-7-yl)-2-phenyl-N-(4-(trifluoromethoxy)benzyl)acetamide A mixture of 2-(5-amino-2-(furan-2-yl)-7H-pyrazolo[4,3-e][1,2,4]triazolo[1,5-c]pyrimidin-7-yl)-2-phenylacetic acid (50 mg, 0.13 mmol), (4-(trifluoromethoxy)phenyl)methanamine (29 mg, 0.15 mmol), HATU (55 mg, 0.15 mmol) and DIPEA (50 mg, 0.39 mmol) in DMF (10 mL) was stirred for 4 hours at RT. The reaction mixture was poured into H$_2$O (20 nit) and extracted with EtOAc (50 mL×3). The combined organic layers were washed with brine, dried over Na$_2$SO$_4$, concentrated and purified by column chromatography (petroleum ether/EtOAc 1:1~100% EtOAc) to give target compound (39.3 mg, 55.2%). $^1$H NMR (400 MHz, DMSO-d6) δ 8.55 (s, 1H), 8.24 (s, 1H), 8.20 (br.s, 2H), 7.95 (s, 1H), 7.47-7.27 (m, 9H), 7.24 (d, J=3.2 Hz, 1H), 6.74 (br.s, 1H), 6.48 (s, 1H), 4.45-4.27 (m, 2H) ppm. MS: M/e 549 (M+1)+.

Example 25: 2-(5-amino-2-(furan-2-yl)-7H-pyrazolo[4,3-e][1,2,4]triazolo[1,5-c]pyrimidin-7-yl)-N-(4-methylbenzyl)-2-phenylacetamide A mixture of 2-(5-amino-2-(furan-2-yl)-7H-pyrazolo[4,3-e][1,2,4]triazolo[1,5-c]pyrimidin-7-yl)-2-phenylacetic acid (50 mg, 0.13 mmol), p-tolylethanolamine (19 mg, 0.15 mmol), HATU (55 mg, 0.15 mmol) and DIPEA (50 mg, 0.39 mmol) in DMF (10 mL) was stirred for 4 hours at RT. The reaction mixture was poured into H$_2$O (20 mL) and extracted with EtOAc (50 mL×3). The combined organic layers were washed with brine, dried over Na$_2$SO$_4$, concentrated and purified by column chromatography (petroleum ether/EtOAc=1:1~100% EtOAc) to give the target compound (15.6 mg, 25.1%). $^1$H NMR (400 MHz, DMSO-d6) δ 8.42 (t, J=5.9 Hz, 1H), 8.23 (s, 1H), 8.18 (br.s, 2H), 7.95 (s, 1H), 7.49-7.31 (m, 5H), 7.24 (d, J=3.3 Hz, 1H), 7.16-7.05 (m, 4H), 6.77-6.71 (m, 1H), 6.46 (s, 1H), 4.28 (d, J=5.9 Hz, 2H), 2.26 (s, 3H). MS: M/e 479 (M+1)+.

Example 26: 2-(5-amino-2-(furan-2-yl)-7H-pyrazolo[4,3-e][1,2,4]triazolo[1,5-c]pyrimidin-7-yl)-N-(4-fluorobenzyl)-2-phenylacetamide A mixture of 2-(5-amino-2-(furan-2-yl)-7H-pyrazolo[4,3-e][1,2,4]triazolo[1,5-c]pyrimidin-7-yl)-2-phenylacetic acid (50 mg, 0.13 mmol), (4-fluorophenyl)methanamine (19 mg, 0.15 mmol), HATU (55 mg, 0.15 mmol) and DIPEA (50 mg, 0.39 mmol) in DMF (10 mL) was stirred for 4 hours at RT. The reaction mixture was poured into H$_2$O (20 mL) and extracted with EtOAc (50 mL×3). The combined organic layers were washed with brine, dried over Na$_2$SO$_4$, concentrated and purified by column chromatography (petroleum ether/EtOAc=1:1~100% EtOAc) to give the target compound (34.7 mg, 55.3%). $^1$H NMR (400 MHz, DMSO-d6) δ 8.51 (s, 1H), 8.23 (s, 1H), 8.19 (br.s, 1H), 7.96 (s, 1H), 7.44-7.19 (m, 8H), 7.18-7.06 (m, 2H), 6.74 (br.s, 1H), 6.46 (s, 1H), 4.30 (t, J=9.7 Hz, 2H). MS: M/e 483 (M+1)+.

Example 27: 2-(5-amino-2-(furan-2-yl)-7H-pyrazolo[4,3-e][1,2,4]triazolo[1,5-c]pyrimidin-7-yl)-N-(2-methoxybenzyl)-4-methylpentanamide

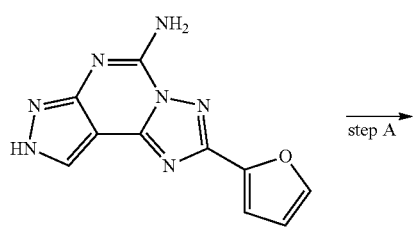

-continued

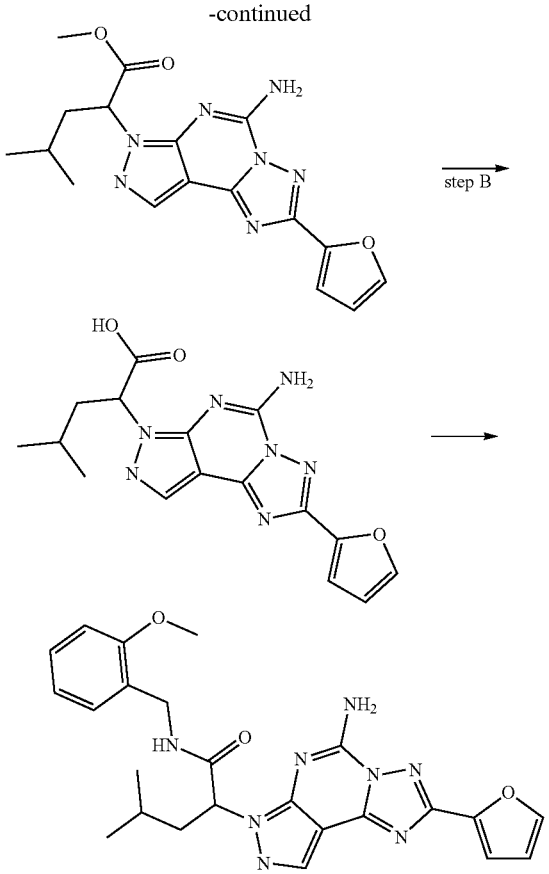

Step A: methyl 2-(5-amino-2-(furan-2-yl)-7H-pyrazolo[4,3-e][1,2,4]triazolo[1,5-c]pyrimidin-7-yl)-4-methylpentanoate To a stirred solution of 2-(furan-2-yl)-8H-pyrazolo[4,3-e][1,2,4]triazolo[1,5-c]pyrimidin-5-amine (482 mg, 2 mmol) in DMF (10 mL) was added $K_2CO_3$ (552 mg, 4 mmol) and methyl 2-bromo-4-methylpentanoate (418 mg, 2 mmol). After addition, the reaction mixture was stirred for a weekend. The reaction mixture was poured into $H_2O$ (20 mL) and extracted with EtOAc (15 mL×3). The combined organic layers were washed with brine, dried over $Na_2SO_4$, concentrated and purified by column chromatography (petroleum ether/EtOAc=3:1~1:1) to give methyl 2-(5-amino-2-(furan-2-yl)-7H-pyrazolo[4,3-e][1,2,4]triazolo[1,5-c]pyrimidin-7-yl)-4-methylpentanoate (280 mg, 37.9%). MS: M/e 370 (M+1)$^+$.

Step B: 2-(5-amino-2-(furan-2-yl)-7H-pyrazolo[4,3-e][1,2,4]triazolo[1,5-c]pyrimidin-7-yl)-4-methylpentanoic acid To a stirred mixture of methyl 2-(5-amino-2-(furan-2-yl)-7H-pyrazolo[4,3-e][1,2,4]triazolo[1,5-c]pyrimidin-7-yl)-4-methylpentanoate (200 mg, 0.54 mmol) in MeOH/$H_2O$ (10 mL/5 mL) was added aq. NaOH (2.0 M, 4 mL). After addition, the reaction mixture was stirred overnight. Most of solvent was removed to give the aqueous layer, then acidified to pH=3-4 with aq. HCl and filtered, the cake was collected, dried to give the target compound (180 mg, 93.8%) as a white solid. MS: M/e 356 (M+1)$^+$.

Step C: 2-(5-amino-2-(furan-2-yl)-7H-pyrazolo[4,3-e][1,2,4]triazolo[1,5-c]pyrimidin-7-yl)-N-(2-methoxybenzyl)-4-methylpentanamide A mixture of 2-(5-amino-2-(furan-2-yl)-7H-pyrazolo[4,3-e][1,2,4]triazolo[1,5-c]pyrimidin-7-yl)-4-methylpentanoic acid (36.9 mg, 0.1 mmol), (2-methoxyphenyl)methanamine (13.7 mg, 0.1 mmol), HATU (46 mg, 0.12 mmol) and DIPEA (25.8 mg, 0.2 mmol) in DMF (3 mL) was stirred overnight. The reaction mixture was poured into $H_2O$ (10 mL) and extracted with EtOAc (20 mL×3). The combined organic layers were washed with brine, dried over $Na_2SO_4$, concentrated and purified by column chromatography (petroleum ether/EtOAc=3:1~1:1) to give the target compound (35 mg, 74.6%). $^1$H NMR (400 MHz, DMSO-d6) δ 8.31 (s, 1H), 8.17 (s, 2H), 7.95 (s, 1H), 7.82 (t, J=5.6 Hz, 1H), 7.29-7.16 (m, 2H), 7.09-7.07 (d, J=7.2 Hz, 1H), 6.98-6.84 (m, 2H), 6.74 (s, 1H), 5.33-5.29 (m, 1H), 4.28-4.13 (m, 2H), 3.75 (s, 3H), 2.43-2.32 (m, 1H), 2.01-1.95 (m, 1H), 1.24 (s, 1H), 0.89-0.83 (m, 6H) ppm. MS: M/e 475 (M+1)$^+$.

Example 28: 2-(5-amino-2-(furan-2-yl)-7H-pyrazolo[4,3-e][1,2,4]triazolo[1,5-c]pyrimidin-7-yl)-N-(4-methoxybenzyl)-2-phenylacetamide A mixture of 2-(5-amino-2-(furan-2-yl)-7H-pyrazolo[4,3-e][1,2,4]triazolo[1,5-c]pyrimidin-7-yl)-2-phenylacetic acid (50 mg, 0.13 mmol), (4-methoxyphenyl)methanamine (30 mg, 0.15 mmol), HATU (55 mg, 0.15 mmol) and DIPEA (50 mg, 0.39 mmol) in DMF (10 mL) was stirred for 4 hours at RT. The reaction mixture was poured into $H_2O$ (20 mL) and extracted with EtOAc (50 mL×3). The combined organic layers were washed with brine, dried over $Na_2SO_4$, concentrated and purified by column chromatography (petroleum ether/EtOAc=1:1~100% EtOAc) to give the target compound (23.6 mg, 36.7%). $^1$H NMR (400 MHz, DMSO-d6) δ 8.40 (t, J=6.0 Hz, 1H), 8.23 (s, 1H), 8.17 (br.s, 2H), 7.95 (s, 1H), 7.46-7.30 (m, 5H), 7.24 (d, J=3.4 Hz, 1H), 7.19-7.13 (m, 2H), 6.89-6.82 (m, 2H), 6.74 (br.s, 1H), 6.45 (s, 1H), 4.25 (d, J=5.8 Hz, 2H), 3.72 (s, 4H). MS: M/e 495 (M+1)$^+$.

Example 29: 2-(5-amino-2-(furan-2-yl)-7H-pyrazolo[4,3-e][1,2,4]triazolo[1,5-c]pyrimidin-7-yl)-2-phenyl-N-(4-(trifluoromethyl)benzyl)acetamide A mixture of 2-(5-amino-2-(furan-2-yl)-7H-pyrazolo[4,3-e][1,2,4]triazolo[1,5-c]pyrimidin-7-yl)-2-phenylacetic acid (50 mg, 0.13 mmol), (4-(trifluoromethyl)phenyl)methanamine (35 mg, 0.15 mmol), HATU (55 mg, 0.15 mmol) and DIPEA (50 mg, 0.39 mmol) in DMF (10 mL) was stirred for 4 hours at RT. The reaction mixture was poured into $H_2O$ (20 mL) and extracted with EtOAc (50 mL×3). The combined organic layers were washed with brine, dried over $Na_2SO_4$, concentrated and purified by column chromatography (petroleum ether/EtOAc=1:1~100% EtOAc) to give target compound (25.7 mg, 37.2%). $^1$H NMR (400 MHz, DMSO-d6) δ 8.58 (t, J=6.0 Hz, 1H), 8.25 (s, 1H), 8.20 (br.s, 2H), 7.95 (s, 1H), 7.68 (d, J=8.1 Hz, 2H), 7.51-7.41 (m, 4H), 7.40-7.30 (m, 3H), 7.24 (d, J=3.3 Hz, 1H), 6.74 (br.s, 1H), 6.49 (s, 1H), 4.53-4.31 (m, 2H). MS: M/e 533 (M+1)$^+$.

Intermediate-I: 2-(5-amino-2-(furan-2-yl)-7H-pyrazolo[4,3-e][1,2,4]triazolo[1,5-c]pyrimidin-7-yl)-2-phenylpropanoic acid

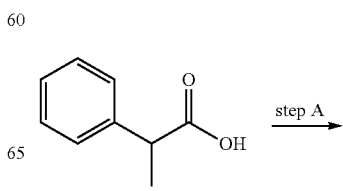

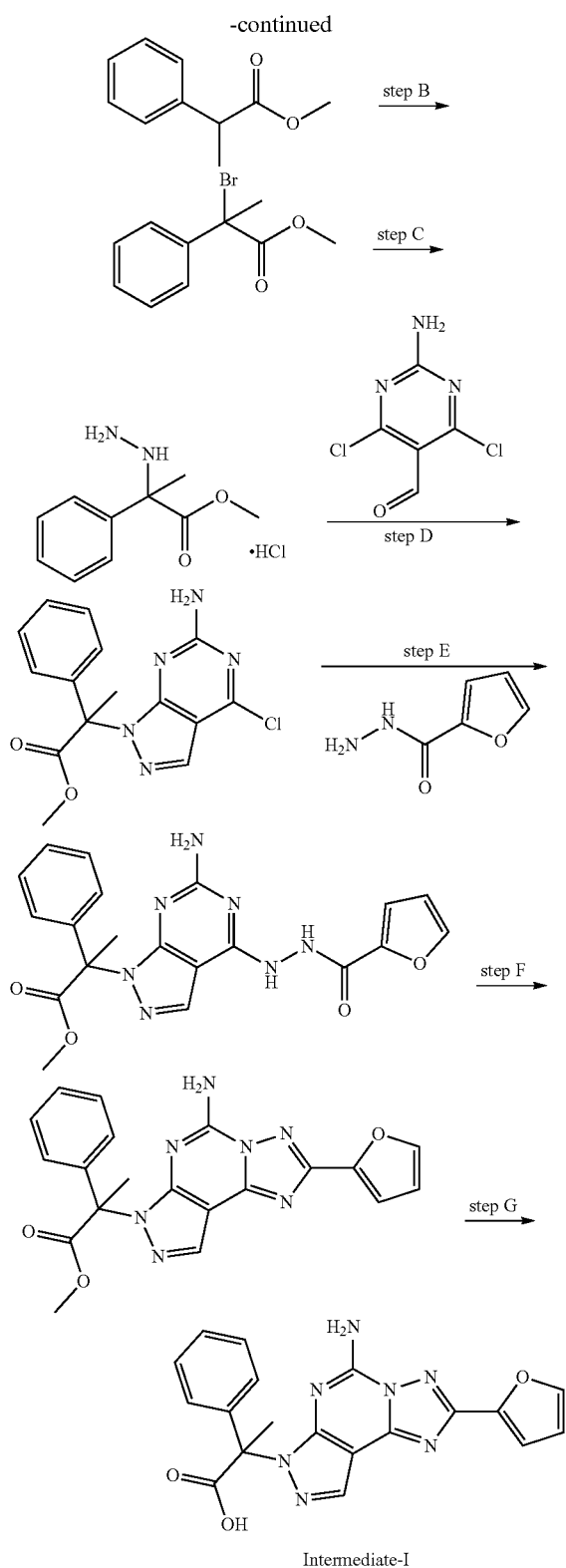

Intermediate-I

Step A: methyl 2-phenylpropanoate

To a solution of 2-phenylpropanoic acid (5 g, 33.33 mmol) in MeOH (15 mL), sulfoxide chloride (5.15 g, 50 mmol) was added dropwise at 0° C. After the addition, the reaction mixture was stirred at rt for 3 h. The mixture was concentrated, quenched with ice water (20 mL), extracted with EtOAc (30 mL×3). The combined organic layers were washed with brine, dried over $Na_2SO_4$, concentrated and purified by column chromatography (petroleum ether/EtOAc=20:1~5:1) to give methyl 2-phenylpropanoate (5.22 g, 95.49%) as yellow oil. MS: M/e 165 $(M+1)^+$.

Step B: methyl 2-bromo-2-phenylpropanoate

A mixture of methyl 2-phenylpropanoate (5.22 g, 31.83 mmol), NBS (6.80 g, 38.19 mmol), BPO (0.385 g, 1.591 mmol) in carbon tetrachloride (20 mL) was stirred at 70° C. overnight. The mixture was concentrated, the residue was washed with PE and filtered, the filtrate was concentrated to give methyl 2-bromo-2-phenylpropanoate (7.57 g, 97.87%) as yellow oil. $^1$H NMR (400 MHz, CDCl3) δ 7.55 (d, J=7.5 Hz, 2H), 7.40-7.27 (m, 3H), 3.80 (s, 3H), 2.30 (s, 3H)

Step C: methyl 2-hydrazinyl-2-phenylpropanoate hydrochloride

To a stirred solution of methyl 2-bromo-2-phenylpropanoate (15 g, 62.2 mmol) in acetonitrile (200 mL) was added hydrazine hydrate (80%, 15.5 g, 249 mmol). After addition, the reaction mixture was warmed up to 50° C. and stirred for 3.5 h. The reaction mixture was concentrated in vacuo. The residue was added $H_2O$ (300 mL) and extracted with EtOAc (200 mL×3). The combined organic layers were washed with brine, dried over $Na_2SO_4$ and concentrated in vacuo. The residue was added EtOAc (50 mL) and added to 4M HCl/EtOAc solution (200 mL) at 0° C. After addition, the mixture was stirred for 1 h at 0° C., then the mixture was filtered and the filter cake was washed with EtOAc EA (50 mL), dried to give the target product as a white solid (9.8 g, 68.5%). $^1$H NMR (400 MHz, DMSO-d6) δ 9.28 (s, 2H), 7.43-7.38 (m, 5H), 6.23 (s, 1H), 3.73 (s, 3H), 1.72 (s, 3H) ppm. MS: M/e 195 $(M+1)^+$.

Step D: methyl 2-(6-amino-4-chloro-1H-pyrazolo[3,4-d]pyrimidin-1-yl)-2-phenylpropanoate To a stirred mixture of methyl 2-hydrazinyl-2-phenylpropanoate hydrochloride (2.38 g, 10.3 mmol) in acetonitrile (30 mL) was added 2-amino-4,6-dichloropyrimidine-5-carbaldehyde (1.96 g, 10.3 mmol). After addition, the reaction mixture was stirred at rt overnight. The reaction mixture was warmed up to 70° C. and stirred for 2 h. 1M $NaHCO_3$ aqueous solution was added to the mixture and the mixture was extracted with EtOAc (50 mL×3). The combine organic phase was dried with $Na_2SO_4$ and concentrated in vacuo. The crude product was purified by column chromatography (petroleum ether/EtOAc=4:1) to give the target compound (2.2 g, 64.3%) as a white solid. $^1$H NMR (400 MHz, DMSO-d6) δ 8.05 (s, 1H), 7.35-7.31 (m, 5H), 7.13-7.11 (m, 2H), 3.71 (s, 3H), 3.25 (s, 3H) ppm. MS: M/e 332 $(M+1)^+$.

Step E: methyl 2-(6-amino-4-(2-(furan-2-carbonyl)hydrazinyl)-1H-pyrazolo[3,4-d]pyrimidin-1-yl)-2-phenylpropanoate To a stirred mixture of methyl 2-(6-amino-4-chloro-1H-pyrazolo[3,4-d]pyrimidin-1-yl)-2-phenylpropanoate (2.03 g, 6.4 mmol) in DMSO (20 mL) was added furan-2-carbohydrazide (0.85 g, 6.7 mmol) and DIEA (2.36 g, 18.3 mmol). After addition, the reaction mixture was stirred at 120° C. overnight. Most of solvent was concentrated in vacuo and the residue was added $H_2O$ (20 mL) and stirred for 1 h. The mixture was filtered and the filter cake was washed with water. The crude product was dried at 40° C. and used directly in next Step (850 mg, 31.5%). MS: M/e 422 (M+1)+.

Step F: methyl 2-(5-amino-2-(furan-2-yl)-7H-pyrazolo[4,3-e][1,2,4]triazolo[1,5-c]pyrimidin-7-yl)-2-phenylpropanoate A mixture of methyl 2-(6-amino-4-(2-(furan-2-carbonyl)hydrazinyl)-1H-pyrazolo[3,4-d]pyrimidin-7-yl)-2-phenylpropanoate (750 mg, 1.78 mmol) in BSA (7.5 mL) and HMDS (7.5 mL) was stirred at 110° C. overnight. The mixture was concentrated in vacuo to remove BSA and HMDS. The residue was added H$_2$O and extracted with EtOAc (20 mL×3). The combined organic phase was washed with brine, dried with Na$_2$SO$_4$ and concentrated in vacuo. The crude product was purified by column chromatography (petroleum ether/EtOAc=4:1~2:1) to give the target compound (150 mg, 20.9%) as a white solid. $^1$H NMR (400 MHz, CDCl$_3$) δ 8.31 (s, 1H), 7.64 (s, 1H), 7.31 (m, 5H), 7.21 (d, J=4.0 Hz, 1H), 6.59-6.58 (m, 1H), 3.76 (s, 3H), 2.4 (s, 3H) ppm MS: M/e 404 (M+1)+.

Step G: 2-(5-amino-2-(furan-2-yl)-7H-pyrazolo[4,3-e][1,2,4]triazolo[1,5-c]pyrimidin-7-yl)-2-phenylpropanoic acid (Intermediate-I)

To a stirred mixture of methyl 2-(5-amino-2-(furan-2-yl)-7H-pyrazolo[4,3-e][1,2,4]triazolo[1,5-c]pyrimidin-7-yl)-2-phenylpropanoate (150 mg, 0.34 mmol) in EtOH (3 mL) was added aq. NaOH (2.0 M, 3 mL). After addition, the reaction mixture was stirred at 70° C. for 1 h. Most of EtOH was removed to give the aqueous layer, then acidified to pH=3-4 with aq. HCl and filtered, the filter cake was collected, dried to give the target compound (130 mg, 98.3%) as a white solid. $^1$H NMR (400 MHz, DMSO-d6) δ 13.31 (s, 1H), 8.21 (s, 1H), 7.99 (s, 2H), 7.95 (s, 1H), 7.33-7.21 (m, 6H), 6.75-6.74 (m, 1H), 2.32 (s, 3H) ppm. MS: M/e 390 (M+1)+.

Intermediate-I was separated into two enantiomeric stereoisomers (Intermediate-Ia, earlier peak, and Intermediate-Ib, later peak) by chiral prep-HPLC. The chiral separation conditions are shown below.

| Column | CHIRALPAK-IC |
|---|---|
| Column size | 5 cm × 15 cm, 5 um |
| Injection | 8 ml |
| Mobile phase | CO$_2$:MeOH(0.1% DEA) = 60:40 |
| Flow rate | 160 ml/min |
| Wave length | UV 220 nm |
| Temperature | 25° C. |
| Sample solution | 15.1 mg/ml in EtOH:ACN:DCM = 1:1:1 |
| Prep-SFC equipment | Prep-SFC-350 |

Intermediate-Ib can be synthesized using the following route: (R)-2-(5-amino-2-(furan-2-yl)-7H-pyrazolo[4,3-e][1,2,4]triazolo[1,5-c]pyrimidin-7-yl)-2-phenylpropanoic acid

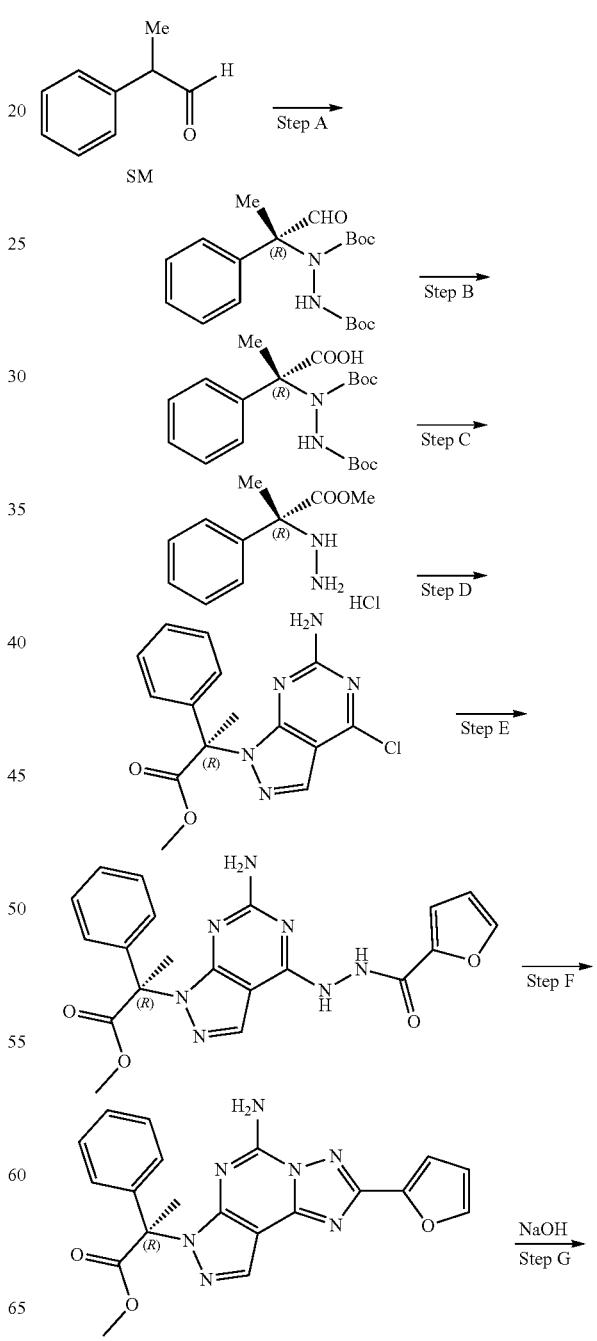

Intermediate-Ia

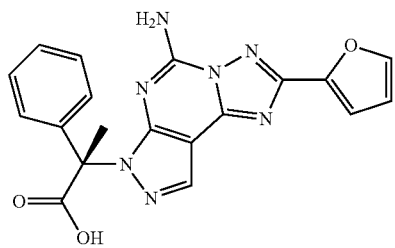

Intermediate-Ib

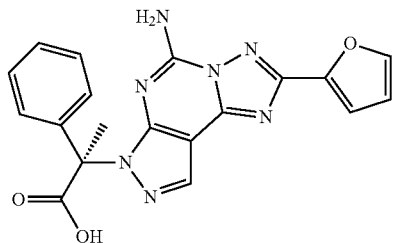

-continued

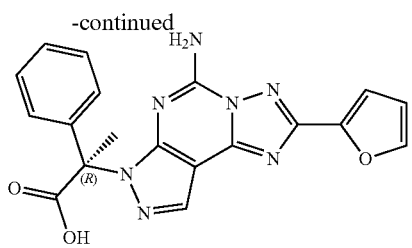

Step A: di-tert-butyl 1-(1-oxo-2-phenylpropan-2-yl)hydrazine-1,2-dicarboxylate To a stirred solution of (S)-2-amino-4-(tert-butoxy)-4-oxobutanoic acid (15 g, 0.08 mol) in dry THF (0.8 L) were added 2-phenylpropanal (53.6 g, 0.4 mol) and DTAD (92 g, 0.4 mol) at 0° C. After addition, the reaction was slowly warmed to rt and stirred overnight under $N_2$. The mixture was diluted with water/brine, extracted with EtOAc (600 mL). The combined organic layers were washed with brine, dried over $Na_2SO_4$, concentrated to give the target compound (160 g, crude) as yellow oil.

Step B: 2-(1,2-bis(tert-butoxycarbonyl)hydrazinyl)-2-phenylpropanoic acid

To a solution of the product of Step A (120 g, 0.3 mol) in DCM (600 mL) was added a solution of $NaH_2PO_4$ (10.08 g, 0.084 mol) in water (150 mL). $H_2O_2$ (150 mL, 1.46 mol about 4.85 eq)) was added at 0° C. Then a solution of 75% $NaClO_2$ (46 g, 0.51 mol, 1.275 eq) in water (300 mL) was added drop wise to keep the temperature below 10° C. After addition, the reaction was warmed to rt overnight. The stirring was stopped and the water layer was discarded. The organic layer was transferred into 10% $NaHSO_3$ solution (300 mL) and the resulting mixture was stirred at rt for one hour. The organic layer was collected and washed with 10% $NaHSO_3$ solution (300 mL), brine, dried over $Na_2SO_4$, filtered, and concentrated. To the residue was added $CH_3CN$ (200 mL) and the mixture was concentrated again. The resulted residue was slurried with EtOAc/PE (⅓~200 mL) and stirred at rt overnight. The precipitate was filtered, washed with EtOAc/PE (⅓, 100 mL) to give the target compound (47, 41% for two Steps) as a white solid.

Step C: methyl 2-hydrazinyl-2-phenylpropanoate hydrochloride

To a mixture of the product of Step B (299 g, 0.787 mol) in MeOH (1.2 L) was added $SOCl_2$ (187 g, 1.57 mmol) dropwise at 10~30° C. The resulting mixture was heated at 65° C. overnight. The mixture was cooled to rt and concentrated to give the residue, which was added EtOAc (100 mL) and concentrated again. The residue was slurry with EtOAc (200 mL) and filtered, the cake was collected to give the target compound (176 g, 97%, ee %=99.3%) as a white solid.

Step D: methyl (R)-2-(6-amino-4-chloro-1H-pyrazolo[3,4-d]pyrimidin-1-yl)-2-phenylpropanoate To a stirred mixture of the product of Step C (11.5 g, 50 mmol) and 2-amino-4,6-dichloropyrimidine-5-carbaldehyde (9.6 g, 50 mmol) in $CH_3CN$ (200 mL) was added $POCl_3$ (7.7 g, 50 mmol) at room temperature. After addition, the reaction mixture was stirred at 30° C. overnight. Then the reaction mixture was added dropwise to a system of EtOAc (200 mL)/aq. $K_3PO_4$ (37 g, 0.175 mol) in $H_2O$ (200 mL) and stirred for 2 h. The organic layer was separated, washed with brine, dried over $Na_2SO_4$, concentrated to give the residue, which was dissolved in EtOAc (40 mL), active-carbon (5 g) was added and petroleum ether (80 mL) was added dropwise. The mixture was stirred for half an hour and filtered. The filtrate was concentrated to give the target compound (15 g, 90%) as a light yellow solid.

Step E: methyl (R)-2-(6-amino-4-(2-(furan-2-carbonyl)hydrazinyl)-1H-pyrazolo[3,4-d]pyrimidin-1-yl)-2-phenylpropanoate To a mixture of the product of Step D (114 g, 0.344 mol) and furan-2-carbohydrazide (65 g, 0.5166 mol) in DMSO (115 mL) was added DIPEA (88 g, 0.6888 mol). The resulting mixture was heated at 80° C. overnight under $N_2$. The mixture was cooled to rt and diluted with PE. The PE layer was discarded. The DMSO layer was slowly add to water (1.1 L) with vigorous stirring. A suspension was formed, filtered and washed with water. The solid was slurry with water (500 mL) at rt for 2 h, filtered and washed with water, dried in the oven over 3 days to give the target compound (125 g, 86%) as brown solid.

Step F: methyl (R)-2-(5-amino-2-(furan-2-yl)-7H-pyrazolo[4,3-e][1,2,4]triazolo[1,5-c]pyrimidin-7-yl)-2-phenylpropanoate To a mixture of BSA (204 g, 1.072 mol) and HMDS (161 g, 1.072 mol) was added the product of Step E (90.3 g, 0.2144 mol). The resulting mixture was heated at 115° C. for 5 hours. The mixture was cooled to rt and concentrated to dryness under reduced pressure. To the residue was added EtOH (200 mL) slowly at rt and the resulting mixture was heated at 75° C. for 1 hour. The suspension was cooled to rt, maintained at rt overnight with stirring, filtered and the cake was washed with PE, dried to give target compound (66 g, 76%) as an off-white solid.

Step G: (R)-2-(5-amino-2-(furan-2-yl)-7H-pyrazolo[4,3-e][1,2,4]triazolo[1,5-c]pyrimidin-7-yl)-2-phenylpropanoic acid To a mixture of the product of Step F (20.4 g, 50.62 mmol) in MeOH/THF (50 mL/150 mL) was added 4N NaOH (63 mL, 253 mmol). The resulting mixture was stirred at 30° C. (inner temperature 25~30° C.) overnight. The solvent was concentrated under reduced pressure (bath temperature 25~30° C.). To the residue were added water (150 mL) and 2N HCl until pH=~3. A suspension was formed, filtered and washed with water. The solid was collected and slurried from EtOAc (60 mL) to give a solid (10 g). The mother liquid was extracted with EtOAc. The organic layer was concentrated. The residue was slurried from EtOAc (20 mL) to give a solid (6.5 g). The filtrate was concentrated and the residue was slurry with EtOH to give the product (1.1 g). The three-batch solids were combined to yield the target compound (17.6 g, 89%) in total.

Example 30: 2-(5-amino-2-(furan-2-yl)-7H-pyrazolo[4,3-e][1,2,4]triazolo[1,5-c]pyrimidin-7-yl)-N-phenethyl-2-phenylpropanamide To a stirred solution of 2-(5-amino-2-(furan-2-yl)-7H-pyrazolo[4,3-e][1,2,4]triazolo[1,5-c]pyrimidin-7-yl)-2-phenylpropanoic acid (70 mg, 0.18 mmol), HATU (75 mg, 0.20 mmol) and DIEA (70 mg, 0.54 mmol) in THF (15 ml) was added 2-phenylethan-1-amine (22 mg, 0.18 mmol). The reaction mixture was stirred at rt for 15 h. After completion, the reaction mixture was diluted with EtOAc (30 ml) and then washed with H₂O (15 ml*2). The organic layer was dried over Na₂SO₄, filtered and then concentrated under reduced pressure to afford a residue. The residue was purified by prep-TLC with PE:EtOAc (1:2) to afford the product (53.6 mg, 61%). $^1$H NMR (400 MHz, DMSO-d6) δ 8.23 (s, 1H), 7.95 (s, 3H), 7.62 (t, J=4 Hz, 1H), 7.31-7.22 (m, 4H), 7.18-7.11 (m, 2H), 7.10-7.01 (m, 5H), 6.74 (dd, J=4 Hz, 2 Hz, 1H), 3.41-3.35 (m, 2H), 2.80-2.66 (m, 2H), 2.25 (s, 3H) ppm. MS: M/e 493 (M+1)⁺.

Example 31: 2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-phenylpropanamide To a stirred solution of 2-(5-amino-2-(furan-2-yl)-7H-pyrazolo[4,3-e][1,2,4]triazolo[1,5-c]pyrimidin-7-yl)-2-phenylpropanoic acid (70 mg, 0.18 mmol), HATU (75 mg, 0.20 mmol) and DIPEA (70 mg, 0.54 mmol) in THF (10 ml) was added 3-(aminomethyl)oxetan-3-ol (19 mg, 0.18 mmol). The reaction mixture was stirred at rt for 15 h. After completion, the reaction mixture was diluted with EtOAc (30 ml) and then washed with H₂O (15 ml×2). The organic layer was dried over Na₂SO₄, filtered and then concentrated under reduced pressure to afford a residue. The residue was purified by prep-TLC with PE:EtOAc (1:5) to the product (35.1 mg, 41%). $^1$H NMR (400 MHz, DMSO-d6) δ 8.26 (s, 1H), 7.95 (s, 3H), 7.45 (t, J=4 Hz, 1H), 7.32-7.10 (m, 6H), 6.74 (s, 1H), 5.69 (s, 1H), 4.39 (t, J=4 Hz, 2H), 4.26 (t, J=4 Hz, 2H), 3.44-3.40 (m, 2H), 2.33 (s, 3H) ppm. MS: M/e 475 (M+1)⁺.

Example 31A: (S)-2-(5-amino-2-(furan-2-yl)-7H-pyrazolo[4,3-e][1,2,4]triazolo[1,5-c]pyrimidin-7-yl)-N-((3-hydroxyoxetan-3-yl))methyl)-2-phenylpropanamide To a stirred solution of (S)-2-(5-amino-2-(furan-2-yl)-7H-pyrazolo[4,3-e][1,2,4]triazolo[1,5-c]pyrimidin-7-yl)-2-phenylpropanoic acid (100 mg, 0.26 mmol), HATU (108 mg, 0.28 mmol) and DIPEA (100 mg, 0.78 mmol) in THF (15 ml) was added 3-(aminomethyl)oxetan-3-ol (27 mg, 0.26 mmol). The reaction mixture was stirred at rt for 15 h. After completion, the reaction mixture was diluted with EtOAc (30 ml) and then washed with H₂O (15 ml×2). The organic layer was dried over Na₂SO₄, filtered and then concentrated under reduced pressure to afford a residue. The residue was purified by prep-TLC with PE:EtOAc (1:5) to afford the product (53.5 mg, 44%). $^1$H NMR (400 MHz, DMSO-d6) δ 8.26 (s, 1H), 7.96 (s, 3H), 7.46 (t, J=4 Hz, 1H), 7.37-7.12 (m, 6H), 6.75 (dd, J=8 Hz, 4 Hz, 1H), 5.70 (s, 1H), 4.40 (t, J=4 Hz, 2H), 4.26 (dd, J=8 Hz, 4 Hz, 2H), 3.42 (dd, J=8 Hz, 4 Hz, 2H), 2.33 (s, 3H) ppm. MS: M/e 475 (M+1)⁺.

Example 31B: (R)-2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-phenylpropanamide To a stirred solution of (R)-2-(5-amino-2-(furan-2-yl)-7H-pyrazolo[4,3-e][1,2,4]triazolo[1,5-c]pyrimidin-7-yl)-2-phenylpropanoic acid (100 mg, 0.26 mmol), HATU (108 mg, 0.28 mmol) and DIPEA (100 mg, 0.78 mmol) in THF (15 ml) was added 3-(aminomethyl)oxetan-3-ol (27 mg, 0.26 mmol). The reaction mixture was stirred at rt for 15 h. After completion, the reaction mixture was diluted with EtOAc (30 ml) and then washed with H₂O (15 ml×2). The organic layer was dried over Na₂SO₄, filtered and then concentrated under reduced pressure to afford a residue. The residue was purified by prep-TLC with PE:EtOAc (1:5) to afford the product (50.3 mg, 41%). $^1$H NMR (400 MHz, DMSO-d6) δ 8.26 (s, 1H), 7.96 (s, 3H), 7.50-7.41 (m, 1H), 7.37-7.10 (m, 6H), 6.74 (d, J=4 Hz, 1H), 5.70 (s, 1H), 4.50-4.35 (m, 2H), 4.32-4.19 (m, 2H), 3.50-3.39 (m, 2H), 2.33 (s, 3H) ppm. MS: M/e 475 (M+1)⁺.

Example 32: 2-(5-amino-2-(furan-2-yl)-7H-pyrazolo[4,3-e][1,2,4]triazolo[1,5-c]pyrimidin-7-yl)-N-methyl-2-phenylpropanamide To a stirred solution of 2-(5-amino-2-(furan-2-yl)-7H-pyrazolo[4,3-e][1,2,4]triazolo[1,5-c]pyrimidin-7-yl)-2-phenylpropanoic acid (70 mg, 0.18 mmol), HATU (75 mg, 0.20 mmol) and DIPEA (70 mg, 0.54 mmol) in THF (10 ml) was added methylamine hydrochloride (12 mg, 0.18 mmol). The reaction mixture was stirred at rt for 15 h. After completion, the reaction mixture was diluted with EtOAc (30 ml) and then washed with H₂O (15 ml×2). The organic layer was dried over Na₂SO₄, filtered and then concentrated under reduced pressure to afford a residue. The residue was purified by prep-TLC with PE:EtOAc (1:5) to afford the product (38.3 mg, 53%). $^1$H NMR (400 MHz, DMSO-d6) δ 8.21 (s, 1H), 7.98 (s, 2H), 7.95 (s, 1H), 7.50 (q, J=4 Hz, 1H), 7.34-7.23 (m, 4H), 7.14 (d, J=4 Hz, 2H), 6.74 (dd, J=4 Hz, 2 Hz, 1H), 2.64 (d, J=4 Hz, 3H), 2.30 (s, 3H) ppm. MS: M/e 403 (M+1)⁺.

Example 33: 2-(5-amino-2-(furan-2-yl)-7H-pyrazolo[4,3-e][1,2,4]triazolo[1,5-c]pyrimidin-7-yl)-(trans)-N-(4-hydroxy-4-methylcyclohexyl)-2-phenylpropanamide To a stirred solution of 2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), HATU (54 mg, 0.14 mmol) and DIPEA (50 mg, 0.39 mmol) in THF (10 ml) was added trans-4-amino-1-methylcyclohexan-1-ol (17 mg, 0.13 mmol). The reaction mixture was stirred at rt for 15 h. After completion, the reaction mixture was diluted with EtOAc (30 ml) and then washed with H₂O (15 ml×2). The organic layer was dried over Na₂SO₄, filtered and then concentrated under reduced pressure to afford a residue. The residue was purified by prep-TLC with PE:EtOAc (1:5) to afford the product (35.7 mg, 56%). $^1$H NMR (400 MHz, DMSO-d6) δ 8.24 (s, 1H), 8.00 (s, 2H), 7.95 (s, 1H), 7.38 (d, J=4 Hz, 1H), 7.32-7.24 (m, 4H), 7.14 (d, J=4 Hz, 2H), 6.74 (dd, J=8 Hz, 4 Hz, 1H), 4.19 (s, 1H), 3.75-3.65 (m, 1H), 2.25 (s, 3H), 1.75-1.66 (m, 1H), 1.64-1.54 (m, 1H), 1.40-1.29 (m, 6H), 0.99 (s, 3H) ppm. MS: M/e 501 (M+1)⁺.

Example 33A: (S)-2-(5-amino-2-(furan-2-yl)-7H-pyrazolo[4,3-e][1,2,4]triazolo[1,5-c]pyrimidin-7-yl)-(trans)-N-(4-hydroxy-4-methylcyclohexyl)-2-phenylpropanamide To a stirred solution of (S)-2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), HATU (54 mg, 0.14 mmol) and DIPEA (50 mg, 0.39 mmol) in TH F (15 ml) was added trans-4-amino-1-methylcyclohexan-1-ol (18 mg, 0.14 mmol). The reaction mixture was stirred at rt for 15 h. After completion, the reaction mixture was diluted with EtOAc (30 ml) and then washed with H₂O (15 ml×2). The organic layer was dried over Na₂SO₄, filtered and then concentrated under reduced pressure to afford a residue. The residue was purified by prep-TLC with PE:EtOAc (1:5) to afford the product (36.6 mg, 57%). $^1$H NMR (400 MHz, DMSO-d6) δ 8.24 (s, 1H), 8.00 (s, 2H), 7.95 (s, 1H), 7.37 (d, J=8 Hz, 1H), 7.33-7.24 (m, 4H), 7.14 (d, J=8 Hz, 2H), 6.80-6.70 (m, 1H), 4.20 (s, 1H), 3.79-3.55 (m, 1H), 2.25 (s, 3H), 1.75-1.66 (m, 1H), 1.64-1.56 (m, 1H), 1.40-1.29 (m, 6H), 0.99 (s, 3H) ppm. MS: M/e 501 (M+1)+.

Example 33B: (R)-2-(5-amino-2-(furan-2-yl)-7H-pyrazolo[4,3-e][1,2,4]triazolo[1,5-c]pyrimidin-7-yl)-(trans)-N-(4-hydroxy-4-methylcyclohexyl)-2-phenylpropanamide To a stirred solution of (R)-2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), HATU (54 mg, 0.14 mmol) and DIPEA (50 mg, 0.39 mmol) in THF (15 ml) was added trans-4-amino-1-methylcyclohexan-1-ol (18 mg, 0.14 mmol). The reaction mixture was stirred at rt for 15 h. After completion, the reaction mixture was diluted with EtOAc (30 ml) and then washed with H$_2$O (15 ml×2). The organic layer was dried over Na$_2$SO$_4$, filtered and then concentrated under reduced pressure to afford a residue. The residue was purified by prep-TLC with PE:EtOAc (1:5) to afford the product (40.4 mg, 63%). $^1$H NMR (400 MHz, DMSO-d6) δ 8.24 (s, 1H), 8.00 (s, 2H), 7.95 (s, 1H), 7.37 (d, J=8 Hz, 1H), 7.33-7.24 (m, 4H), 7.14 (d, J=8 Hz, 2H), 6.74 (dd, J=4 Hz, 2 Hz, 1H), 4.20 (s, 1H), 3.76-3.63 (m, 1H), 2.25 (s, 3H), 1.77-1.65 (m, 1H), 1.62-1.53 (m, 1H), 1.40-1.29 (m, 6H), 0.99 (s, 3H) ppm. MS: M/e 501 (M+1)+.

Example 34: 2-(5-amino-2-(furan-2-yl)-7H-pyrazolo[4,3-e][1,2,4]triazolo[1,5-c]pyrimidin-7-yl)-N,2-diphenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (30 mg, 0.077 mmol), aniline (7.2 mg, 0.077 mmol), HATU (35.3 mg, 0.092 mmol) and DIPEA (20 mg, 0.154 mmol) in DMF (3 mL) was stirred overnight. The reaction mixture was poured into H$_2$O (10 mL) and extracted with EtOAc (10 mL×3). The combined organic layers were washed with brine, dried over Na$_2$SO$_4$, concentrated and purified by prep-TLC (petroleum ether/EtOAc=1:2) to give the target compound (25 mg, 70%). $^1$H NMR (400 MHz, DMSO-d6) δ 9.77 (s, 1H), 8.29 (s, 1H), 8.04 (s, 2H), 7.95 (s, 1H), 7.58 (d, J=8.4 Hz, 2H), 7.38-7.22 (m, 6H), 7.13 (d, J=7.6 Hz, 2H), 7.05 (t, J=6.8 Hz, 1H), 6.79-6.70 (m, 1H), 2.47 (s, 3H) ppm. MS: M/e 465 (M+1)+.

Example 35: 2-(5-amino-2-(furan-2-yl)-7H-pyrazolo[4,3-e][1,2,4]triazolo[1,5-c]pyrimidin-7-yl)-N-benzyl-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (30 mg, 0.077 mmol), phenylmethanamine (8.2 mg, 0.077 mmol), HATU (35.3 mg, 0.092 mmol) and DIPEA (20 mg, 0.154 mmol) in DMF (3 mL) was stirred overnight. The reaction mixture was poured into H$_2$O (10 mL) and extracted with EtOAc (10 mL×3). The combined organic layers were washed with brine, dried over Na$_2$SO$_4$, concentrated and purified by prep-TLC (petroleum ether/EtOAc=1:2) to give the target compound (18 mg, 48.9%). $^1$H NMR (400 MHz, DMSO-d6) 8.23 (s, 1H), 8.09 (t, J=6.0 Hz, 1H), 8.02 (s, 2H), 7.95 (s, 1H), 7.34-7.14 (m, 11H), 6.75 (d, J=7.2 Hz, 1H), 4.34 (d, J=6.0 Hz, 2H), 2.37 (s, 3H) ppm. MS: M/e 479 (M+1)+.

Example 36: 2-(5-amino-2-(furan-2-yl)-7H-pyrazolo[4,3-e][1,2,4]triazolo[1,5-c]pyrimidin-7-yl)-N-(3-hydroxycyclopentyl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), 3-aminocyclopentan-1-ol hydrochloride (21 mg, 0.15 mmol), HATU (57 mg, 0.15 mmol) and DIPEA (34 mg, 0.26 mmol) in DMF (5 mL) was stirred at rt for 2 hrs. The solution was added with water (5 mL), extracted with ethyl acetate (10 mL) and washed with brine (10 mL). The organic layer was dried, concentrated and purified by preparative TLC (EtOAc) to get the desired product (23 mg, 38%). $^1$H NMR (400 MHz, DMSO-d6) δ 8.21 (d, J=12.0 Hz, 1H), 7.97 (br.s, 2H), 7.95 (s, 1H), 7.43-7.39 (m, 1H), 7.32-7.24 (m, 4H), 7.18-7.12 (m, 2H), 6.74 (d, J=4.0 Hz, 1H), 4.47 (d, J=4.0 Hz, 1H), 4.18 (br.s, 1H), 4.00 (s, 1H), 2.27 (s, 3H), 1.92-1.73 (m, 2H), 1.67-1.59 (m, 2H), 1.40-1.37 (m, 2H) ppm. MS: M/e 473 (M+1)+

Example 37: 2-(5-amino-2-(furan-2-yl)-7H-pyrazolo[4,3-e][1,2,4]triazolo[1,5-c]pyrimidin-7-yl)-N-(1-(hydroxymethyl)cyclopropyl)-2-phenylpropanamide To a mixture of 2-(5-amino-2-(furan-2-yl)-7H-pyrazolo[4,3-e][1,2,4]triazolo[1,5-c]pyrimidin-7-yl)-2-phenylpropanoic acid (40 mg, 0.1 mmol), (1-aminocyclopropyl)methanol hydrochloride (16 mg, 0.13 mmol), DIPEA (60 mg, 0.46 mmol) in DMF (1 mL) was added HATU (50 mg, 0.13 mmol) at rt and the mixture was stirred at rt for 3 hrs. The mixture was diluted with 15 mL of EtOAc, washed with brine (5 mL×3), dried over Na$_2$SO$_4$, concentrated and the resulted oil was purified by prep-TLC (EtOAc: 100%) to give the title product (28.0 mg, yield: 61%) after lyophilization. $^1$H NMR (400 MHz, DMSO-d6) δ 8.22 (s, 1H), 8.10-7.82 (m, 3H), 7.75 (s, 1H), 7.35-7.19 (m, 4H), 7.11 (d, J=8.0 Hz, 2H), 6.79-6.69 (m, 1H), 4.55 (t, J=5.6 Hz, 1H), 3.59 (dd, J=11.2, 6.0 Hz, 1H), 3.41 (dd, J=11.2, 5.6 Hz, 1H), 2.25 (s, 3H), 0.73-0.50 (m, 4H). MS: M/e 459 (M+1)+.

Example 38: 2-(5-amino-2-(furan-2-yl)-7H-pyrazolo[4,3-e][1,2,4]triazolo[1,5-c]pyrimidin-7-yl)-N—((R)-2-hydroxypropyl)-2-phenylpropanamide To a mixture of 2-(5-amino-2-(furan-2-yl)-7H-pyrazolo[4,3-e][1,2,4]triazolo[1,5-c]pyrimidin-7-yl)-2-phenylpropanoic acid (40 mg, 0.1 mmol), (R)-1-aminopropan-2-ol (20 mg, 0.26 mmol), DIPEA (60 mg, 0.46 mmol) in DMF (1 mL) was added HATU (50 mg, 0.13 mmol) at rt and the mixture was stirred at rt for 3 hrs. The mixture was treated with 15 mL of EtOAc and 5 mL of brine. The aqueous layer was extracted with EtOAc (5 mL×3). The combined organics were washed with brine (5 mL×5), dried over Na$_2$SO$_4$, concentrated and purified by prep-TLC (EtOAc: 100%) to give the title product (12.0 mg, yield: 27%) after lyophilization. $^1$H NMR (400 MHz, DMSO-d6) δ 8.24 (d, J=6.4 Hz, 1H), 8.07-7.85 (m, 3H), 7.45-7.21 (m, 5H), 7.14 (dd, J=13.2, 7.6 Hz, 2H), 6.74 (s, 1H), 4.55 (dd, J=11.2, 4.8 Hz, 1H), 3.78-3.61 (m, 1H), 3.14-3.04 (m, 2H), 2.32 (s, 3H), 0.94 (d, J=6.0 Hz, 3H). MS: M/e 447 (M+1)+.

Example 39: 2-(5-amino-2-(furan-2-yl)-7H-pyrazolo[4,3-e][1,2,4]triazolo[1,5-c]pyrimidin-7-yl)-N-(2-methoxyethyl)-2-phenylpropanamide A mixture of 2-methoxyethan-1-amine (11.6 mg, 0.15 mmol), 2-(5-amino-2-(furan-2-yl)-7H-pyrazolo[4,3-e][1,2,4]triazolo[1,5-c]pyrimidin-7-yl)-2-phenylpropanoic acid (40 mg, 0.1 mmol), HATU (43 mg, 0.11 mmol) and DIPEA (0.2 mL) in DMF (2 mL) was stirred at RT overnight. The reaction mixture was poured into water (20 mL) and extracted with EtOAc (15 mL×3). The combined organic layers were washed with brine, dried over Na$_2$SO$_4$ and concentrated under reduced pressure. The residue was purified by prep-TLC (EtOAc: 100%) to afford the title compound (10 mg, yield: 21.8%). $^1$H NMR (400 MHz, DMSO-d6) δ 8.24 (s, 1H), 7.99 (br.s, 2H), 7.96 (s, 1H), 7.66-7.55 (m, 1H), 7.35-7.22 (m, 4H), 7.20-7.08 (m, 2H), 6.78-6.64 (m, 1H), 3.34-3.22 (m, 4H), 3.16 (s, 3H), 2.30 (s, 3H) ppm. MS: M/e 447 (M+1)⁺.

Example 40: 2-(5-amino-2-(furan-2-yl)-7H-pyrazolo[4,3-e][1,2,4]triazolo[1,5-c]pyrimidin-7-yl)-N-cyclopropyl-2-phenylpropanamide To a mixture of 2-(5-amino-2-(furan-2-yl)-7H-pyrazolo[4,3-e][1,2,4]triazolo[1,5-c]pyrimidin-7-yl)-2-phenylpropanoic acid (40 mg, 0.1 mmol), (1-aminocyclopropyl)methanol hydrochloride (10 mg, 0.17 mmol), DIPEA (55 mg, 0.42 mmol) in DMF (1 mL) was added HATU (46 mg, 0.12 mmol) at rt and the mixture was stirred at rt for 16 hrs. The mixture was diluted with 10 mL of EtOAc, washed with brine (5 mL×3), dried over Na₂SO₄, concentrated and the resulted oil was purified by prep-TLC (EtOAc: 100%) to give the title product (18.0 mg, yield: 42%) after lyophilization. ¹H NMR (400 MHz, DMSO-d6) δ 8.21 (s, 1H), 8.11-7.87 (m, 3H), 7.77 (d, J=3.6 Hz, 1H), 7.34-7.21 (m, 4H), 7.12 (d, J=8.0 Hz, 2H), 6.77-6.70 (m, 1H), 2.70-2.62 (m, 1H), 2.27 (s, 3H), 0.60-0.39 (m, 4H). MS: M/e 429 (M+1)⁺.

Example 41: 2-(5-amino-2-(furan-2-yl)-7H-pyrazolo[4,3-e][1,2,4]triazolo[1,5-c]pyrimidin-7-yl)-N-(2-morpholinoethyl)-2-phenylpropanamide To a stirred solution of 2-(5-amino-2-(furan-2-yl)-7H-pyrazolo[4,3-e][1,2,4]triazolo[1,5-c]pyrimidin-7-yl)-2-phenylpropanoic acid (80 mg, 0.21 mmol), HATU (86 mg, 0.23 mmol) and DIPEA (80 mg, 0.62 mmol) in THF (15 ml) was added 2-morpholinoethan-1-amine (27 mg, 0.21 mmol). The reaction mixture was stirred at rt for 15 h. After completion, the reaction mixture was diluted with EtOAc (30 ml) and then washed with H₂O (15 ml×2). The organic layer was dried over Na₂SO₄, filtered and then concentrated under reduced pressure to afford a residue. The residue was purified by prep-TLC with DCM:MeOH (5:1) to afford the product (16.2 mg, 16%). ¹H NMR (400 MHz, DMSO-d6) δ 8.32 (s, 1H), 8.06 (s, 2H), 7.99-7.94 (m, 2H), 7.42-7.23 (m, 5H), 7.09-7.00 (m, 2H), 6.80-6.71 (m, 1H), 4.00-3.94 (m, 2H), 3.69-3.51 (m, 8H), 3.15-3.00 (m, 4H), 2.27 (s, 3H) ppm. MS: M/e 502 (M+1)⁺.

Example 42: 2-(5-amino-2-(furan-2-yl)-7H-pyrazolo[4,3-e][1,2,4]triazolo[1,5-c]pyrimidin-7-yl)-N-(benzo[d][1,3]dioxol-5-ylmethyl)-2-phenylpropanamide To a stirred solution of 2-(5-amino-2-(furan-2-yl)-7H-pyrazolo[4,3-e][1,2,4]triazolo[1,5-c]pyrimidin-7-yl)-2-phenylpropanoic acid (100 mg, 0.26 mmol), HATU (108 mg, 0.28 mmol) and DIPEA (100 mg, 0.78 mmol) in THF (15 ml) was added benzo[d][1,3]dioxol-5-ylmethanamine (43 mg, 0.28 mmol). The reaction mixture was stirred at rt for 15 h. After completion, the reaction mixture was diluted with EtOAc (30 ml) and then washed with H₂O (15 ml×2). The organic layer was dried over Na₂SO₄, filtered and then concentrated under reduced pressure to afford a residue. The residue was purified by prep-TLC with PE:EtOAc (1:1) to afford the product (23.2 mg, 17%). ¹H NMR (400 MHz, DMSO-d6) δ 8.23 (s, 1H), 8.05 (t, J=8 Hz, 1H), 7.98 (s, 2H), 7.95 (s, 1H), 7.32-7.24 (m, 4H), 7.21-7.17 (m, 2H), 6.80 (d, J=8 Hz, 1H), 6.79-6.71 (m, 3H), 5.94 (s, 2H), 4.31-4.12 (m, 2H), 2.35 (s, 3H) ppm. MS: M/e 523 (M+1)⁺.

Example 43: 2-(5-amino-2-(furan-2-yl)-7H-pyrazolo[4,3-e][1,2,4]triazolo[1,5-c]pyrimidin-7-yl)-N-cyclohexyl-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (30 mg, 0.077 mmol), cyclohexanamine (7.6 mg, 0.077 mmol), HATU (35.3 mg, 0.092 mmol) and DIPEA (20 mg, 0.154 mmol) in DMF (3 mL) was stirred overnight. The reaction mixture was poured into H₂O (10 mL) and extracted with EtOAc (10 mL×3). The combined organic layers were washed with brine, dried over Na₂SO₄, concentrated and purified by prep-TLC (petroleum ether/EtOAc=1:2) to give the target compound (19 mg, 52.4%). ¹H NMR (400 MHz, DMSO-d6) δ 8.23 (s, 1H), 7.98 (s, 2H), 7.95 (s, 1H), 7.48 (d, J=8.0 Hz, 1H), 7.35-7.21 (m, 4H), 7.14 (d, J=6.8 Hz, 2H), 6.74 (m, 1H), 4.10 (s, 1H), 3.64 (m, 1H), 2.26 (s, 3H), 1.79 (d, J=11.2 Hz, 1H), 1.61 (s, 5H), 1.20-1.09 (m, 5H) ppm. MS: M/e 471 (M+1)⁺.

Example 44: 2-(5-amino-2-(furan-2-yl)-7H-pyrazolo[4,3-e][1,2,4]triazolo[1,5-c]pyrimidin-7-yl)-N-(2-(4-(4-(2-methoxyethoxy)phenyl)piperazin-1-yl)ethyl)-2-phenylpropanamide

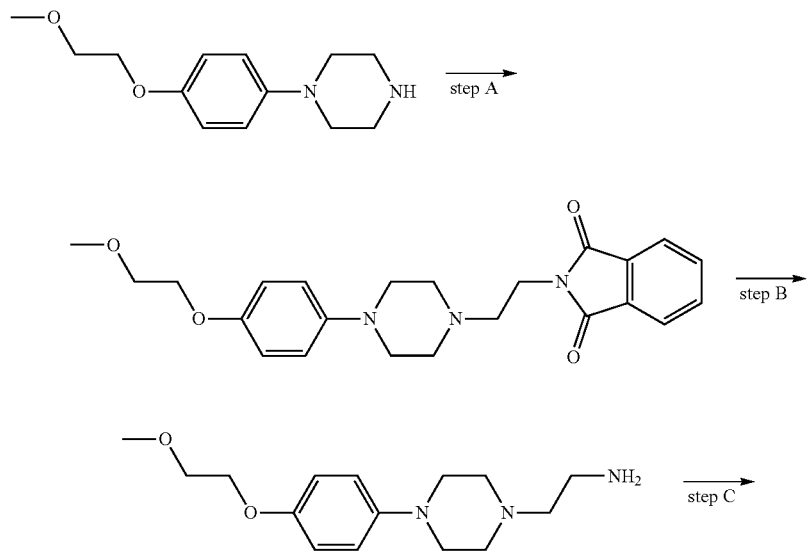

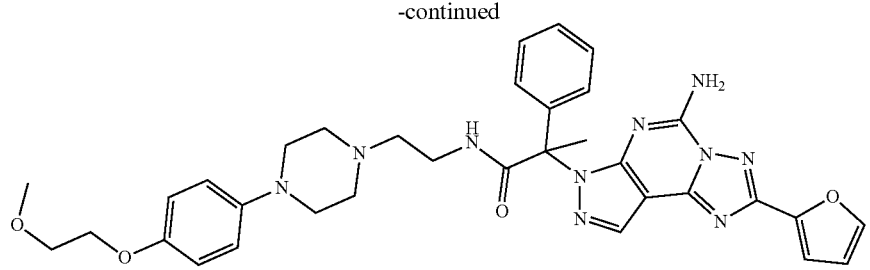

Step A: 2-(2-(4-(4-(2-methoxyethoxy)phenyl)piperazin-1-yl)ethyl)isoindoline-1,3-dione A mixture of 1-(4-(2-methoxyethoxy)phenyl)piperazine (1 g, 4.24 mmol), 2-(2-bromoethyl)isoindoline-1,3-dione (1.08 g, 4.24 mmol) and K$_2$CO$_3$ (1.17 g, 8.48 mmol) in DMF (20 mL) was stirred at 60° C. overnight. The reaction mixture was poured into H$_2$O (50 mL) and filtered. The cake was collected, dried to give the target compound (800 mg, 46.1%) as a white solid. MS: M/e 410 (M+1)$^+$.

Step B: 2-(4-(4-(2-methoxyethoxy)phenyl)piperazin-1-yl)ethan-1-amine

To a stirred solution of the product of Step A (800 mg, 1.96 mmol) in EtOH (20 mL) was added N$_2$H$_4$.H$_2$O (196 mg, 3.91 mmol). After addition, the reaction was stirred at 80° C. overnight. The reaction was concentrated to give the residue, which was washed with EtOAc (40 mL) and filtered. The filtrate was concentrated to give the target compound (490 mg, 89.6%) as a white syrup. MS: M/e 280 (M+1)$^+$.

Step C: 2-(5-amino-2-(furan-2-yl)-7H-pyrazolo[4,3-e][1,2,4]triazolo[1,5-c]pyrimidin-7-yl)-N-(2-(4-(4-(2-methoxyethoxy)phenyl)piperazin-1-yl)ethyl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (38.9 mg, 0.1 mmol), the product of Step B (28 mg, 0.1 mmol), HATU (46 mg, 0.12 mmol) and DIPEA (25.8 mg, 0.2 mmol) in DMF (3 mL) was stirred overnight. The reaction mixture was poured into H$_2$O (15 mL) and extracted with EtOAc (10 mL×3). The combined organic layers were washed with brine, dried over Na$_2$SO$_4$, concentrated and purified by prep-TLC (petroleum ether/EtOAc=1:2) to give the target compound, which was further purified by washed with EtOH and filtered. The cake was collected, dried to give the target compound (15 mg, 23%). $^1$H NMR (400 MHz. DMSO-d6) δ 8.25 (s, 1H), 8.05 (s, 1H), 8.00-7.96 (m, 1H), 7.34-7.15 (m, 7H), 6.78-6.73 (m, 1H), 6.69-6.62 (m, 4H), 3.96-3.92 (m, 2H), 3.64-3.57 (m, 2H), 3.31-3.24 (m, 2H), 3.29 (s, 3H) 2.72-2.58 (m, 4H), 2.43-2.31 (m, 6H), 2.29 (s, 3H) ppm. MS: M/e 651 (M+1)$^+$.

Example 45: 2-(5-amino-2-(furan-2-yl)-7H-pyrazolo[4,3-e][1,2,4]triazolo[1,5-c]pyrimidin-7-yl)-2-phenyl-N-(2-(piperazin-1-yl)ethyl)propanamide

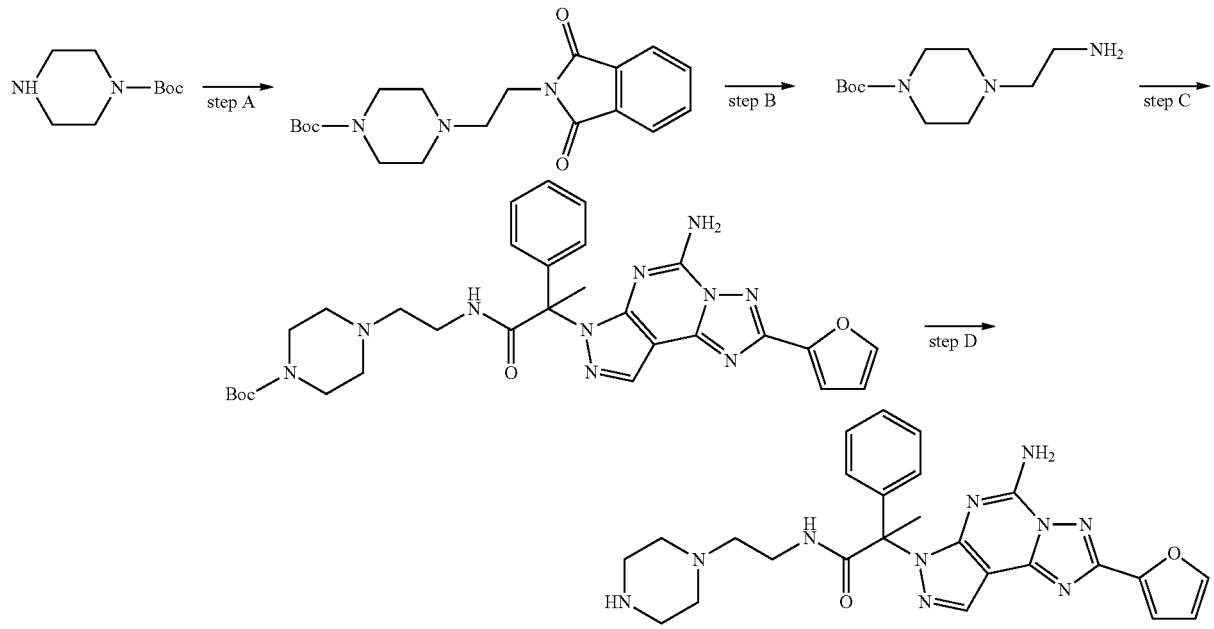

Step A: tert-butyl 4-(2-(1,3-dioxoisoindolin-2-yl)ethyl)piperazine-1-carboxylate A mixture of tert-butyl piperazine-1-carboxylate (1 g, 5.38 mmol), 2-(2-bromoethyl)isoindoline-1,3-dione (1.36 g, 5.38 mmol) and K$_2$CO$_3$ (1.48 g, 10.76 mmol) in DMF (20 mL) was stirred at 60° C. overnight. The reaction mixture was poured into H$_2$O (50 mL) and filtered. The cake was collected, dried to give the target compound (700 mg, 36.2%) as a white solid. MS: M/e 360 (M+1)$^+$.

Step B: tert-butyl 4-(2-aminoethyl)piperazine-1-carboxylate

To a stirred solution of the product of Step A (700 mg, 1.95 mmol) in EtOH (20 mL) was added N$_2$H$_4$.H$_2$O (195 mg, 3.9 mmol). After addition, the reaction was stirred at 80° C. overnight. The reaction was concentrated to give the residue, which was washed with EtOAc (40 mL) and filtered. The filtrate was concentrated to give the target compound (460 mg, 100%) as colorless syrup. MS: M/e 230 (M+1)$^+$.

Step B: tert-butyl 4-(2-(2-(5-amino-2-(furan-2-yl)-7H-pyrazolo[4,3-e][1,2,4]triazolo[1,5-c]pyrimidin-7-yl)-2-phenylpropanamido)ethyl)piperazine-1-carboxylate A mixture of 2-(5-amino-2-(furan-2-yl)-7H-pyrazolo[4,3-e][1,2,4]triazolo[1,5-c]pyrimidin-7-yl)-2-phenylpropanoic acid (60 mg, 0.154 mmol), the product of Step B (35.3 mg, 0.154 mmol), HATU (70.6 mg, 0.18 mmol) and DIPEA (40 mg, 0.308 mmol) in DMF (3 mL) was stirred overnight. The reaction mixture was poured into H$_2$O (15 mL) and extracted with EtOAc (10 mL×3). The combined organic layers were washed with brine, dried over Na$_2$SO$_4$, concentrated and purified by prep-TLC (petroleum ether/EtOAc=1:2) to give the target compound (34 mg, 36.8%) as a white solid. MS: M/e 601 (M+1)$^+$.

Step D: 2-(5-amino-2-(furan-2-yl)-7H-pyrazolo[4,3-e][1,2,4]triazolo[1,5-c]pyrimidin-7-yl)-2-phenyl-N-(2-(piperazin-1-yl)ethyl)propanamide To a stirred solution of the product of Step C (34 mg, 0.057 mmol) in EtOAc (3 mL) was added EtOAc/HCl (g) (4.0 M, 3 mL). After addition, the reaction was stirred overnight. The reaction mixture was concentrated to ~3 mL and filtered. The cake was collected, dried to give the target product (28 mg, 52.2%). $^1$H NMR (400 MHz, DMSO-d6) δ 11.83 (s, 1H), 9.55 (s, 2H), 8.30 (s, 1H), 8.04 (s, 1H), 7.96 (s, 2H), 7.27 (dd, J=8.4, 5.1 Hz, 4H), 7.15-7.05 (m, 2H), 6.75 (dd, J=3.1, 1.6 Hz, 1H), 3.44 (dd, J=39.8, 33.2 Hz, 13H), 2.29 (s, 3H) ppm. MS: M/e 501 (M+1)$^+$.

Example 46: 2-(5-amino-2-(furan-2-yl)-7H-pyrazolo[4,3-e][1,2,4]triazolo[1,5-c]pyrimidin-7-yl)-N-(1-(4-(2-methoxyethoxy)phenyl)piperidin-4-yl)-2-phenyl-propanamide

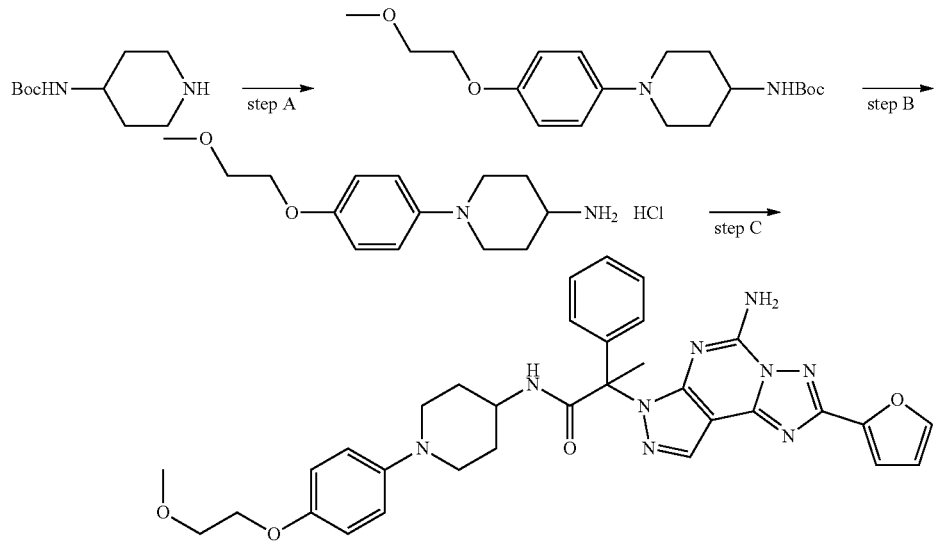

Step A: tert-butyl(1-(4-(2-methoxyethoxy)phenyl)piperidin-4-yl)carbamate

A mixture of tert-butyl piperidin-4-ylcarbamate (2.3 g, 10 mmol), 1-bromo-4-(2-methoxyethoxy)benzene (2 g, 10 mmol), Pd$_2$(dba)$_3$ (0.905 g, 1 mmol), X-phos (0.952 g, 2 mmol) and Cs$_2$CO$_3$ (6.52 g, 20 mmol) in toluene (30 mL) was stirred at 120° C. for 3 hours under N$_2$. The reaction was concentrated to give the residue, which was treated with EtOAc/H$_2$O (50 mL/20 mL). The organic layer was separated, washed with brine, dried over Na$_2$SO$_4$, concentrated and purified by column chromatography (petroleum ether/EtOAc=8:1~3:1) to give the target compound (0.9 g, 25.8%) as yellow oil. MS: M/e 351 (M+1)$^+$.

Step B: 1-(4-(2-methoxyethoxy)phenyl)piperidin-4-amine hydrochloride

To a stirred solution of the product of Step A (0.9 g, 2.57 mmol) in CH$_2$Cl$_2$ (10 mL) was added EtOAc/HCl(g) (4.0 M, 4 mL). After addition, the reaction was stirred overnight. The reaction was concentrated to ~5 mL and filtered. The cake was collected, dried to give the target compound (680 mg, 92.4%) as a white solid. MS: M/e 251 (M+1)$^+$.

Step C: 2-(5-amino-2-(furan-2-yl)-7H-pyrazolo[4,3-e][1,2,4]triazolo[1,5-c]pyrimidin-7-yl)-N-(1-(4-(2-methoxyethoxy)phenyl)piperidin-4-yl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (38.9 mg, 0.1 mmol), the product of Step B (28.6 mg, 0.1 mmol), HATU (46 mg, 0.12 mmol) and DIPEA (25.8 mg, 0.2 mmol) in DMF (3 mL) was stirred overnight. The reaction mixture was poured into H$_2$O (15 mL) and extracted with EtOAc (10 mL×3). The combined organic layers were washed with brine, dried over Na$_2$SO$_4$, concentrated and purified by prep-TLC (petroleum ether/EtOAc=1:2) to give the target compound (27 mg, 43.4%). $^1$H NMR (400 MHz, DMSO-d6) δ 8.23 (s, 1H), 8.01 (s, 1H), 7.95 (s, 1H), 7.62 (d, J=7.6 Hz, 1H), 7.35-7.23 (m, 4H), 7.21-7.13 (m, 2H), 6.87-6.71 (m, 5H), 4.00-3.92 (m, 2H), 3.88-3.75 (m, 1H), 3.62-3.57 (m, 2H), 3.46-3.35 (m, 2H), 3.28 (s, 3H), 2.71-2.58 (m, 2H), 2.27 (s, 3H), 1.91-1.69 (m, 2H), 1.61-1.45 (m, 2H) ppm. MS: M/e 622 (M+1)$^+$.

Example 47: 2-(5-amino-2-(furan-2-yl)-7H-pyrazolo[4,3-e][1,2,4]triazolo[1,5-c]pyrimidin-7-yl)-N-((1S,2R)-2-hydroxycyclopentyl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (38.9 mg, 0.1 mmol), (1R,2S)-2-aminocyclopentan-1-ol hydrochloride (13.7 mg, 0.1 mmol), HATU (45 mg, 0.12 mmol) and DIPEA (25.8 mg, 0.2 mmol) in DMF (3 mL) was stirred overnight. The reaction mixture was poured into H$_2$O (10 mL) and extracted with EtOAc (10 mL×3). The combined organic layers were washed with brine, dried over Na$_2$SO$_4$, concentrated and purified by prep-TLC (petroleum ether/EtOAc=1:2) to give the target compound (27 mg, 57%). $^1$H NMR (400 MHz, DMSO-d6) δ 8.28-8.25 (m, 1H), 7.98 (s, 2H), 7.96 (s, 1H), 7.38-7.22 (m, 4H), 7.19-7.07 (m, 2H), 6.95-6.81 (m, 1H), 6.79-6.70 (m, 1H), 4.66-4.56 (m, 1H), 4.00-3.79 (m, 2H), 2.34 (d, J=10.4 Hz, 3H), 1.89 (m, 1H), 1.78-1.54 (m, 3H), 1.31-1.21 (m, 2H) ppm. MS: M/e 473 (M+1)$^+$.

Example 48: 2-(5-amino-2-(furan-2-yl)-7H-pyrazolo[4,3-e][1,2,4]triazolo[1,5-c]pyrimidin-7-yl)-N-((1R,2S)-2-hydroxycyclopentyl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (38.9 mg, 0.1 mmol), (1S,2R)-2-aminocyclopentan-1-ol hydrochloride (13.7 mg, 0.1 mmol), HATU (45 mg, 0.12 mmol) and DIPEA (25.8 mg, 0.2 mmol) in DMF (3 mL) was stirred overnight. The reaction mixture was poured into H$_2$O (10 mL) and extracted with EtOAc (10 mL×3). The combined organic layers were washed with brine, dried over Na$_2$SO$_4$, concentrated and purified by prep-TLC (EtOAc) to give the target compound (31 mg, 65%). $^1$H NMR (400 MHz, DMSO-d6) δ 8.28-8.25 (m, 1H), 7.98 (s, 2H), 7.96 (s, 1H), 7.38-7.22 (m, 4H), 7.19-7.07 (m, 2H), 6.95-6.81 (m, 1H), 6.79-6.70 (m, 1H), 4.66-4.56 (m, 1H), 4.00-3.79 (m, 2H), 2.34 (d, J=10.4 Hz, 3H), 1.89 (m, 1H), 1.78-1.54 (m, 3H), 1.31-1.21 (m, 2H) ppm. MS: M/e 473 (M+1)$^+$.

Example 48A: (S)-2-(5-amino-2-(furan-2-yl)-7H-pyrazolo[4,3-e][1,2,4]triazolo[1,5-c]pyrimidin-7-yl)-N-((1R,2S)-2-hydroxycyclopentyl)-2-phenylpropanamide A mixture of(S)-2-(5-amino-2-(furan-2-yl)-7H-pyrazolo[4,3-e][1,2,4]triazolo[1,5-c]pyrimidin-7-yl)-2-phenylpropanoic acid (100 mg, 0.26 mmol), (1S,2R)-2-aminocyclopentan-1-ol hydrochloride (35.3 mg, 0.26 mmol), HATU (120 mg, 0.31 mmol) and DIPEA (67 mg, 0.52 mmol) in DMF (4 mL) was stirred overnight. The reaction mixture was poured into H$_2$O (10 mL) and extracted with EtOAc (10 mL×3). The combined organic layers were washed with brine, dried over Na$_2$SO$_4$, concentrated and purified by prep-TLC (EtOAc) to give the target compound (53 mg, 52.4%). $^1$H NMR (400 MHz, DMSO-d6) δ 8.28-8.25 (m, 1H), 7.98 (s, 2H), 7.96 (s, 1H), 7.38-7.22 (m, 4H), 7.19-7.07 (m, 2H), 6.95-6.81 (m, 1H), 6.79-6.70 (m, 1H), 4.66-4.56 (m, 1H), 4.00-3.79 (m, 2H), 2.34 (d, J=10.4 Hz, 3H), 1.89 (m, 1H), 1.78-1.54 (m, 3H), 1.31-1.21 (m, 2H) ppm. MS: M/e 473 (M+1)$^+$.

Example 48B: (R)-2-(5-amino-2-(furan-2-yl)-7H-pyrazolo[4,3-e][1,2,4]triazolo[1,5-c]pyrimidin-7-yl)-N-((1R,2S)-2-hydroxycyclopentyl)-2-phenylpropanamide A mixture of (R)-2-(5-amino-2-(furan-2-yl)-7H-pyrazolo[4,3-e][1,2,4]triazolo[1,5-c]pyrimidin-7-yl)-2-phenylpropanoic acid (100 mg, 0.26 mmol), (1S,2R)-2-aminocyclopentan-1-ol hydrochloride (35.3 mg, 0.26 mmol), HATU (120 mg, 0.31 mmol) and DIPEA (67 mg, 0.52 mmol) in DMF (4 mL) was stirred overnight. The reaction mixture was poured into H$_2$O (10 mL) and extracted with EtOAc (10 mL×3). The combined organic layers were washed with brine, dried over Na$_2$SO$_4$, concentrated and purified by prep-TLC (EtOAc) to give the target compound (50 mg, 52.4%). $^1$H NMR (400 MHz, DMSO-d6) δ 8.28-8.25 (m, 1H), 7.98 (s, 2H), 7.96 (s, 1H), 7.38-7.22 (m, 4H), 7.19-7.07 (m, 2H), 6.95-6.81 (m, 1H), 6.79-6.70 (m, 1H), 4.66-4.56 (m, 1H), 4.00-3.79 (m, 2H), 2.34 (d, J=10.4 Hz, 3H), 1.89 (m, 1H), 1.78-1.54 (m, 3H), 1.31-1.21 (m, 2H) ppm. MS: M/e 473 (M+1)$^+$.

Example 49: 2-(5-amino-2-(furan-2-yl)-7H-pyrazolo[4,3-e][1,2,4]triazolo[1,5-c]pyrimidin-7-yl)-2-phenyl-N-((tetrahydrofuran-2-yl)methyl)propanamide A mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.12 mmol), tetrahydrofuran-2-ylmethanamine (16 mg, 0.15 mmol), HATU (57 mg, 0.15 mmol) and DIPEA (31 mg, 0.24 mmol) in DMF (5 mL) was stirred at rt for 2 hrs. The solution was added with water (10 mL), extracted with ethyl acetate (10 mL) and washed with brine (10 mL). The organic layer was dried, concentrated and purified by preparative TLC (EtOAc) to get the desired product (20 mg, 33%). $^1$H NMR (400 MHz, DMSO-d6) δ 8.25 (d, J=8.0 Hz, 1H), 7.94 (br.s, 2H), 7.96 (s, 1H), 7.47-7.43 (m, 1H), 7.31-7.25 (m, 4H), 7.18-7.12 (m, 2H), 6.74 (d, J=4.0 Hz, 1H), 3.92-3.87 (m, 1H), 3.63-3.47 (m, 2H), 3.28-3.08 (m, 2H), 2.31 (s, 3H), 1.81-1.61 (m, 3H), 1.49-1.40 (m, 1H)) ppm. MS: M/e 473 (M+1)$^+$ Example 50: 2-(5-amino-2-(furan-2-yl)-7H-pyrazolo[4,3-e][1,2,4]triazolo[1,5-c]pyrimidin-7-yl)-2-phenyl-N—(((R)-tetrahydrofuran-2-yl)methyl)propanamide A mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.12 mmol), (R)-(tetrahydrofuran-2-yl)methanamine (16 mg, 0.15 mmol), HATU (57 mg, 0.15 mmol) and DIPEA (31 mg, 0.24 mmol) in DMF (5 mL) was stirred at rt for 2 hrs. The solution was added with water (10 mL), extracted with ethyl acetate (10 mL) and washed with brine (10 mL). The organic layer was dried, concentrated and purified by preparative TLC (EtOAc) to get the desired product (20 mg, 33%). $^1$H NMR (400 MHz, DMSO-d6) δ 8.25 (d, J=8.0 Hz, 1H), 7.94 (br.s, 2H), 7.96 (s, 1H), 7.47-7.43 (m, 1H), 7.31-7.25 (m, 4H), 7.19-7.12 (m, 2H), 6.74 (s, 1H), 3.92-3.87 (m, 1H), 3.63-3.47 (m, 2H), 3.27-3.07 (m, 2H), 2.31 (s, 3H), 1.79-1.63 (m, 3H), 1.49-1.40 (m, 1H) ppm. MS: M/e 473 (M+1)$^+$

Example 51: 2-(5-amino-2-(furan-2-yl)-7H-pyrazolo[4,3-e][1,2,4]triazolo[1,5-c]pyrimidin-7-yl)-2-phenyl-N—(((S)-tetrahydrofuran-2-yl)methyl)propanamide A mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.12 mmol), (S)-(tetrahydrofuran-2-yl)methanamine (16 mg, 0.15 mmol), HATU (57 mg, 0.15 mmol) and DIPEA (31 mg, 0.24 mmol) in DMF (5 mL) was stirred at rt for 2 hrs. The solution was added with water (10 mL), extracted with ethyl acetate (10 mL) and washed with brine (10 mL). The organic layer was dried, concentrated and purified by preparative TLC (EtOAc) to get the desired product (26 mg, 43%). $^1$H NMR (400 MHz, DMSO-d6) δ 8.25 (d, J=8.0 Hz, 1H), 7.94 (br.s, 2H), 7.95 (s, 1H), 7.47-7.43 (m, 1H), 7.31-7.25 (m, 4H), 7.18-7.12 (m, 2H), 6.74 (d, J=4.0 Hz, 1H), 3.92-3.87 (m, 1H), 3.63-3.47 (m, 2H), 3.28-3.08 (m, 2H), 2.31 (s, 3H), 1.81-1.61 (m, 3H), 1.49-1.40 (m, 1H)) ppm. MS: M/e 473 (M+1)$^+$

Example 52: 2-(5-amino-2-(furan-2-yl)-7H-pyrazolo[4,3-e][1,2,4]triazolo[1,5-c]pyrimidin-7-yl)-(trans)-N-(4-hydroxycyclohexyl)-2-phenylpropanamide To a stirred solution of 2-(5-amino-2-(furan-2-yl)-7H-pyrazolo[4,3-e][1,2,4]triazolo[1,5-c]pyrimidin-7-yl)-2-phenylpropanoic acid (100 mg, 0.26 mmol), HATU (108 mg, 0.28 mmol) and DIPEA (100 mg, 0.78 mmol) in THF (15 ml) was added trans-4-aminocyclohexan-1-ol (33 mg, 0.28 mmol). The reaction mixture was stirred at rt for 15 h. After completion, the reaction mixture was diluted with EtOAc (30 ml) and then washed with H$_2$O (15 ml×2). The organic layer was dried over Na$_2$SO$_4$, filtered and then concentrated under reduced pressure to afford a residue. The residue was purified by prep-TLC with PE:EtOAc (1:5) to afford the product (71.0 mg, 57%). $^1$H NMR (400 MHz, DMSO-d6) δ 8.22 (s, 1H), 7.96 (s, 2H), 7.95 (s, 1H), 7.48 (d, J=8 Hz, 1H), 7.31-7.22 (m, 4H), 7.14 (d, J=8 Hz, 2H), 6.74 (dd, J=4 Hz, 2 Hz, 1H), 3.62-3.56 (m, 1H), 3.30-3.28 (m, 1H), 3.17 (s, 1H), 2.24 (s, 3H), 1.82-1.65 (m, 4H), 1.24-1.11 (m, 4H) ppm. MS: M/e 487 (M+1)$^+$.

Example 52B: (R)-2-(5-amino-2-(furan-2-yl)-7H-pyrazolo[4,3-e][1,2,4]triazolo[1,5-c]pyrimidin-7-yl)-N-((trans)-4-hydroxycyclohexyl)-2-phenylpropanamide To a mixture of (R)-2-(5-amino-2-(furan-2-yl)-7H-pyrazolo[4,3-e][1,2,4]triazolo[1,5-c]pyrimidin-7-yl)-2-phenylpropanoic acid (6.0 g, 15.4 mmol), (trans)-4-aminocyclohexan-1-ol hydrochloride (2.7 g, 17.9 mmol), DIPEA (7.9 g, 61.2 mmol) in THF (60 mL) was added HATU (6.4 g, 16.8 mmol) at rt and the mixture was stirred at rt for 16 hrs. The reaction mixture was filtered and the filtrate was added 50 mL of aq. NaHCO$_3$, stirred for 10 min and extracted with EtOAc (50 mL×2). The combined extract was washed with brine (50 mL×2), dried over Na$_2$SO$_4$ and concentrated. The resulted residue was purified by column chromatography to give 6.8 g of crude product, which was recrystallized in Heptane/Acetone (3:7, 100 mL). The suspension was filtered, washed with Heptane/Acetone (1:1, 20 mL), dried under high vacuum for 2 hrs to give the title product (4.5 g, yield: 60%). $^1$H NMR (400 MHz, DMSO-d6) δ 8.22 (s, 1H), 8.13-7.82 (m, 3H), 7.48 (d, J=8.0 Hz, 1H), 7.33-7.22 (m, 4H), 7.18-7.11 (m, 2H), 6.74 (dd, J=3.2, 1.6 Hz, 1H), 4.49 (s, 1H), 3.60 (s, 1H), 3.28 (s, 1H), 2.24 (s, 3H), 1.86-1.63 (m, 4H), 1.27-1.12 (m, 4H). MS: M/e 487 (M+1)$^+$.

Example 53: 2-(5-amino-2-(furan-2-yl)-7H-pyrazolo[4,3-e][1,2,4]triazolo[1,5-c]pyrimidin-7-yl)-2-phenyl-N—(((S)-tetrahydrofuran-3-yl)methyl)propanamide To a mixture of 2-(5-amino-2-(furan-2-yl)-7H-pyrazolo[4,3-e][1,2,4]triazolo[1,5-c]pyrimidin-7-yl)-2-phenylpropanoic acid (40 mg, 0.1 mmol), (S)-(tetrahydrofuran-3-yl)methanamine (10 mg, 0.1 mmol) and DIPEA (25 mg, 0.2 mmol) in DMF (2 mL) was added HATU (38 mg, 0.1 mmol). The mixture was stirred at rt overnight. The mixture was quenched with water, extracted with EtOAc (30 mL×2), washed with brine, dried over Na$_2$SO$_4$, filtered and concentrated. The residue was purified by prep-TLC (100% EtOAc) to give the title product (20 mg, 43%). $^1$H NMR (400 MHz, DMSO-d6) δ 8.24 (d, J=2.0 Hz, 1H), 7.98 (br.s, 2H), 7.95 (s, 1H), 7.77 (dd, J=10.8 Hz, 5.2 Hz, 1H), 7.35-7.22 (m, 4H), 7.16 (t, J=6.0 Hz, 2H), 6.74 (t, J=2.0 Hz, 1H), 3.70-3.45 (m, 3H), 3.36-3.28 (m, 1H), 3.21-2.95 (m, 2H), 2.47-2.38 (m, 1H), 2.29 (s, 3H), 1.90-1.71 (m, 1H), 1.55-1.38 (m, 1H). MS: M/e 473 (M+1)$^+$.

Example 54: 2-(5-amino-2-(furan-2-yl)-7H-pyrazolo[4,3-e][1,2,4]triazolo[1,5-c]pyrimidin-7-yl)-2-phenyl-N—(((R)-tetrahydrofuran-3-yl)methyl)propanamide To a mixture of 2-(5-amino-2-(furan-2-yl)-7H-pyrazolo[4,3-e][1,2,4]triazolo[1,5-c]pyrimidin-7-yl)-2-phenylpropanoic acid (40 mg, 0.1 mmol), (R)-(tetrahydrofuran-3-yl)methanamine (10 mg, 0.1 mmol) and DIPEA (25 mg, 0.2 mmol) in DMF (2 mL) was added HATU (38 mg, 0.1 mmol). The mixture was stirred at rt overnight. The mixture was quenched with water, extracted with EtOAc (30 mL×2), washed with brine, dried over Na$_2$SO$_4$, filtered and concentrated. The residue was purified by prep-TLC (100% EtOAc) to give the title product (28 mg, 60%). $^1$H NMR (400 MHz, DMSO-d6) δ 8.24 (d, J=2.0 Hz, 1H), 7.98 (br.s, 2H), 7.95 (s, 1H), 7.76 (dd, J=10.4 Hz, 5.2 Hz, 1H), 7.35-7.21 (m, 4H), 7.16 (t, J=5.6 Hz, 2H), 6.76-6.72 (m, 1H), 3.70-3.46 (m, 3H), 3.32-3.25 (m, 1H), 3.21-2.95 (m, 2H), 2.46-2.36 (m, 1H), 2.29 (s, 3H), 1.90-1.69 (m, 1H), 1.55-1.38 (m, 1H). MS: M/e 473 (M+1)$^+$.

Example 55: 2-(5-amino-2-(furan-2-yl)-7H-pyrazolo[4,3-e][1,2,4]triazolo[1,5-c]pyrimidin-7-yl)-N-(2-hydroxyethyl)-2-phenylpropanamide To a mixture of 2-(5-amino-2-(furan-2-yl)-7H-pyrazolo[4,3-e][1,2,4]triazolo[1,5-c]pyrimidin-7-yl)-2-phenylpropanoic acid (40 mg, 0.1 mmol), 2-aminoethane-1-ol (10 mg, 0.16 mmol), DIPEA (55 mg, 0.42 mmol) in DMF (1 mL) was added HATU (46 mg, 0.12 mmol) at rt and the mixture was stirred at rt for 16 hrs. The mixture was diluted with 10 mL of EtOAc, washed with brine (5 mL×3), dried over Na$_2$SO$_4$, concentrated and the resulted oil was purified by prep-TLC (EtOAc: 100%) to give the title product (7.0 mg, yield: 16%) after lyophilization. $^1$H NMR (400 MHz, DMSO-d6) δ 8.23 (s, 1H), 8.10-7.83 (m, 3H), 7.47 (t, J=5.6 Hz, 1H), 7.35-7.22 (m, 4H), 7.14 (d, J=6.8 Hz, 2H), 6.78-6.70 (m, 1H), 4.56 (t, J=5.6 Hz, 1H), 3.47-3.36 (m, 2H), 3.26-3.14 (m, 2H), 2.30 (s, 3H). MS: M/e 433 (M+1)$^+$.

Example 56: 2-(5-amino-2-(furan-2-yl)-7H-pyrazolo[4,3-e][1,2,4]triazolo[1,5-c]pyrimidin-7-yl)-N-((1S,2R)-2-hydroxycyclohexyl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (30 mg, 0.077 mmol), (1R,2S)-2-aminocyclohexan-1-ol (8.9 mg, 0.077 mmol), HATU (35 mg, 0.092 mmol) and DIPEA (30 mg, 0.23 mmol) in DMF (5 mL) was stirred overnight at RT. The reaction mixture was poured into H$_2$O (60 mL) and extracted with EtOAc (20 mL×3). The combined organic layers were washed with brine, dried over Na$_2$SO$_4$, concentrated and purified by column chromatography (EtOAc) to give the target compound (14 mg, 37.3%). $^1$H NMR (400 MHz, DMSO-d6) $^1$H NMR (400 MHz, DMSO-d6) δ 8.26 (d, J=5.5 Hz, 1H), 8.01-7.92 (m, 3H), 7.31 (q, J=6.6 Hz, 3H), 7.25 (d, J=3.4 Hz, 1H), 7.18 (d, J=6.6 Hz, 1H), 7.11 (d, J=6.9 Hz, 1H), 6.78-6.74 (m, 2H), 4.51 (dd, J=11.8, 4.0 Hz, 1H), 3.70 (s, 1H), 3.59 (s, 1H), 2.32 (d, J=3.1 Hz, 3H), 1.54-1.39 (m, 6H), 1.24 (m, 2H). MS: M/e 487 (M+1)$^+$.

Example 57: 2-(5-amino-2-(furan-2-yl)-7H-pyrazolo[4,3-e][1,2,4]triazolo[1,5-c]pyrimidin-7-yl)-N-((1S,2S)-2-hydroxycyclohexyl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (30 mg, 0.077 mmol), (1S,2S)-2-aminocyclohexan-1-ol (8.9 mg, 0.077 mmol), HATU (35 mg, 0.092 mmol) and DIPEA (30 mg, 0.23 mmol) in DMF (5 mL) was stirred overnight at RT. The reaction mixture was poured into H$_2$O (60 mL) and extracted with EtOAc (20 mL×3). The combined organic layers were washed with brine, dried over Na$_2$SO$_4$, concentrated and purified by column chromatography (EtOAc) to give the target compound (23.5 mg, 62.7%). $^1$H NMR (400 MHz, DMSO-d6) δ 8.25 (d, J=6.5 Hz, 1H), 7.97 (d, J=8.2 Hz, 3H), 7.42 (dd, J=22.1, 7.9 Hz, 1H), 7.29-7.24 (m, 4H), 7.19 (d, J=7.7 Hz, 1H), 7.10 (d, J=7.8 Hz, 1H), 6.75-6.74 (m, 1H), 4.41 (m, 1H), 3.52-3.47 (m, 1H), 3.25-3.15 (m, 1H), 2.30 (d, J=13.4 Hz, 3H), 1.79 (m, 2H), 1.59-1.53 (m, 2H), 1.18-1.08 (m, 4H). MS: M/e 487 (M+1)$^+$.

Example 58: 2-(5-amino-2-(furan-2-yl)-7H-pyrazolo[4,3-e][1,2,4]triazolo[1,5-c]pyrimidin-7-yl)-N-((1R,2S)-2-hydroxycyclohexyl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (30 mg, 0.077 mmol), (S,2R)-2-aminocyclohexan-1-ol (8.9 mg, 0.077 mmol), HATU (35 mg, 0.092 mmol) and DIPEA (30 mg, 0.23 mmol) in DMF (5 mL) was stirred overnight at RT. The reaction mixture was poured into H$_2$O (60 mL) and extracted with EtOAc (20 mL×3). The combined organic layers were washed with brine, dried over Na$_2$SO$_4$, concentrated and purified by column chromatography (EtOAc) to give the target compound (22 mg, 58.7%). $^1$H NMR (400 MHz, DMSO-d6) δ 8.26 (d, J=5.5 Hz, 1H), 7.95 (s, 3H), 7.31 (q, J=6.5 Hz, 1H), 7.25 (d, J=3.3 Hz, 1H), 7.18 (d, J=6.9 Hz, 1H), 7.11 (d, J=7.0 Hz, 1H), 6.76 (d, J=8.6 Hz, 2H), 4.50 (s, 1H), 3.70 (s, 1H), 3.59 (s, 1H), 2.32 (d, J=2.7 Hz, 3H), 1.54-1.39 (m, 6H), 1.23 (m, 2H). MS: M/e 487 (M+1)$^+$.

Compound 58 A: 2-(5-amino-2-(furan-2-yl)-7H-pyrazolo[4,3-e][1,2,4]triazolo[1,5-c]pyrimidin-7-yl)-N-((1S,2R)-2-hydroxycyclohexyl)-2-phenylpropanamide A mixture of(S)-2-(5-amino-2-(furan-2-yl)-7H-pyrazolo[4,3-e][1,2,4]triazolo[1,5-c]pyrimidin-7-yl)-2-phenylpropanoic acid (100 mg, 0.257 mmol), (S,2R)-2-aminocyclohexan-1-ol (29.5 mg, 0.257 mmol), HATU (117 mg, 0.308 mmol) and DIPEA (99 mg, 0.77 mmol) in DMF (5 mL) was stirred overnight at RT. The reaction mixture was poured into H$_2$O (60 mL) and extracted with EtOAc (20 mL×3). The combined organic layers were washed with brine, dried over Na$_2$SO$_4$, concentrated and purified by column chromatography (EtOAc) to give the target compound (35 mg, 28.2%). $^1$H NMR (400 MHz, DMSO-d6) δ 8.25 (s, 1H), 7.96 (s, 3H), 7.28 (m, 4H), 7.18 (d, J=7.4 Hz, 2H), 6.76 (d, J=10.6 Hz, 2H), 4.52 (d, J=3.0 Hz, 1H), 3.70 (s, 2H), 3.30 (s, 1H), 2.33 (s, 3H), 1.49-1.33 (m, 6H), 1.23 (m, 2H). MS: M/e 487 (M+1)$^+$.

Compound 58B: (R)-2-(5-amino-2-(furan-2-yl)-7H-pyrazolo[4,3-e][1,2,4]triazolo[1,5-c]pyrimidin-7-yl)-N-((1R,2S)-2-hydroxycyclohexyl)-2-phenylpropanamide A mixture of (R)-2-(5-amino-2-(furan-2-yl)-7H-pyrazolo[4,3-e][1,2,4]triazolo[1,5-c]pyrimidin-7-yl)-2-phenylpropanoic acid (100 mg, 0.257 mmol), (1S,2R)-2-aminocyclohexan-1-ol (29.5 mg, 0.257 mmol), HATU (117 mg, 0.308 mmol) and DIPEA (99 mg, 0.77 mmol) in DMF (5 mL) was stirred overnight at RT. The reaction mixture was poured into H$_2$O (60 mL) and extracted with EtOAc (20 mL×3). The combined organic layers were washed with brine, dried over Na$_2$SO$_4$, concentrated and purified by column chromatography (EtOAc) to give the target compound (40 mg, 32%). $^1$H NMR (400 MHz, DMSO-d6) δ 8.27 (s, 1H), 7.96 (s, 3H), 7.28 (m, 4H), 7.11 (d, J=7.3 Hz, 2H), 6.76 (d, J=9.1 Hz, 2H), 4.49 (s, 1H), 3.69 (s, 1H), 3.59 (s, 1H), 2.32 (s, 3H), 1.47 (m, 6H), 1.24 (s, 2H). MS: M/e 487 (M+1)$^+$.

Example 59: 2-(5-amino-2-(furan-2-yl)-7H-pyrazolo[4,3-e][1,2,4]triazolo[1,5-c]pyrimidin-7-yl)-2-phenyl-N—((S)-tetrahydro-2H-pyran-3-yl)propanamide A mixture of(S)-tetrahydro-2H-pyran-3-amine hydrochloride (21 mg, 0.15 mmol), 2-(5-amino-2-(furan-2-yl)-7H-pyrazolo[4,3-e][1,2,4]triazolo[1,5-c]pyrimidin-7-yl)-2-phenylpropanoic acid (40 mg, 0.1 mmol), HATU (43 mg, 0.11 mmol) and DIPEA (0.2 mL) in DMF (5 mL) was stirred at RT overnight. The reaction mixture was poured into water (10 mL) and extracted with EtOAc (15 mL×3). The combined organic layers were washed with brine, dried over Na$_2$SO$_4$ and concentrated under reduced pressure. The residue was purified by prep-TLC (EtOAc: 100%) to afford the title compound (5 mg, yield: 10.3%). $^1$H NMR (400 MHz, DMSO-d6) δ8.32-8.18 (m, 1H), 8.07-7.92 (m, 3H), 7.62-7.45 (m, 1H), 7.35-7.21 (m, 4H), 7.19-7.04 (m, 2H), 6.75 (s, 1H), 3.90-3.59 (m, 3H), 3.30-3.13 (m, 1H), 3.12-2.94 (m, 1H), 2.27 (s, 3H), 1.88-1.68 (m, 1H), 1.60-1.40 (m, 3H) ppm. MS: M/e 473 (M+1)$^+$.

Example 60: 2-(5-amino-2-(furan-2-yl)-7H-pyrazolo[4,3-e][1,2,4]triazolo[1,5-c]pyrimidin-7-yl)-2-phenyl-N—((R)-tetrahydro-2H-pyran-3-yl)propanamide A mixture of (R)-tetrahydro-2H-pyran-3-amine hydrochloride (21 mg, 0.15 mmol), 2-(5-amino-2-(furan-2-yl)-7H-pyrazolo[4,3-e][1,2,4]triazolo[1,5-c]pyrimidin-7-yl)-2-phenylpropanoic acid (40 mg, 0.1 mmol), HATU (43 mg, 0.11 mmol) and DIPEA (0.1 mL) in DMF (5 mL) was stirred at RT overnight. The reaction mixture was poured into water (10 mL) and extracted with EtOAc (15 mL×3). The combined organic layers were washed with brine, dried over Na$_2$SO$_4$ and concentrated under reduced pressure. The residue was purified by prep-TLC (EtOAc: 100%) to afford the title compound (25 mg, yield: 51.3%). $^1$H NMR (400 MHz, DMSO-d6) δ8.31-8.19 (m, 1H), 8.09-7.88 (m, 3H), 7.60-

7.44 (m, 1H), 7.35-7.20 (m, 4H), 7.19-7.12 (m, 1H), 7.12-7.02 (m, 1H), 6.77-6.69 (m, 1H), 3.88-3.56 (m, 3H), 3.27-3.13 (m, 1H), 3.09-2.94 (m, 1H), 2.32-2.21 (m, 3H), 1.87-1.70 (m, 1H), 1.60-1.35 (m, 3H) ppm. MS: M/e 473 (M+1)$^+$.

Example 61: 2-(5-amino-2-(furan-2-yl)-7H-pyrazolo[4,3-e][1,2,4]triazolo[1,5-c]pyrimidin-7-yl)-2-phenyl-N-((tetrahydro-2H-pyran-3-yl)methyl)propanamide A mixture of (tetrahydro-2H-pyran-3-yl)methanamine (18 mg, 0.15 mmol), 2-(5-amino-2-(furan-2-yl)-7H-pyrazolo[4,3-e][1,2,4]triazolo[1,5-c]pyrimidin-7-yl)-2-phenyl-propanoic acid (40 mg, 0.1 mmol), HATU (43 mg, 0.11 mmol) and DIPEA (0.1 mL) in DMF (5 mL) was stirred at RT overnight. The reaction mixture was poured into water (10 mL) and extracted with EtOAc (15 mL×3). The combined organic layers were washed with brine, dried over Na$_2$SO$_4$ and concentrated under reduced pressure. The residue was purified by prep-TLC (EtOAc: 100%) to afford the title compound (25 mg, yield: 62.7%). $^1$H NMR (400 MHz, DMSO-d6) δ8.31-8.12 (m, 1H), 8.07-7.83 (m, 3H), 7.72-7.53 (m, 1H), 7.36-7.22 (m, 4H), 7.20-7.10 (m, 2H), 6.86-6.62 (m, 1H), 3.73-3.59 (m, 2H), 3.28-3.19 (m, 1H), 3.05-2.90 (m, 3H), 2.29 (s, 3H), 1.81-1.55 (m, 2H), 1.54-1.32 (m, 2H), 1.16-1.06 (m, 1H) ppm. MS: M/e 487 (M+1)$^+$.

Example 62: 2-(5-amino-2-(furan-2-yl)-7H-pyrazolo[4,3-e][1,2,4]triazolo[1,5-c]pyrimidin-7-yl)-N-(2-(dimethylamino)ethyl)-2-phenylpropanamide A mixture of N',N'-dimethylethane-1,2-diamine (14 mg, 0.15 mmol), 2-(5-amino-2-(furan-2-yl)-7H-pyrazolo[4,3-e][1,2,4]triazolo[1,5-c]pyrimidin-7-yl)-2-phenylpropanoic acid (40 mg, 0.1 mmol), HATU (43 mg, 0.11 mmol) and DIPEA (0.1 mL) in DMF (5 mL) was stirred at RT overnight. The reaction mixture was poured into water (10 mL) and extracted with EtOAc (15 mL×3). The combined organic layers were washed with brine, dried over Na$_2$SO$_4$ and concentrated under reduced pressure. The residue was purified by prep-TLC (MeOH/DCM:1/5) to afford the title compound (12 mg, yield: 31.8%). $^1$H NMR (400 MHz, DMSO-d6) δ8.28 (s, 1H), 8.15-7.90 (m, 3H), 7.78 (br.s, 1H), 7.38-7.20 (m, 4H), 7.16-6.96 (m, 2H), 6.79-6.64 (m, 1H), 3.50-3.37 (m, 2H), 3.37-3.25 (m, 6H), 2.99-2.72 (m, 2H), 2.29 (s, 3H) ppm. MS: M/e 460 (M+1)$^+$.

Example 63: 2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-(o-tolyl)propanamide A mixture of 2-(5-amino-2-(furan-2-yl)-7H-pyrazolo[4,3-e][1,2,4]triazolo[1,5-c]pyrimidin-7-yl)-2-(o-tolyl)propanoic acid (35 mg, 0.09 mmol), 3-(aminomethyl)oxetan-3-ol (14 mg, 0.13 mmol), HATU (50 mg, 0.13 mmol) and DIPEA (24 mg, 0.18 mmol) in DMF (5 mL) was stirred at rt for 2 hrs. The solution was added with water (5 mL), extracted with ethyl acetate (10 mL) and washed with brine (10 mL). The organic layer was dried, concentrated and purified by preparative TLC (EtOAc) to get the desired product (20 mg, 48%). $^1$H NMR (400 MHz, DMSO-d6) δ 8.27 (s, 1H), 8.00 (br.s, 2H), 7.95 (d, J=4.0 Hz, 1H), 7.58 (t, J=8.0 Hz, 1H), 7.25-7.12 (m, 4H), 6.84 (d, J=8.0 Hz, 1H), 6.74 (d, J=4.0 Hz, 1H), 5.74 (br.s, 1H), 4.25 (s, 2H), 4.15 (dd, J$_1$=12.0 Hz, J$_2$=8.0 Hz, 2H), 3.55 (dd, J$_1$=12.0 Hz, J$_2$=8.0 Hz, 1H), 3.35-3.33 (m, 1H), 2.34 (s, 3H), 1.97 (s, 3H) ppm. MS: M/e 489 (M+1)$^+$.

Example 64: 2-(5-amino-2-(furan-2-yl)-7H-pyrazolo[4,3-e][1,2,4]triazolo[1,5-c]pyrimidin-7-yl)-2-phenyl-N-(pyridin-3-yl)propanamide To a mixture of 2-(5-amino-2-(furan-2-yl)-7H-pyrazolo[4,3-e][1,2,4]triazolo[1,5-c]pyrimidin-7-yl)-2-phenylpropanoic acid (40 mg, 0.1 mmol), pyridin-3-amine (15 mg, 0.16 mmol), DIPEA (75 mg, 0.58 mmol) in DMF (1 mL) was added HATU (46 mg, 0.12 mmol) at rt and the mixture was stirred at rt for 16 hrs. The mixture was diluted with 10 mL of EtOAc, washed with brine (5 mL×3), dried over Na$_2$SO$_4$, concentrated and the resulted oil was purified by prep-TLC (EtOAc: 100%) to give the title product (12 mg, yield: 26%) after lyophilization. $^1$H NMR (400 MHz, DMSO-d6) δ 9.99 (s, 1H), 8.71 (d, J=2.4 Hz, 1H), 8.33 (s, 1H), 8.26 (d, J=3.2 Hz, 1H), 8.17-7.97 (m, 3H), 7.95 (s, 1H), 7.38-7.26 (m, 4H), 7.25 (d, J=3.6 Hz, 1H), 7.10 (d, J=6.4 Hz, 2H), 6.74 (dd, J=3.2, 1.6 Hz, 1H), 2.47 (s, 3H). MS: M/e 466 (M+1)$^+$.

Example 65: 2-(5-amino-2-(furan-2-yl)-7H-pyrazolo[4,3-e][1,2,4]triazolo[1,5-c]pyrimidin-7-yl)-2-phenyl-N-(pyridin-4-yl)propanamide To a mixture of 2-(5-amino-2-(furan-2-yl)-7H-pyrazolo[4,3-e][1,2,4]triazolo[1,5-c]pyrimidin-7-yl)-2-phenylpropanoic acid (40 mg, 0.1 mmol), pyridin-3-amine (15 mg, 0.16 mmol), DIEA (75 mg, 0.58 mmol) in DMF (1 mL) was added HATU (46 mg, 0.12 mmol) at rt and the mixture was stirred at rt for 16 hrs. The mixture was diluted with 10 mL of EtOAc, washed with brine (5 mL×3), dried over Na$_2$SO$_4$, concentrated and the resulted oil was purified by prep-TLC (EtOAc: 100%) to give the title product (25 mg, yield: 54%) after lyophilization. $^1$H NMR (400 MHz, DMSO-d6) δ 10.21 (s, 1H), 8.41 (d, J=6.0 Hz, 2H), 8.33 (s, 1H), 8.04 (s, 2H), 7.95 (s, 1H), 7.65 (d, J=6.0 Hz, 2H), 7.37-7.22 (m, 4H), 7.05 (d, J=6.4 Hz, 2H), 6.78-6.70 (m, 1H), 2.51 (s, 3H). MS: M/e 466 (M+1)$^+$.

Example 66: 2-(5-amino-2-(furan-2-yl)-7H-pyrazolo[4,3-e][1,2,4]triazolo[1,5-c]pyrimidin-7-yl)-2-phenyl-N-(pyridin-2-ylmethyl)propanamide A mixture of 2-(5-amino-2-(furan-2-yl)-7H-pyrazolo[4,3-e][1,2,4]triazolo[1,5-c]pyrimidin-7-yl)-2-phenylpropanoic acid (38.9 mg, 0.1 mmol), pyridin-2-ylmethanamine (10 mg, 0.1 mmol), HATU (45 mg, 0.12 mmol) and DIPEA (25.8 mg, 0.2 mmol) in DMF (3 mL) was stirred overnight. The reaction mixture was poured into H$_2$O (10 mL) and extracted with EtOAc (10 mL×3). The combined organic layers were washed with brine, dried over Na$_2$SO$_4$, concentrated and purified by prep-TLC (petroleum ether/EtOAc=1:2) to give the target compound (23 mg, 48%). $^1$H NMR (400 MHz, DMSO-d6) δ8.40 (d, J=4.4 Hz, 1H), 8.26 (s, 1H), 8.17 (t, J=5.6 Hz, 1H), 8.05 (s, 2H), 7.95 (s, 1H), 7.74 (t, J=7.6 Hz, 1H), 7.41 (d, J=7.6 Hz, 1H), 7.36-7.18 (m, 7H), 6.74 (s, 1H), 4.51-4.34 (m, 2H), 2.39 (s, 3H) ppm. MS: M/e 480 (M+1)$^+$.

Example 66B: (R)-2-(5-amino-2-(furan-2-yl)-7H-pyrazolo[4,3-e][1,2,4]triazolo[1,5-c]pyrimidin-7-yl)-2-phenyl-N-(pyridin-2-ylmethyl)propanamide A mixture of (R)-2-(5-amino-2-(furan-2-yl)-7H-pyrazolo[4,3-e][1,2,4]triazolo[1,5-c]pyrimidin-7-yl)-2-phenylpropanoic acid (38.9 mg, 0.1 mmol), pyridin-2-ylmethanamine (10 mg, 0.1 mmol), HATU (45 mg, 0.12 mmol) and DIPEA (25.8 mg, 0.2 mmol) in DMF (3 mL) was stirred overnight. The reaction mixture was poured into H$_2$O (10 mL) and extracted with EtOAc (10 mL×3). The combined organic layers were washed with brine, dried over Na$_2$SO$_4$, concentrated and purified by prep-TLC (petroleum ether/EtOAc=1:2) to give the target compound (26 mg, 54%). $^1$H NMR (400 MHz, DMSO-d6) δ 8.40 (d, J=4.4 Hz, 1H), 8.26 (s, 1H), 8.17 (t, J=5.6 Hz, 1H), 8.05 (s, 2H), 7.95 (s, 1H), 7.74 (t, J=7.6 Hz, 1H), 7.41 (d, J=7.6 Hz, 1H), 7.36-7.18 (m, 7H), 6.74 (s, 1H), 4.51-4.34 (m, 2H), 2.39 (s, 3H) ppm. MS: M/e 480 (M+1)⁺.

Example 67: 2-(5-amino-2-(furan-2-yl)-7H-pyrazolo[4,3-e][1,2,4]triazolo[1,5-c]pyrimidin-7-yl)-2-phenyl-N—((R)-piperidin-3-yl)propanamide

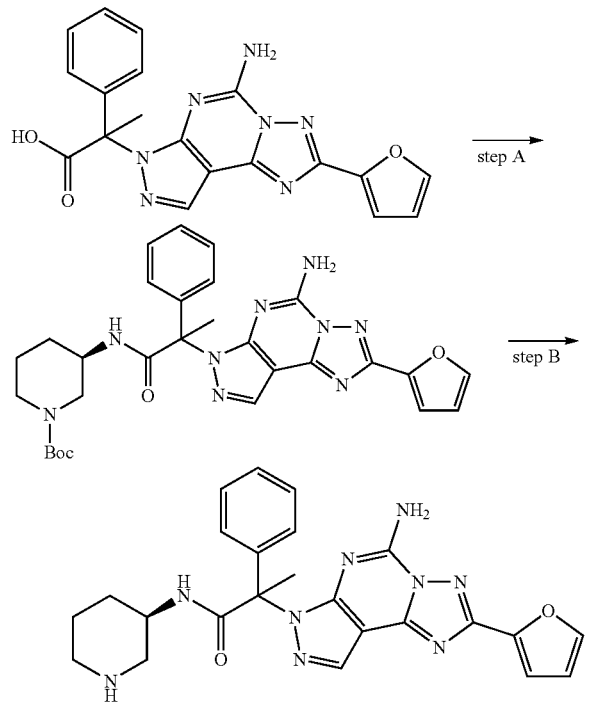

Step A: tert-butyl (3S)-3-(2-(5-amino-2-(furan-2-yl)-7H-pyrazolo[4,3-e][1,2,4]triazolo[1,5-c]pyrimidin-7-yl)-2-phenylpropanamido)piperidine-1-carboxylate A mixture of 2-(5-amino-2-(furan-2-yl)-7H-pyrazolo[4,3-e][1,2,4]triazolo[1,5-c]pyrimidin-7-yl)-2-phenylpropanoic acid (38.9 mg, 0.1 mmol), tert-butyl (R)-3-aminopiperidine-1-carboxylate (20 mg, 0.1 mmol), HATU (45 mg, 0.12 mmol) and DIPEA (25.8 mg, 0.2 mmol) in DMF (3 mL) was stirred overnight. The reaction mixture was poured into $H_2O$ (10 mL) and extracted with EtOAc (10 mL×3). The combined organic layers were washed with brine, dried over $Na_2SO_4$, concentrated and purified by prep-TLC (petroleum ether/EtOAc=1:2) to give the target compound (23 mg, 40.3%) as a white solid. MS: M/e 572 (M+1)⁺.

Step B: 2-(5-amino-2-(furan-2-yl)-7H-pyrazolo[4,3-e][1,2,4]triazolo[1,5-c]pyrimidin-7-yl)-2-phenyl-N—((R)-piperidin-3-yl)propanamide To a stirred solution of the product of Step A (23 mg, 0.04 mmol) in $CH_2Cl_2$ (4 mL) was added EtOAc/HCl(g) (4.0 M, 1 mL). After addition, the reaction was stirred overnight. The reaction mixture was concentrated to give the target compound (22 mg, 100%). ¹H NMR (400 MHz, DMSO-d6) δ 9.18-8.85 (m, 2H), 8.27 (d, J=2.0 Hz, 1H), 8.03 (s, 2H), 7.96 (s, 1H), 7.88 (dd, J=25.6, 8.0 Hz, 1H), 7.33-7.21 (m, 4H), 7.18-7.07 (m, 2H), 6.78-6.72 (m, 1H), 4.21-4.04 (m, 1H), 3.26 (dd, J=40.8, 12.4 Hz, 1H), 3.15-3.03 (m, 1H), 2.77-2.55 (m, 2H), 2.27 (s, 3H), 1.89-1.38 (m, 4H) ppm. MS: M/e 472 (M+1)⁺.

Example 68: 2-(5-amino-2-(furan-2-yl)-7H-pyrazolo[4,3-e][1,2,4]triazolo[1,5-c]pyrimidin-7-yl)-2-phenyl-N—((S)-piperidin-3-yl)propanamide

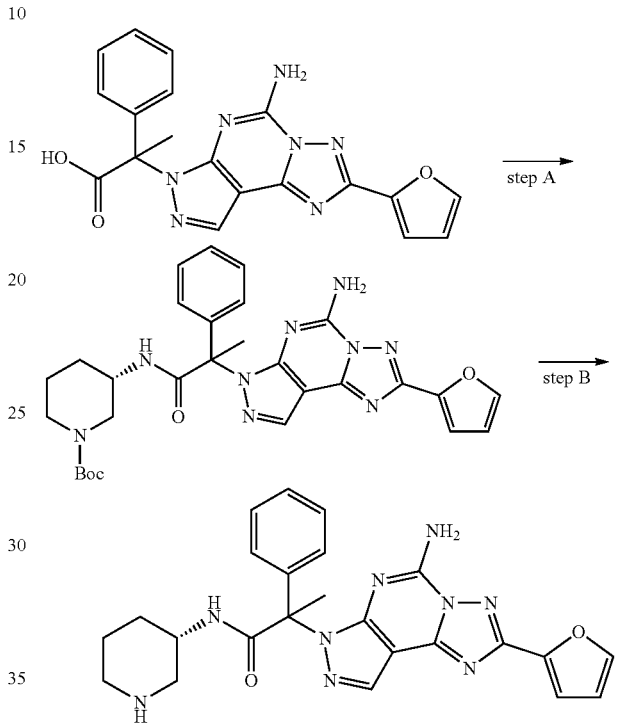

Step A: tert-butyl (3S)-3-(2-(5-amino-2-(furan-2-yl)-7H-pyrazolo[4,3-e][1,2,4]triazolo[1,5-c]pyrimidin-7-yl)-2-phenylpropanamido)piperidine-1-carboxylate A mixture of 2-(5-amino-2-(furan-2-yl)-7H-pyrazolo[4,3-e][1,2,4]triazolo[1,5-c]pyrimidin-7-yl)-2-phenylpropanoic acid (38.9 mg, 0.1 mmol), tert-butyl (S)-3-aminopiperidine-1-carboxylate (20 mg, 0.1 mmol), HATU (45 mg, 0.12 mmol) and DIPEA (25.8 mg, 0.2 mmol) in DMF (3 mL) was stirred overnight. The reaction mixture was poured into $H_2O$ (10 mL) and extracted with EtOAc (10 mL×3). The combined organic layers were washed with brine, dried over $Na_2SO_4$, concentrated and purified by prep-TLC (petroleum ether/EtOAc=1:2) to give the target compound (10 mg, 18.7%) as a white solid. MS: M/e 572 (M+1)⁺.

Step B: 2-(5-amino-2-(furan-2-yl)-7H-pyrazolo[4,3-e][1,2,4]triazolo[1,5-c]pyrimidin-7-yl)-2-phenyl-N—((R)-piperidin-3-yl)propanamide To a stirred solution of the product of Step A (23 mg, 0.04 mmol) in $CH_2Cl_2$ (4 mL) was added EtOAc/HCl(g) (4.0 M, 1 mL). After addition, the reaction was stirred overnight. The reaction mixture was concentrated to give the target compound (9 mg, 100%). ¹H NMR (400 MHz, DMSO-d6) δ 9.18-8.85 (m, 2H), 8.27 (d, J=2.0 Hz, 1H), 8.03 (s, 2H), 7.96 (s, 1H), 7.88 (dd, J=25.6, 8.0 Hz, 1H), 7.33-7.21 (m, 4H), 7.18-7.07 (m, 2H), 6.78-6.72 (m, 1H), 4.21-4.04 (m, 1H), 3.26 (dd, J=40.8, 12.4 Hz, 1H), 3.15-3.03 (m, 1H), 2.77-2.55 (m, 2H), 2.27 (s, 3H), 1.89-1.38 (m, 4H) ppm. MS: M/e 472 (M+1)+.

Example 69: 2-(5-amino-2-(furan-2-yl)-7H-pyrazolo[4,3-e][1,2,4]triazolo[1,5-c]pyrimidin-7-yl)-(cis)-N-(4-hydroxy-4-methylcyclohexyl)-2-phenylpropanamide To a stirred solution of 2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), HATU (54 mg, 0.14 mmol) and DIPEA (50 mg, 0.39 mmol) in THF (15 ml) was added cis-4-amino-1-methylcyclohexan-1-ol (17 mg, 0.13 mmol). The reaction mixture was stirred at rt for 15 h. After completion, the reaction mixture was diluted with EtOAc (30 ml) and then washed with $H_2O$ (15 ml×2). The organic layer was dried over $Na_2SO_4$, filtered and then concentrated under reduced pressure to afford a residue. The residue was purified by prep-TLC with PE:EtOAc (1:5) to afford the product (39.2 mg, 61%). $^1$H NMR (400 MHz, DMSO-d6) δ 8.21 (s, 1H), 7.95 (s, 3H), 7.47 (d, J=8 Hz, 1H), 7.31-7.23 (m, 4H), 7.17 (d, J=8 Hz, 2H) 6.73 (dd, J=4, 2 Hz, 1H), 3.93 (s, 1H), 3.61-3.52 (m, 1H), 2.27 (s, 3H), 1.56-1.43 (m, 6H), 1.32-1.25 (m, 2H), 1.06 (s, 3H) ppm. MS: M/e 501 (M+1)+.

Example 69A: (S)-2-(5-amino-2-(furan-2-yl)-7H-pyrazolo[4,3-e][1,2,4]triazolo[1,5-c]pyrimidin-7-yl)-(cis)-N-(4-hydroxy-4-methylcyclohexyl)-2-phenylpropanamide To a stirred solution of (S)-2-(5-amino-2-(furan-2-yl)-7H-pyrazolo[4,3-e][1,2,4]triazolo[1,5-c]pyrimidin-7-yl)-2-phenylpropanoic acid (100 mg, 0.26 mmol), HATU (108 mg, 0.28 mmol) and DIPEA (100 mg, 0.78 mmol) in THF (15 ml) was added cis-4-amino-1-methylcyclohexan-1-ol (33 mg, 0.26 mmol). The reaction mixture was stirred at rt for 15 h. After completion, the reaction mixture was diluted with EtOAc (30 ml) and then washed with $H_2O$ (15 ml×2). The organic layer was dried over $Na_2SO_4$, filtered and then concentrated under reduced pressure to afford a residue. The residue was purified by prep-TLC with PE:EtOAc (1:4) to afford the product (70.1 mg, 54%). $^1$H NMR (400 MHz, DMSO-d6) δ 8.21 (s, 1H), 8.06-7.88 (m, 3H), 7.47 (d, J=8 Hz, 1H), 7.31-7.22 (m, 4H), 7.16 (d, J=8 Hz, 2H), 6.79-6.70 (m, 1H), 3.93 (s, 1H), 3.64-3.52 (m, 1H), 2.26 (s, 3H), 1.56-1.45 (m, 6H), 1.32-1.22 (m, 2H), 1.05 (s, 3H) ppm. MS: M/e 501 (M+1)+.

Example 69B: (R)-2-(5-amino-2-(furan-2-yl)-7H-pyrazolo[4,3-e][1,2,4]triazolo[1,5-c]pyrimidin-7-yl)-(cis)-N-(4-hydroxy-4-methylcyclohexyl)-2-phenylpropanamide To a stirred solution of (R)-2-(5-amino-2-(furan-2-yl)-7H-pyrazolo[4,3-e][1,2,4]triazolo[1,5-c]pyrimidin-7-yl)-2-phenylpropanoic acid (100 mg, 0.26 mmol), HATU (108 mg, 0.28 mmol) and DIPEA (100 mg, 0.78 mmol) in THF (15 ml) was added cis-4-amino-1-methylcyclohexan-1-ol (33 mg, 0.26 mmol). The reaction mixture was stirred at rt for 15 h. After completion, the reaction mixture was diluted with EtOAc (30 ml) and then washed with $H_2O$ (15 ml×2). The organic layer was dried over $Na_2SO_4$, filtered and then concentrated under reduced pressure to afford a residue. The residue was purified by prep-TLC with PE:EtOAc (1:4) to afford the product (65.5 mg, 51%). $^1$H NMR (400 MHz, DMSO-d6) δ 8.21 (s, 1H), 8.10-7.88 (m, 3H), 7.48 (d, J=8 Hz, 1H), 7.32-7.24 (m, 4H), 7.16 (d, J=8 Hz, 2H), 6.73 (dd, J=4 Hz, 2 Hz, 1H), 3.93 (s, 1H), 3.66-3.51 (m, 1H), 2.26 (s, 3H), 1.58-1.42 (m, 6H), 1.32-1.22 (m, 2H), 1.05 (s, 3H) ppm. MS: M/e 501 (M+1)+.

Example 70: 2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-(2-methoxyphenyl)propanamide To a mixture of 2-(5-amino-2-(furan-2-yl)-7H-pyrazolo[4,3-e][1,2,4]triazolo[1,5-c]pyrimidin-7-yl)-2-(2-methoxyphenyl)propanoic acid (50 mg, 0.1 mmol), 3-(aminomethyl)oxetan-3-ol (13 mg, 0.13 mmol), DIPEA (70 mg, 0.54 mmol) in DMF (2 mL) was added HATU (50 mg, 0.13 mmol) at rt and the mixture was stirred at rt for 16 hrs. The mixture was diluted with 20 mL of EtOAc, washed with brine (10 mL×3), dried over $Na_2SO_4$, concentrated and the resulted oil was purified by prep-TLC (EtOAc/MeOH=2:1) to give the title product (16 mg, yield: 32%) after lyophilization. $^1$H NMR (400 MHz, DMSO-d6) δ 8.23 (s, 1H), 8.03-7.83 (m, 3H), 7.37-7.19 (m, 3H), 7.07 (d, J=8.0 Hz, 1H), 6.82 (t, J=7.6 Hz, 1H), 6.74 (dd, J=3.2, 1.6 Hz, 1H), 6.38 (dd, J=7.6, 1.2 Hz, 1H), 5.73 (s, 1H), 4.38-4.18 (m, 4H), 3.69 (s, 3H), 3.51-3.38 (m, 2H), 2.37 (s, 3H). MS: M/e 505 (M+1)+.

Example 71: 2-(5-amino-2-(furan-2-yl)-7H-pyrazolo[4,3-e][1,2,4]triazolo[1,5-c]pyrimidin-7-yl)-N-((1-hydroxycyclobutyl)methyl)-2-phenylpropanamide To a mixture of 2-(5-amino-2-(furan-2-yl)-7H-pyrazolo[4,3-e][1,2,4]triazolo[1,5-c]pyrimidin-7-yl)-2-phenylpropanoic acid (40 mg, 0.1 mmol), 1-(aminomethyl)cyclobutan-1-ol (12 mg, 0.12 mmol), DIPEA (50 mg, 0.39 mmol) in DMF (1 mL) was added HATU (46 mg, 0.12 mmol) at rt and the mixture was stirred at rt for 16 hrs. The mixture was diluted with 20 mL of EtOAc, washed with brine (10 mL×3), dried over $Na_2SO_4$, concentrated and the resulted oil was purified by prep-TLC (EA 100%) to give the title product (39 mg, yield: 83%) after lyophilization. $^1$H NMR (400 MHz, DMSO-d6) δ 8.26 (s, 1H), 8.08-7.83 (m, 3H), 7.36-7.27 (m, 3H), 7.25 (dd, J=3.2, 0.4 Hz, 1H), 7.19-7.10 (m, 2H), 6.98 (t, J=5.6 Hz, 1H), 6.74 (dd, J=3.2, 1.6 Hz, 1H), 5.02 (s, 1H), 3.27 (d, J=5.6 Hz, 2H), 2.35 (s, 3H), 1.96-1.68 (m, 4H), 1.60-1.48 (m, 1H), 1.43-1.30 (m, 1H). MS: M/e 473 (M+1)+.

Example 72: 2-(5-amino-2-(furan-2-yl)-7H-pyrazolo[4,3-e][1,2,4]triazolo[1,5-c]pyrimidin-7-yl)-N-((1-hydroxycyclohexyl)methyl)-2-phenylpropanamide To a mixture of 2-(5-amino-2-(furan-2-yl)-7H-pyrazolo[4,3-e][1,2,4]triazolo[1,5-c]pyrimidin-7-yl)-2-phenylpropanoic acid (40 mg, 0.1 mmol), 1-(aminomethyl) cyclohexan-1-ol (20 mg, 0.12 mmol), DIPEA (50 mg, 0.39 mmol) in DMF (1 mL) was added HATU (46 mg, 0.12 mmol) at rt and the mixture was stirred at rt for 16 hrs. The mixture was diluted with 20 mL of EtOAc, washed with brine (10 mL×3), dried over $Na_2SO_4$, concentrated and the resulted oil was purified by prep-TLC (EA 100%) to give the title product (27 mg, yield: 54%) after lyophilization. $^1$H NMR (400 MHz, DMSO-d6) δ 8.27 (s, 1H), 8.14-7.78 (m, 3H), 7.39-7.27 (m, 3H), 7.25 (d, J=3.2 Hz, 1H), 7.20-7.05 (m, 2H), 6.98 (t, J=5.6 Hz, 1H), 6.74 (dd, J=3.2, 1.6 Hz, 1H), 4.17 (s, 1H), 3.13 (d, J=5.2 Hz, 2H), 2.35 (s, 3H), 1.50-1.02 (m, 10H). MS: M/e 501 (M+1)+.

Example 73: 2-(5-amino-2-(furan-2-yl)-7H-pyrazolo[4,3-e][1,2,4]triazolo[1,5-c]pyrimidin-7-yl)-2-phenyl-N-(2-(tetrahydro-2H-pyran-4-yl)ethyl)propanamide A mixture of 2-(5-amino-2-(furan-2-yl)-7H-pyrazolo[4,3-e][1,2,4]triazolo[1,5-c]pyrimidin-7-yl)-2-phenylpropanoic acid (100 mg, 0.2570 mmol), 2-(tetrahydro-2H-pyran-4-yl)ethan-1-amine (40 mg, 0.3085 mmol), HATU (146 mg, 0.3856 mmol), DIPEA (99 mg, 0.7712 mmol) in DMF (3 mL) was stirred at rt for 3 hours. The reaction mixture was poured into H$_2$O (10 mL) and extracted with EtOAc (15 mL×3). The combined organic layers were washed with brine, dried over Na$_2$SO$_4$, concentrated and purified by column chromatography (DCM/MeOH=40:1~0:1) to give the product (62 mg, 48.2%). $^1$H NMR (400 MHz, DMSO-d6) δ 8.24 (s, 1H), 8.00 (s, 2H), 7.95 (d, J=0.9 Hz, 1H), 7.53 (t, J=5.6 Hz, 1H), 7.34-7.20 (m, 4H), 7.15 (dd, J=8.0, 1.4 Hz, 2H), 6.74 (dd, J=3.4, 1.8 Hz, 1H), 3.76-3.66 (m, 2H), 3.15 (q, J=6.6 Hz, 2H), 3.04 (dd, J=23.4, 11.6 Hz, 2H), 2.28 (s, 3H), 1.51-1.39 (m, 2H), 1.37-1.27 (m, 2H), 1.26-1.17 (m, 1H), 1.02 (ddd, J=23.9, 12.0, 4.2 Hz, 2H). MS: M/e 501 (M+1)$^+$.

Example 74: 2-(5-amino-2-(furan-2-yl)-7H-pyrazolo[4,3-e][1,2,4]triazolo[1,5-c]pyrimidin-7-yl)-2-phenyl-N-(2-(tetrahydrofuran-3-yl)ethyl)propanamide A mixture of 2-(5-amino-2-(furan-2-yl)-7H-pyrazolo[4,3-e][1,2,4]triazolo[1,5-c]pyrimidin-7-yl)-2-phenylpropanoic acid (100 mg, 0.2570 mmol), 2-(tetrahydrofuran-3-yl)ethan-1-amine (35 mg, 0.3085 mmol), HATU (146 mg, 0.3856 mmol), DIPEA (99 mg, 0.7712 mmol) in DMF (3 mL) was stirred at rt for 3 hours. The reaction mixture was poured into H$_2$O (10 mL) and extracted with EtOAc (15 mL×3). The combined organic layers were washed with brine, dried over Na$_2$SO$_4$, concentrated and purified by column chromatography (DCM/MeOH=40:1~10:1) to give the product (64 mg, 51.2%). $^1$HNMR (400 MHz, DMSO-d6) δ 8.23 (s, 1H), 7.97 (s, 2H), 7.95 (s, 1H), 7.62 (t, J=6.1 Hz, 1H), 7.27 (dd, J=14.1, 5.7 Hz, 4H), 7.15 (d, J=7.4 Hz, 2H), 6.74 (dd, J=3.3, 1.7 Hz, 1H), 3.74-3.67 (m, 1H), 3.65 (dd, J=9.3, 4.7 Hz, 1H), 3.53 (dd, J=7.6, 3.5 Hz, 1H), 3.19-3.04 (m, 3H), 2.29 (s, 3H), 2.03-1.84 (m, 2H), 1.47 (dd, J=12.0, 5.6 Hz, 2H), 1.41-1.33 (m, 1H). MS: M/e 487 (M+1)$^+$.

Example 75: 2-(5-amino-2-(furan-2-yl)-7H-pyrazolo[4,3-e][1,2,4]triazolo[1,5-c]pyrimidin-7-yl)-N-(2-(2-methoxyethoxy)ethyl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (100 mg, 0.2570 mmol), 2-(2-methoxyethoxy)ethan-1-amine (37 mg, 0.3085 mmol), HATU (146 mg, 0.3856 mmol), DIPEA (99 mg, 0.7712 mmol) in DMF (3 mL) was stirred at rt for 3 hours. The reaction mixture was poured into H$_2$O (10 mL) and extracted with EtOAc (15 mL×3). The combined organic layer was washed with brine, dried over Na$_2$SO$_4$, concentrated and purified by column chromatography (DCM/MeOH=40:1~0:1) to give the target product (85 mg, 67.48%). $^1$HNMR (400 MHz, DMSO-d6) δ 8.24 (s, 1H), 7.98 (s, 2H), 7.95 (s, 1H), 7.56 (t, J=5.6 Hz, 1H), 7.34-7.22 (m, 4H), 7.15 (dd, J=7.7, 1.5 Hz, 2H), 6.74 (dd, J=3.3, 1.8 Hz, 1H), 3.46-3.37 (m, 4H), 3.29 (dd, J=5.6, 3.0 Hz, 3H), 3.22 (dd, J=13.2, 6.0 Hz, 1H), 3.13 (s, 3H), 2.28 (s, 3H). MS: M/e 491 (M+1)$^+$.

Example 76: 2-(5-amino-2-(furan-2-yl)-7H-pyrazolo[4,3-e][1,2,4]triazolo[1,5-c]pyrimidin-7-yl)-(cis)-N-(4-hydroxycyclohexyl)-2-phenylpropanamide To a stirred solution of 2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), HATU (54 mg, 0.14 mmol) and DIPEA (50 mg, 0.39 mmol) in THF (15 ml) was added cis-4-aminocyclohexan-1-ol hydrochloride (20 mg, 0.13 mmol). The reaction mixture was stirred at rt for 15 h. After completion, the reaction mixture was diluted with EtOAc (30 ml) and then washed with H$_2$O (15 ml×2). The organic layer was dried over Na$_2$SO$_4$, filtered and then concentrated under reduced pressure to afford a residue. The residue was purified by prep-TLC with PE:EtOAc (1:5) to afford the product (37.4 mg, 60%). $^1$H NMR (400 MHz, DMSO-d6) δ 8.23 (s, 1H), 8.10-7.90 (m, 3H), 7.41 (d, J=8 Hz, 1H), 7.32-7.23 (m, 4H), 7.15 (d, J=8 Hz, 2H) 6.74 (dd, J=4 Hz, 2 Hz, 1H), 4.25 (s, 1H), 3.71-3.62 (m, 2H), 2.28 (s, 3H), 1.56-1.37 (m, 8H) ppm. MS: M/e 487 (M+1)$^+$.

Example 76A: (S)-2-(5-amino-2-(furan-2-yl)-7H-pyrazolo[4,3-e][1,2,4]triazolo[1,5-c]pyrimidin-7-yl)-(cis)-N-(4-hydroxycyclohexyl)-2-phenylpropanamide To a stirred solution of (S)-2-(5-amino-2-(furan-2-yl)-7H-pyrazolo[4,3-e][1,2,4]triazolo[1,5-c]pyrimidin-7-yl)-2-phenylpropanoic acid (150 mg, 0.39 mmol), HATU (161 mg, 0.42 mmol) and DIPEA (149 mg, 1.16 mmol) in THF (20 ml) was added cis-4-aminocyclohexan-1-ol hydrochloride (58 mg, 0.39 mmol). The reaction mixture was stirred at rt for 15 h. After completion, the reaction mixture was diluted with EtOAc (30 ml) and then washed with H$_2$O (15 ml×2). The organic layer was dried over Na$_2$SO$_4$, filtered and then concentrated under reduced pressure to afford a residue. The residue was purified by prep-TLC with PE:EtOAc (1:4) to afford the product (103.9 mg, 55%). $^1$H NMR (400 MHz, DMSO-d6) δ 8.23 (s, 1H), 8.09-7.90 (m, 3H), 7.42 (d, J=8 Hz, 1H), 7.35-7.24 (m, 4H), 7.15 (d, J=8 Hz, 2H), 6.86-6.70 (m, 1H), 4.27 (s, 1H), 3.75-3.60 (m, 2H), 2.28 (s, 3H), 1.59-1.38 (m, 8H) ppm. MS: M/e 487 (M+1)$^+$.

Example 76B: (R)-2-(5-amino-2-(furan-2-yl)-7H-pyrazolo[4,3-e][1,2,4]triazolo[1,5-c]pyrimidin-7-yl)-(cis)-N-(4-hydroxycyclohexyl)-2-phenylpropanamide To a stirred solution of (R)-2-(5-amino-2-(furan-2-yl)-7H-pyrazolo[4,3-e][1,2,4]triazolo[1,5-c]pyrimidin-7-yl)-2-phenylpropanoic acid (150 mg, 0.39 mmol), HATU (161 mg, 0.42 mmol) and DIPEA (149 mg, 1.16 mmol) in THF (20 ml) was added cis-4-aminocyclohexan-1-ol hydrochloride (58 mg, 0.39 mmol). The reaction mixture was stirred at rt for 15 h. After completion, the reaction mixture was diluted with EtOAc (30 ml) and then washed with H$_2$O (15 ml×2). The organic layer was dried over Na$_2$SO$_4$, filtered and then concentrated under reduced pressure to afford a residue. The residue was purified by prep-TLC with PE:EtOAc (1:4) to afford the product (123.1 mg, 66%). $^1$H NMR (400 MHz, DMSO-d6) δ 8.23 (s, 1H), 8.08-7.90 (m, 3H), 7.42 (d, J=8 Hz, 1H), 7.33-7.24 (m, 4H), 7.15 (d, J=8 Hz, 2H), 6.74 (dd, J=4 Hz, 2 Hz, 1H), 4.27 (d, J=4 Hz, 1H), 3.71-3.61 (m, 2H), 2.28 (s, 3H), 1.57-1.38 (m, 8H) ppm. MS: M/e 487 (M+1)$^+$.

Example 77: 2-(5-amino-2-(furan-2-yl)-7H-pyrazolo[4,3-e][1,2,4]triazolo[1,5-c]pyrimidin-7-yl)-2-phenyl-N-(pyridin-2-yl)propanamide

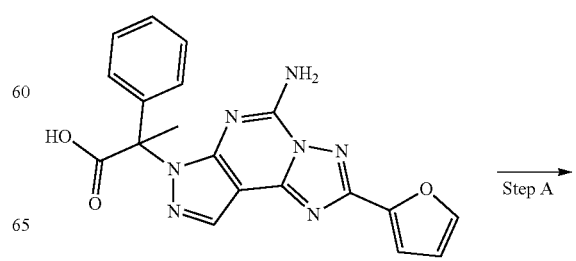

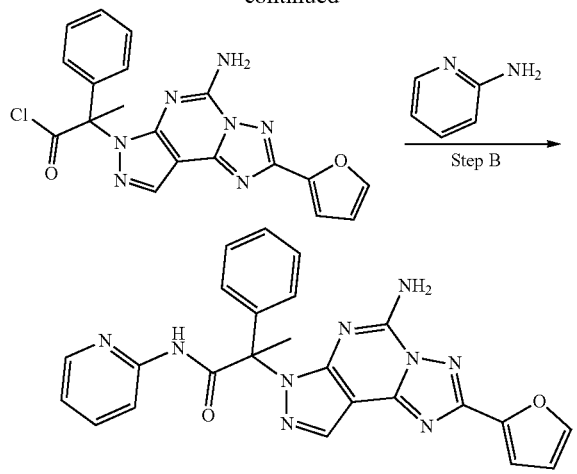

Step A: 2-(5-amino-2-(furan-2-yl)-7H-pyrazolo[4,3-e][1,2,4]triazolo[1,5-c]pyrimidin-7-yl)-2-phenylpropanoyl chloride 40 mg of 2-(5-amino-2-(furan-2-yl)-7H-pyrazolo[4,3-e][1,2,4]triazolo[1,5-c]pyrimidin-7-yl)-2-phenylpropanoic acid in SOCl$_2$ (10 mL) was heated at 70° C. for 1 hour. The solution was concentrated to dryness. 20 mL of CH$_2$Cl$_2$ was added and the resulted mixture was concentrated again to remove the SOCl$_2$ residue to give the title product (45 mg, crude) as a light brown oil which was used for the next directly.

Step B: 2-(5-amino-2-(furan-2-yl)-7H-pyrazolo[4,3-e][1,2,4]triazolo[1,5-c]pyrimidin-7-yl)-2-phenyl-N-(pyridin-2-yl)propanamide To a stirred mixture of pyridin-2-amine (25 mg, 0.27 mmol) and DIEA (130 mg, 1.0 mmol) in CH$_2$Cl$_2$ (2 mL) was added a solution of 2-(5-amino-2-(furan-2-yl)-7H-pyrazolo[4,3-e][1,2,4]triazolo[1,5-c]pyrimidin-7-yl)-2-phenylpropanoyl chloride (45 mg, crude) in CH$_2$Cl$_2$ (3 mL) at rt and the mixture was stirred at rt for 16 hrs. The mixture was diluted with 10 mL of CH$_2$Cl$_2$, washed with NaHCO$_3$ (5 mL×2), brine (5 mL×2), dried over Na$_2$SO$_4$, concentrated and the resulted oil was purified by prep-TLC (EtOAc: 100%) to give the title product (8 mg, yield: 17%) after lyophilization. $^1$H NMR (400 MHz, CD$_3$OD/CDCl$_3$=2:1) δ 8.29 (s, 1H), 8.25-8.16 (m, 2H), 7.86 (t, J=8.8 Hz, 1H), 7.71 (d, J=0.8 Hz, 1H), 7.39-7.28 (m, 3H), 7.25 (d, J=3.6 Hz, 1H), 7.20-7.14 (m, 1H), 7.12-7.05 (m, 2H), 6.64 (dd, J=3.6, 2.0 Hz, 1H), 2.38 (s, 3H). MS: M/e 466 (M+1)$^+$.

Example 78: 2-(5-amino-2-(3-methylpyrazin-2-yl)-7H-pyrazolo[4,3-e][1,2,4]triazolo[1,5-c]pyrimidin-7-yl)-N-((3-hydroxyoxetan-3-yl)methyl)-2-phenylpropanamide

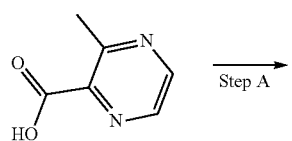

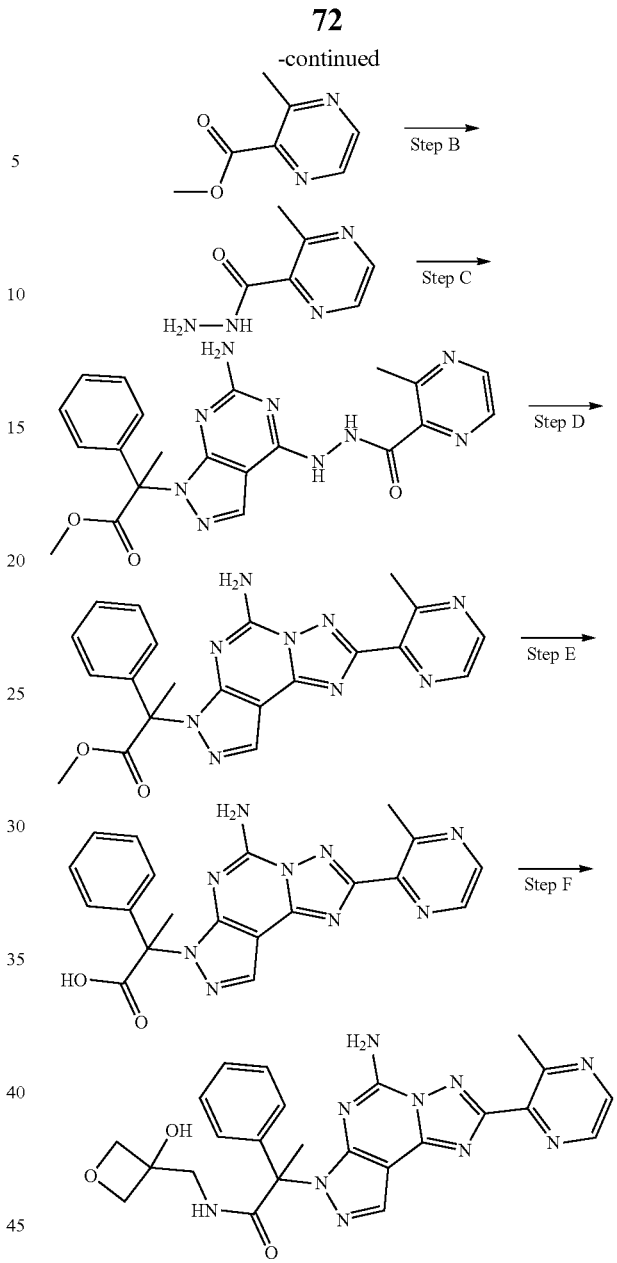

Step A: methyl 3-methylpyrazine-2-carboxylate

To a stirred solution of MeOH (50 mL) was added SOCl$_2$ (8.6 g, 72.4 mmol) dropwise at 0° C. Then 3-methylpyrazine-2-carboxylic acid (5 g, 36.2 mmol) was added to the reaction. The mixture was stirred at 60° C. overnight. The mixture was concentrated under reduced pressure and the residue was dissolved into EtOAc (50 mL). The organic phase was washed with saturated aq.NaHCO$_3$ (50 mL). The organic phase was washed with brine, dried over Na$_2$SO$_4$ and concentrated under reduced pressure. The residue was purified by silica gel chromatography (eluted with: EtOAc/PE=1/1) to afford the title compound as yellow solid (3.9 g, yield: 70.9%). MS: M/e 153 (M+1)$^+$.

Step B: 3-methylpyrazine-2-carbohydrazide

To a stirred solution of the product of Step A (0.9 g, 5.9 mmol) in MeOH (20 mL) was added hydrazine hydrate (1.5 g, 23.7 mmol) at RT. The mixture was stirred at 60° C. overnight.

The mixture was concentrated and the residue was dissolved into EtOAc (30 mL). The organic phase was washed with brine, dried over $Na_2SO_4$ and concentrated under reduced pressure. The residue (460 mg, yield: 51.1%) was used into next Step directly. MS: M/e 153 $(M+1)^+$.

Step C: methyl 2-(6-amino-4-(2-(3-methylpyrazine-2-carbonyl)hydrazinyl)-1H-pyrazolo[3,4-d]pyrimidin-1-yl)-2-phenylpropanoate A mixture of methyl 2-(6-amino-4-chloro-1H-pyrazolo[3,4-d]pyrimidin-1-yl)-2-phenylpropanoate (1 g, 3 mmol), the product of Step B (460 mg, 3 mmol) and $Et_3N$ (610 mg, 6 mmol) in DMSO (10 mL) was stirred at 100° C. overnight. The reaction was cooled to RT. The mixture was poured into water (30 mL). The precipitate was formed from the system. After stirring at RT for 30 mins, the mixture was filtered. The solid was collected and dried in air. The yellow solid (1.6 g, crude) was used into next Step directly. MS: M/e 448 $(M+1)^+$.

Step D: methyl 2-(5-amino-2-(3-methylpyrazin-2-yl)-7H-pyrazolo[4,3-e][1,2,4]triazolo[1,5-c]pyrimidin-7-yl)-2-phenylpropanoate A mixture of the product of Step C (1 g, 2.2 mmol) in BSA (5 mL) and HMDS (5 mL) was stirred at 100° C. overnight. The reaction was cooled to RT and concentrated under reduced pressure. The residue was dissolved into $H_2O$ (10 mL) and MeOH (10 mL). The mixture was stirred at 80° C. for 2 hours. MeOH was removed and the solid was precipitated from the system. The solid was filtered and dried in air. The brown solid (300 mg, yield for two Steps: 37.5%) was used into next Step directly. MS: M/e 430 $(M+1)^+$.

Step E: 2-(5-amino-2-(3-methylpyrazin-2-yl)-7H-pyrazolo[4,3-e][1,2,4]triazolo[1,5-c]pyrimidin-7-yl)-2-phenylpropanoic acid To a stirred solution of the product of Step D in MeOH (6 mL) was added aq.NaOH (2 mL) at RT. The mixture was stirred at RT overnight. The solvents were removed and the residue was dissolved into water (20 mL). The mixture was acidified to pH=3~4 with aq. HCl (2M). The solid was precipitated from the system. The mixture was filtered and the solid was collected. The white solid was dried in air and used into next Step directly. MS: M/e 416 $(M+1)^+$.

Step F: 2-(5-amino-2-(3-methylpyrazin-2-yl)-7H-pyrazolo[4,3-e][1,2,4]triazolo[1,5-c]pyrimidin-7-yl)-N-((3-hydroxyoxetan-3-yl)methyl)-2-phenylpropanamide A mixture of 3-(aminomethyl)oxetan-3-ol (33 mg, 0.32 mmol), 2-(5-amino-2-(3-methylpyrazin-2-yl)-7H-pyrazolo[4,3-e][1,2,4]triazolo[1,5-c]pyrimidin-7-yl)-2-phenylpropanoic acid (89 mg, 0.21 mmol), HATU (102 mg, 0.26 mmol) and DIPEA (0.1 mL) in DMF (5 mL) was stirred at 0° C. for 2 hours. Then the mixture was warmed to RT and stirred overnight. The reaction mixture was poured into water (10 mL) and extracted with EtOAc (15 mL×3). The combined organic layers were washed with brine, dried over $Na_2SO_4$ and concentrated under reduced pressure. The residue was purified by prep-TLC (EtOAc: 100%) to afford the title compound (15 mg, yield: 14.3%). $^1$H NMR (400 MHz, DMSO-d6) δ8.73-8.64 (m, 2H), 8.30 (s, 1H), 8.05 (br.s, 2H), 7.53-7.46 (m, 1H), 7.36-7.25 (m, 3H), 7.21-7.13 (m, 2H), 5.71 (s, 1H), 4.46-4.36 (m, 2H), 4.28 (t, J=8 Hz, 2H), 3.44 (t, J=8 Hz, 2H), 2.88 (s, 3H), 2.35 (s, 3H) ppm. MS: M/e 501 $(M+1)^+$.

Example 79: 2-(5-amino-2-(furan-2-yl)-7H-pyrazolo[4,3-e][1,2,4]triazolo[1,5-c]pyrimidin-7-yl)-N-(oxetan-3-ylmethyl)-2-phenylpropanamide A mixture of oxetan-3-ylmethanamine (13.4 mg, 0.15 mmol), 2-(5-amino-2-(furan-2-yl)-7H-pyrazolo[4,3-e][1,2,4]triazolo[1,5-c]pyrimidin-7-yl)-2-phenylpropanoic acid (40 mg, 0.1 mmol), HATU (43 mg, 0.11 mmol) and DIPEA (0.1 mL) in DMF (5 mL) was stirred at RT overnight. The reaction mixture was poured into water (15 mL) and extracted with EtOAc (15 mL×3). The combined organic layers were washed with brine, dried over $Na_2SO_4$ and concentrated under reduced pressure. The residue was purified by prep-TLC (EtOAc: 100%) to afford the title compound (18 mg, yield: 38.1%). $^1$H NMR (400 MHz, DMSO-d6) δ8.24 (s, 1H), 8.00 (br.s, 2H), 7.97-7.93 (m, 1H), 7.83 (t, J=8 Hz, 1H), 7.32-7.24 (m, 4H), 7.19-7.13 (m, 2H), 6.78-6.71 (m, 1H), 4.60-4.45 (m, 2H), 4.29-4.16 (m, 2H), 3.47-3.39 (m, 1H), 3.35-3.28 (m, 1H), 3.21-3.07 (m, 1H), 2.28 (s, 3H) ppm. MS: M/e 459 $(M+1)^+$.

Example 80: 2-(5-amino-2-(furan-2-yl)-7H-pyrazolo[4,3-e][1,2,4]triazolo[1,5-c]pyrimidin-7-yl)-N-((4-hydroxytetrahydro-2H-pyran-4-yl)methyl)-2-phenylpropanamide A mixture of 4-(aminomethyl)tetrahydro-2H-pyran-4-ol (20 mg, 0.15 mmol), 2-(5-amino-2-(furan-2-yl)-7H-pyrazolo[4,3-e][1,2,4]triazolo[1,5-c]pyrimidin-7-yl)-2-phenylpropanoic acid (40 mg, 0.1 mmol), HATU (43 mg, 0.11 mmol) and DIPEA (0.1 mL) in DMF (5 mL) was stirred at RT overnight. The reaction mixture was poured into water (15 mL) and extracted with EtOAc (15 mL×3). The combined organic layers were washed with brine, dried over $Na_2SO_4$ and concentrated under reduced pressure. The residue was purified by prep-TLC (EtOAc: 100%) to afford the title compound (22 mg, yield: 41.7%). $^1$H NMR (400 MHz, DMSO-d6) δ8.27 (s, 1H), 8.05-7.87 (m, 3H), 7.35-7.23 (m, 4H), 7.22-7.09 (m, 3H), 6.77-6.70 (m, 1H), 4.44 (s, 1H), 3.57-3.46 (m, 4H), 3.19-3.11 (m, 2H), 2.34 (s, 3H), 1.54-1.42 (m, 2H), 1.33-1.23 (m, 2H) ppm. MS: M/e 503 $(M+1)^+$.

Example 81: 2-(5-amino-2-(furan-2-yl)-7H-pyrazolo[4,3-e][1,2,4]triazolo[1,5-c]pyrimidin-7-yl)-N-(2-(methylamino)ethyl)-2-phenylpropanamide A mixture of $N^1$-methylethane-1,2-diamine (11.4 mg, 0.15 mmol), 2-(5-amino-2-(furan-2-yl)-7H-pyrazolo[4,3-e][1,2,4]triazolo[1,5-c]pyrimidin-7-yl)-2-phenylpropanoic acid (40 mg, 0.1 mmol), HATU (43 mg, 0.11 mmol) and DIPEA (0.1 mL) in DMF (5 mL) was stirred at RT overnight. The reaction mixture was poured into water (15 mL) and extracted with EtOAc (15 mL×3). The combined organic layers were washed with brine, dried over $Na_2SO_4$ and concentrated under reduced pressure. The residue was purified by prep-TLC (EtOAc: 100%) to afford the title compound (5 mg, yield: 10.9%). $^1$H NMR (400 MHz, DMSO-d6) δ8.28 (s, 1H), 8.01-7.90 (m, 1H), 7.88-7.80 (m, 1H), 7.33-7.21 (m, 4H), 7.14-7.06 (m, 2H), 6.79-6.69 (m, 1H), 3.37-3.26 (m, 2H), 2.96-2.74 (m, 2H), 2.45 (s, 3H), 2.30 (s, 3H) ppm. MS: M/e 446 $(M+1)^+$.

Example 82: 2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-phenylacetamide A mixture of 3-(aminomethyl)oxetan-3-ol (132 mg, 1.28 mmol), 2-(5-amino-2-(furan-2-yl)-7H-pyrazolo[4,3-e][1,2, 4]triazolo[1,5-c]pyrimidin-7-yl)-2-phenylpropanoic acid (400 mg, 1.07 mmol), HATU (43 mg, 1.07 mmol) and DIPEA (276 mg, 2.14 mmol) in DMF (20 mL) was stirred at RT overnight. The reaction mixture was poured into water (60 mL) and extracted with EtOAc (40 mL×3). The combined organic layers were washed with brine, dried over $Na_2SO_4$ and concentrated under reduced pressure. The residue was purified by silica gel chromatography (EtOAc: 100%) to afford the title compound (120 mg, yield: 24.4%). $^1$H NMR (400 MHz, DMSO-d6) δ8.24 (s, 1H), 8.17 (br.s, 2H), 8.09 (t, J=8 Hz, 1H), 7.98-7.91 (m, 1H), 7.44-7.30 (m, 5H), 7.24 (d, J=4 Hz, 1H), 6.74 (dd, J=4, 2 Hz, 1H), 6.48 (s, 1H), 5.86 (s, 1H), 4.42-4.29 (m, 4H), 3.51-3.42 (m, 2H) ppm. MS: M/e 461 (M+1)$^+$.

Example 82 was separated into two enantiomeric stereoisomers (Example 82A, earlier peak, and Example 82B, later peak) by chiral prep-HPLC. The chiral separation conditions are shown below.

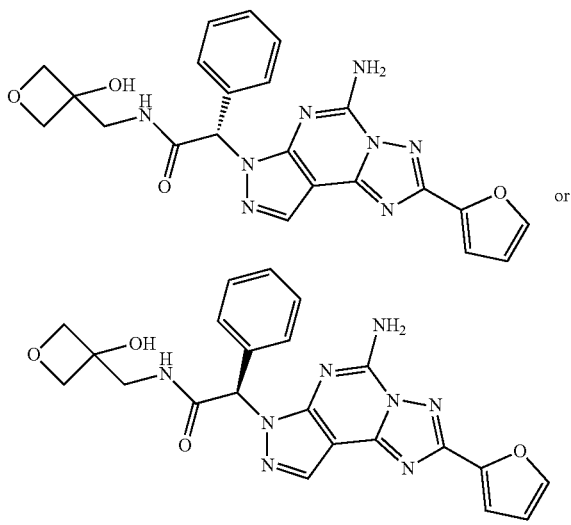

| Column | CHIRALPAK IA |
|---|---|
| Column size | 2 cm × 15 cm, 5 um |
| Injection | 0.5 ml |
| Mobile phase | Hex:ETOH = 50:50 |
| Flow rate | 20 ml/min |
| Wave length | UV 220 nm |
| Temperature | 25° C. |
| Sample solution | 12.5 mg/ml in EtOH:DCM = 3:1 |
| Prep-HPLC equipment | Prep-HPLC-Gilson |

Example 83: 2-(5-amino-2-(furan-2-yl)-7H-pyrazolo[4,3-e][1,2,4]triazolo[1,5-c]pyrimidin-7-yl)-2-phenyl-N-(pyridin-4-ylmethyl)propenamide A mixture of 2-(5-amino-2-(furan-2-yl)-7H-pyrazolo[4,3-e][1,2,4]triazolo[1,5-c]pyrimidin-7-yl)-2-phenylpropanoic acid (38.9 mg, 0.1 mmol), pyridin-4-ylmethanamine (10 mg, 0.1 mmol), HATU (45 mg, 0.12 mmol) and DIPEA (25.8 mg, 0.2 mmol) in DMF (3 mL) was stirred overnight. The reaction mixture was poured into $H_2O$ (10 mL) and extracted with EtOAc (10 mL×3). The combined organic layers were washed with brine, dried over $Na_2SO_4$, concentrated and purified by prep-TLC (petroleum ether/EtOAc=1: 2) to give the target compound (26 mg, 54.2%). $^1$H NMR (400 MHz, DMSO-d6) δ 8.47 (d, J=6.0 Hz, 2H), 8.26 (s, 1H), 8.21 (d, J=5.6 Hz, 1H), 8.08 (s, 2H), 7.97-7.93 (m, 1H), 7.42-7.14 (m, 8H), 6.77-6.71 (m, 1H), 4.41-4.29 (m, 2H), 2.38 (s, 3H) ppm. MS: M/e 480 (M+1)$^+$.

Example 84: 2-(5-amino-2-(furan-2-yl)-7H-pyrazolo[4,3-e][1,2,4]triazolo[1,5-c]pyrimidin-7-yl)-2-phenyl-N-(pyridin-3-ylmethyl)propenamide A mixture of 2-(5-amino-2-(furan-2-yl)-7H-pyrazolo[4,3-e][1,2,4]triazolo[1,5-c]pyrimidin-7-yl)-2-phenylpropanoic acid (38.9 mg, 0.1 mmol), pyridin-3-ylmethanamine (10 mg, 0.1 mmol), HATU (45 mg, 0.12 mmol) and DIPEA (25.8 mg, 0.2 mmol) in DMF (3 mL) was stirred overnight. The reaction mixture was poured into $H_2O$ (10 mL) and extracted with EtOAc (10 mL×3). The combined organic layers were washed with brine, dried over $Na_2SO_4$, concentrated and purified by prep-TLC (petroleum ether/EtOAc=1: 2) to give the target compound (22 mg, 45.9%). $^1$H NMR (400 MHz, DMSO-d6) δ 8.53-8.49 (m, 1H), 8.42 (dd, J=5.2, 2.8 Hz, 1H), 8.25-8.19 (m, 2H), 8.02 (s, 2H), 7.95 (s, 1H), 7.73 (m, 1H), 7.37-7.15 (m, 7H), 6.77-6.69 (m, 1H), 4.44-4.29 (m, 2H), 2.35 (s, 3H) ppm. MS: M/e 480 (M+1)$^+$.

Example 85: 2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-(m-tolyl)propanamide

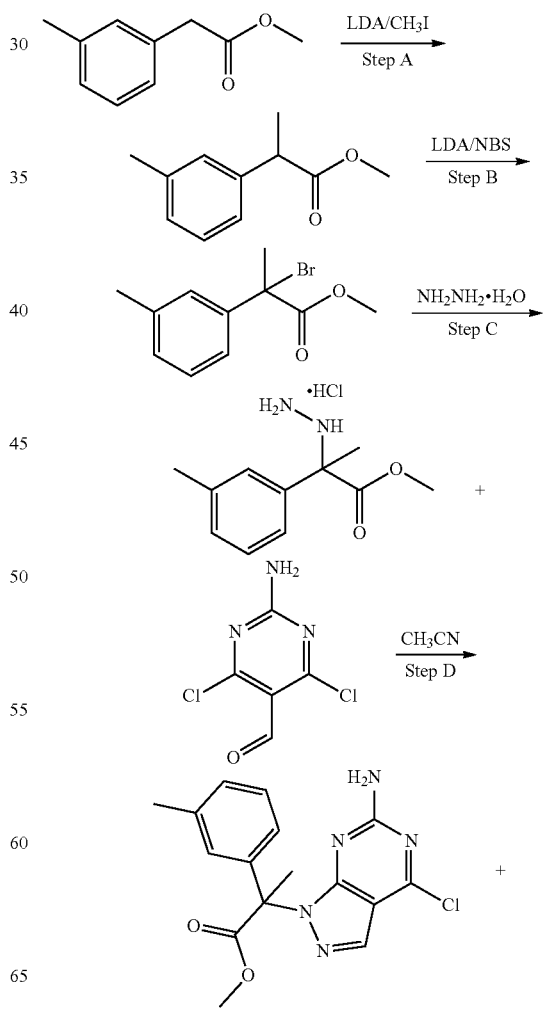

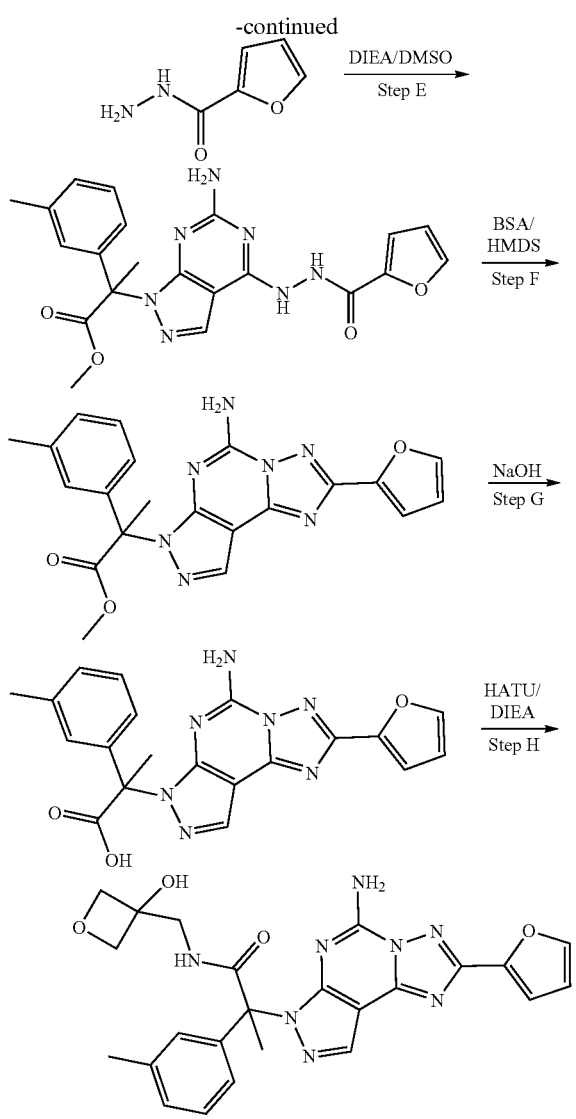

Step A: methyl 2-(m-tolyl)propanoate

To a cooled solution of lithium diisopropylamide (LDA) (2M in THF, 10 mL, 20 mmol) in THF (60 mL) at −78° C. under N$_2$ atmosphere was added with a solution of methyl 2-(m-tolyl)acetate (3 g, 18 mmol) in THF (5 mL) dropwise. After additional, the solution was stirred for a further 20 mins before CH$_3$I (7.8 g, 55 mmol) was added dropwise. The mixture was allowed to warm to rt for 2 hrs. TLC showed the reaction was complete. The reaction mixture was quenched with water (5 mL), extracted with ethyl acetate (30 mL) and washed with brine (20 mL). The organic layer was dried, concentrated and purified by column chromatography (PE:EtOAc=50:1) to get the product as an colorless oil (2.6 g, 81%). $^1$H NMR (400 MHz, CDCl$_3$) δ 7.26-7.20 (m, 1H), 7.11-7.07 (m, 3H), 3.70-3.68 (m, 1H), 3.66 (s, 3H), 2.35 (s, 3H), 1.49 (d, J=8.0 Hz, 3H) ppm.

Step B: methyl 2-bromo-2-(m-tolyl)propanoate

To a cooled solution of lithium diisopropylamide (LDA) (2M in THF, 3.1 mL, 6.2 mmol) in THF (30 mL) at −78° C. under N$_2$ atmosphere was added with a solution of methyl 2-(m-tolyl) propanoate (1 g, 5.6 mmol) in THF (2 mL) dropwise. The solution was stirred for a further 30 mins before the dropwise addition of trimethyl chlorosilane (TMSCl) (671 mg, 6.2 mmol). The mixture was allowed to warm to rt for 2 hrs before being cooled to −78° C. NBS (2 g, 11.2 mmol) was added in portions and the solution was stirred at −78° C. for 1 hr. The reaction mixture was allowed to reach to rt over 1 hr, then quenched with saturated NaHCO$_3$ solution, and extracted with ethyl acetate (20 mL). The organic layer was dried, concentrated and purified by column chromatography (PE:EtOAc=50:1) to get the product (1 g, 70%).

Step C: methyl 2-hydrazinyl-2-(m-tolyl)propanoate

NH$_2$NH$_2$.H$_2$O (625 mg, 10 mmol) was added to a solution of methyl 2-bromo-2-(m-tolyl)propanoate (500 mg, 2 mmol) in CH$_3$CN (5 mL). The reaction mixture was heated at 60° C. for 1 hr. TLC showed the reaction was complete. The solution was concentrated, added with water (10 mL) and extracted with ethyl acetate (10 mL). The organic phase was concentrated, added with HCl/EtOAc (2 M, 2 mL) and evaporated to get the product as HCl salt (380 mg, 80%). MS: M/e 209 (M+1)$^+$.

Step D: methyl 2-(6-amino-4-chloro-1H-pyrazolo[3,4-d]pyrimidin-1-yl)-2-(m-tolyl)propanoate A mixture of methyl 2-hydrazinyl-2-(m-tolyl)propanoate hydrochloride (380 mg, 1.5 mmol) and 2-amino-4,6-dichloropyrimidine-5-carbaldehyde (300 mg, 1.5 mmol) in CH$_3$CN (10 mL) was stirred at rt overnight, and then heated at 50° C. for 3 hrs. The reaction mixture was evaporated, added with water (10 mL) and extracted with ethyl acetate (10 mL). The organic phase was dried, concentrated and further purified by column chromatography (PE:EtOAc=6:1) to get the desired product as a white solid (300 mg, 56%). MS: M/e 346 (M+1)$^+$ Step E: methyl 2-(6-amino-4-(2-(furan-2-carbonyl) hydrazinyl)-1H-pyrazolo[3,4-d]pyrimidin-1-yl)-2-(m-tolyl)propanoate A mixture of methyl 2-(6-amino-4-chloro-1H-pyrazolo[3,4-d]pyrimidin-1-yl)-2-(m-tolyl)propanoate (300 mg, 0.87 mmol), furan-2-carbohydrazide (109 mg, 0.87 mmol) and DIPEA (225 mg, 1.74 mmol) in DMSO (10 mL) was heated at 120° C. overnight. The solvent was evaporated under oil pump. The residue was added with water (10 mL), slurried and filtered. The cake was washed with water, dried to get the crude product, which was used in the next Step directly (260 mg, 68%). MS: M/e 436 (M+1)$^+$ Step F: methyl 2-(5-amino-2-(furan-2-yl)-7H-pyrazolo[4,3-e][1,2,4]triazolo[1,5-c]pyrimidin-7-yl)-2-(m-tolyl)propanoate A solution of methyl 2-(6-amino-4-(2-(furan-2-carbonyl) hydrazinyl)-1H-pyrazolo[3,4-d]pyrimidin-1-yl)-2-(m-tolyl) propanoate (260 mg, 0.60 mmol) in BSA (2 mL) and HMDS (2 mL) was heated at 120° C. for 3 hrs. The solvent was evaporated under oil pump. The residue was added with water (5 mL), extracted with ethyl acetate (10 mL) and washed with brine (10 mL). The organic layer was dried, concentrated and purified by column chromatography (PE:EtOAc=5:1) to get the desired product as a white solid (110 mg, 44%). MS: M/e 418 (M+1)$^+$ Step G: 2-(5-amino-2-(furan-2-yl)-7H-pyrazolo[4,3-e][1,2,4]triazolo[1,5-c]pyrimidin-7-yl)-2-(m-tolyl) propanoic acid NaOH solution (50 mg, 1.25 mmol, in 1 mL of water) was added to a solution of methyl 2-(5-amino-2-(furan-2-yl)-7H- pyrazolo[4,3-e][1,2,4]triazolo[1,5-c]pyrimidin-7-yl)-2-(m-tolyl)propanoate (110 mg, 0.26 mmol) in methanol (5 mL). The solution was stirred at rt overnight. The solvent was evaporated. The residue was added with water (5 mL), acidified with 2 M HCl to pH=2~3. The precipitated solid was filtered and dried to get the product as a white solid (40 mg, 38%). MS: M/e 404 (M+1)⁺

Step H: 2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-(m-tolyl)propanamide A mixture of 2-(5-amino-2-(furan-2-yl)-7H-pyrazolo[4,3-e][1,2,4]triazolo[1,5-c]pyrimidin-7-yl)-2-(m-tolyl)propanoic acid (50 mg, 0.12 mmol), 3-(amino methyl)oxetan-3-ol (19 mg, 0.18 mmol), HATU (69 mg, 0.18 mmol) and DIPEA (31 mg, 0.24 mmol) in DMF (5 mL) was stirred at rt for 2 hrs. The solution was added with water (5 mL), extracted with ethyl acetate (10 mL) and washed with brine (10 mL). The organic layer was dried, concentrated and purified by preparative TLC (EtOAc) to get the desired product (25 mg, 42%). ¹H NMR (400 MHz, DMSO-d6) δ 8.24 (s, 1H), 7.95 (br.s, 3H), 7.43 (t, J=8.0 Hz, 1H), 7.25 (d, J=4.0 Hz, 1H), 7.18 (t, J=8.0 Hz, 1H), 7.11 (s, 1H), 7.08 (br.s, 1H), 6.90 (d, J=8.0 Hz, 1H), 6.74 (d=4.0 Hz, 1H), 5.72 (s, 1H), 4.40 (t, J=8.0 Hz, 2H), 4.30-4.26 (m, 2H), 3.43 (t, J=8.0 Hz, 2H), 2.27 (s, 3H), 2.08 (s, 3H) ppm. MS: M/e 489 (M+1)⁺

Example 86: 2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-(4-methoxyphenyl)propanamide

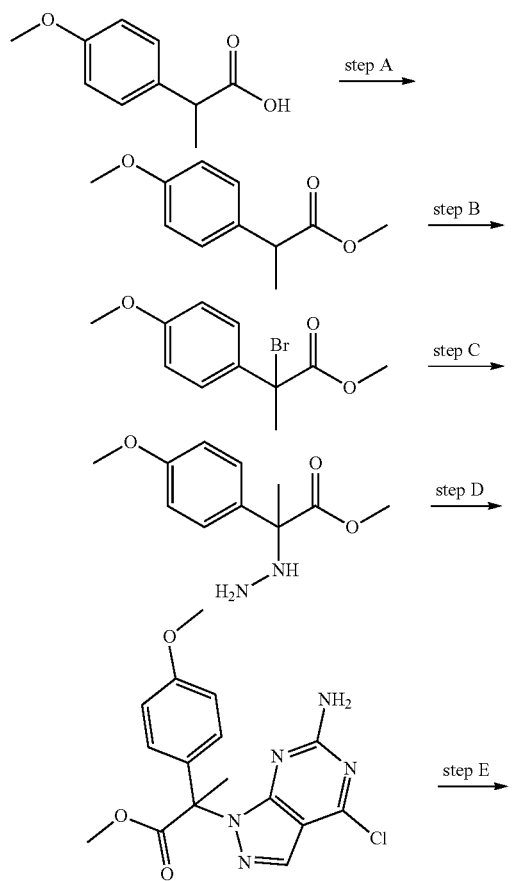

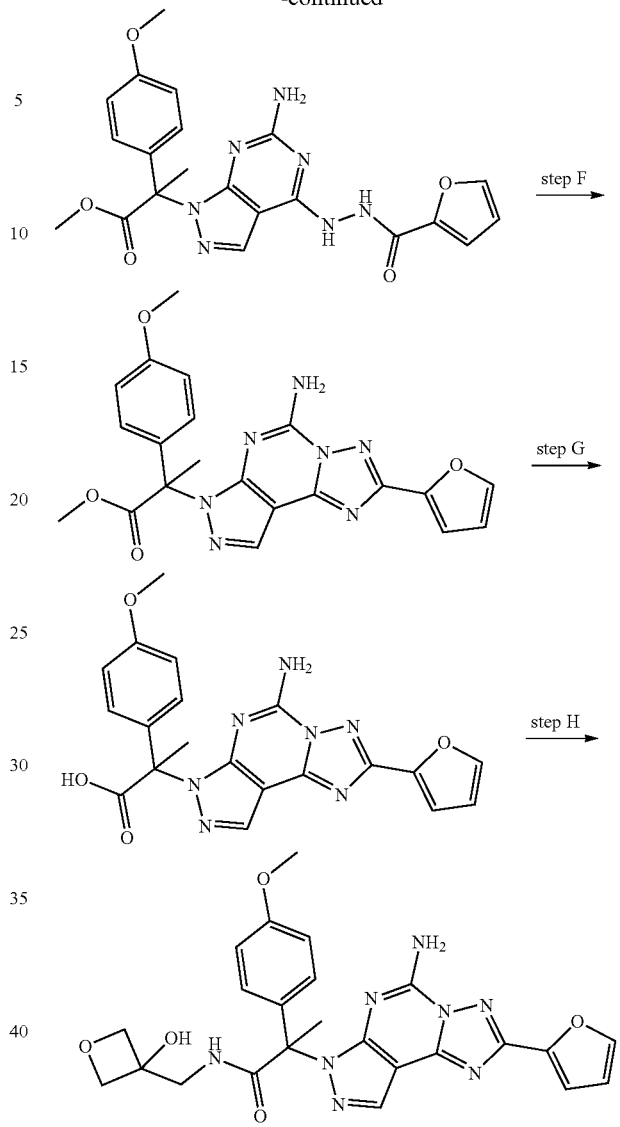

Step A: methyl 2-(4-methoxyphenyl)propanoate

To a solution of 2-(4-methoxyphenyl)propanoic acid (5 g, 27.78 mmol) in MeOH (15 mL), sulfoxide chloride (4.96 g, 41.67 mmol) was added dropwise at 0° C., After addition, the reaction mixture was stirred at rt for 3 h. The mixture was concentrated, quenched with ice water (20 mL), extracted with EtOAc (30 mL×3). The combined organic layers were washed with brine, dried over Na₂SO₄, concentrated and purified by column chromatography (petroleum ether/EtOAc=20:1~5:1) to give methyl 2-(4-methoxyphenyl)propanoate (5.20 g, 96.49%) as yellow oil. MS: M/e 195 (M+1)⁺.

Step B: methyl 2-bromo-2-(4-methoxyphenyl)propanoate

To a solution of methyl 2-(4-methoxyphenyl)propanoate (5.20 g, 26.80 mmol) in THF (20 mL) was added lithium diisopropylamide (LDA) (20 mL, 40.21 mmol) dropwise at −78° C. and stirred for 1 h. Then the reaction mixture was added trimethyl chlorosilane (TMSCl) (3.51 g, 32.16 mmol)

dropwise at −78° C. and stirred for 1 h. Then the reaction mixture was added NBS (7.16 g, 40.21 mmol) at −78° C. and stirred for 1 h. After addition, the reaction mixture was warmed slowly to rt and stirred for 2 h. The mixture was filtered, the filtrate was concentrated and washed with PE and filtered, the filtrate was concentrated to give methyl 2-bromo-2-(4-methoxyphenyl)propanoate (4.31 g, 58.90%) as yellow oil. $^1$H NMR (400 MHz, DMSO-d6) δ 7.22 (d, J=8.6 Hz, 2H), 6.87 (d, J=2.7 Hz, 2H), 3.65 (s, 3H), 2.67 (s, 3H), 2.30 (s, 3H).

Step C: methyl 2-hydrazinyl-2-(4-methoxyphenyl)propanoate

A mixture of methyl 2-bromo-2-(4-methoxyphenyl)propanoate (4.31 g, 15.79 mmol), hydrazinium hydroxide (3.95 g, 63.15 mmol) in ACN (20 mL) was stirred at 60° C. overnight. The mixture was extracted with DCM (30 mL×3). The combined organic layers were washed with water (10 mL×3) and brine, dried over $Na_2SO_4$, concentrated to give methyl 2-hydrazinyl-2-(4-methoxyphenyl)propanoate (2.36 g, 66.73%) as brown oil. MS: M/e 225 (M+1)$^+$.

Step D: methyl 2-(6-amino-4-chloro-1H-pyrazolo[3,4-d]pyrimidin-1-yl)-2-(4-methoxyphenyl)propanoate A mixture of methyl 2-hydrazinyl-2-(4-methoxyphenyl)propanoate (2.36 g, 10.54 mmol), 2-amino-4,6-dichloro-1,6-dihydropyrimidine-5-carbaldehyde (2.01 g, 10.54 mmol) in ACN (10 mL) was stirred at rt overnight, then warmed to 70° C. and stirred for 2 h. The reaction mixture was poured into $H_2O$ (10 mL) and extracted with EtOAc (10 mL×3). The combined organic layers were washed with brine, dried over $Na_2SO_4$, concentrated and purified by column chromatography (petroleum ether/EtOAc=10:1~2:1) to give the product (2.10 g, 55.06%) as yellow solid. MS: M/e 362 (M+1)$^+$.

Step E: methyl 2-(6-amino-4-(2-(furan-2-carbonyl)hydrazinyl)-1H-pyrazolo[3,4-d]pyrimidin-1-yl)-2-(4-methoxyphenyl)propanoate A mixture of methyl 2-(6-amino-4-chloro-1H-pyrazolo[3,4-d]pyrimidin-1-yl)-2-(4-methoxyphenyl)propanoate (2.10 g, 5.801 mmol), furan-2-carbohydrazide (1.46 g, 11.60 mmol), DIPEA (2.24 g, 17.40 mmol) in DMSO (5 mL) was stirred at 120° C. overnight. The reaction mixture was poured into $H_2O$ (10 mL) and extracted with EtOAc (20 mL×3). The combined organic layers were washed with brine, dried over $Na_2SO_4$, concentrated and purified by column chromatography (petroleum ether/EtOAc=10:1~1:1) to give the product (2.01 g, 76.83%) as yellow solid. MS: M/e 452 (M+1)$^+$.

Step F: methyl 2-(5-amino-2-(furan-2-yl)-7H-pyrazolo[4,3-e][1,2,4]triazolo[1,5-c]pyrimidin-7-yl)-2-(4-methoxyphenyl)propanoate A mixture of methyl 2-(6-amino-4-(2-(furan-2-carbonyl)hydrazinyl)-1H-pyrazolo[3,4-d]pyrimidin-1-yl)-2-(4-methoxyphenyl)propanoate (2.01 g, 4.457 mmol), trimethylsilyl (E)-N-(trimethylsilyl)acetamidate (3 mL), HMDS (3 mL) was stirred at 120° C. overnight. The reaction mixture was concentrated, stirred in MeOH (10 mL) and water (2 mL) at 50° C. for 1 h. Then concentrated and purified by column chromatography (petroleum ether/EtOAc=10:1~1:1) to give the product (1.66 g, 86.02%) as white solid. MS: M/e 434 (M+1)$^+$.

Step G: 2-(5-amino-2-(furan-2-yl)-7H-pyrazolo[4,3-e][1,2,4]triazolo[1,5-c]pyrimidin-7-yl)-2-(4-methoxyphenyl)propanoic acid A mixture of methyl 2-(5-amino-2-(furan-2-yl)-7H-pyrazolo[4,3-e][1,2,4]triazolo[1,5-c]pyrimidin-7-yl)-2-(4-methoxyphenyl)propanoate (1.66 g, 3.834 mmol), lithium hydroxide (1.53 g, 38.34 mmol) in MeOH (5 mL) and water (2 mL) was stirred at 50° C. overnight. The reaction mixture was acidified with hydrochloric acid, extracted with EtOAc (20 mL×3). The combined organic layers were washed with brine, dried over $Na_2SO_4$, concentrated and purified by column chromatography (petroleum ether/EtOAc=10:1~1:2) to give the product (1.33 g, 82.80%) as a white solid. MS: M/e 420 (M+1)$^+$.

Step H: 2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-(4-methoxyphenyl)propanamide A mixture of 2-(5-amino-2-(furan-2-yl)-7H-pyrazolo[4,3-e][1,2,4]triazolo[1,5-c]pyrimidin-7-yl)-2-(4-methoxyphenyl)propanoic acid (100 mg, 0.2387 mmol), 3-(aminomethyl)oxetan-3-ol (49 mg, 0.4773 mmol), HATU (181 mg, 0.4773 mmol), DIPEA (92 mg, 0.7160 mmol) in DMF (3 mL) was stirred at rt overnight. The reaction mixture was poured into $H_2O$ (10 mL) and extracted with EtOAc (15 mL×3). The combined organic layers were washed with brine, dried over $Na_2SO_4$, concentrated and purified by column chromatography (DCM/MeOH=40:1~10:1) to give the product (70 mg, 58.19%). $^1$H NMR (400 MHz, DMSO-d6) δ 8.22 (s, 1H), 7.96 (s, 1H), 7.93 (s, 2H), 7.42 (t, J=5.5 Hz, 1H), 7.24 (d, J=2.7 Hz, 1H), 7.13 (d, J=8.7 Hz, 2H), 6.86 (d, J=8.6 Hz, 2H), 6.77-6.71 (m, 1H), 5.75 (s, 1H), 4.41 (t, J=6.3 Hz, 2H), 4.28 (dd, J=10.4, 6.5 Hz, 2H), 3.73 (s, 3H), 3.42 (d, J=5.6 Hz, 2H), 2.31 (s, 3H). MS: M/e 505 (M+1)$^+$.

Example 87: 2-(5-amino-2-(furan-2-yl)-7H-pyrazolo[4,3-e][1,2,4]triazolo[1,5-c]pyrimidin-7-yl)-2-(2-fluorophenyl)-N-((3-hydroxyoxetan-3-yl)methyl)propanamide A mixture of 2-(5-amino-2-(furan-2-yl)-7H-pyrazolo[4,3-e][1,2,4]triazolo[1,5-c]pyrimidin-7-yl)-2-(2-fluorophenyl)propanoic acid (100 mg, 0.2457 mmol), 3-(aminomethyl)oxetan-3-ol (38 mg, 0.3685 mmol), HATU (146 mg, 0.3685 mmol), DIPEA (95 mg, 0.73712 mmol) in DMF (3 mL) was stirred at rt for 3 hours. The reaction mixture was poured into $H_2O$ (5 mL) and extracted with EtOAc (5 mL×3). The combined organic layers were washed with brine, dried over $Na_2SO_4$, concentrated and purified by column chromatography (DCM/MeOH=40:1~10:1) to give the product (82 mg, 67.83%). $^1$H NMR (400 MHz, DMSO-d6) δ 8.26 (s, 1H), 8.00 (s, 2H), 7.96 (s, 1H), 7.44 (t, J=5.7 Hz, 1H), 7.38 (dd, J=12.7, 7.2 Hz, 1H), 7.25 (d, J=3.1 Hz, 1H), 7.20 (dd, J=11.8, 8.4 Hz, 1H), 7.10 (t, J=7.6 Hz, 1H), 6.80-6.65 (m, 2H), 5.69 (s, 1H), 4.36 (d, J=6.3 Hz, 1H), 4.33 (d, J=6.3 Hz, 1H), 4.27 (d, J=6.3 Hz, 1H), 4.21 (d, J=6.3 Hz, 1H), 3.52 (dd, J=13.5, 6.3 Hz, 1H), 3.37 (d, J=5.4 Hz, 1H), 2.44 (s, 3H). MS: M/e 493 (M+1)$^+$.

Example 88: 2-(5-amino-2-(furan-2-yl)-7H-pyrazolo[4,3-e][1,2,4]triazolo[1,5-c]pyrimidin-7-yl)-N-((1-hydroxycyclopropyl)methyl)-2-phenylpropanamide A mixture of 1-(aminomethyl)cyclopropan-1-ol (23.8 mg, 0.19 mmol), 2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), HATU (54 mg, 0.14 mmol) and DIPEA (33 mg, 0.26 mmol) in DMF (10 mL) was stirred at RT overnight. The reaction mixture was poured into water (10 mL) and the solid was precipitated from the system. The solid was filtered and purified by prep-TLC (EtOAc: 100%) to afford the title compound (5 mg, yield: 8.4%). ¹H NMR (400 MHz, DMSO-d6) δ8.22 (s, 1H), 8.02-7.88 (m, 3H), 7.76 (s, 1H), 7.35-7.21 (m, 4H), 7.16-7.04 (m, 2H), 6.79-6.68 (m, 1H), 4.56 (t, J=4 Hz, 1H), 3.64-3.53 (m, 1H), 3.48-3.38 (m, 1H), 2.25 (s, 3H), 0.77-0.62 (m, 3H), 0.60-0.46 (m, 1H) ppm. MS: M/e 459 (M+1)⁺.

Example 89: 2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-(pyridin-3-yl)propanamide

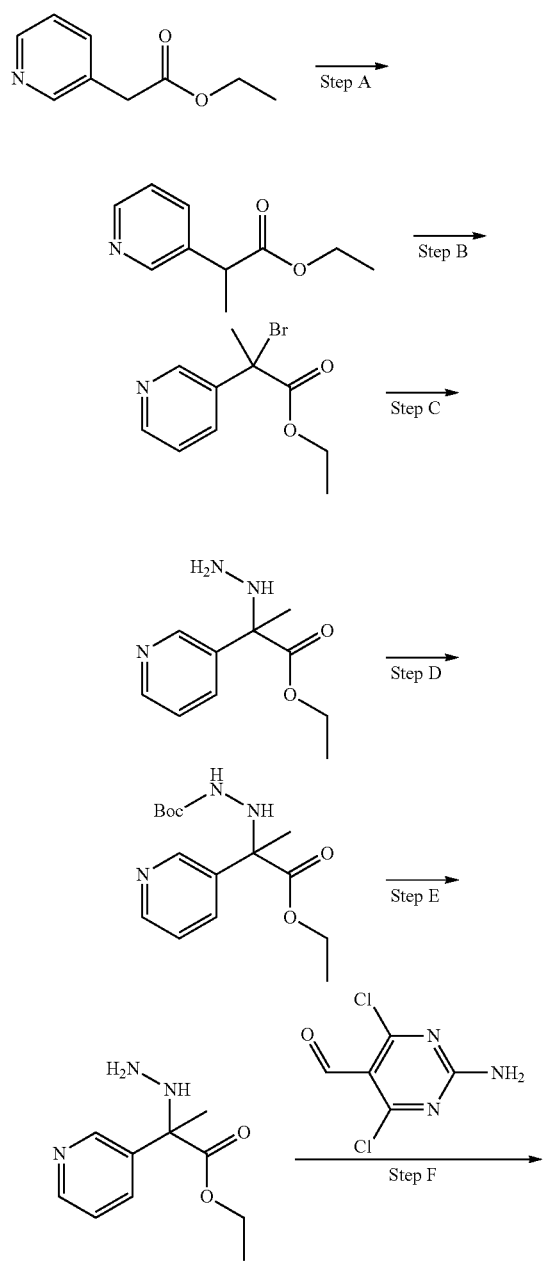

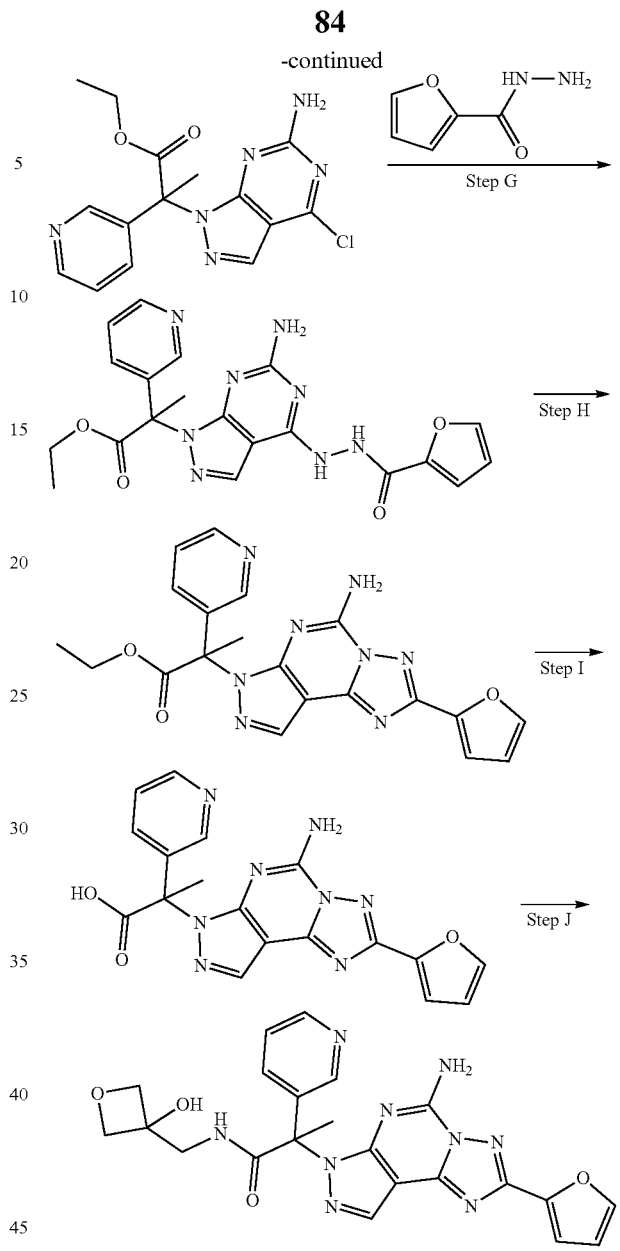

Step A: ethyl 2-(pyridin-3-yl)propanoate

To a stirred solution of ethyl 2-(pyridin-3-yl)acetate (13.7 g, 85 mmol) in 150 mL of THF was added LDA (47 mL, 2.0 M) at −78° C. under N₂. The resulted mixture was stirred for 30 min. MeI (32.0 g, 225 mmol) was added in drops. The reaction mixture was allowed warm to rt and stirred for 20 hrs. The mixture was quenched with 150 mL of H₂O, extracted with EtOAc (150 mL×3). The organic extracts were combined, washed with brine (150 mL×2), dried over Na₂SO₄ and concentrated. The residue was purified by column chromatography eluted with PE/EtOAc (5:1~3:1) to give the title product (8.1 g, 53%) as a light-yellow oil. MS: M/e 180 (M+1)⁺.

Step B: ethyl 2-bromo-2-(pyridin-3-yl)propanoate

To a stirred solution of ethyl 2-(pyridin-3-yl)propanoate (8.1 g, 45.2 mmol) in THF (100 mL) was added LDA (25 mL, 2.0 M) at −78° C. under N₂. The resulted was stirred for 30 min. TMSCl (5.4 g, 50 mmol) was added and the resulted mixture was stirred at rt for 1 hour. After been cooled to −78° C. again, the mixture was added NBS (12.0 g, 67 mmol). The resulted mixture was stirred at −78° C. for 30 min, and stirred at rt for 2 hrs. The mixture was quenched with 100 mL of H$_2$O extracted with EtOAc (100 mL×3). The organic extracts were combined, washed with brine (100 mL×2), dried over Na$_2$SO$_4$ and concentrated to dryness to give the title product (9.8 g, crude) as a brown oil which was used for the next Step directly. $^1$H NMR (400 MHz, CDCl$_3$) δ 8.80 (d, J=2.4 Hz, 1H), 8.56 (dd, J=4.8, 1.2 Hz, 1H), 7.96 (ddd, J=8.0, 2.4, 1.6 Hz, 1H), 7.31 (dd, J=8.0, 4.8 Hz, 1H), 4.31-4.23 (m, 2H), 2.33 (s, 3H), 1.28 (t, J=7.2 Hz, 3H).

Step C: ethyl 2-hydrazinyl-2-(pyridin-3-yl)propanoate

To a stirred solution of ethyl 2-bromo-2-(pyridin-3-yl)propanoate (9.8 g, crude) in MeCN (100 mL) was added hydrazine hydrate (20 mL, 320 mmol) at rt and the resulted mixture was stirred at 50° C. for 16 hrs. The mixture was treated with 100 mL of EtOAc and 100 mL of brine. Aqueous layer was extracted with EtOAc (100 mL×3). The combined organics were washed with brine (100 mL×2), dried over Na$_2$SO$_4$, and concentrated to dryness to give the title product (7.8 g, crude) as a brown oil. MS: M/e 210 (M+1)$^+$.

Step D: tert-butyl 2-(1-ethoxy-1-oxo-2-(pyridin-3-yl)propan-2-yl)hydrazine-1-carboxylate To a mixture of ethyl 2-hydrazinyl-2-(pyridin-3-yl)propanoate (7.8 g, crude) and Et$_3$N (12.0 g, 120 mmol) in CH$_2$Cl$_2$ (100 mL) was added Boc$_2$O (9.5 g, 43.5 mmol) in drops at 0° C. and the resulted mixture was stirred at rt for 3 hrs. The mixture was concentrated and the resulted residue was purified by column chromatography eluted with PE/EtOAc (2:1~1:1) to give the title product (3.05 g, 22% for 3 Steps) as a brown oil. MS: M/e 310 (M+1)$^+$.

Step E: ethyl 2-hydrazinyl-2-(pyridin-3-yl)propanoate hydrochloride

To a stirred solution of tert-butyl 2-(1-ethoxy-1-oxo-2-(pyridin-3-yl)propan-2-yl)hydrazine-1-carboxylate (3.05 g, 9.8 mmol) in EtOAc (20 mL) was added HC/Dioxane (20 mL, 4M), and the resulted mixture was stirred at rt for 40 hrs. The mixture was concentrated to dryness to give the title product (2.7 g, yield: 95%) as a brown solid. MS: M/e 210 (M+1)$^+$.

Step F: ethyl 2-(6-amino-4-chloro-H-pyrazolo[3,4-d]pyrimidin-1-yl)-2-(pyridin-3-yl)propanoate A mixture of ethyl 2-hydrazinyl-2-(pyridin-3-yl)propanoate hydrochloride (550 mg, 2.24 mmol) and 2-amino-4,6-dichloropyrimidine-5-carbaldehyde (430 mg, 2.25 mmol) in POCl$_3$ (10 mL) was stirred at 60° C. for 4 hrs. The resulted mixture was concentrated to dryness and the resulted oil was diluted with 20 mL of EtOAc, treated with aqueous solution of Na$_2$CO$_3$, washed with brine (10 mL×2), dried over Na$_2$SO$_4$, and concentrated. The resulted residue was purified by column chromatography (PE/EtOAc=3:1~1:1) to give the title product (180 mg, 23%) as a light yellow solid. MS: We 347 (M+1)$^+$.

Step G: ethyl 2-(6-amino-4-(2-(furan-2-carbonyl)hydrazinyl)-1H-pyrazolo[3,4-d]pyrimidin-1-yl)-2-(pyridin-3-yl)propanoate A mixture of ethyl 2-(6-amino-4-chloro-1H-pyrazolo[3,4-d]pyrimidin-1-yl)-2-(pyridin-3-yl)propanoate (25 mg, 0.072 mmol), furan-2-carbohydrazide (20 mg, 0.158 mmol) and DIEA (50 mg, 0.387 mmol) in DMSO (1 mL) was heated at 110° C. for 4 hrs. The mixture was diluted with 20 mL of EtOAc, washed with brine (5 mL×3), dried over Na$_2$SO$_4$, and concentrated. The resulted residue was purified by prep-TLC (EtOAc/MeOH=30:1) to give the title product (15 mg, crude) as a light brown solid. MS: We 437 (M+1)$^+$.

Step H: ethyl 2-(5-amino-2-(furan-2-yl)-7H-pyrazolo[4,3-e][1,2,4]triazolo[1,5-c]pyrimidin-7-yl)-2-(pyridin-3-yl)propanoate A mixture of ethyl 2-(6-amino-4-(2-(furan-2-carbonyl)hydrazinyl)-1H-pyrazolo[3,4-d]pyrimidin-1-yl)-2-(pyridin-3-yl)propanoate (15 mg, crude), HMDS (2.5 mL) and BSA (2.5 mL) was heated at 110° C. for 7 hrs. The mixture was concentrated to dryness. 2 mL of MeOH was added and the solution was stirred at 60° C. for 20 min. The resulted residue was diluted with 10 mL of EtOAc, washed with NaHCO$_3$ (2 mL), brine (2 mL×2), dried over Na$_2$SO$_4$, concentrated. The resulted residue was purified by prep-TLC (EA 100%) to give the title product (5 mg, crude) as a white solid which was used for the next Step directly. M/e 419 (M+1)$^+$.

Step I: 2-(5-amino-2-(furan-2-yl)-7H-pyrazolo[4,3-e][1,2,4]triazolo[1,5-c]pyrimidin-7-yl)-2-(pyridin-3-yl)propanoic acid To a solution of ethyl 2-(5-amino-2-(furan-2-yl)-7H-pyrazolo[4,3-e][1,2,4]triazolo[1,5-c]pyrimidin-7-yl)-2-(pyridin-3-yl)propanoate (5 mg, crude) in THF (2 mL) was added aqueous solution of NaOH (2 M, 2 mL) at rt and the resulted mixture was stirred at 50° C. for 3 hrs. The mixture was acidified by HCl (1M) to pH~3 and concentrated to dryness. The resulted white solid was treated with CH$_2$Cl$_2$/MeOH (3:1, 10 mL). The suspension was filtered and the filtrate was concentrated to dryness to give the title product (6 mg, crude) as a light yellow solid which was used for the next Step directly. M/e 391 (M+1)$^+$.

Step J: 2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-(pyridin-3-yl)propanamide To a mixture of 2-(5-amino-2-(furan-2-yl)-7H-pyrazolo[4,3-e][1,2,4]triazolo[1,5-c]pyrimidin-7-yl)-2-(pyridin-3-yl)propanoic acid (6 mg, crude), 3-(aminomethyl)oxetan-3-ol (10 mg, 0.1 mmol), DIPEA (30 mg, 0.23 mmol) in DMF (I mL) was added HATU (15 mg, 0.04 mmol) at rt and the mixture was stirred at rt for 2 hrs. The mixture was diluted with 10 mL of EtOAc, washed with brine (3 mL×3), dried over Na$_2$SO$_4$, concentrated and the resulted oil was purified by prep-TLC (CH2Cl2/MeOH=10:1) for 2 times to give the title product (2.5 mg, yield: 7.2% for 4 Steps) after lyophilization. $^1$H NMR (400 MHz, CD$_3$OD) δ 8.49 (d, J=2.0 Hz, 1H), 8.45 (dd, J=4.8, 1.2 Hz, 1H), 8.23 (s, 1H), 7.76 (dd, J=1.6, 0.4 Hz, 1H), 7.74-7.68 (m, 1H), 7.39 (dd, J=8.0, 4.0 Hz, 1H), 7.26 (d, J=2.8 Hz, 1H), 6.67 (dd, J=3.2, 1.6 Hz, 1H), 4.54 (t, J=6.4 Hz, 2H), 4.43 (dd, J=6.4, 2.4 Hz, 2H), 3.67-3.50 (m, 2H), 2.42 (s, 3H). MS: M/e 476 (M+1)$^+$.

Example 90: 2-(5-amino-2-(furan-2-yl)-7H-pyrazolo[4,3-e][1,2,4]triazolo[1,5-c]pyrimidin-7-yl)-N-((1R,2S)-2-hydroxycyclopentyl)-2-phenylacetamide A mixture of 2-(5-amino-2-(furan-2-yl)-7H-pyrazolo[4,3-e][1,2,4]triazolo[1,5-c]pyrimidin-7-yl)-2-phenylacetic acid (37.5 mg, 0.1 mmol), (1S,2R)-2-aminocyclopentan-1-ol (13.76 mg, 0.1 mmol), HATU (45 mg, 0.12 mmol) and DIPEA (25.8 mg, 0.2 mmol) in DMF (3 mL) was stirred overnight. The reaction mixture was poured into H₂O (10 mL) and extracted with EtOAc (10 mL×3). The combined organic layers were washed with brine, dried over Na₂SO₄, concentrated and purified by prep-TLC (100% EtOAc) to give the target compound (20 mg, 43.7%). ¹H NMR (400 MHz, DMSO-d6) δ8.29 (s, 1H), 8.22 (s, 2H), 7.97-7.94 (m, 1H), 7.75-7.68 (m, 1H), 7.44-7.31 (m, 5H), 7.24 (d, J=3.2 Hz, 1H), 6.76-6.71 (m, 1H), 6.46 (d, J=5.2 Hz, 1H), 4.82 (dd, J=16.4, 11.0 Hz, 1H), 4.05-3.82 (m, 2H), 1.96-1.39 (m, 6H) ppm. MS: M/e 459 (M+1)⁺.

Example 91: 2-(5-amino-2-(furan-2-yl)-7H-pyrazolo[4,3-e][1,2,4]triazolo[1,5-c]pyrimidin-7-yl)-N-((1S, 2R)-2-hydroxycyclohexyl)-2-phenylacetamide To a mixture of 2-(5-amino-2-(furan-2-yl)-7H-pyrazolo[4,3-e][1,2,4]triazolo[1,5-c]pyrimidin-7-yl)-2-phenylacetic acid (50 mg, 0.13 mmol), (1R,2S)-2-aminocyclohexan-1-ol (25 mg, 0.16 mmol), DIPEA (85 mg, 0.66 mmol) in DMF (2 mL) was added HATU (61 mg, 0.16 mmol) at rt and the mixture was stirred at rt for 3 hrs. The mixture was diluted with 10 mL of EtOAc, washed with brine (5 mL×3), dried over Na₂SO₄, concentrated and the resulted oil was purified by prep-TLC (EtOAc: 100%) to give the title product (35 mg, yield: 57%) after lyophilization. ¹H NMR (400 MHz, DMSO-d6) ¹H NMR (400 MHz, DMSO-d6) δ 8.43-8.05 (m, 3H), 7.95 (s, 1H), 7.69 (dd, J=22.4, 8.4 Hz, 1H), 7.47-7.28 (m, 5H), 7.24 (d, J=3.6 Hz, 1H), 6.74 (s, 1H), 6.44 (d, J=5.2 Hz, 1H), 4.69 (dd, J=41.2, 4.0 Hz, 1H), 3.82-3.58 (m, 2H), 1.63-1.38 (m, 6H), 1.29-1.20 (m, 2H). MS: M/e 473 (M+1)⁺.

Example 92: 2-(5-amino-2-(furan-2-yl)-7H-pyrazolo[4,3-e][1,2,4]triazolo[1,5-c]pyrimidin-7-yl)-(cis)-N-(4-hydroxycyclohexyl)-2-phenylacetamide To a stirred solution of 2-(5-amino-2-(furan-2-yl)-7H-pyrazolo[4,3-e][1,2,4]triazolo[1,5-c]pyrimidin-7-yl)-2-phenylacetic acid (50 mg, 0.13 mmol), HATU (56 mg, 0.15 mmol) and DIPEA (52 mg, 0.40 mmol) in THF (15 ml) was added cis-4-aminocyclohexan-1-ol hydrochloride (20 mg, 0.13 mmol). The reaction mixture was stirred at rt for 15 h. After completion, the reaction mixture was diluted with EtOAc (30 ml) and then washed with H₂O (15 ml×2). The organic layer was dried over Na₂SO₄, filtered and then concentrated under reduced pressure to afford a residue. The residue was purified by prep-TLC with PE:EtOAc (1:10) to afford the product (35.3 mg, 56%). ¹H NMR (400 MHz, DMSO-d6) δ 8.22 (s, 1H), 8.16 (s, 2H), 8.01-7.92 (m, 2H), 7.40-7.32 (m, 5H), 7.24 (d, J=4 Hz, 1H), 6.74 (dd, J=4 Hz, 2 Hz, 1H), 6.41 (s, 1H), 4.37 (d, J=4 Hz, 1H), 3.71-3.60 (m, 2H), 1.61-1.39 (m, 8H) ppm. MS: M/e 473 (M+1)⁺.

Example 92 was separated into two enantiomeric stereoisomers, EXAMPLE 92A (earlier peak), and EXAMPLE 92B (later peak) by chiral prep-HPLC. The chiral separation conditions are shown below.

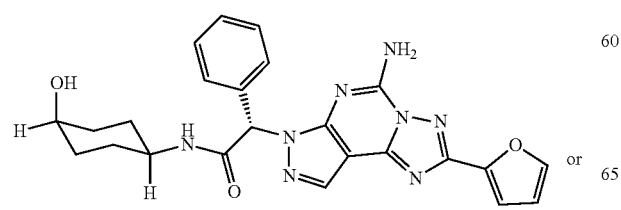

or

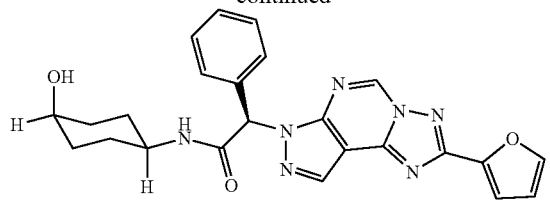

| Column | CHIRAL ART Cellulose-SA |
|---|---|
| Column size | 2 cm × 25 cm, 5 um |
| Injection | 4.5 ml |
| Mobile phase | CO₂:(IPA:ACN = 1:1) = 50:50 |
| Flow rate | 40 ml/min |
| Wave length | UV 270 nm |
| Temperature | 25° C. |
| Sample solution | 3.9 mg/ml in MeOH:DCM = 1:1 |
| Prep-SFC equipment | Prep-SFC-80 |

Example 93: 1-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-1,2,3,4-tetrahydronaphthalene-1-carboxamide

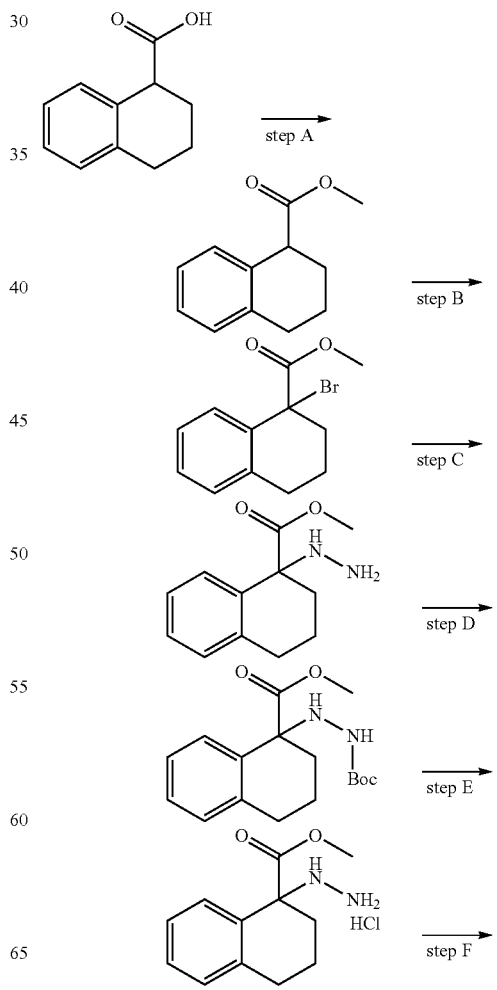

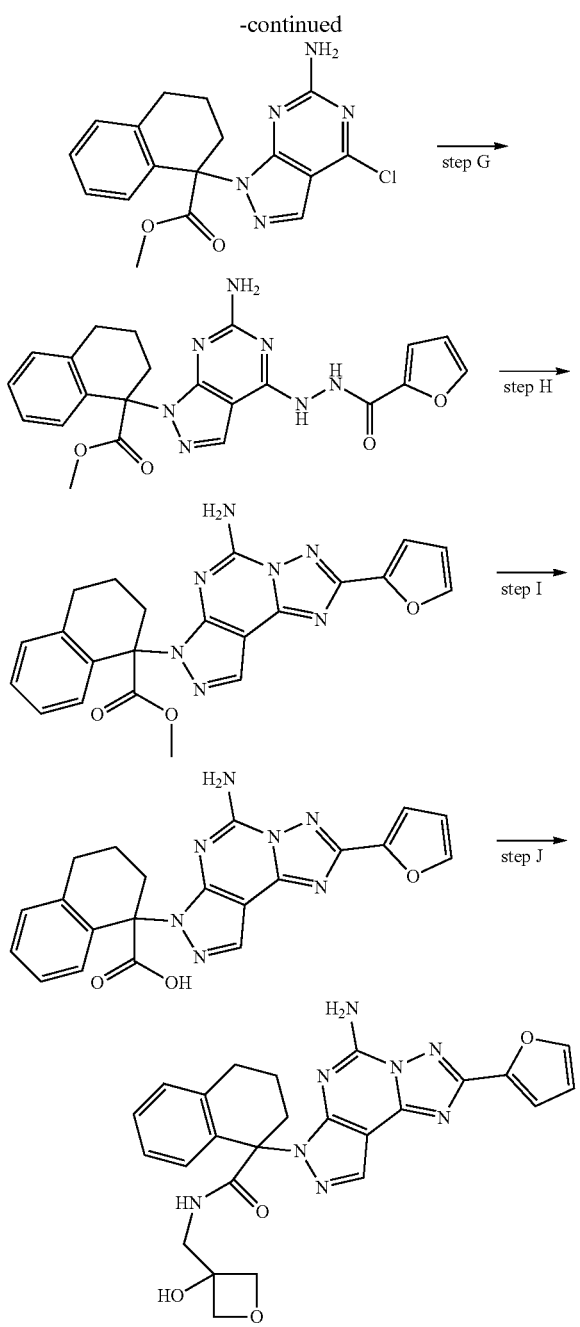

Step A: methyl 1,2,3,4-tetrahydronaphthalene-1-carboxylate

To a mixture of 1,2,3,4-tetrahydronaphthalene-1-carboxylic acid (7.04 g, 40 mmol) in CH₃OH (60 mL) was added SOCl₂ (9.52 g, 80 mmol) drop wise at rt. The reaction was heated at 65° C. overnight. The mixture was cooled to rt and concentrated to dryness. The residue was diluted with EtOAc (160 mL), washed with saturated NaHCO₃ solution, brine, dried over Na₂SO₄, filtered and concentrated to give the product (7.2 g, 95%) as oil. $^1$H NMR (400 MHz, CDCl₃) δ 7.18-7.09 (m, 4H), 3.84 (t, J=5.6 Hz, 1H), 3.71 (s, 3H), 2.91-2.70 (m, 2H), 2.22-2.08 (m, 1H), 2.05-1.91 (m, 2H), 1.85-1.70 (m, 1H). MS: M/e 191 (M+1)$^+$.

Step B: methyl 1-bromo-1,2,3,4-tetrahydronaphthalene-1-carboxylate

To a mixture of LDA (20.5 mL, 2 mol/L, 41.1 mmol) in THF (60 mL) was added a solution of the product of Step A (7.1 g, 37.3 mmol) in THF (30 mL) drop wise at −70° C. The reaction was stirred at −70° C. for 0.5 hour and chlorotrimethylsilane (4.83 g, 44.7 mmol) was added drop wise. Then the reaction mixture was warmed to rt for 2 hours. The mixture was cooled to −70° C. and NBS (7.97 g, 44.7 mmol) was added in some portions. After addition, the reaction was stirred at −70° C. for one hour and the reaction mixture was warmed to rt. The mixture was quenched with saturated NH₄Cl solution, extracted with EtOAc (50 mL), washed with brine, dried over Na₂SO₄, filtered and concentrated to give the product (10 g, crude) as oil.

Step C: methyl 1-hydrazinyl-1,2,3,4-tetrahydronaphthalene-1-carboxylate

To a mixture of the product of Step B (10 g, crude) in CH₃CN (100 mL) was added NH₂NH₂.H₂O (8.15 g, 130 mmol). The reaction was heated at 50° C. for 3 hours. The mixture was cooled to rt and concentrated. The residue was diluted with EtOAc (100 mL), washed with water, brine, dried over Na₂SO₄, filtered and concentrated to give the product (8 g, crude) MS: M/e 221 (M+1)$^+$.

Step D: tert-butyl 2-(1-(methoxycarbonyl)-1,2,3,4-tetrahydronaphthalen-1-yl) hydrazine-1-carboxylate To a mixture of the product of Step C (8 g, crude) in DCM (150 mL) were added BOC₂O (6.34 g, 29 mmol) and Triethylamine (TEA) (10.9 g, 108 mmol). The reaction was stirred at rt for 5 hours. The reaction was quenched with water, extracted with DCM (50 mL×2), washed with brine, dried over Na₂SO₄, filtered and concentrated. The residue was purified by column chromatography (EtOAc:PE=1:6) to give the title product (4 g, 33.4% for 3 Steps) as solid. $^1$H NMR (400 MHz, CDCl₃) δ 7.24-7.17 (m, 1H), 7.16-7.05 (m, 3H), 6.49 (s, 1H), 3.71 (s, 3H), 2.95-2.76 (m, 2H), 2.35-2.09 (m, 3H), 1.91-1.82 (m, 1H), 1.42 (s, 9H) MS: M/e 321 (M+1)$^+$.

Step E: methyl 1-hydrazinyl-1,2,3,4-tetrahydronaphthalene-1-carboxylate hydrochloride To a mixture of the product of Step D (4 g, 12.5 mmol) in DCM (20 mL) was added a solution of 4M HCl in EtOAc (10 mL, 40 mmol). The reaction was stirred at rt overnight. The mixture was concentrated to give a white solid (3.2 g, ~100%). MS: M/e 221 (M+1)$^+$.

Step F: methyl 1-(6-amino-4-chloro-1H-pyrazolo[3,4-d]pyrimidin-1-yl)-1,2,3,4-tetrahydronaphthalene-1-carboxylate A solution of methyl 1-hydrazinyl-1,2,3,4-tetrahydronaphthalene-1-carboxylate hydrochloride (0.7 g, 2.7 mmol) and 2-amino-4,6-dichloropyrimidine-5-carbaldehyde (0.52 g, 2.7 mmol) in MeCN (30 ml) was stirred at rt overnight and then heated to 70° C. The reaction mixture was stirred at 70° C. for 1 h. After completion, the mixture was filtered. The filtrate was concentrated under reduced pressure. The resulting residue was purified by column chromatography with PE:EtOAc (5:1) to afford product (0.66 g, 68%) as a light yellow solid. MS: M/e 358 (M+1)$^+$.

Step G: Methyl 1-(6-amino-4-(2-(furan-2-carbonyl)hydrazinyl)-1H-pyrazolo[3,4-d]pyrimidin-1-yl)-1,2,3,4-tetrahydronaphthalene-1-carboxylate A solution of methyl 1-(6-amino-4-chloro-1H-pyrazolo[3,4-d]pyrimidin-1-yl)-1,2,3,4-tetrahydronaphthalene-1-carboxylate (0.66 g, 1.8 mmol), furan-2-carbohydrazide (0.28 g, 2.2 mmol) and DIPEA (0.48 g, 3.7 mmol) in DMSO (15 ml) was stirred at 110° C. overnight. After completion, the reaction mixture was concentrated under reduced pressure to remove DMSO. $H_2O$ was added to the residue and stirred. The slurry was filtered to afford crude product (0.97 g) as a light yellow solid, which was used directly for the next Step without further purification. MS: M/e 448 (M+1)$^+$.

Step H: methyl 1-(5-amino-2-(furan-2-yl)-7H-pyrazolo[4,3-e][1,2,4]triazolo[1,5-c]pyrimidin-7-yl)-1,2,3,4-tetrahydronaphthalene-1-carboxylate A solution of Methyl 1-(6-amino-4-(2-(furan-2-carbonyl)hydrazinyl)-1H-pyrazolo[3,4-d]pyrimidin-1-yl)-1,2,3,4-tetrahydronaphthalene-1-carboxylate (0.97 g, crude) in BSA (15 ml) was stirred at 110° C. overnight. After completion, the reaction mixture was concentrated under reduced pressure. The residue was diluted with EtOH and then stirred at 80° C. for 2 h. The solution was cooled to rt naturally and then filtered to afford product (0.24 g) as a light yellow solid. MS: M/e 430 (M+1)$^+$.

Step I: 1-(5-amino-2-(furan-2-yl)-7H-pyrazolo[4,3-e][1,2,4]triazolo[1,5-c]pyrimidin-7-yl)-1,2,3,4-tetrahydronaphthalene-1-carboxylic acid To a solution of 1-(5-amino-2-(furan-2-yl)-7H-pyrazolo[4,3-e][1,2,4]triazolo[1,5-c]pyrimidin-7-yl)-1,2,3,4-tetrahydronaphthalene-1-carboxylate (0.24 g, 0.56 mmol) in EtOH (10 ml), was added a solution of NaOH (0.22 g, 5.5 mmol) in $H_2O$ (2 ml). The mixture was heated to 80° C. and then stirred for 3 h. After completion, the reaction mixture was concentrated under reduced pressure to remove EtOH. The residue was diluted with $H_2O$ and then acidified with aq. HCl (4N) to pH=3~4. The precipitate was filtered, washed and then dried to afford product (0.2 g, 86%) as a light yellow solid. MS: M/e 416 (M+1)$^+$.

Step J: 1-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-1,2,3,4-tetrahydronaphthalene-1-carboxamide To a stirred solution of 1-(5-amino-2-(furan-2-yl)-7H-pyrazolo[4,3-e][1,2,4]triazolo[1,5-c]pyrimidin-7-yl)-1,2,3,4-tetrahydronaphthalene-1-carboxylic acid (100 mg, 0.24 mmol) and HATU (138 mg, 0.36 mmol) in THF (10 ml), was added 3-(aminomethyl)oxetan-3-ol (28 mg, 0.27 mmol) and DIPEA (94 mg, 0.73 mmol). The mixture was stirred at rt for 2 h. After completion, the reaction mixture was concentrated under reduced pressure to remove solvent. The residue was diluted with DCM (20 ml) and then washed with $H_2O$ (10 ml×2). The organic solution was dried, filtered and concentrated under reduced pressure. The residue was purified by prep-TLC with DCM:MeOH (30:1) to afford product (30.8 mg, 26%). $^1$H NMR (400 MHz, DMSO-d6) δ 8.12 (s, 1H), 8.04-7.90 (m, 3H), 7.44 (t, J=8 Hz, 1H), 7.28-7.16 (m, 4H), 7.11 (t, J=8 Hz, 1H), 6.76-6.71 (m, 1H), 5.72 (s, 1H), 4.46 (t, J=8 Hz, 2H), 4.33 (d, J=4 Hz, 1H), 4.30 (d, J=8 Hz, 1H), 3.48-3.42 (m, 2H), 2.92-2.76 (m, 2H), 1.27-1.23 (m, 4H) ppm. MS: M/e 501 (M+1)$^+$.

Example 94: 2-(5-amino-2-(furan-2-yl)-7H-pyrazolo[4,3-e][1,2,4]triazolo[1,5-c]pyrimidin-7-yl)-N-((1R,3R)-3-hydroxycyclopentyl)-2-phenylpropanamide A mixture of (1R,3R)-3-aminocyclopentan-1-ol (17 mg, 0.12 mmol), 2-(5-amino-2-(furan-2-yl)-7H-pyrazolo[4,3-e][1,2,4]triazolo[1,5-c]pyrimidin-7-yl)-2-phenylpropanoic acid (40 mg, 0.1 mmol), HATU (46.9 mg, 0.12 mmol) and DIPEA (0.2 mL) in DMF (2 mL) was stirred at RT overnight. The reaction mixture was poured into water (10 mL) and extracted with EtOAc (15 mL×3). The combined organic layers were washed with brine, dried over $Na_2SO_4$ and concentrated under reduced pressure. The residue was purified by combiflash (EtOAc: 100%) to afford the title compound (35 mg, yield: 74.5%). $^1$H NMR (400 MHz, DMSO-d6) δ8.27-8.20 (m, 1H), 8.03-7.92 (m, 3H), 7.61-7.55 (m, 1H), 7.33-7.23 (m, 4H), 7.18-7.08 (m, 2H), 6.76-6.70 (m, 1H), 4.41 (t, J=4 Hz, 1H), 4.37-4.24 (m, 1H), 4.12-4.02 (m, 1H), 2.27 (s, 3H), 2.01-1.88 (m, 1H), 1.84-1.68 (m, 2H), 1.63-1.49 (m, 1H), 1.45-1.29 (m, 2H) ppm. MS: M/e 473 (M+1)$^+$.

Example 95: 2-(5-amino-2-(furan-2-yl)-7H-pyrazolo[4,3-e][1,2,4]triazolo[1,5-c]pyrimidin-7-yl)-N-((1S,3S)-3-hydroxycyclopentyl)-2-phenylpropanamide A mixture of (1S,3S)-3-aminocyclopentan-1-ol (17 mg, 0.12 mmol), 2-(5-amino-2-(furan-2-yl)-7H-pyrazolo[4,3-e][1,2,4]triazolo[1,5-c]pyrimidin-7-yl)-2-phenylpropanoic acid (40 mg, 0.1 mmol), HATU (46.9 mg, 0.12 mmol) and DIPEA (0.2 mL) in DMF (2 mL) was stirred at RT overnight. The reaction mixture was poured into water (10 mL) and extracted with EtOAc (15 mL×3). The combined organic layers were washed with brine, dried over $Na_2SO_4$ and concentrated under reduced pressure. The residue was purified by combiflash (EtOAc: 100%) to afford the title compound (30 mg, yield: 63.8%). $^1$H NMR (400 MHz, DMSO-d6) δ8.27-8.18 (m, 1H), 8.04-7.85 (m, 3H), 7.63-7.52 (m, 1H), 7.35-7.21 (m, 4H), 7.17-7.04 (m, 2H), 6.79-6.68 (m, 1H), 4.41 (t, J=4 Hz, 1H), 4.36-4.22 (m, 1H), 4.15-3.94 (m, 1H), 2.27 (s, 3H), 2.05-1.85 (m, 1H), 1.84-1.67 (m, 2H), 1.65-1.49 (m, 1H), 1.46-1.27 (m, 2H) ppm. MS: M/e 473 (M+1)$^+$.

Example 96: 2-(5-amino-2-(furan-2-yl)-7H-pyrazolo[4,3-e][1,2,4]triazolo[1,5-c]pyrimidin-7-yl)-(cis)-N-(4-hydroxy-4-methylcyclohexyl)-2-phenylacetamide To a stirred solution of 2-(5-amino-2-(furan-2-yl)-7H-pyrazolo[4,3-e][1,2,4]triazolo[1,5-c]pyrimidin-7-yl)-2-phenylacetic acid (50 mg, 0.13 mmol), HATU (56 mg, 0.15 mmol) and DIPEA (52 mg, 0.40 mmol) in THF (15 ml) was added cis-4-amino-1-methylcyclohexan-1-ol (17 mg, 0.13 mmol). The reaction mixture was stirred at rt for 15 h. After completion, the reaction mixture was diluted with EtOAc (30 ml) and then washed with $H_2O$ (15 ml×2). The organic layer was dried over $Na_2SO_4$, filtered and then concentrated under reduced pressure to afford a residue. The residue was purified by prep-TLC with DCM:MeOH (30:1) to afford the product (26.2 mg, 40%). $^1$H NMR (400 MHz, DMSO-d6) δ 8.20 (s, 1H), 8.16 (s, 2H), 7.95 (s, 1H), 7.91 (d, J=8 Hz, 1H), 7.42-7.32 (m, 5H), 7.25 (d, J=4 Hz, 1H), 6.73 (dd, J=4 Hz, 2 Hz, 1H), 6.38 (s, 1H), 4.01 (s, 1H), 3.57-3.47 (m, 1H), 1.56-1.43 (m, 5H), 1.34-1.28 (m, 3H), 1.07 (s, 3H) ppm. MS: M/e 487 (M+1)$^+$.

Example 97: 2-(5-amino-2-(furan-2-yl)-7H-pyrazolo[4,3-e][1,2,4]triazolo[1,5-c]pyrimidin-7-yl)-2-phenyl-N-((tetrahydro-2H-pyran-4-yl)methyl)propenamide A mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.128 mmol), (tetrahydro-2H-pyran-4-yl)methanamine (29.6 mg, 0.257 mmol), HATU (53.5 mg, 0.14 mmol) and DIPEA (33 mg, 0.256 mmol) in DMF (5 mL) was stirred overnight at RT. The reaction mixture was poured into H$_2$O (60 mL) and extracted with EtOAc (20 mL×3). The combined organic layers were washed with brine, dried over Na$_2$SO$_4$, concentrated in vacuo and purified by column chromatography (EtOAc) to give the target compound (30 mg, 48.2%). $^1$H NMR (400 MHz, DMSO-d6) δ 8.24 (s, 1H), 7.96 (d, J=5.9 Hz, 3H), 7.64 (t, J=5.9 Hz, 1H), 7.27 (dt, J=9.9, 4.8 Hz, 4H), 7.15 (d, J=6.8 Hz, 2H), 6.78-6.71 (m, 1H), 3.74 (s, 2H), 3.20 (t, J=11.7 Hz, 2H), 2.99 (m, 2H), 2.29 (s, 3H), 1.71 (s, 1H), 1.48-1.35 (m, 2H), 1.05 (m, 2H). MS: M/e 487 (M+1)$^+$.

Example 98: 2-(5-amino-2-(furan-2-yl)-7H-pyrazolo[4,3-e][1,2,4]triazolo[1,5-c]pyrimidin-7-yl)-2-phenyl-N-(tetrahydro-2H-pyran-4-yl)propanamide A mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.128 mmol), tetrahydro-2H-pyran-4-amine (26 mg, 0.257 mmol), HATU (53.5 mg, 0.141 mmol) and DIPEA (33 mg, 0.256 mmol) in DMF (5 mL) was stirred overnight at RT. The reaction mixture was poured into H$_2$O (60 mL) and extracted with EtOAc (20 mL×3). The combined organic layers were washed with brine, dried over Na$_2$SO$_4$, concentrated and purified by column chromatography (EtOAc) to give the target compound (22 mg, 36.3%). $^1$H NMR (400 MHz, DMSO-d6) δ 8.24 (s, 1H), 7.97 (d, J=10.1 Hz, 3H), 7.67 (d, J=7.8 Hz, 1H), 7.26 (dd, J=12.6, 5.4 Hz, 4H), 7.14 (d, J=6.9 Hz, 2H), 6.74 (s, 1H), 3.88 (s, 1H), 3.76 (d, J=4.6 Hz, 2H), 3.30 (s, 2H), 2.26 (s, 3H), 1.68 (m, 2H), 1.41 (m, 2H). MS: M/e 473 (M+1)$^+$.

Example 99: 2-(5-amino-2-(furan-2-yl)-7H-pyrazolo[4,3-e][1,2,4]triazolo[1,5-c]pyrimidin-7-yl)-N-(3-hydroxycyclohexyl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.128 mmol), 3-aminocyclohexan-1-ol (14.8 mg, 0.128 mmol), HATU (53.5 mg, 0.14 mmol) and DIPEA (33 mg, 0.256 mmol) in DMF (5 mL) was stirred overnight at RT. The reaction mixture was poured into H$_2$O (60 mL) and extracted with EtOAc (20 mL×3). The combined organic layers were washed with brine, dried over Na$_2$SO$_4$, concentrated and purified by column chromatography (EtOAc) to give the target compound (16 mg, 25.7%). δ 8.21 (d, J=4.7 Hz, 1H), 7.95 (s, 3H), 7.61 (d, J=7.9 Hz, 1H), 7.36-7.21 (m, 4H), 7.19-7.11 (m, 2H), 6.74 (s, 1H), 3.71 (s, 1H), 3.42 (s, 1H), 3.10-3.05 (m, 1H), 2.27 (s, 3H), 1.61 (m, 3H), 1.24-1.09 (m, 5H). MS: M/e 487 (M+1)$^+$.

Example 100: 2-(5-amino-2-(furan-2-yl)-7H-pyrazolo[4,3-e][1,2,4]triazolo[1,5-c]pyrimidin-7-yl)-N—((S)-5-oxopyrrolidin-3-yl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.128 mmol), (S)-4-aminopyrrolidin-2-one (25.6 mg, 0.256 mmol), HATU (53.5 mg, 0.128 mmol) and DIPEA (33 mg, 0.256 mmol) in DMF (5 mL) was stirred overnight at RT. The reaction mixture was poured into H$_2$O (60 mL) and extracted with EtOAc (20 mL×3). The combined organic layers were washed with brine, dried over Na$_2$SO$_4$, concentrated and purified by column chromatography (EtOAc) to give the target compound (25 mg, 41.6%). $^1$H NMR (400 MHz, DMSO-d6) δ 8.22 (d, J=24.4 Hz, 1H), 7.95 (s, 3H), 7.84 (s, 1H), 7.74 (d, J=10.1 Hz, 1H), 7.27 (dd, J=14.7, 7.1 Hz, 5H), 7.17 (d, J=7.1 Hz, 1H), 6.74 (s, 1H), 4.31 (m, 1H), 3.13 (d, J=5.5 Hz, 2H), 2.31 (s, 3H), 2.27 (s, 2H). MS: M/e 472 (M+1)$^+$.

Example 101: 2-(5-amino-2-(furan-2-yl)-7H-pyrazolo[4,3-e][1,2,4]triazolo[1,5-c]pyrimidin-7-yl)-2-phenyl-N-(piperidin-4-yl)propanamide

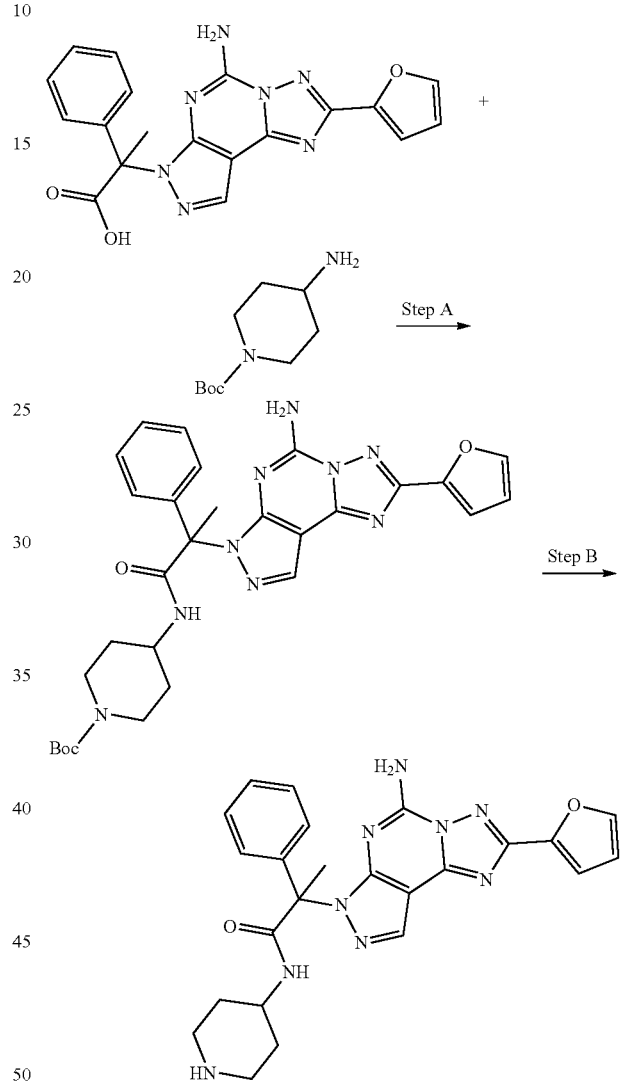

Step A: 4-(2-(5-amino-2-(furan-2-yl)-7H-pyrazolo[4,3-e][1,2,4]triazolo[1,5-c]pyrimidin-7-yl)-2-phenylpropanamido)piperidine-1-carboxylate A mixture of 2-(5-amino-2-(furan-2-yl)-7H-pyrazolo[4,3-e][1,2,4]triazolo[1,5-c]pyrimidin-7-yl)-2-phenylpropanoic acid (100 mg, 0.256 mmol), tert-butyl 4-aminopiperidine-1-carboxylate (102.8 mg, 0.514 mmol), HATU (117.2 mg, 0.308 mmol) and DIPEA (66 mg, 0.514 mmol) in DMF (5 mL) was stirred overnight at RT. The reaction mixture was poured into H$_2$O (60 mL) and extracted with EtOAc (20 mL×3). The combined organic layers were washed with brine, dried over Na$_2$SO$_4$, concentrated and purified by column chromatography (EtOAc) to give the target compound (120 mg, 82%) as a white solid. $^1$H NMR (400 MHz, DMSO-d6) δ 8.23 (s, 1H), 7.97 (d, J=11.6 Hz, 3H), 7.64 (d, J=8.0 Hz, 1H), 7.32-7.21 (m, 4H), 7.15 (d, J=6.5 Hz, 2H), 6.74 (dd, J=3.3, 1.7 Hz, 1H), 3.85 (s, 3H), 2.71 (d, J=16.8 Hz, 2H), 2.25 (s, 3H), 1.71 (m, 2H), 1.35 (s, 9H), 1.26 (m, 2H). MS: M/e 572 (M+1)+.

Step B: 2-(5-amino-2-(furan-2-yl)-7H-pyrazolo[4,3-e][1,2,4]triazolo[1,5-c]pyrimidin-7-yl)-2-phenyl-N-(piperidin-4-yl)propanamide A mixture of tert-butyl 4-(2-(5-amino-2-(furan-2-yl)-7H-pyrazolo[4,3-e][1,2,4]triazolo[1,5-c]pyrimidin-7-yl)-2-phenylpropanamido)piperidine-1-carboxylate (190 mg, 0.33 mmol) in 4M HCl/EtOAc (20 ml) was stirred at rt overnight. The mixture was filtered and the filter cake was washed with EtOAc. The product was added to 1M NaHCO₃ solution and extracted with DCM (20 mL×2). The combined organic phase was washed with brine, dried over Na₂SO₄ and concentrated in vacuo to give the product (120 mg, 77.4%). ¹H NMR (400 MHz, DMSO-d6) δ 8.23 (s, 1H), 7.95 (s, 3H), 7.54 (d, J=7.6 Hz, 1H), 7.26 (dd, J=13.8, 5.6 Hz, 4H), 7.14 (d, J=7.3 Hz, 2H), 6.74 (s, 1H), 3.70 (s, 1H), 2.85 (s, 2H), 2.44 (s, 2H), 2.27 (s, 3H), 2.08 (s, 1H), 1.66 (m, 2H), 1.24 (m, 2H). MS: M/e 472 (M+1)+.

Example 102: 2-(5-amino-2-(furan-2-yl)-7H-pyrazolo[4,3-e][1,2,4]triazolo[1,5-c]pyrimidin-7-yl)-(trans)-N-(3-hydroxycyclobutyl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.128 mmol), trans-3-aminocyclobutan-1-ol (17.5 mg, 0.141 mmol), HATU (53.5 mg, 0.128 mmol) and DIPEA (33 mg, 0.256 mmol) in DMF (5 mL) was stirred overnight at RT. The reaction mixture was poured into H₂O (60 mL) and extracted with EtOAc (20 mL×3). The combined organic layers were washed with brine, dried over Na₂SO₄, concentrated and purified by column chromatography (EtOAc) to give the target compound (35 mg, 59.7%). ¹H NMR (400 MHz, DMSO-d6) δ 8.24 (s, 1H), 7.96 (d, J=10.3 Hz, 3H), 7.89 (d, J=6.6 Hz, 1H), 7.26 (dd, J=11.0, 5.4 Hz, 4H), 7.11 (d, J=7.3 Hz, 2H), 6.74 (s, 1H), 4.90 (s, 1H), 4.26 (d, J=6.2 Hz, 1H), 4.08 (s, 1H), 2.28 (s, 3H), 2.21-2.11 (m, 2H), 2.03 (m, 2H). MS: M/e 459 (M+1)+.

Example 102B: (R)-2-(5-amino-2-(furan-2-yl)-7H-pyrazolo[4,3-e][1,2,4]triazolo[1,5-c]pyrimidin-7-yl)-(trans)-N-(3-hydroxycyclobutyl)-2-phenylpropanamide To a stirred solution of (R)-2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), HATU (54 mg, 0.14 mmol) and DIPEA (50 mg, 0.39 mmol) in THF (15 ml) was added trans-3-aminocyclobutan-1-ol hydrochloride (18 mg, 0.15 mmol). The reaction mixture was stirred at rt for 15 h. After completion, the reaction mixture was diluted with EtOAc (30 ml) and then washed with H₂O (15 ml×2). The organic layer was dried over Na₂SO₄, filtered and then concentrated under reduced pressure to afford a residue. The residue was purified by prep-TLC with DCM:MeOH (20:1) to afford the product (41.8 mg, 71%). ¹H NMR (400 MHz, DMSO-d6) δ 8.24 (s, 1H), 7.98 (s, 2H), 7.95 (s, 1H), 7.89 (d, J=8 Hz, 1H), 7.30-7.23 (m, 4H), 7.11 (d, J=8 Hz, 2H), 6.74 (dd, J=4 Hz, 2 Hz, 1H), 4.91 (s, 1H), 4.30-4.22 (m, 1H), 4.13-4.05 (m, 1H), 2.28 (s, 3H), 2.24-2.11 (m, 2H), 2.07-1.98 (m, 2H) ppm. MS: M/e 459 (M+1)+.

Example 103: 2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-phenylbutanamide

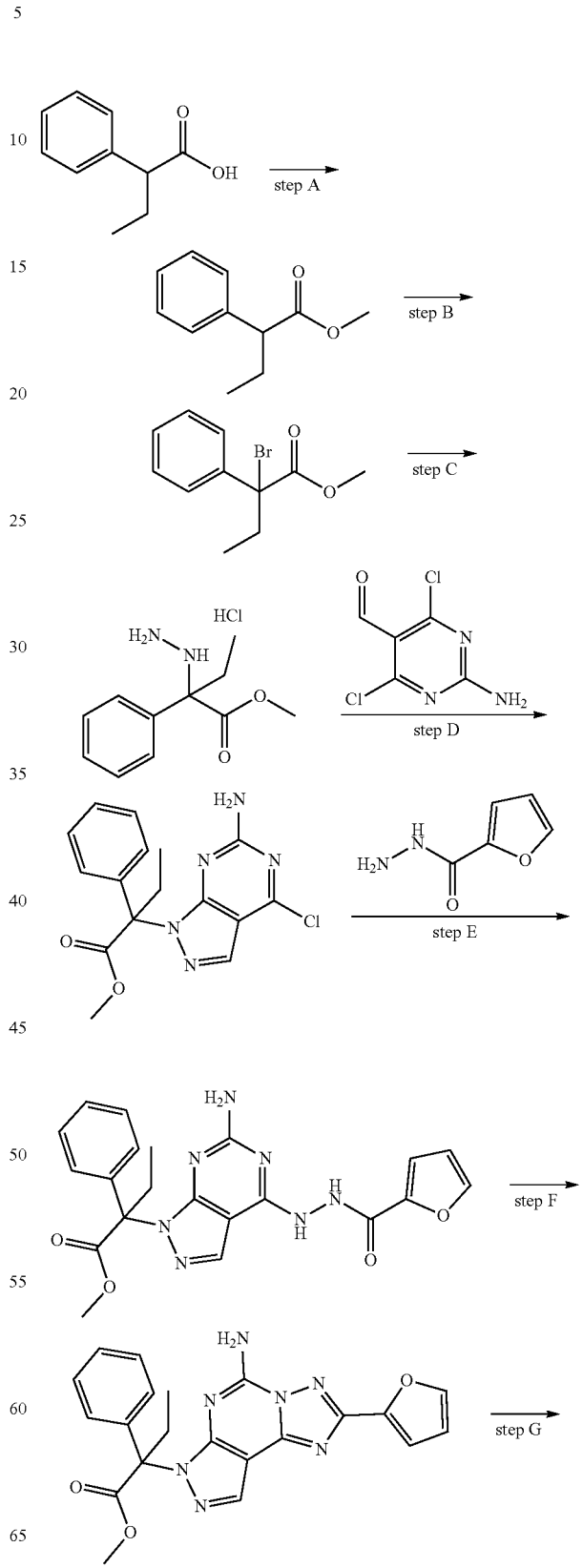

-continued

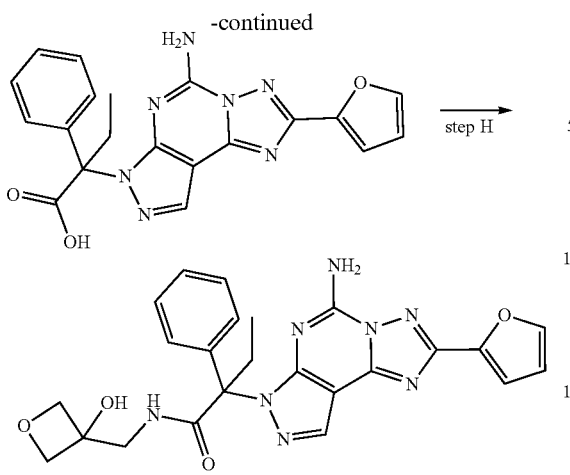

Step A: methyl 2-phenylbutanoate

To a solution of 2-phenylbutanoic acid (5 g, 30.49 mmol) in MeOH (15 mL), sulfoxide chloride (54.4 g, 45.73 mmol) was added dropwise at 0° C., After the addition, the reaction mixture was stirred at rt for 3 h. The mixture was concentrated, quenched with ice water (20 mL), extracted with EtOAc (30 mL×3). The combined organic layers were washed with brine, dried over $Na_2SO_4$, concentrated and purified by column chromatography (petroleum ether/EtOAc=20:1~5:1) to give methyl 2-phenylbutanoate (5.12 g, 94.35%) as yellow oil. MS: M/e 179 (M+1)$^+$.

Step B: methyl 2-bromo-2-phenylbutanoate

A mixture of methyl 2-phenylbutanoate (5.12 g, 28.76 mmol), NBS (6.14 g, 34.52 mmol), BPO (0.348 g, 1.438 mmol) in carbon tetrachloride (20 mL) was stirred at 70° C. overnight. The mixture was concentrated, the residue was washed with PE and filtered, the filtrate was concentrated to give methyl 2-bromo-2-phenylbutanoate (7.08 g, 95.77%) as yellow oil. $^1$H NMR (400 MHz, CDCl$_3$) δ 7.46 (d, J=7.8 Hz, 2H), 7.38-7.28 (m, J=19.2, 6.3 Hz, 3H), 3.78 (s, 3H), 2.57-2.38 (m, 2H), 0.98 (t, J=7.2 Hz, 3H).

Step C: methyl 2-hydrazinyl-2-phenylbutanoate hydrochloride

To a stirred solution of methyl 2-bromo-2-phenylbutanoate (2 g, 7.8 mmol) and $K_2CO_3$ (2.16 mg, 15.7 mmol) in DMF (20 ml) was added hydrazine hydrate (1.95 g, 31.2 mmol). The reaction mixture was stirred at rt for 24 h. After completion, the reaction mixture was poured into water (30 ml), which was then extracted with EtOAc (30 ml×3). The combined organic layer was concentrated under reduced pressure to remove solvent. The residue was diluted with EtOAc (50 ml) and then washed with $H_2O$ (25 ml×2) to remove hydrazine hydrate. The resulted organic solution was concentrated to afford a residue. The residue was acidified with aq. HCl (4M) and then washed with EtOAc (25 ml×2) to remove impurities which are easily soluble in EtOAc. The aqueous solution was concentrated under reduced pressure and dried to afford the product (1.0 g, 52.6%) as a white solid, which was used directly for the next Step without further purification. $^1$H NMR (400 MHz, DMSO-d6) δ 7.41 (d, J=4 Hz, 4H), 7.39-7.35 (m, 1H), 3.72 (s, 3H), 2.21-2.14 (m, 2H), 0.74 (t, J=8 Hz, 3H) ppm. MS: M/e 209 (M+1)$^+$.

Step D: methyl 2-(6-amino-4-chloro-1H-pyrazolo[3,4-d]pyrimidin-1-yl)-2-phenylbutanoate To a stirred solution of methyl 2-hydrazinyl-2-phenylbutanoate hydrochloride (1 g, 4.09 mmol) in acetonitrile (30 ml) was added 2-amino-4,6-dichloropyrimidine-5-carbaldehyde (0.94 g, 4.90 mmol). The reaction mixture was stirred at rt for 15 h and then heated to 60° C., which was stirred at 60° C. for 2 h. After completion, the reaction mixture was filtered. The filtrate was concentrated under reduced pressure to afford a residue. The residue was purified by column chromatography with PE:EtOAc (4:1) to afford the product (0.55 g, 39%) as a yellow solid. MS: M/e 346 (M+1)$^+$.

Step E: methyl 2-(6-amino-4-(2-(furan-2-carbonyl)hydrazinyl)-1H-pyrazolo[3,4-d]pyrimidin-1-yl)-2-phenylbutanoate A mixture of methyl 2-(6-amino-4-chloro-1H-pyrazolo[3,4-d]pyrimidin-1-yl)-2-phenylbutanoate (0.55 g, 1.59 mmol), furan-2-carbohydrazide (0.20 g, 1.59 mmol) and DIEA (0.41 g, 3.18 mmol) in DMSO (15 ml) was stirred at 110° C. for 15 h. After completion, the reaction mixture was poured into $H_2O$ (15 ml) and then extracted with EtOAc (20 ml×3). The combined organic layer was dried over $Na_2SO_4$, filtered and then concentrated under reduced pressure to afford a residue. The residue was purified by column chromatography with PE:EtOAc (1:2) to afford the product (0.57 g, 82%) as a light-yellow solid. MS: M/e 436 (M+1)$^+$.

Step F: methyl 2-(5-amino-2-(furan-2-yl)-7H-pyrazolo[4,3-e][1,2,4]triazolo[1,5-c]pyrimidin-7-yl)-2-phenylbutanoate A solution of methyl 2-(6-amino-4-(2-(furan-2-carbonyl)hydrazinyl)-1H-pyrazolo[3,4-d]pyrimidin-1-yl)-2-phenylbutanoate (0.57 g, 1.31 mmol) in BSA (5 ml) and HMDS (5 ml) was stirred at 110° C. for 15 h. After completion, the reaction mixture was concentrated. The residue was diluted with aq. $NaHCO_3$ (sat., 15 ml) and then extracted with EtOAc (20 ml×3). The combined organic layer was dried over $Na_2SO_4$, filtered and then concentrated under reduced pressure to afford a residue. The residue was purified by column chromatography with PE:EtOAc (10:1) to afford the product (0.28 g, 51%) as a yellow solid. MS: M/e 418 (M+1)$^+$.

Step G: 2-(5-amino-2-(furan-2-yl)-7H-pyrazolo[4,3-e][1,2,4]triazolo[1,5-c]pyrimidin-7-yl)-2-phenylbutanoic acid To a stirred solution of methyl 2-(5-amino-2-(furan-2-yl)-7H-pyrazolo[4,3-e][1,2,4]triazolo[1,5-c]pyrimidin-7-yl)-2-phenylbutanoate (0.28 g, 0.67 mmol) in ethanol (15 ml) was added a solution of NaOH (0.27 g, 6.75 mmol) in $H_2O$ (5 ml). The mixture was stirred at 70° C. for 4 h. After completion, the reaction mixture was concentrated to remove ethanol. The residue was diluted with $H_2O$ (15 ml) and then acidified with aq. HCl (4M) to pH=3~4. The precipitate was filtered. The filtration cake was washed with $H_2O$ (15 ml) and then dried to afford the product (0.25 g, 92%) as a white solid. MS: M/e 404 (M+1)$^+$.

Step H: 2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-phenylbutanamide To a stirred solution of 2-(5-amino-2-(furan-2-yl)-7H-pyrazolo[4,3-e][1,2,4]triazolo[1,5-c]pyrimidin-7-yl)-2-phenylbutanoic acid (50 mg, 0.12 mmol), HATU (54 mg, 0.14 mmol) and DIPEA (47 mg, 0.36 mmol) in THF (15 ml) was added 3-(aminomethyl)oxetan-3-ol (14 mg, 0.13 mmol). The reaction mixture was stirred at rt for 15 h. After completion, the reaction mixture was diluted with EtOAc (30 ml) and then washed with $H_2O$ (15 ml×2). The organic layer was dried over $Na_2SO_4$, filtered and then concentrated under reduced pressure to afford a residue. The residue was purified by prep-TLC with DCM:MeOH (20:1) to afford the target product (21.0 mg, 35%). $^1$H NMR (400 MHz, DMSO-d6) δ 8.32 (s, 1H), 7.95 (s, 1H), 7.92 (s, 2H), 7.69 (t, J=4 Hz, 1H), 7.38-7.19 (m, 6H), 6.74 (s, 1H), 5.68 (s, 1H), 4.34 (t, J=4 Hz, 2H), 4.22 (d, J=4 Hz, 2H), 3.47-3.37 (m, 2H), 2.84 (q, J=8 Hz, 2H), 0.79 (t, J=8 Hz, 3H) ppm. MS: M/e 489 (M+1)$^+$.

Example 104: 2-(5-amino-2-(furan-2-yl)-7H-pyrazolo[4,3-e][1,2,4]triazolo[1,5-c]pyrimidin-7-yl)-N-((1s,3s)-3-hydroxycyclobutyl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.129 mmol), (1s,3s)-3-aminocyclobutan-1-ol (17.5 mg, 0.141 mmol), HATU (53.7 mg, 0.141 mmol) and DIPEA (49.7 mg, 0.385 mmol) in THF (5 mL) was stirred overnight at RT. The reaction mixture was poured into $H_2O$ (20 mL) and extracted with EtOAc (20 mL×3). The combined organic layer was washed with brine, dried over $Na_2SO_4$, concentrated and purified by column chromatography (petroleum ether/EtOAc=0:1) to give target compound (26 mg, 44%). $^1$H NMR (400 MHz, DMSO-d6) δ 8.23 (s, 1H), 7.95 (s, 3H), 7.84 (d, J=7.2 Hz, 1H), 7.27 (t, J=6.6 Hz, 4H), 7.12 (d, J=7.1 Hz, 2H), 6.74 (s, 1H), 4.95 (d, J=5.6 Hz, 1H), 3.75 (d, J=6.8 Hz, 2H), 2.28 (s, 3H), 2.08 (s, 2H), 1.73 (dd, J=18.1, 9.3 Hz, 2H). ppm.MS: M/e 459 (M+1)$^+$.

Example 104B: (R)-2-(5-amino-2-(furan-2-yl)-7H-pyrazolo[4,3-e][1,2,4]triazolo[1,5-c]pyrimidin-7-yl)-(cis)-N-(3-hydroxycyclobutyl)-2-phenylpropanamide To a stirred solution of (R)-2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), HATU (54 mg, 0.14 mmol) and DIPEA (50 mg, 0.39 mmol) in THF (15 ml) was added cis-3-aminocyclobutan-1-ol hydrochloride (18 mg, 0.15 mmol). The reaction mixture was stirred at rt for 15 h. After completion, the reaction mixture was diluted with EtOAc (30 ml) and then washed with $H_2O$ (15 ml×2). The organic layer was dried over $Na_2SO_4$, filtered and then concentrated under reduced pressure to afford a residue. The residue was purified by prep-TLC with DCM:MeOH (20:1) to afford the product (32.7 mg, 55%). $^1$H NMR (400 MHz, DMSO-d6) δ 8.23 (s, 1H), 8.04-7.93 (m, 3H), 7.84 (d, J=8 Hz, 1H), 7.31-7.24 (m, 4H), 7.12 (d, J=8 Hz, 2H), 6.74 (dd, J=4 Hz, 2 Hz, 1H), 4.95 (s, 1H), 3.81-3.71 (m, 2H), 2.49-2.39 (m, 2H), 2.28 (s, 3H), 1.74 (q, J=8 Hz, 2H) ppm. MS: M/e 459 (M+1)$^+$.

Example 105: 2-(5-amino-2-(furan-2-yl)-7H-pyrazolo[4,3-e][1,2,4]triazolo[1,5-c]pyrimidin-7-yl)-N-((1S,3S)-3-hydroxy-3-methylcyclobutyl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.129 mmol), (1s,3s)-3-amino-1-methylcyclobutan-1-ol (20 mg, 0.198 mmol), HATU (53.7 mg, 0.141 mmol) and DIPEA (33 mg, 0.256 mmol) in THF (5 mL) was stirred overnight at RT. The reaction mixture was concentrated in vacuo and purified by column chromatography (petroleum ether/EtOAc=0:1) to give the target compound (32 mg, 53.3%). $^1$H NMR (400 MHz, DMSO-d6) δ 8.23 (s, 1H), 7.96 (d, J=5.4 Hz, 3H), 7.83 (d, J=7.1 Hz, 1H), 7.35-7.18 (m, 4H), 7.11 (d, J=6.7 Hz, 2H), 6.74 (dd, J=3.3, 1.7 Hz, 1H), 4.82 (s, 1H), 3.84 (m, 1H), 2.27 (s, 3H), 2.19 (m, 2H), 1.92 (t, J=8.1 Hz, 2H), 1.20 (s, 3H). ppm.MS: M/e 473 (M+1)$^+$.

Example 105B: (R)-2-(5-amino-2-(furan-2-yl)-7H-pyrazolo[4,3-e][1,2,4]triazolo[1,5-c]pyrimidin-7-yl)-(cis)-N-(3-hydroxy-3-methylcyclobutyl)-2-phenylpropanamide To a stirred solution of (R)-2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), HATU (54 mg, 0.14 mmol) and DIEA (50 mg, 0.39 mmol) in THF (15 ml) was added (cis)-3-amino-1-methylcyclobutan-1-ol hydrochloride (20 mg, 0.15 mmol). The reaction mixture was stirred at rt for 15 h. After completion, the reaction mixture was diluted with EtOAc (30 ml) and then washed with $H_2O$ (15 ml×2). The organic layer was dried over $Na_2SO_4$, filtered and then concentrated under reduced pressure to afford a residue. The residue was purified by prep-TLC with DCM:MeOH (20:1) to afford the product (42.1 mg, 69%). $^1$H NMR (400 MHz, DMSO-d6) δ 8.23 (s, 1H), 8.05-7.91 (m, 3H), 7.82 (d, J=8 Hz, 1H), 7.32-7.24 (m, 4H), 7.12 (d, J=8 Hz, 2H), 6.74 (dd, J=4 Hz, 2 Hz, 1H), 4.79 (s, 1H), 3.90-3.78 (m, 1H), 2.28 (s, 3H), 2.24-2.15 (m, 2H), 1.96-1.88 (m, 2H), 1.20 (s, 3H) ppm. MS: M/e 473 (M+1)$^+$.

Example 106: 2-(5-amino-2-(furan-2-yl)-7H-pyrazolo[4,3-e][1,2,4]triazolo[1,5-c]pyrimidin-7-yl)-N-((3S,4R)-4-hydroxytetrahydrofuran-3-yl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (38.9 mg, 0.1 mmol), (3R,4S)-4-aminotetrahydrofuran-3-ol hydrochloride (13.9 mg, 0.1 mmol), HATU (45 mg, 0.12 mmol) and DIPEA (25.8 mg, 0.2 mmol) in DMF (3 mL) was stirred overnight. The reaction mixture was poured into $H_2O$ (10 mL) and extracted with EtOAc (10 mL×3). The combined organic layer was washed with brine, dried over $Na_2SO_4$, concentrated and purified by prep-TLC (EtOAc 100%) to give the target compound (20 mg, 42.2%). $^1$H NMR (400 MHz, DMSO-d6) δ 8.29 (d, J=12.9 Hz, 1H), 8.05-7.92 (m, 3H), 7.37-7.23 (m, 4H), 7.15-7.02 (m, 3H), 6.77-6.70 (m, 1H), 5.21 (s, 1H), 4.23-4.07 (m, 2H), 3.98-3.76 (m, 2H), 3.48-3.36 (m, 2H), 2.33 (d, J=4.4 Hz, 3H) ppm. MS: M/e 475 (M+1)$^+$.

Example 106B: (R)-2-(5-amino-2-(furan-2-yl)-7H-pyrazolo[4,3-e][1,2,4]triazolo[1,5-c]pyrimidin-7-yl)-N-((3S,4R)-4-hydroxytetrahydrofuran-3-yl)-2-phenylpropanamide A mixture of (R)-2-(5-amino-2-(furan-2-yl)-7H-pyrazolo[4,3-e][1,2,4]triazolo[1,5-c]pyrimidin-7-yl)-2-phenylpropanoic acid (38.9 mg, 0.1 mmol), (3R,4S)-4-aminotetrahydrofuran-3-ol hydrochloride (13.9 mg, 0.1 mmol), HATU (45 mg, 0.12 mmol) and DIPEA (25.8 mg, 0.2 mmol) in DMF (3 mL) was stirred overnight. The reaction mixture was poured into $H_2O$ (10 mL) and extracted with EtOAc (10 mL×3). The combined organic layer was washed with brine, dried over $Na_2SO_4$, concentrated and purified by prep-TLC (EtOAc 100%) to give the target compound (24 mg, 50.6%). $^1$H NMR (400 MHz, DMSO-d6) δ 8.24 (d, J=1.2 Hz, 1H), 8.08-7.92 (m, 3H), 7.83 (dd, J=22.4, 6.8 Hz, 1H), 7.45-7.20 (m, 4H), 7.16-7.05 (m, 2H), 6.79-6.70 (m, 1H), 5.19-5.09

(m, 1H), 4.26-4.04 (m, 2H), 3.96-3.84 (m, 1H), 3.69-3.48 (m, 2H), 3.47-3.38 (m, 1H), 2.29 (s, 3H) ppm. MS: M/e 475 (M+1)$^+$.

Example 107: 2-(5-amino-2-(furan-2-yl)-7H-pyrazolo[4,3-e][1,2,4]triazolo[1,5-c]pyrimidin-7-yl)-N-((3S,4S)-4-hydroxytetrahydrofuran-3-yl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (38.9 mg, 0.1 mmol), (3S,4S)-4-aminotetrahydrofuran-3-ol (10.3 mg, 0.1 mmol), HATU (45 mg, 0.12 mmol) and DIPEA (25.8 mg, 0.2 mmol) in DMF (3 mL) was stirred overnight. The reaction mixture was poured into H$_2$O (10 mL) and extracted with EtOAc (10 mL×3). The combined organic layer was washed with brine, dried over Na$_2$SO$_4$, concentrated and purified by Pre-TLC (EtOAc 100%) to give the target compound (21 mg, 44.3%). $^1$H NMR (400 MHz, DMSO-d6) δ8.25 (d, J=1.6 Hz, 1H), 8.08-7.93 (m, 3H), 7.92-7.78 (m, 1H), 7.36-7.21 (m, 4H), 7.19-7.04 (m, 2H), 6.82-6.70 (m, 1H), 5.15 (dd, J=10.8, 4.1 Hz, 1H), 4.29-4.03 (m, 2H), 3.95-3.60 (m, 2H), 3.56-3.39 (m, 2H), 2.29 (s, 3H) ppm. MS: M/e 475 (M+1)$^+$.

Example 107B: (R)-2-(5-amino-2-(furan-2-yl)-7H-pyrazolo[4,3-e][1,2,4]triazolo[1,5-c]pyrimidin-7-yl)-N-((3S,4S)-4-hydroxytetrahydrofuran-3-yl)-2-phenylpropanamide A mixture of (R)-2-(5-amino-2-(furan-2-yl)-7H-pyrazolo[4,3-e][1,2,4]triazolo[1,5-c]pyrimidin-7-yl)-2-phenylpropanoic acid (38.9 mg, 0.1 mmol), (3S,4S)-4-aminotetrahydrofuran-3-ol (10.3 mg, 0.1 mmol), HATU (45 mg, 0.12 mmol) and DIPEA (25.8 mg, 0.2 mmol) in DMF (3 mL) was stirred overnight. The reaction mixture was poured into H$_2$O (10 mL) and extracted with EtOAc (10 mL×3). The combined organic layer was washed with brine, dried over Na$_2$SO$_4$, concentrated and purified by prep-TLC (EtOAc 100%) to give the target compound (23 mg, 48.5%). $^1$H NMR (400 MHz, DMSO-d6) δ 8.28 (s, 1H), 7.96 (s, 3H), 7.39-7.21 (m, 4H), 7.18-6.99 (m, 3H), 6.84-6.67 (m, 1H), 5.21 (d, J=3.6 Hz, 1H), 4.22-4.09 (m, 2H), 3.93-3.73 (m, 2H), 3.49-3.39 (m, 2H), 2.34 (s, 3H) ppm. MS: M/e 475 (M+1)$^+$.

Example 108: 2-(5-amino-2-(furan-2-yl)-7H-pyrazolo[4,3-e][1,2,4]triazolo[1,5-c]pyrimidin-7-yl)-N-((6-methylpyridin-2-yl)methyl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), (6-methylpyridin-2-yl)methanamine (24 mg, 0.19 mmol), HATU (72 mg, 0.19 mmol) and DIPEA (34 mg, 0.26 mmol) in DMF (5 mL) was stirred at rt for 2 hrs. The solution was added with water (5 mL), extracted with ethyl acetate (10 mL) and washed with brine (10 mL). The organic layer was dried, concentrated and purified by Pre-TLC (EtOAc) to get the desired product (35 mg, 56%). $^1$H NMR (400 MHz, DMSO-d6) δ 8.26 (s, 1H), 8.08 (t, J=4.0 Hz, 1H), 8.02 (br.s, 2H), 7.95 (s, 1H), 7.61 (t, J=8.0 Hz, 1H), 7.34-7.23 (m, 6H), 7.18 (d, J=8.0 Hz, 1H), 7.05 (d, J=4.0 Hz, 1H), 6.74 (dd, J=3.2, 1.6 Hz, 1H), 4.43-4.33 (m, 2H), 2.39 (s, 3H), 2.33 (s, 3H) ppm. MS: M/e 494 (M+1)$^+$.

Example 108B: (R)-2-(5-amino-2-(furan-2-yl)-7H-pyrazolo[4,3-e][1,2,4]triazolo[1,5-c]pyrimidin-7-yl)-N-((6-methylpyridin-2-yl)methyl)-2-phenylpropanamide A mixture of (R)-2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), (6-methyl pyridin-2-yl)methanamine (24 mg, 0.19 mmol), HATU (72 mg, 0.19 mmol) and DIPEA (34 mg, 0.26 mmol) in DMF (5 mL) was stirred at rt for 2 hrs. The solution was added with water (5 mL), extracted with ethyl acetate (10 mL) and washed with brine (10 mL). The organic layer was dried, concentrated and purified by Pre-TLC (EtOAc) to get the desired product (12 mg, 19%). $^1$H NMR (400 MHz, DMSO-d6) δ 8.26 (s, 1H), 8.09 (t, J=4.0 Hz, 1H), 8.02 (br.s, 2H), 7.95 (s, 1H), 7.63 (s, 1H), 7.34-7.30 (m, 3H), 7.27-7.19 (m, 4H), 7.07 (s, 1H), 6.74 (dd, J$_1$=3.2 Hz, J$_2$=1.6 Hz, 1H), 4.44-4.33 (m, 2H), 2.39 (s, 3H), 2.34 (s, 3H) ppm. MS: M/e 494 (M+1)$^+$.

Example 109: 2-(5-amino-2-(furan-2-yl)-7H-pyrazolo[4,3-e][1,2,4]triazolo[1,5-c]pyrimidin-7-yl)-N-((5-methylpyridin-2-yl)methyl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), (6-(aminomethyl)pyridin-3-yl)methanamine (24 mg, 0.19 mmol), HATU (72 mg, 0.19 mmol) and DIPEA (34 mg, 0.26 mmol) in DMF (5 mL) was stirred at rt for 2 hrs. The solution was added with water (5 mL), extracted with ethyl acetate (10 mL) and washed with brine (10 mL). The organic layer was dried, concentrated and purified by Prep-TLC (EtOAc) to get the desired product (42 mg, 66%). $^1$H NMR (400 MHz, DMSO-d6) δ 8.26 (s, 2H), 8.14 (t, J=4.0 Hz, 1H), 8.03 (br.s, 2H), 7.95 (s, 1H), 7.60 (s, 1H), 7.34-7.21 (m, 7H), 6.74 (dd, J=3.2, 1.6 Hz, 1H), 4.44-4.35 (m, 2H), 2.38 (s, 3H), 2.25 (s, 3H) ppm. MS: M/e 494 (M+1)$^+$.

Example 109B: (R)-2-(5-amino-2-(furan-2-yl)-7H-pyrazolo[4,3-e][1,2,4]triazolo[1,5-c]pyrimidin-7-yl)-N-((5-methylpyridin-2-yl)methyl)-2-phenylpropanamide A mixture of (R)-2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), (6-(aminomethyl)pyridin-3-yl) methanamine (24 mg, 0.19 mmol), HATU (72 mg, 0.19 mmol) and DIPEA (34 mg, 0.26 mmol) in DMF (5 mL) was stirred at rt for 2 hrs. The solution was added with water (5 mL), extracted with ethyl acetate (10 mL) and washed with brine (10 mL). The organic layer was dried, concentrated and purified by Prep-TLC (EtOAc) to get the desired product (40 mg, 63%). $^1$H NMR (400 MHz, DMSO-d6) δ 8.25 (s, 1H), 8.23 (br.s, 1H), 8.11 (t, J=4.0 Hz, 1H), 8.03 (br.s, 2H), 7.95 (s, 1H), 7.55 (d, J=8.0 Hz, 1H), 7.33-7.28 (m, 4H), 7.25-7.22 (m, 3H), 6.74 (dd, J=3.2 Hz, 1.6 Hz, 11H), 4.43-4.33 (m, 2H), 2.38 (s, 3H), 2.23 (s, 3H) ppm. MS: M/e 494 (M+1)$^+$.

Example 110: 2-(5-amino-2-(furan-2-yl)-7H-pyrazolo[4,3-e][1,2,4]triazolo[1,5-c]pyrimidin-7-yl)-N-((4-methylpyridin-2-yl)methyl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), (4-methylpyridin-2-yl)methanamine (24 mg, 0.19 mmol), HATU (72 mg, 0.19 mmol) and DIPEA (34 mg, 0.26 mmol) in DMF (5 mL) was stirred at rt for 2 hrs. The solution was added with water (5 mL), extracted with ethyl acetate (10 mL) and washed with brine (10 mL). The organic layer was dried, concentrated and purified by Prep-TLC (EtOAc) to get the desired product (24 mg, 38%). $^1$H NMR (400 MHz, DMSO-d6) δ 8.27 (s, 1H), 8.24 (d, J=8.0 Hz, 1H), 8.12 (t, J=4.0 Hz, 1H), 8.02 (br.s, 2H), 7.95 (s, 1H), 7.34-7.22 (m, 6H), 7.01 (d, J=4.0 Hz, 1H), 6.97 (s, 1H), 6.74 (dd, J=3.2, 1.6 Hz, 1H), 4.45-4.34 (m, 2H), 2.39 (s, 3H), 2.20 (s, 3H) ppm. MS: M/e 494 (M+1)$^+$.

Example 110B: (R)-2-(5-amino-2-(furan-2-yl)-7H-pyrazolo[4,3-e][1,2,4]triazolo[1,5-c]pyrimidin-7-yl)-N-((4-methylpyridin-2-yl)methyl)-2-phenylpropanamide A mixture of (R)-2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), (4-methylpyridin-2-yl)methanamine (24 mg, 0.19 mmol), HATU (72 mg, 0.19 mmol) and DIPEA (34 mg, 0.26 mmol) in DMF (5 mL) was stirred at rt for 2 hrs. The solution was added with water (5 mL), extracted with ethyl acetate (10 mL) and washed with brine (10 mL). The organic layer was dried, concentrated and purified by Prep-TLC (EtOAc) to get the desired product (40 mg, 63%). $^1$H NMR (400 MHz, DMSO-d6) δ 8.27 (s, 1H), 8.24 (d, J=8.0 Hz, 1H), 8.12 (t, J=4.0 Hz, 1H), 8.03 (br.s, 2H), 7.95 (d, J=4.0 Hz, 1H), 7.34-7.29 (m, 3H), 7.26-7.21 (m, 3H), 7.01 (d, J=4.0 Hz, 1H), 6.97 (s, 1H), 6.74 (dd, J$_1$=3.2 Hz, J$_2$=1.6 Hz, 1H), 4.45-4.35 (m, 2H), 2.39 (s, 3H), 2.20 (s, 3H) ppm. MS: M/e 494 (M+1)$^+$.

Example 111: 2-(5-amino-2-(furan-2-yl)-7H-pyrazolo[4,3-e][1,2,4]triazolo[1,5-c]pyrimidin-7-yl)-N-((3-methylpyridin-2-yl)methyl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), (3-methylpyridin-2-yl)methanamine (24 mg, 0.19 mmol), HATU (72 mg, 0.19 mmol) and DIPEA (34 mg, 0.26 mmol) in DMF (5 mL) was stirred at rt for 2 hrs. The solution was added with water (5 mL), extracted with ethyl acetate (10 mL) and washed with brine (10 mL). The organic layer was dried, concentrated and purified by Prep-TLC (EtOAc) to get the desired product (54 mg, 85%). $^1$H NMR (400 MHz, DMSO-d6) δ 8.27 (s, 1H), 8.07 (d, J=4.0 Hz, 1H), 7.93 (m, 4H), 7.54 (d, J=8.0 Hz, 1H), 7.35-7.20 (m, 6H), 7.14 (t, J=4.0 Hz, 1H), 6.74 (dd, J=3.2, 1.6 Hz, 1H), 4.45 (d, J=4.0 Hz, 2H), 2.39 (s, 3H), 2.24 (s, 3H) ppm. MS: M/e 494 (M+1)$^+$.

Example 111B: (R)-2-(5-amino-2-(furan-2-yl)-7H-pyrazolo[4,3-e][1,2,4]triazolo[1,5-c]pyrimidin-7-yl)-N-((3-methylpyridin-2-yl)methyl)-2-phenylpropanamide A mixture of (R)-2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), (3-methylpyridin-2-yl)methanamine (24 mg, 0.19 mmol), HATU (72 mg, 0.19 mmol) and DIPEA (34 mg, 0.26 mmol) in DMF (5 mL) was stirred at rt for 2 hrs. The solution was added with water (5 mL), extracted with ethyl acetate (10 mL) and washed with brine (10 mL). The organic layer was dried, concentrated and purified by Prep-TLC (EtOAc) to get the desired product (45 mg, 71%). $^1$H NMR (400 MHz, DMSO-d6) δ 8.27 (s, 1H), 8.07 (d, J=4.0 Hz, 1H), 7.96-7.92 (m, 4H), 7.53 (d, J=8.0 Hz, 1H), 7.36-7.31 (m, 3H), 7.25-7.20 (m, 3H), 7.15-7.12 (m, 1H), 6.74 (dd, J$_1$=3.2 Hz, J$_2$=1.6 Hz, 1H), 4.44 (d, J=4.0 Hz, 2H), 2.39 (s, 3H), 2.23 (s, 3H) ppm. MS: M/e 494 (M+1)$^+$.

Example 112: 2-(5-amino-2-(furan-2-yl)-7H-pyrazolo[4,3-e][1,2,4]triazolo[1,5-c]pyrimidin-7-yl)-N-((6-methoxypyridin-2-yl)methyl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.129 mmol), (6-methoxypyridin-2-yl)methanamine (32.7 mg, 0.256 mmol), HATU (53.7 mg, 0.141 mmol) and DIPEA (49.7 mg, 0.385 mmol) in DMF (5 mL) was stirred overnight at RT. The reaction mixture was poured into H$_2$O (20 mL) and extracted with EtOAc (20 mL×3). The combined organic layer was washed with brine, dried over Na$_2$SO$_4$, concentrated and purified by column chromatography (EtOAc) to give target compound (40 mg, 61.5%). $^1$H NMR (400 MHz, DMSO-d6) δ 8.26 (d, J=2.4 Hz, 1H), 8.01-7.95 (m, 4H), 7.65 (dd, J=11.0, 4.6 Hz, 1H), 7.30-7.22 (m, 6H), 6.98 (d, J=6.8 Hz, 1H), 6.77-6.69 (m, 1H), 6.63 (d, J=8.1 Hz, 1H), 4.35 (s, 2H), 3.70 (d, J=1.9 Hz, 3H), 2.40 (s, 3H). ppm.MS: M/e 510 (M+1)$^+$.

Example 112B: (R)-2-(5-amino-2-(furan-2-yl)-7H-pyrazolo[4,3-e][1,2,4]triazolo[1,5-c]pyrimidin-7-yl)-N-((6-methoxypyridin-2-yl)methyl)-2-phenylpropanamide A mixture of (R)-2-(5-amino-2-(furan-2-yl)-7H-pyrazolo[4,3-e][1,2,4]triazolo[1,5-c]pyrimidin-7-yl)-2-phenylpropanoic acid (100 mg, 0.256 mmol), (6-methoxypyridin-2-yl)methanamine (42 mg, 0.307 mmol), HATU (116 mg, 0.307 mmol) and DIPEA (66 mg, 0.512 mmol) in THF (10 mL) was stirred overnight at RT. The reaction mixture was concentrated in vacuo. The residue was purified by column chromatography (Methanol/EtOAc=1:50) to give the target compound (120 mg, 92.3%). $^1$H NMR (400 MHz, DMSO-d6) δ 8.27 (s, 1H), 8.24 (d, J=5.3 Hz, 1H), 8.13 (t, J=5.5 Hz, 1H), 7.96 (d, J=0.8 Hz, 3H), 7.30 (t, J=7.0 Hz, 3H), 7.25 (d, J=3.4 Hz, 1H), 7.20 (d, J=8.0 Hz, 2H), 6.82 (d, J=5.6 Hz, 2H), 6.74 (dd, J=3.4, 1.8 Hz, 1H), 4.39 (d, J=5.6 Hz, 2H), 3.76 (s, 3H), 2.40 (s, 3H). ppm.MS: M/e 510 (M+1)$^+$.

Example 113B: (R)-2-(5-amino-2-(furan-2-yl)-7H-pyrazolo[4,3-e][1,2,4]triazolo[1,5-c]pyrimidin-7-yl)-N-((5-methoxypyridin-2-yl)methyl)-2-phenylpropanamide To a mixture of (R)-2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), and DIPEA (70 mg, 0.54 mmol) in THF (1 mL) was added HATU (54 mg, 0.14 mmol) at rt and the mixture was stirred at rt for 10 min. A solution of (5-methoxypyridin-2-yl)methanamine (20 mg, 0.14 mmol) was added, and the mixture was stirred at rt for 16 hrs. The mixture was diluted with 5 mL of EtOAc, washed with brine (3 mL×3), dried over Na$_2$SO$_4$, and concentrated. The resulted residue was purified by prep-TLC (EtOAc, 100%) and the resulted solid was lyophilized to give the title product (45 mg, yield: 69%). $^1$H NMR (400 MHz, DMSO-d6) δ 8.25 (s, 1H), 8.17-8.07 (m, 2H), 8.02 (s, 2H), 7.97-7.92 (m, 1H), 7.38-7.26 (m, 5H), 7.26-7.19 (m, 3H), 6.74 (dd, J=3.2, 1.6 Hz, 1H), 4.46-4.26 (m, 2H), 3.78 (s, 3H), 2.38 (s, 3H). MS: M/e 510 (M+1)$^+$.

Example 114: 2-(5-amino-2-(furan-2-yl)-7H-pyrazolo[4,3-e][1,2,4]triazolo[1,5-c]pyrimidin-7-yl)-N-((4-methoxypyridin-2-yl)methyl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.129 mmol), (4-methoxypyridin-2-yl)methanamine (32.7 mg, 0.256 mmol), HATU (53.7 mg, 0.141 mmol) and DIPEA (49.7 mg, 0.385 mmol) in DMF (5 mL) was stirred overnight at RT. The reaction mixture was poured into H$_2$O (20 mL) and extracted with EtOAc (20 mL×3). The combined organic layer was washed with brine, dried over Na$_2$SO$_4$, concentrated and purified by column chromatography (EtOAc) to give the target compound (42 mg, 64.5%). ¹H NMR (400 MHz, DMSO-d6) δ 8.26 (d, J=2.4 Hz, 1H), 8.26-8.23 (m, 2H), 8.14-8.10 (m, 3H), 7.31-7.19 (m, 6H), 6.82-6.80 (m, 2H), 6.74-6.70 (m, 1H), 4.35 (s, 2H), 3.70 (d, J=1.9 Hz, 3H), 2.40 (s, 3H). MS: M/e 510 (M+1)⁺.

Example 114B: (R)-2-(5-amino-2-(furan-2-yl)-7H-pyrazolo[4,3-e][1,2,4]triazolo[1,5-c]pyrimidin-7-yl)-N-((4-methoxypyridin-2-yl)methyl)-2-phenylpropanamide A mixture of (R)-2-(5-amino-2-(furan-2-yl)-7H-pyrazolo[4,3-e][1,2,4]triazolo[1,5-c]pyrimidin-7-yl)-2-phenylpropanoic acid (100 mg, 0.256 mmol), (4-methoxypyridin-2-yl)methanamine (42 mg, 0.307 mmol), HATU (116 mg, 0.307 mmol) and DIPEA (66 mg, 0.512 mmol) in THF (10 mL) was stirred overnight at RT. The reaction mixture was concentrated in vacuo. The residue was purified by column chromatography (Methanol/EtOAc=1:50) to give the target compound (120 mg, 92.3%). ¹H NMR (400 MHz, DMSO-d6) δ 8.27 (s, 1H), 8.24 (d, J=5.3 Hz, 1H), 8.13 (t, J=5.5 Hz, 1H), 7.96 (d, J=0.8 Hz, 3H), 7.30 (t, J=7.0 Hz, 3H), 7.25 (d, J=3.4 Hz, 1H), 7.20 (d, J=8.0 Hz, 2H), 6.82 (d, J=5.6 Hz, 2H), 6.74 (dd, J=3.4, 1.8 Hz, 1H), 4.39 (d, J=5.6 Hz, 2H), 3.76 (s, 3H), 2.40 (s, 3H). ppm.MS: M/e 510 (M+1)⁺.

Example 115: 2-(5-amino-2-(furan-2-yl)-7H-pyrazolo[4,3-e][1,2,4]triazolo[1,5-c]pyrimidin-7-yl)-N-((3-methoxypyridin-2-yl)methyl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.129 mmol), (3-methoxypyridin-2-yl)methanamine (35 mg, 0.257 mmol), HATU (73 mg, 0.19 mmol) and DIPEA (64 mg, 0.5 mmol) in THF (5 mL) was stirred overnight at RT. The reaction mixture was concentrated in vacuo and purified by column chromatography (EtOAc) to give target compound (12 mg, 18.4%). ¹H NMR (400 MHz, DMSO-d6)) δ 8.27 (s, 1H), 7.95 (s, 2H), 7.84 (d, J=4.9 Hz, 1H), 7.70 (s, 1H), 7.38-7.27 (m, 4H), 7.23 (t, J=8.0 Hz, 4H), 6.74 (s, 1H), 4.44 (d, J=4.3 Hz, 2H), 3.79 (s, 3H), 2.38 (s, 3H). MS: M/e 510.1 (M+1)⁺.

Example 115B: (R)-2-(5-amino-2-(furan-2-yl)-7H-pyrazolo[4,3-e][1,2,4]triazolo[1,5-c]pyrimidin-7-yl)-N-((3-methoxypyridin-2-yl)methyl)-2-phenylpropanamide A mixture of (R)-2-(5-amino-2-(furan-2-yl)-7H-pyrazolo[4,3-e][1,2,4]triazolo[1,5-c]pyrimidin-7-yl)-2-phenylpropanoic acid (100 mg, 0.256 mmol), (3-methoxypyridin-2-yl)methanamine (42 mg, 0.307 mmol), HATU (116 mg, 0.307 mmol) and DIPEA (66 mg, 0.512 mmol) in THF (10 mL) was stirred overnight at RT. The reaction mixture was concentrated in vacuo. The residue was purified by column chromatography (Methanol/EtOAc=1:50) to give target product (110 mg, 84.6%). ¹H NMR (400 MHz, DMSO-d6) δ 8.26 (s, 1H), 8.01-7.95 (m, 3H), 7.94 (d, J=0.9 Hz, 1H), 7.64 (t, J=7.8 Hz, 1H), 7.35-7.27 (m, 3H), 7.27-7.18 (m, 3H), 6.98 (d, J=7.4 Hz, 1H), 6.74 (dd, J=3.4, 1.7 Hz, 1H), 6.62 (d, J=8.2 Hz, 1H), 4.35 (d, J=5.1 Hz, 2H), 3.70 (s, 3H), 2.40 (s, 3H). ppm.MS: M/e 510 (M+1)⁺.

Example 116: 2-(5-amino-2-(furan-2-yl)-7H-pyrazolo[4,3-e][1,2,4]triazolo[1,5-c]pyrimidin-7-yl)-N-((6-fluoropyridin-2-yl)methyl)-2-phenylpropanamide To a mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.12 mmol), (6-fluoropyridin-2-yl)methanamine dihydrochloride (30 mg, 0.15 mmol), DIPEA (100 mg, 0.77 mmol) in DMF (1 mL) was added HATU (60 mg, 0.16 mmol) at rt and the mixture was stirred at rt for 16 hrs. The mixture was diluted with 20 mL of EtOAc, washed with NaHCO₃ (10 mL), brine (10 mL×3), dried over Na₂SO₄, concentrated. 3 mL of EtOAc was added and the suspension was stirred for 30 min and filtered. The filter cake was lyophilized to give the title product (25 mg, yield: 42%). ¹H NMR (400 MHz, DMSO-d6) δ 8.27 (s, 1H), 8.22 (t, J=6.0 Hz, 1H), 8.06 (s, 2H), 7.98-7.88 (m, 2H), 7.39 (dd, J=7.6, 2.0 Hz, 1H), 7.36-7.19 (m, 6H), 7.00 (dd, J=8.0, 2.0 Hz, 1H), 6.74 (dd, J=3.2, 1.6 Hz, 1H), 4.45-4.27 (m, 2H), 2.39 (s, 3H). MS: M/e 498 (M+1)⁺.

Example 117: 2-(5-amino-2-(furan-2-yl)-7H-pyrazolo[4,3-e][1,2,4]triazolo[1,5-c]pyrimidin-7-yl)-N-((5-fluoropyridin-2-yl)methyl)-2-phenylpropanamide To a stirred solution of 2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), HATU (54 mg, 0.14 mmol) and DIPEA (50 mg, 0.39 mmol) in THF (15 ml) was added (5-fluoropyridin-2-yl)methanamine (18 mg, 0.14 mmol). The reaction mixture was stirred at rt for 15 h. After completion, the reaction mixture was washed with H₂O (15 ml) and then extracted with DCM (20 ml×2). The organic layer was dried over Na₂SO₄, filtered and then concentrated under reduced pressure to afford a residue. The residue was purified by prep-TLC with DCM:MeOH (30:1) to afford the product (35.7 mg, 56%). 1H NMR (400 MHz, DMSO-d6) δ 8.41 (d, J=4 Hz, 1H), 8.26 (s, 1H), 8.23 (t, J=4 Hz, 1H), 8.06 (s, 2H), 7.95 (s, 1H), 7.67 (td, J=8 Hz, 4 Hz, 1H), 7.53 (dd, J=8 Hz, 4 Hz, 1H), 7.34-7.21 (m, 6H), 6.74 (dd, J=4 Hz, 2 Hz, 1H), 4.41 (qd, J=16 Hz, 4 Hz, 2H), 2.38 (s, 3H) ppm. MS: M/e 498 (M+1)⁺.

Example 117B: (R)-2-(5-amino-2-(furan-2-yl)-7H-pyrazolo[4,3-e][1,2,4]triazolo[1,5-c]pyrimidin-7-yl)-N-((5-fluoropyridin-2-yl)methyl)-2-phenylpropanamide To a stirred solution of (R)-2-(5-amino-2-(furan-2-yl)-7H-pyrazolo[4,3-e][1,2,4]triazolo[1,5-c]pyrimidin-7-yl)-2-phenylpropanoic acid (1.54 g, 3.96 mmol), HATU (1.65 g, 4.34 mmol) and DIPEA (1.53 g, 15.15 mmol) in THF (30 ml) was added (5-fluoropyridin-2-yl)methanamine (0.50 g, 3.97 mmol). The reaction mixture was stirred at r.t. for 15 h. After completion, the reaction mixture was washed with H₂O (20 ml) and then extracted with DCM (25 ml×2). The organic layer was dried over Na₂SO₄, filtered and then concentrated under reduced pressure to afford a residue. The residue was purified by column chromatography with DCM:MeOH (30:1) to afford the product (1.37 g, 70%). ¹H NMR (400 MHz, DMSO-d6) δ 8.41 (d, J=4 Hz, 1H), 8.26 (s, 1H), 8.23 (t, J=4 Hz, 1H), 8.05 (s, 2H), 7.95 (s, 1H), 7.67 (td, J=8 Hz, 4 Hz, 1H), 7.53 (dd, J=8 Hz, 4 Hz, 1H), 7.34-7.20 (m, 6H), 6.74 (s, 1H), 4.41 (qd, J=16 Hz, 4 Hz, 2H), 2.38 (s, 3H) ppm. MS: M/e 498 (M+1)⁺.

Example 118: 2-(5-amino-2-(furan-2-yl)-7H-pyrazolo[4,3-e][1,2,4]triazolo[1,5-c]pyrimidin-7-yl)-N-((4-fluoropyridin-2-yl)methyl)-2-phenylpropanamide To a stirred solution of 2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), HATU (54 mg, 0.14 mmol) and DIPEA (50 mg, 0.39 mmol) in THF (15 ml) was added (4-fluoropyridin-2-yl)methanamine (18 mg, 0.14 mmol). The reaction mixture was stirred at rt for 15 h. After completion, the reaction mixture was washed with H₂O (15 ml) and then extracted with DCM (20 ml×2). The organic layer was dried over Na₂SO₄, filtered and then concentrated under reduced pressure to afford a residue. The residue was purified by prep-TLC with DCM:MeOH (30:1) to afford the product (26.2 mg, 41%). ¹H NMR (400 MHz, DMSO-d6) δ 8.46 (dd, J=8 Hz, 4 Hz, 1H), 8.27 (s, 1H), 8.23 (t, J=4 Hz, 1H), 8.02 (s, 2H), 7.96 (s, 1H), 7.35-7.08 (m, 8H), 6.78-6.71 (m, 1H), 4.45 (d, J=8 Hz, 2H), 2.40 (s, 3H) ppm. MS: M/e 498 (M+1)⁺.

Example 118B: (R)-2-(5-amino-2-(furan-2-yl)-7H-pyrazolo[4,3-e][1,2,4]triazolo[1,5-c]pyrimidin-7-yl)-N-((4-fluoropyridin-2-yl)methyl)-2-phenylpropanamide To a stirred solution of (R)-2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), HATU (54 mg, 0.14 mmol) and DIPEA (50 mg, 0.39 mmol) in THF (15 ml) was added (4-fluoropyridin-2-yl)methanamine (18 mg, 0.14 mmol). The reaction mixture was stirred at rt for 15 h. After completion, the reaction mixture was washed with H₂O (15 ml) and then extracted with DCM (20 ml×2). The organic layer was dried over Na₂SO₄, filtered and then concentrated under reduced pressure to afford a residue. The residue was purified by prep-TLC with DCM:MeOH (30:1) to afford the product (25.0 mg, 39%). ¹H NMR (400 MHz, DMSO-d6) δ 8.46 (dd, J=8 Hz, 4 Hz, 1H), 8.27 (s, 1H), 8.23 (t, J=4 Hz, 1H), 8.01 (s, 2H), 7.96 (d, J=4 Hz, 1H), 7.34-7.08 (m, 8H), 6.74 (dd, J=4 Hz, 2 Hz, 1H), 4.45 (d, J=4 Hz, 2H), 2.40 (s, 3H) ppm. MS: M/e 498 (M+1)⁺.

Example 119: 2-(5-amino-2-(furan-2-yl)-7H-pyrazolo[4,3-e][1,2,4]triazolo[1,5-c]pyrimidin-7-yl)-N-((3-fluoropyridin-2-yl)methyl)-2-phenylpropanamide To a stirred solution of 2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), HATU (54 mg, 0.14 mmol) and DIPEA (50 mg, 0.39 mmol) in THF (15 ml) was added (3-fluoropyridin-2-yl)methanamine (18 mg, 0.14 mmol). The reaction mixture was stirred at rt for 15 h. After completion, the reaction mixture was washed with H₂O (15 ml) and then extracted with DCM (20 ml×2). The organic layer was dried over Na₂SO₄, filtered and then concentrated under reduced pressure to afford a residue. The residue was purified by prep-TLC with DCM:MeOH (30:1) to afford the product (33.6 mg, 53%). ¹H NMR (400 MHz, DMSO-d6) δ 8.23 (s, 2H), 8.05-7.88 (m, 4H), 7.65 (t, J=8 Hz, 1H), 7.37-7.18 (m, 7H), 6.74 (s, 1H), 4.53 (qd, J=16 Hz, 4 Hz, 2H), 2.35 (s, 3H) ppm. MS: M/e 498 (M+1)⁺.

Example 119B: (R)-2-(5-amino-2-(furan-2-yl)-7H-pyrazolo[4,3-e][1,2,4]triazolo[1,5-c]pyrimidin-7-yl)-N-((3-fluoropyridin-2-yl)methyl)-2-phenylpropanamide To a stirred solution of (R)-2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), HATU (54 mg, 0.14 mmol) and DIPEA (50 mg, 0.39 mmol) in THF (15 ml) was added (3-fluoropyridin-2-yl)methanamine (18 mg, 0.14 mmol). The reaction mixture was stirred at rt for 15 h. After completion, the reaction mixture was washed with H₂O (15 ml) ml) and then extracted with DCM (20 ml×2). The organic layer was dried over Na₂SO₄, filtered and then concentrated under reduced pressure to afford a residue. The residue was purified by prep-TLC with DCM:MeOH (30:1) to afford the product (45.2 mg, 71%). ¹H NMR (400 MHz, DMSO-d6) δ 8.25-8.21 (m, 2H), 8.02-7.90 (m, 4H), 7.64 (t, J=8 Hz, 1H), 7.37-7.18 (m, 7H), 6.74 (dd, J=8 Hz, 4 Hz, 1H), 4.53 (qd, J=16 Hz, 4 Hz, 2H), 2.35 (s, 3H) ppm. MS: M/e 498 (M+1)⁺.

Example 120: 2-(5-amino-2-(furan-2-yl)-7H-pyrazolo[4,3-e][1,2,4]triazolo[1,5-c]pyrimidin-7-yl)-N-((1R,3R)-3-hydroxycyclohexyl)-2-phenylacetamide Example 121: 2-(5-amino-2-(furan-2-yl)-7H-pyrazolo[4,3-e][1,2,4]triazolo[1,5-c]pyrimidin-7-yl)-N-((1S,3R)-3-hydroxycyclohexyl)-2-phenylpropanamide Example 122: 2-(5-amino-2-(furan-2-yl)-7H-pyrazolo[4,3-e][1,2,4]triazolo[1,5-c]pyrimidin-7-yl)-N-((1S,3S)-3-hydroxycyclohexyl)-2-phenylacetamide Example 123: 2-(5-amino-2-(furan-2-yl)-7H-pyrazolo[4,3-e][1,2,4]triazolo[1,5-c]pyrimidin-7-yl)-N-((1S,3R)-3-hydroxycyclohexyl)-2-phenylpropanamide To a mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), (1R,3S)-3-aminocyclohexan-1-ol hydrochloride (23 mg, 0.15 mmol), DIPEA (70 mg, 0.54 mmol) in DMF (1 mL) was added HATU (60 mg, 0.16 mmol) at rt and the mixture was stirred at rt for 5 hrs. The mixture was diluted with 15 mL of EA, washed with NaHCO₃ (10 mL), brine (10 mL×3), dried over Na₂SO₄, and concentrated. The resulted residue was purified by prep-TLC (EtOAc 100%) to give the title product (16 mg, yield: 26%). ¹H NMR (400 MHz, DMSO-d6) δ 8.22 (d, J=4.4 Hz, 1H), 8.12-7.78 (m, 3H), 7.61 (d, J=8.0 Hz, 1H), 7.34-7.22 (m, 4H), 7.21-7.10 (m, 2H), 6.74 (dd, J=3.2, 1.6 Hz, 1H), 4.53 (dd, J=7.2, 4.0 Hz, 1H), 3.80-3.65 (m, 1H), 3.51-3.37 (m, 1H), 2.27 (s, 3H), 1.95-1.75 (m, 1H), 1.72-1.51 (m, 3H), 1.22-1.07 (m, 3H), 1.06-0.93 (m, 1H). MS: M/e 487 (M+1)⁺.

Example 124

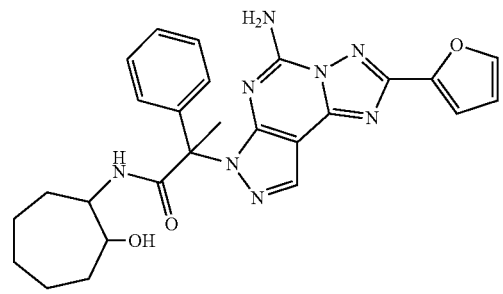 [SMILES: CC(C(=O)NC1CCCCCC1O)(c1ccccc1)n1ncc2c1nc(N)n1nc(-c3ccco3)nc21]

Example 125

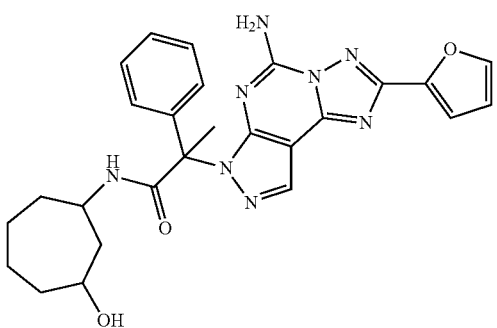 [SMILES: CC(C(=O)NC1CCCCC(O)C1)(c1ccccc1)n1ncc2c1nc(N)n1nc(-c3ccco3)nc21]

Example 126

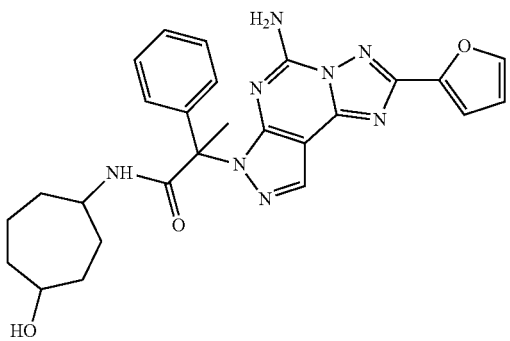 [SMILES: CC(C(=O)NC1CCCC(O)CC1)(c1ccccc1)n1ncc2c1nc(N)n1nc(-c3ccco3)nc21]

Example 127

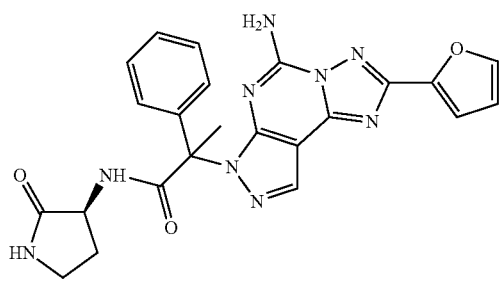 [SMILES: CC(C(=O)N[C@H]1CCNC1=O)(c1ccccc1)n1ncc2c1nc(N)n1nc(-c3ccco3)nc21]

Example 128: 2-(5-amino-2-(furan-2-yl)-7H-pyrazolo[4,3-e][1,2,4]triazolo[1,5-c]pyrimidin-7-yl)-N-(4-oxocyclohexyl)-2-phenylpropanamide To a mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), 4-aminocyclohexan-1-one hydrochloride (50 mg, 0.3 mmol), DIPEA (100 mg, 0.77 mmol) in DMF (1 mL) was added HATU (60 mg, 0.16 mmol) at rt and the mixture was stirred at rt for 16 hrs. The mixture was diluted with 20 mL of EtOAc, washed with brine (10 mL×3), dried over Na$_2$SO$_4$, and concentrated. The resulted residue was purified by prep-TLC and the resulted solid was lyophilized to give the title product (39 mg, yield: 62%). $^1$H NMR (400 MHz. DMSO-d6) δ 8.24 (s, 1H), 8.12-7.86 (m, 3H), 7.73 (d, J=7.6 Hz, 1H), 7.34-7.22 (m, 4H), 7.14 (d, J=6.8 Hz, 2H), 6.74 (dd, J=2.8, 1.6 Hz, 1H), 4.25-4.13 (m, 1H), 2.46-2.37 (m, 2H), 2.27 (s, 3H), 2.21-2.12 (m, 2H), 2.07-2.01 (m, 1H), 1.98-1.91 (m, 1H), 1.72-1.57 (m, 2H). MS: M/e 485 (M+1)$^+$.

Example 128B: (R)-2-(5-amino-2-(furan-2-yl)-7H-pyrazolo[4,3-e][1,2,4]triazolo[1,5-c]pyrimidin-7-yl)-N-(4-oxocyclohexyl)-2-phenylpropanamide

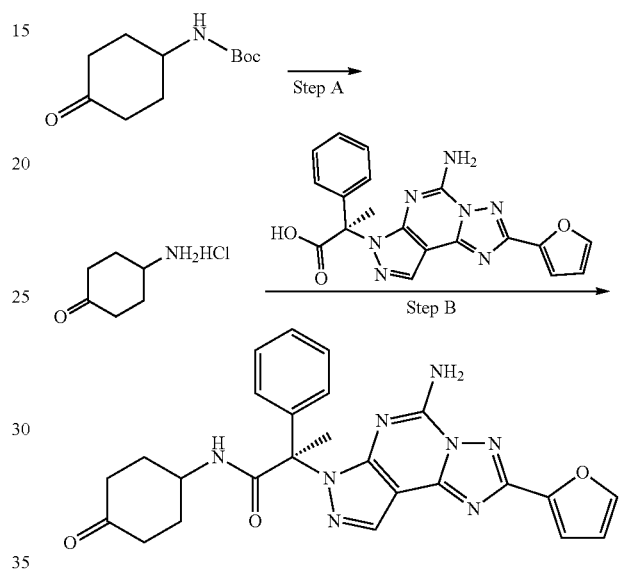

Step A: 4-aminocyclohexan-1-one hydrochloride

To a stirred solution of tert-butyl (4-oxocyclohexyl)carbamate (1.0 g, 4.7 mmol) in EtOAc was added a solution of HCl/Dioxane (4 M, 10 mL) and the resulted mixture was stirred at rt for 4 hrs. A white solid precipitated, which was filtered, washed with EtOAc (5 mL), dried under high vacuum to give the title product (650 mg, yield: 92%) as a white solid. $^1$H NMR (400 MHz, CD$_3$OD) δ 3.23-3.07 (m, 1H), 2.14-2.04 (m, 2H), 1.97-1.86 (m, 2H), 1.67-1.52 (m, 2H), 1.51-1.39 (m, 2H).

Step B: (R)-2-(5-amino-2-(furan-2-yl)-7H-pyrazolo[4,3-e][1,2,4]triazolo[1,5-c]pyrimidin-7-yl)-N-(4-oxocyclohexyl)-2-phenylpropanamide To a mixture of (R)-2-(5-amino-2-(furan-2-yl)-7H-pyrazolo[4,3-e][1,2,4]triazolo[1,5-c]pyrimidin-7-yl)-2-phenylpropanoic acid (400 mg, 1.03 mmol), 4-aminocyclohexan-1-one hydrochloride (180 mg, 1.2 mmol), DIPEA (650 mg, 5 mmol) in DMF (5 mL) was added HATU (450 mg, 1.2 mmol) at rt and the mixture was stirred at rt for 16 hrs. The mixture was diluted with 30 mL of EtOAc, washed with brine (20 mL×3), dried over Na$_2$SO$_4$, and concentrated. The resulted residue was purified by column chromatography eluted with PE/EtOAc (1:1~1:2) and the resulted solid was lyophilized to give the title product (255 mg, yield: 53%). $^1$H NMR (400 MHz, DMSO-d6) δ 8.25 (s, 1H), 8.13-7.88 (m, 3H), 7.74 (d, J=8.0 Hz, 1H), 7.34-7.22 (m, 4H), 7.17-7.10 (m, 2H), 6.74 (dd, J=3.2, 1.6 Hz, 1H), 4.25-4.13 (m, 1H), 2.48-2.37 (m, 2H), 2.22-2.11 (m, 2H), 2.11-2.02 (m, 1H), 2.01-0.92 (m, 1H), 1.73-1.58 (m, 2H). MS: M/e 485 (M+1)$^+$.

Example 129

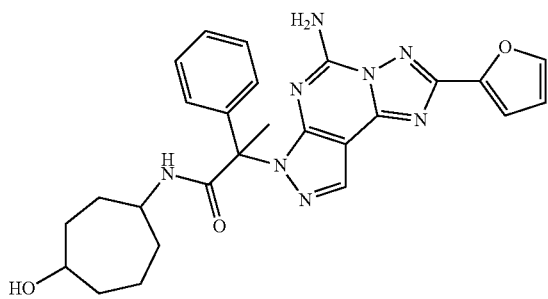 [SMILES: CC(C(=O)NC1CCCC(O)CC1)(c1ccccc1)n1ncc2c1nc(N)n1nc(-c3ccco3)nc21]

Example 130: 2-(5-amino-2-(furan-2-yl)-7H-pyrazolo[4,3-e][1,2,4]triazolo[1,5-c]pyrimidin-7-yl)-N-((6-(1-hydroxycyclobutyl)pyridin-2-yl)methyl)-2-phenylpropanamide

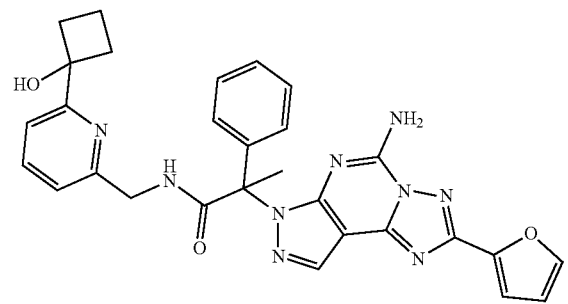

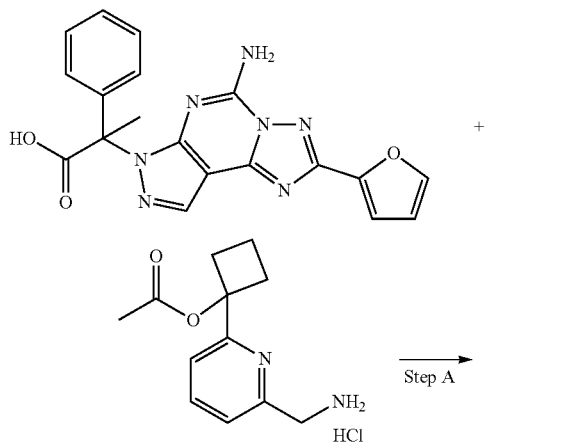

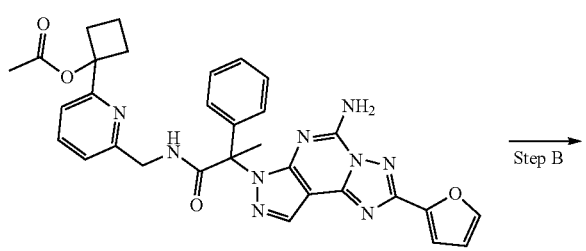

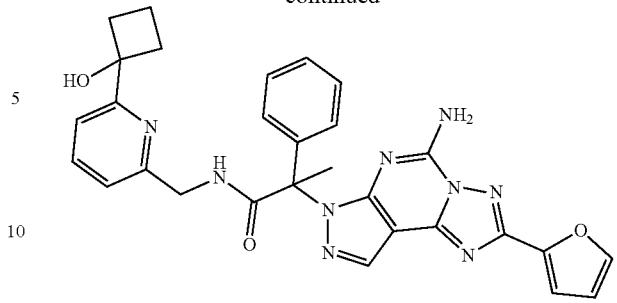

Step A: 1-(6-((2-(5-amino-2-(furan-2-yl)-7H-pyrazolo[4,3-e][1,2,4]triazolo[1,5-c]pyrimidin-7-yl)-2-phenylpropanamido)methyl)pyridin-2-yl)cyclobutyl acetate To a mixture of 2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), 1-(6-(aminomethyl)pyridin-2-yl)cyclobutyl acetate hydrochloride (40 mg, 0.15 mmol) and DIEA (100 mg, 0.77 mmol) in DMF (1 mL) was added HATU (60 mg, 0.16 mmol) at rt and the mixture was stirred at rt for 16 hrs. The mixture was diluted with 20 mL of EtOAc, washed with NaHCO₃ (10 mL), brine (10 mL×3), dried over Na₂SO₄, concentrated to give the title product (90 mg, crude) as a light yellow oil which was used for the next step directly. MS: M/e 592 (M+1)⁺.

Step B: 2-(5-amino-2-(furan-2-yl)-7H-pyrazolo[4,3-e][1,2,4]triazolo[1,5-c]pyrimidin-7-yl)-N-((6-(1-hydroxycyclobutyl)pyridin-2-yl)methyl)-2-phenylpropanamide To a stirred solution of 1-(6-((2-(5-amino-2-(furan-2-yl)-7H-pyrazolo[4,3-e][1,2,4]triazolo[1,5-c]pyrimidin-7-yl)-2-phenylpropanamido)methyl)pyridin-2-yl)cyclobutyl acetate (90 mg, crude) in MeOH (2 mL) was added an aqueous solution of NaOH (2 M, 2 mL) at rt and the resulted mixture was stirred for 5 hrs. The mixture was neutralized by HCl (1 M) to pH~7. The mixture was extracted with EtOAc (5 mL×3). The combined extract was washed with brine (5 mL×2), dried over Na₂SO₄ and concentrated. The resulted residue was purified by column chromatography and prep-TLC (EA, 100%) to give the title product (48 mg, yield: 68% for 2 steps). ¹H NMR (400 MHz, DMSO-d6) δ 8.25 (s, 1H), 8.13-7.98 (m, 3H), 7.97-7.92 (m, 1H), 7.70 (t, J=7.6 Hz, 1H), 7.38 (d, J=8.0 Hz, 1H), 7.34-7.20 (m, 7H), 6.74 (dd, J=3.2, 1.6 Hz, 1H), 5.62 (s, 1H), 4.47 (d, J=5.2 Hz, 2H), 2.43-2.31 (m, 5H), 2.15-2.03 (m, 2H), 1.85-1.71 (m, 1H), 1.68-1.55 (m, 1H). MS: M/e 550 (M+1)⁺.

Example 131

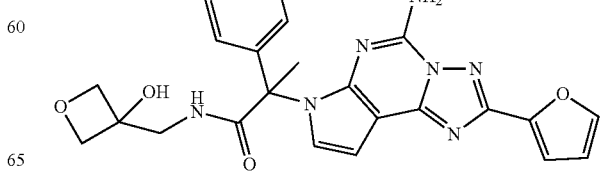

Example 132: 2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-methyl-3-phenylpropanamide A mixture of 2-(5-amino-2-(furan-2-yl)-7H-pyrazolo[4,3-e][1,2,4]triazolo[1,5-c]pyrimidin-7-yl)-2-methyl-3-phenylpropanoic acid (70 mg, 0.17 mmol), 3-(amino methyl)oxetan-3-ol (27 mg, 0.26 mmol), HATU (99 mg, 0.26 mmol) and DIPEA (44 mg, 0.34 mmol) in DMF (5 mL) was stirred at rt for 2 hrs. The solution was added with water (10 mL), extracted with ethyl acetate (10 mL) and washed with brine (10 mL). The organic layer was dried, concentrated and purified by preparative TLC (EtOAc) to get the desired product (50 mg, 60%). $^1$H NMR (400 MHz, DMSO-d6) δ 8.11 (s, 1H), 8.01 (br.s, 2H), 7.96 (s, 1H), 7.25-7.20 (m, 2H), 7.11-7.07 (m, 3H), 6.77-6.73 (m, 1H), 6.70 (d, J=6.7 Hz, 2H), 5.62 (s, 1H), 4.42-4.33 (m, 2H), 4.22 (dd, $J_1$=19.5 Hz, $J_2$=6.4 Hz, 2H), 4.10 (d, J=13.7 Hz, 1H), 3.49-3.40 (m, 2H), 3.24 (dd, J=13.6 Hz, $J_2$=5.6 Hz, 1H), 1.73 (s, 3H) ppm. MS: M/e 489 (M+1)$^+$.

Example 133: 2-(5-amino-2-(thiazol-2-yl)-7H-pyrazolo[4,3-e][1,2,4]triazolo[1,5-c]pyrimidin-7-yl)-N-((3-hydroxyoxetan-3-yl)methyl)-2-phenylpropanamide

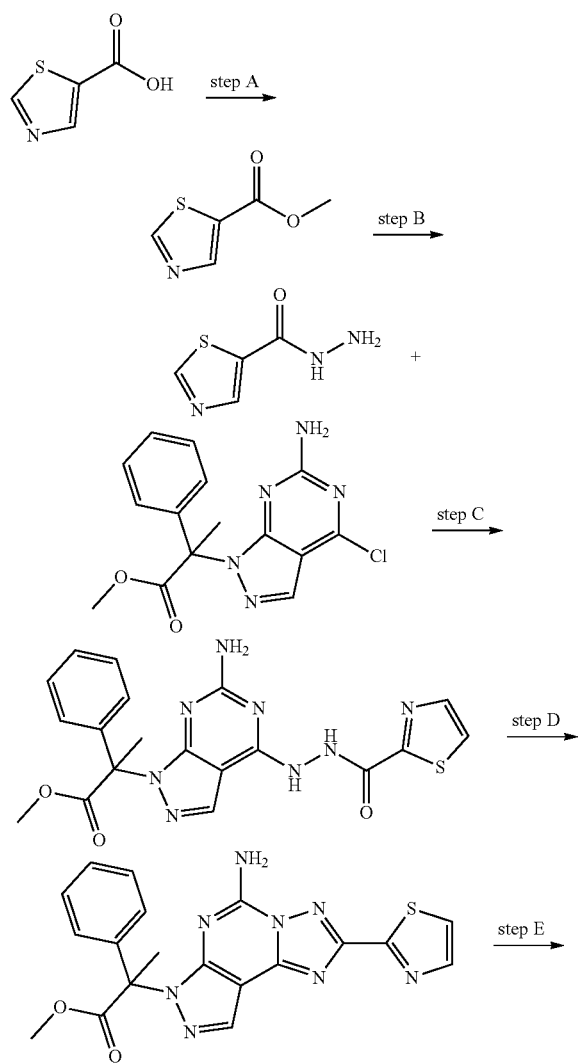

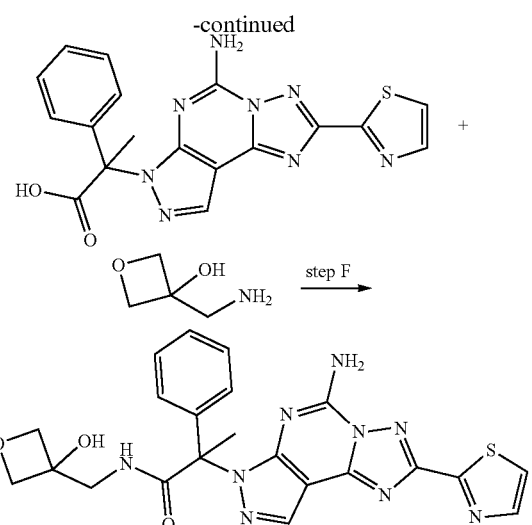

Step A: methyl thiazole-5-carboxylate

To a stirred solution of methyl thiazole-5-carboxylic acid (1 g, 7.75 mmol) in DCM (20 mL) was added oxalyl chloride (2 ml, 24 mmol) and DMF (50 mg, 0.67 mmol). After the addition, the reaction mixture was stirred at rt for 2 h. The mixture was concentrated in vacuo and the residue was added DCM (20 ml) followed by methanol (1.5 ml). After the addition, the reaction mixture was stirred at rt overnight. The reaction mixture was concentrated in vacuo to give a colorless oil which was used directly in next step (1.3 g, 100%). MS: M/e 144.0 (M+1)$^+$.

Step B: thiazole-5-carbohydrazide

To a stirred mixture of methyl thiazole-5-carboxylate (1.3 g, 7.75 mmol) in ethanol (30 mL) was added hydrazine hydrate (2 ml). After the addition, the reaction mixture was stirred at rt for 3 h. The reaction mixture was filtered. The filter cake was washed with EtOH (10 ml) and dried at 50° C. to give a white solid which was used directly in next step (820 mg, 74%). MS: M/e 144.0 (M+1)$^+$.

Step C: methyl 2-(6-amino-4-(2-(thiazole-2-carbonyl)hydrazinyl)-1H-pyrazolo[3,4-d]pyrimidin-1-yl)-2-phenylpropanoate To a stirred mixture of methyl 2-(6-amino-4-chloro-1H-pyrazolo[3,4-d]pyrimidin-1-yl)-2-phenylpropanoate (331 mg, 1 mmol) in t-BuOH (5 mL) was added thiazole-5-carbohydrazide (143 mg, 1 mmol). After the addition, the reaction mixture was stirred at 120° C. overnight. The mixture was cooled to rt and filtered. The filter cake was washed with t-BuOH and dried to give the product as a white solid which could be used directly in next step (400 mg, 91.3%). MS: M/e 439.0 (M+1)$^+$.

Step D: methyl 2-(5-amino-2-(thiazol-2-yl)-7H-pyrazolo[4,3-e][1,2,4]triazolo[1,5-c]pyrimidin-7-yl)-2-phenylpropanoate A mixture of methyl 2-(6-amino-4-(2-(thiazole-2-carbonyl)hydrazinyl)-1H-pyrazolo[3,4-d]pyrimidin-1-yl)-2-phenylpropanoate (460 mg, 1.09 mmol) in BSA (5 mL) and HMDS (5 mL) was stirred at 110° C. overnight. The mixture was concentrated in vacuo to remove BSA and HMDS. The residue was added EtOH (20 ml) and stirred at 70° C. for 1 h. A white precipitate was formed. The mixture was cooled down to rt and filtered. The filter cake was washed by EtOH and dried at 50° C. to give the product as a white solid (220 mg, 52.3%). $^1$H NMR (400 MHz, DMSO-d6) δ 8.31 (s, 1H), 8.17 (s, 2H), 8.11 (d, J=3.1 Hz, 1H), 8.04 (d, J=3.1 Hz, 1H), 7.31 (d, J=6.0 Hz, 3H), 7.16-7.05 (m, 2H), 3.75 (s, 3H), 2.31 (s, 3H). ppm MS: M/e 421.0 (M+1)$^+$.

Step E: 2-(5-amino-2-(thiazol-2-yl)-7H-pyrazolo[4,3-e][1,2,4]triazolo[1,5-c]pyrimidin-7-yl)-2-phenylpropanoic acid To a stirred mixture of methyl 2-(5-amino-2-(thiazol-2-yl)-7H-pyrazolo[4,3-e][1,2,4]triazolo[1,5-c]pyrimidin-7-yl)-2-phenylpropanoate (100 mg, 0.34 mmol) in EtOH (10 mL) was added aq. NaOH (2.0 M, 10 mL). After the addition, the reaction mixture was stirred at rt overnight. The mixture was concentrated in vacuo. The residue was added H$_2$O and adjusted pH=3~4 with aq. HC. The mixture was filtered, the filter cake was collected, dried to give the target compound (70 mg, 71.8%) as a white solid. MS: M/e 407.0 (M+1)$^+$.

Step F: 2-(5-amino-2-(thiazol-2-yl)-7H-pyrazolo[4,3-e][1,2,4]triazolo[1,5-c]pyrimidin-7-yl)-N-((3-hydroxyoxetan-3-yl)methyl)-2-phenylpropanamide A mixture of the product of step E (50 mg, 0.123 mmol), 3-(aminomethyl)oxetan-3-ol (25 mg, 0.246 mmol), HATU (71 mg, 0.184 mmol) and DIPEA (30 mg, 0.246 mmol) in DMF (5 mL) was stirred overnight at RT. The reaction mixture was poured into H$_2$O (20 mL) and extracted with EtOAc (20 mL×3). The combined organic layer was washed with brine, dried over Na$_2$SO$_4$, concentrated and purified by column chromatography (Methanol/EtOAc=1/50) to give target compound (48 mg, 80%). $^1$H NMR (400 MHz, DMSO-d6) δ 8.32 (s, 1H), 8.11 (d, J=3.2 Hz, 1H), 8.09-7.98 (m, 3H), 7.43 (d, J=6.0 Hz, 1H), 7.30 (t, J=6.8 Hz, 3H), 7.17 (d, J=6.6 Hz, 2H), 5.70 (s, 1H), 4.46-4.36 (m, 2H), 4.34-4.19 (m, 2H), 3.42 (d, J=3.2 Hz, 2H), 2.34 (s, 3H). ppm.MS: M/e 492.1 (M+1)$^+$.

Example 134

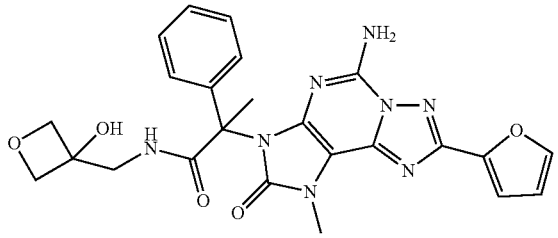 [SMILES: Cn1c(=O)n(C(C)(C(=O)NCC2(O)COC2)c2ccccc2)c2nc(N)n3nc(-c4ccco4)nc3c21]

Example 135: 2-(5-amino-2-(furan-2-yl)-7H-pyrazolo[4,3-e][1,2,4]triazolo[1,5-c]pyrimidin-7-yl)-N-((1R,3S)-3-hydroxycyclopentyl)-2-phenylpropanamide To a mixture of 2-(5-amino-2-(furan-2-yl)-7H-pyrazolo[4,3-e][1,2,4]triazolo[1,5-c]pyrimidin-7-yl)-2-phenylpropanoic acid (40 mg, 0.1 mmol), (1S,3R)-3-aminocyclopentan-1-ol hydrochloride (17 mg, 0.12 mmol), DIEA (50 mg, 0.39 mmol) in DMF (1 mL) was added HATU (46 mg, 0.12 mmol) at rt and the mixture was stirred at rt for 16 hrs. The mixture was diluted with 20 mL of EtOAc, washed with brine (10 mL×3), dried over Na$_2$SO$_4$, concentrated and the resulted oil was purified by prep-TLC (EtOAc) to give the title product (28 mg, yield: 58%) after lyophilization. $^1$H NMR (400 MHz, DMSO-d6) δ 8.22 (d, J=10.8 Hz, 1H), 8.11-7.78 (m, 3H), 7.41 (dd, J=10.8, 8.0 Hz, 1H), 7.35-7.22 (m, 4H), 7.17 (d, J=6.8 Hz, 1H), 7.13 (d, J=6.8 Hz, 1H), 6.78-6.69 (m, 1H), 4.56-4.42 (m, 1H), 4.27-4.09 (m, 1H), 4.08-3.94 (m, 1H), 2.28 (d, J=3.6 Hz, 3H), 1.92-1.70 (m, 2H), 1.68-1.55 (m, 2H), 1.46-1.32 (m, 2H). MS: M/e 473 (M+1)$^+$.

Example 136: 2-(5-amino-2-(furan-2-yl)-7H-pyrazolo[4,3-e][1,2,4]triazolo[1,5-c]pyrimidin-7-yl)-N-((1S,3R)-3-hydroxycyclopentyl)-2-phenylpropanamide To a mixture of 2-(5-amino-2-(furan-2-yl)-7H-pyrazolo[4,3-e][1,2,4]triazolo[1,5-c]pyrimidin-7-yl)-2-phenylpropanoic acid (40 mg, 0.1 mmol), (1R,3S)-3-aminocyclopentan-1-ol hydrochloride (17 mg, 0.12 mmol), DIPEA (50 mg, 0.39 mmol) in DMF (1 mL) was added HATU (46 mg, 0.12 mmol) at rt and the mixture was stirred at rt for 16 hrs. The mixture was diluted with 20 mL of EtOAc, washed with brine (10 mL×3), dried over Na$_2$SO$_4$, concentrated and the resulted oil was purified by prep-TLC (EtOAc) to give the title product (25 mg, yield: 52%) after lyophilization. $^1$H NMR (400 MHz, DMSO-d6) δ 8.20 (d, J=11.2 Hz, 1H), 8.13-7.77 (m, 3H), 7.46-7.35 (m, 1H), 7.34-7.21 (m, 4H), 7.17 (d, J=6.8 Hz, 1H), 7.13 (d, J=6.8 Hz, 1H), 6.74 (dd, J=3.6, 2.0 Hz, 1H), 4.51-4.43 (m, 1H), 4.24-4.11 (m, 1H), 4.08-3.95 (m, 1H), 2.28 (d, J=4.0 Hz, 3H), 1.95-1.72 (m, 2H), 1.67-1.54 (m, 2H), 1.47-1.32 (m, 2H). MS: M/e 473 (M+1)$^+$.

Example 137: 2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-(3-methoxyphenyl)propanamide

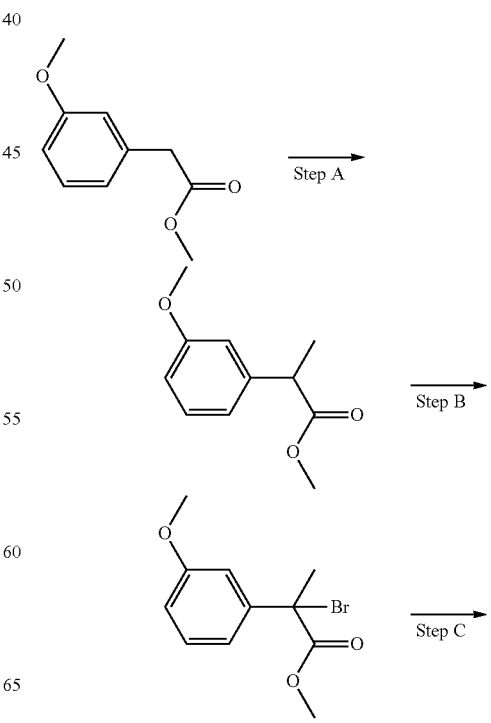

117

-continued

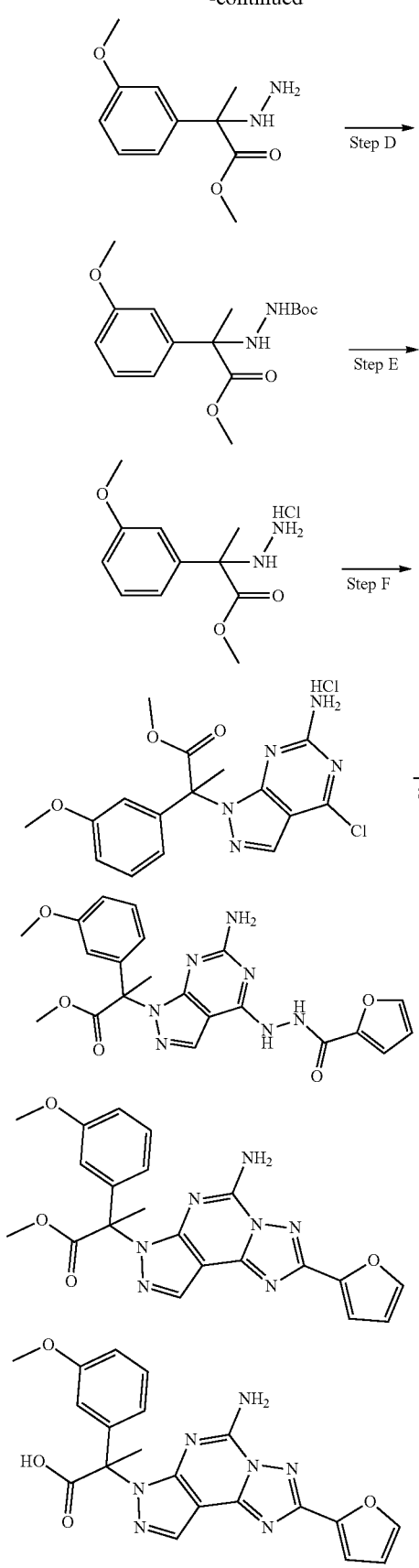

118

-continued

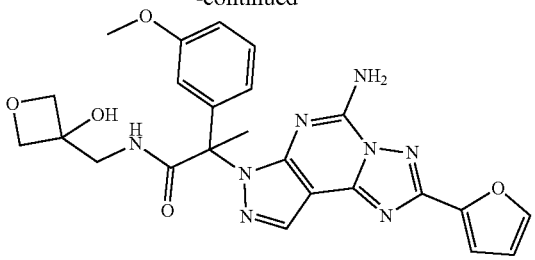

Step A: methyl 2-(3-methoxyphenyl)propanoate

To a stirred solution of methyl 2-(3-methoxyphenyl) acetate (10 g, 55.6 mmol) in THF (100 mL) was added LDA (2M, 33 mL, 66.7 mmol) slowly at −78° C. for 1 hour. Then MeI (10.4 mL, 167 mmol) was added to the reaction. The mixture was warmed to RT and stirred overnight. The reaction was quenched with saturated aq. $NH_4Cl$ and extracted with EtOAc (100 mL×2). The combined organic phase was washed with brine, dried over $Na_2SO_4$ and concentrated under reduced pressure. The residue was purified by silica gel chromatography (EtOAc:PE=1:5) to afford the title compound as yellow oil. $^1H$ NMR (400 MHz, DMSO-d6) δ7.31-7.17 (m, 1H), 6.94-6.76 (m, 3H), 3.80-3.75 (m, 1H), 3.74 (s, 3H), 3.58 (s, 3H), 1.37 (d, J=8 Hz, 3H) ppm. MS: M/e 195 $(M+1)^+$.

Step B: methyl 2-bromo-2-(3-methoxyphenyl)propanoate

To a stirred solution of the product of Step A (1 g, 5.2 mmol) in THF (20 mL) was added LDA (2M, 2.7 mL, 5.4 mmol) slowly at −78° C. under $N_2$. The reaction was stirred at −78° C. for 30 min. Then TBSCl (0.6 g, 5.5 mmol) was added to the reaction slowly. The reaction was warmed to RT and stirred at 50° C. for 2 hours. The reaction was cooled to −78° C. and NBS (1.38 g, 7.7 mmol) was added to the reaction. Then the mixture was warmed to RT and stirred overnight. The mixture was quenched with saturated aq. $NH_4Cl$ and extracted with EtOAc (20 mL×3). The combined organic phase was washed with brine, dried over $Na_2SO_4$ and concentrated under reduced pressure. The residue (crude, 1.7 g, yellow oil) was used into next Step directly. MS: M/e 193 $(M-79)^+$.

Step C: methyl 2-hydrazinyl-2-(3-methoxyphenyl)propanoate

To a stirred solution of the product of Step B (3.4 g, 12.6 mmol) in $CH_3CN$ (40 mL) was added hydrazine hydrate (80%, 3.1 g, 50.4 mmol) at RT. The mixture was stirred at 50° C. overnight. The solvents were concentrated under reduced pressure. The residue was dissolved into water (40 mL) and extracted with EtOAc (40 mL×3). The combined organic phase was washed with brine, dried over $Na_2SO_4$ and concentrated under reduced pressure. The residue (crude, 2.82 g, yellow oil) was used into next Step directly. MS: M/e 225 $(M+1)^+$.

Step D: tert-butyl 2-(1-methoxy-2-(3-methoxyphenyl)-1-oxopropan-2-yl)hydrazine-1-carboxylate To a stirred solution of the product of Step C (2.82 g, 12.6 mmol) and $Et_3N$ (1.9 mL, 15.1 mmol) in DCM (40 mL) was added $(Boc)_2O$ (2.7 g, 12.6 mmol) at 0° C. The mixture was stirred at RT overnight. The reaction was quenched with water (40 mL) and extracted with DCM (50 mL×2). The combined organic phase was washed with brine, dried over Na₂SO₄ and concentrated under reduced pressure. The residue was purified by silica gel chromatography (EtOAc:PE=1:2) to afford the title compound (1.6 g, yield: 39% for three Steps) as yellow solid. ¹H NMR (400 MHz, DMSO-d6) δ7.96 (br.s, 1H), 7.23 (t, J=8.0 Hz, 1H), 6.99 (s, 1H), 6.94-6.87 (m, 1H), 6.86-6.79 (m, 1H), 3.75 (s, 3H), 3.62 (s, 3H), 1.47 (s, 3H), 1.35 (s, 9H) ppm. MS: M/e 325 (M+1)⁺.

Step E: methyl 2-hydrazinyl-2-(3-methoxyphenyl)propanoate hydrochloride

The product of Step D (1.6 g, 4.9 mmol) was dissolved into HCl/1,4-dioxane (4M, 50 mL) at RT. The mixture was stirred at RT for 4 hours. The mixture was concentrated under reduced pressure. The residue (1 g, yield: 90.9%) as yellow solid was used into next Step directly. MS: M/e 225 (M+1)⁺.

Step F: methyl 2-(6-amino-4-chloro-H-pyrazolo[3,4-d]pyrimidin-1-yl)-2-(3-methoxyphenyl)propanoate hydrochloride To a stirred solution of the product of Step E (410 mg, 1.6 mmol) in CH₃CN was added 2-amino-4,6-dichloropyrimidine-5-carbaldehyde (300 mg, 1.6 mmol) at RT. The mixture was stirred at RT overnight. Then the mixture was stirred at 40° C. for 4 hours. The mixture was filtered and the solid was dried in air. The yellow solid (606 mg, 95.4%) was used into next step directly. MS: M/e 362 (M+1)⁺.

Step G: methyl 2-(6-amino-4-(2-(furan-2-carbonyl)hydrazinyl)-1H-pyrazolo[3,4-d]pyrimidin-1-yl)-2-(3-methoxyphenyl)propanoate A mixture of furan-2-carbohydrazide (192 mg, 1.5 mmol), the product of Step F (606 mg, 1.5 mmol) and Et₃N (308 mg, 3 mmol) in DMSO (2 mL) was stirred at 100° C. overnight. The reaction was cooled to RT. The mixture was poured into water (10 mL). The precipitate was formed from the system. After stirring at RT for 30 mins, the mixture was filtered. The solid was collected and dried in air. The yellow solid (400 mg, yield: 59.1%) was used into next step directly. MS: M/e 452 (M+1)⁺.

Step H: methyl 2-(5-amino-2-(furan-2-yl)-7H-pyrazolo[4,3-e][1,2,4]triazolo[1,5-c]pyrimidin-7-yl)-2-(3-methoxyphenyl)propanoate A mixture of the product of Step G (400 mg, 0.89 mmol) in BSA (8 mL) and HMDS (8 mL) was stirred at 100° C. overnight. The reaction was cooled to RT and concentrated under reduced pressure. The residue was dissolved into H₂O (10 mL) and MeOH (10 mL). The mixture was stirred at 60° C. for 2 hours. MeOH was removed and the solid was precipitated from the system. The solid was filtered and dried in air. The brown solid (350 mg, yield: 90.9%) was used into next step directly. MS: M/e 434 (M+1)⁺.

Step I: 2-(5-amino-2-(furan-2-yl)-7H-pyrazolo[4,3-e][1,2,4]triazolo[1,5-c]pyrimidin-7-yl)-2-(3-methoxyphenyl)propanoic acid To a stirred solution of the product of Step H (350 mg, 0.81 mmol) in MeOH (6 mL) was added aq.NaOH (2M, 2 mL) at RT. The mixture was stirred at 60° C. for 3 hours. The reaction was concentrated under reduced pressure. The residue was dissolved into water (10 mL) and neutralized by aq. HCl (2M) to PH=3~4. The solid was precipitated from the system. The mixture was filtered and the solid was collected. The white solid (210 mg, yield: 61.9%) was dried in air and used into next step directly. MS: We 420 (M+1)⁺.

Step J: 2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-(3-methoxyphenyl)propanamide A mixture of 3-(aminomethyl)oxetan-3-ol (17.2 mg, 0.17 mmol), the product of Step I (70 mg, 0.17 mmol), HATU (63.5 mg, 0.17 mmol) and DIEA (0.1 mL, excess) in DMF (2 mL) was stirred at RT overnight. The reaction mixture was poured into water (10 mL) and extracted with EtOAc (15 mL×3). The combined organic layers were washed with brine, dried over Na₂SO₄ and concentrated under reduced pressure. The residue was purified by prep-TLC (EtOAc: 100%) to afford the title compound (32 mg, yield: 38%). ¹H NMR (400 MHz, DMSO-d6) δ8.25 (s, 1H), 8.04-7.87 (m, 3H), 7.44 (t, J=6 Hz, 1H), 7.25 (d, J=3 Hz, 1H), 7.21 (d, J=8 Hz, 1H), 6.86 (dd, J=8, 3 Hz, 1H), 6.77-6.72 (m, 2H), 6.69 (d, J=8.0 Hz, 1H), 5.71 (s, 1H), 4.47-4.38 (m, 2H), 4.28 (t, J=6 Hz, 2H), 3.69 (s, 3H), 3.46-3.39 (m, 2H), 2.32 (s, 3H) ppm. MS: M/e 505 (M+1)⁺.

Example 138: 2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-methylpropanamide

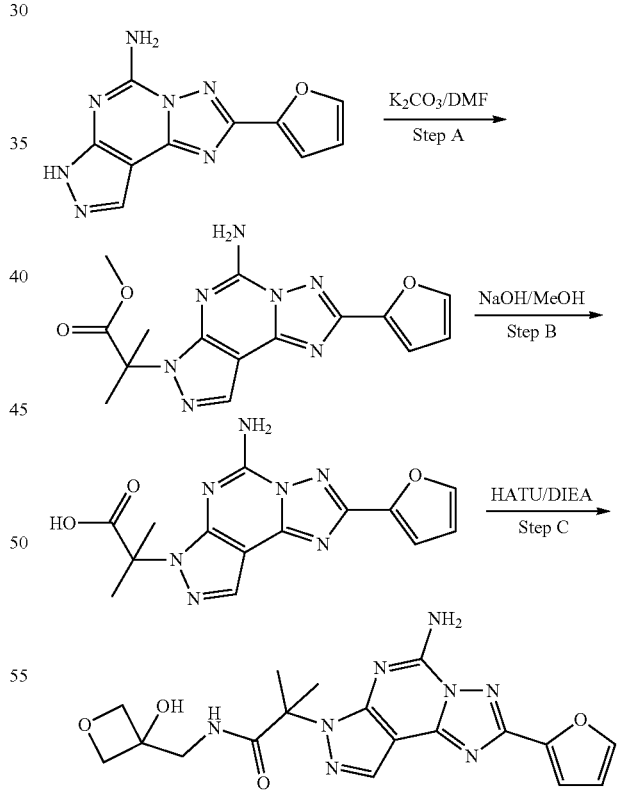

Step A: methyl 2-(5-amino-2-(furan-2-yl)-7H-pyrazolo[4,3-e][1,2,4]triazolo[1,5-c]pyrimidin-7-yl)-2-methylpropanoate A mixture of 2-(furan-2-yl)-7H-pyrazolo[4,3-e][1,2,4]triazolo[1,5-c]pyrimidin-5-amine (1.5 g, 6.2 mmol), methyl 2-bromo-2-methylpropanoate (1.3 g, 7.4 mmol) and K$_2$CO$_3$ (1.7 g, 12.4 mmol) in DMF (80 mL) was stirred at r.t overnight. The solution was added with water (50 mL), extracted with ethyl acetate (50 mL) and washed with brine (50 mL). The organic layer was dried over Na$_2$SO$_4$, concentrated and purified by column chromatography (PE: EtOAc=3:1 to 1:1) to get methyl 2-(5-amino-2-(furan-2-yl)-7H-pyrazolo[4,3-e][1,2,4]triazolo[1,5-c]pyrimidin-7-yl)-2-methylpropanoate (65 mg, 3%). $^1$H NMR (400 MHz, DMSO-d6) δ 8.19 (s, 1H), 8.06 (br.s, 2H), 7.95 (d, J=4.0 Hz, 1H), 7.23 (d, J=4.0 Hz, 1H), 6.73 (t, J=4.0 Hz, 1H), 3.67 (s, 3H), 1.87 (s, 6H) ppm. MS: M/e 342 (M+1)$^+$.

Step B: 2-(5-amino-2-(furan-2-yl)-7H-pyrazolo[4,3-e][1,2,4]triazolo[1,5-c]pyrimidin-7-yl)-2-methylpropanoic acid NaOH solution (30 mg, in 2 mL of water) was added to a solution of methyl 2-(5-amino-2-(furan-2-yl)-7H-pyrazolo[4,3-e][1,2,4]triazolo[1,5-c]pyrimidin-7-yl)-2-methylpropanoate (65 mg, 0.19 mmol) in methanol (5 mL). The reaction mixture was stirred at r.t overnight. The solution was concentrated, added with water (5 mL) and acidified with 1N HCl solution to pH=5. The precipitated solid was filtered and dried to get the desired product as a white solid (53 mg, 85%). MS: M/e 328 (M+1)$^+$.

Step C: 2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-methylpropanamide A mixture of 2-(5-amino-2-(furan-2-yl)-7H-pyrazolo[4,3-e][1,2,4]triazolo[1,5-c]pyrimidin-7-yl)-2-methylpropanoic acid (50 mg, 0.15 mmol), 3-(amino methyl)oxetan-3-ol (24 mg, 0.22 mmol), HATU (84 mg, 0.22 mmol) and DIPEA (39 mg, 0.30 mmol) in DMF (5 mL) was stirred at r.t for 2 hrs. The solution was added with water (5 mL), extracted with ethyl acetate (10 mL) and washed with brine (10 mL). The organic layer was dried, concentrated and purified by preparative TLC (EtOAc) to get the desired product (15 mg, 24%). $^1$H NMR (400 MHz, DMSO-d6) δ 8.22 (s, 1H), 7.94 (br.s, 3H), 7.23 (d, J=4.0 Hz, 1H), 7.17 (t, J=4.0 Hz, 1H), 6.74-6.73 (m, 1H), 5.64 (s, 1H), 4.36 (d, J=8.0 Hz, 2H), 4.22 (d, J=8.0 Hz, 2H), 3.34 (s, 2H), 1.87 (s, 6H) ppm. MS: M/e 413 (M+1)$^+$.

Example 139: 2-(5-amino-2-(furan-2-yl)-7H-pyrazolo[4,3-e][1,2,4]triazolo[1,5-c]pyrimidin-7-yl)-N-((cis)-4-hydroxycyclohexyl)-2-(2-methoxyphenyl)propanamide To a mixture of 2-(5-amino-2-(furan-2-yl)-7H-pyrazolo[4,3-e][1,2,4]triazolo[1,5-c]pyrimidin-7-yl)-2-(2-methoxyphenyl)propanoic acid (50 mg, 0.12 mmol), cis-4-aminocyclohexan-1-ol hydrochloride (22 mg, 0.15 mmol), DIPEA (65 mg, 0.5 mmol) in DMF (2 mL) was added HATU (57 mg, 0.15 mmol) at rt and the mixture was stirred at rt for 16 hrs. The mixture was diluted with 20 mL of EtOAc, washed with brine (10 mL×3), dried over Na$_2$SO$_4$, concentrated and the resulted oil was purified by prep-TLC (EA/MeOH=50:1) to give the title product (23 mg, yield: 37%). $^1$H NMR (400 MHz, DMSO-d6) δ 8.23 (s, 1H), 8.10-7.83 (m, 3H), 7.38-7.18 (m, 3H), 7.05 (d, J=8.4 Hz, 1H), 6.84 (t, J=7.6 Hz, 1H), 6.79-6.68 (m, 1H), 6.56 (d, J=6.8 Hz, 1H), 4.29 (s, 1H), 3.73-3.55 (m, 5H), 2.27 (s, 3H), 1.64-1.25 (m, 8H). MS: M/e 517 (M+1)+

Example 140: 2-(5-amino-2-(furan-2-yl)-7H-pyrazolo[4,3-e][1,2,4]triazolo[1,5-c]pyrimidin-7-yl)-N-((cis)-4-hydroxy-4-methylcyclohexyl)-2-(2-methoxyphenyl)propanamide To a mixture of 2-(5-amino-2-(furan-2-yl)-7H-pyrazolo[4,3-e][1,2,4]triazolo[1,5-c]pyrimidin-7-yl)-2-(2-methoxyphenyl)propanoic acid (50 mg, 0.12 mmol), (cis)-4-amino-1-methylcyclohexan-1-ol (19 mg, 0.15 mmol), DIPEA (65 mg, 0.5 mmol) in DMF (2 mL) was added HATU (57 mg, 0.15 mmol) at rt and the mixture was stirred at rt for 16 hrs. The mixture was diluted with 20 mL of EtOAc, washed with brine (10 mL×3), dried over Na$_2$SO$_4$, concentrated and the resulted oil was purified by prep-TLC (EtOAc) to give the title product (39 mg, yield: 61%). $^1$H NMR (400 MHz, DMSO-d6) δ 8.22 (s, 1H), 8.07-7.87 (m, 3H), 7.34-7.21 (m, 3H), 7.05 (d, J=7.6 Hz, 1H), 6.83 (t, J=7.2 Hz, 1H), 6.78-6.71 (m, 1H), 6.53 (d, J=6.8 Hz, 1H), 3.96 (s, 1H), 3.66 (s, 3H), 3.58-3.40 (m, 1H), 2.25 (s, 3H), 1.68-1.58 (m, 1H), 1.55-1.38 (m, 4H), 1.35-1.21 (m, 3H), 1.05 (s, 3H). MS: We 531 (M+1)$^+$.

Example 141B: (R)-2-(5-amino-2-(furan-2-yl)-7H-pyrazolo[4,3-e][1,2,4]triazolo[1,5-c]pyrimidin-7-yl)-2-phenyl-N-((3-(trifluoromethyl)pyridin-2-yl)methyl)propanamide To a mixture of (R)-2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), and DIPEA (70 mg, 0.54 mmol) in THF (1 mL) was added HATU (54 mg, 0.14 mmol) at rt and the mixture was stirred at rt for 10 min. a suspension of (3-(trifluoromethyl)pyridin-2-yl)methanamine hydrochloride (30 mg, 0.14 mmol) in THF (1 mL) was added, and the mixture was stirred at rt for 16 hrs. The mixture was diluted with 5 mL of EtOAc, washed with brine (3 mL×3), dried over Na$_2$SO$_4$, concentrated. And the resulted residue was purified by prep-TLC (PE/EA, 1:1) and the resulted solid was lyophilized to give the title product (28 mg, yield: 40%). $^1$H NMR (400 MHz, DMSO-d6) δ 8.61 (d, J=4.4 Hz, 1H), 8.26 (s, 1H), 8.14 (d, J=7.6 Hz, 1H), 8.10-7.80 (m, 4H), 7.58-7.41 (m, 1H), 7.40-7.19 (m, 6H), 6.74 (s, 1H), 4.75-4.56 (m, 2H), 2.38 (s, 3H). MS: M/e 548 (M+1)$^+$.

Example 142B: (R)-2-(5-amino-2-(furan-2-yl)-7H-pyrazolo[4,3-e][1,2,4]triazolo[1,5-c]pyrimidin-7-yl)-2-phenyl-N-((5-(trifluoromethyl)pyridin-2-yl)methyl)propanamide To a mixture of (R)-2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), (5-(trifluoromethyl)pyridin-2-yl)methanamine dihydrochloride (35 mg, 0.14 mmol), DIPEA (70 mg, 0.54 mmol) in THF (1 mL) was added HATU (56 mg, 0.15 mmol) at rt and the mixture was stirred at rt for 16 hrs. The mixture was diluted with 10 mL of EA, washed with brine (5 mL×3), dried over Na$_2$SO$_4$, concentrated. The resulted residue was purified by prep-TLC (PE/EA=1:2) and the resulted solid was lyophilized to give the title product (55 mg, yield: 78%). $^1$H NMR (400 MHz, DMSO-d6) δ 8.83 (s, 1H), 8.32 (t, J=5.6 Hz, 1H), 8.28 (s, 1H), 8.19 (dd, J=8.4, 2.0 Hz, 1H), 8.10 (s, 2H), 7.95 (s, 1H), 7.75 (d, J=8.0 Hz, 1H), 7.36-7.28 (m, 3H), 7.27-7.22 (m, 3H), 6.74 (dd, J=3.2, 1.6 Hz, 1H), 4.60-4.40 (m, 2H), 2.39 (s, 3H). MS: M/e 548 (M+1)$^+$.

Example 143B: (R)-2-(5-amino-2-(furan-2-yl)-7H-pyrazolo[4,3-e][1,2,4]triazolo[1,5-c]pyrimidin-7-yl)-2-phenyl-N-((4-(trifluoromethyl)pyridin-2-yl)methyl)propanamide To a mixture of (R)-2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), (4-(trifluoromethyl)pyridin-2-yl)methanamine dihydrochloride (35 mg, 0.14 mmol), DIPEA (70 mg, 0.54 mmol) in THF (1 mL) was added HATU (56 mg, 0.15 mmol) at rt and the mixture was stirred at rt for 16 hrs. The mixture was diluted with 10 mL of EtOAc, washed with brine (5 mL×3), dried over Na$_2$SO$_4$, concentrated. The resulted residue was purified by prep-TLC (PE/EA=1:2) and the resulted solid was lyophilized to give the title product (42 mg, yield: 54%). $^1$H NMR (400 MHz, DMSO-d6) δ 8.78-8.67 (m, 1H), 8.34 (t, J=6.0 Hz, 1H), 8.24 (s, 1H), 8.15-7.87 (m, 3H), 7.64-7.57 (m, 2H), 7.35-7.28 (m, 3H), 7.26 (d, J=3.2 Hz, 1H), 7.19-7.10 (m, 2H), 6.75 (dd, J=3.2, 1.6 Hz, 1H), 4.55 (d, J=6.0 Hz, 2H), 2.41 (s, 3H). MS: M/e 548 (M+1)$^+$.

Example 144B: (R)-2-(5-amino-2-(furan-2-yl)-7H-pyrazolo[4,3-e][1,2,4]triazolo[1,5-c]pyrimidin-7-yl)-2-phenyl-N-((6-(trifluoromethyl)pyridin-2-yl)methyl)propanamide To a mixture of (R)-2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), (6-(trifluoromethyl)pyridin-2-yl)methanamine dihydrochloride (35 mg, 0.14 mmol), DIPEA (70 mg, 0.54 mmol) in THF (1 mL) was added HATU (56 mg, 0.15 mmol) at rt and the mixture was stirred at rt for 16 hrs. The mixture was diluted with 10 mL of EtOAc, washed with brine (5 mL×3), dried over Na$_2$SO$_4$, concentrated. The resulted residue was purified by prep-TLC (PE/EA=1:2) and the resulted solid was lyophilized to give the title product (28 mg, yield: 36%). $^1$H NMR (400 MHz, DMSO-d6) δ 8.34-8.24 (m, 2H), 8.19-7.98 (m, 3H), 7.95 (s, 1H), 7.80-7.71 (m, 2H), 7.36-7.27 (m, 3H), 7.27-7.20 (m, 3H), 6.74 (dd, J=3.2, 1.6 Hz, 1H), 4.62-4.37 (m, 2H), 2.39 (s, 3H). MS: M/e 548 (M+1)$^+$.

Example 145B: (R)-2-(5-amino-2-(furan-2-yl)-7H-pyrazolo[4,3-e][1,2,4]triazolo[1,5-c]pyrimidin-7-yl)-2-phenyl-N-(tetrahydro-2H-thiopyran-4-yl)propanamide To a mixture of (R)-2-(5-amino-2-(furan-2-yl)-7H-pyrazolo[4,3-e][1,2,4]triazolo[1,5-c]pyrimidin-7-yl)-2-phenylpropanoic acid (236 mg, 1.54 mmol), tetrahydro-2H-thiopyran-4-amine hydrochloride (500 mg, 1.28 mmol), DIPEA (660 mg, 5.12 mmol) in DMF (5 mL) was added HATU (585 mg, 1.54 mmol) at rt and the mixture was stirred at rt for 16 hrs. The mixture was diluted with 50 mL of EtOAc, washed with brine (20 mL×3), dried over Na$_2$SO$_4$, and concentrated. The resulted residue was purified by column chromatography to give a crude product which was slurried in heptane/EtOAc (1:1, 10 mL) at rt for 20 min, filtered. The filter cake was dried under high vacuum for 10 min to give the title product (560 mg, yield: 75%). $^1$H NMR (400 MHz, DMSO-d6) δ 8.23 (s, 1H), 8.11-7.85 (m, 3H), 7.69 (d, J=8.0 Hz, 1H), 7.32-7.22 (m, 4H), 7.20-7.10 (m, 2H), 6.74 (dd, J=3.2, 1.6 Hz, 1H), 3.79-3.62 (m, 1H), 2.70-2.52 (m, 4H), 2.25 (s, 3H), 2.11-1.91 (m, 2H), 1.57-1.42 (m, 2H). MS: M/e 489 (M+1)$^+$.

Example 146B-1 or 146B-2: (R)-2-(5-amino-2-(furan-2-yl)-7H-pyrazolo[4,3-e][1,2,4]triazolo[1,5-c]pyrimidin-7-yl)-N-((1S,4s)-1-oxidotetrahydro-2H-thiopyran-4-yl)-2-phenylpropanamide or (R)-2-(5-amino-2-(furan-2-yl)-7H-pyrazolo[4,3-e][1,2,4]triazolo[1,5-c]pyrimidin-7-yl)-N-((1R,4r)-1-oxidotetrahydro-2H-thiopyran-4-yl)-2-phenylpropanamide

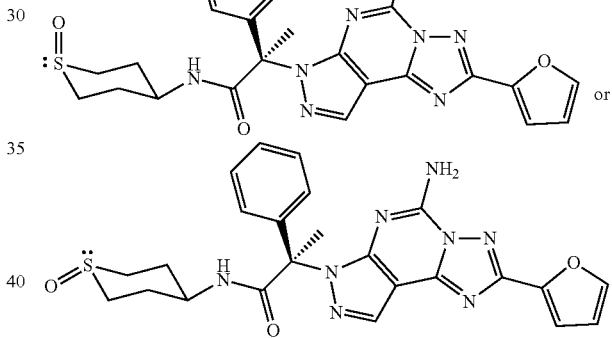

To a solution of (R)-2-(5-amino-2-(furan-2-yl)-7H-pyrazolo[4,3-e][1,2,4]triazolo[1,5-c]pyrimidin-7-yl)-2-phenyl-N-(tetrahydro-2H-thiopyran-4-yl)propanamide (160 mg, 0.33 mmol) in MeOH (5 mL) was added a solution of NaIO$_4$ (85 mg, 0.4 mmol) in H$_2$O (1 mL) at rt and the resulted mixture was stirred at rt for 3 hrs. The mixture was added 5 mL of H$_2$O, extracted with CH$_2$Cl$_2$ (10 mL×3). The combined extract was washed with brine (20 mL×2), dried over Na$_2$SO$_4$, and concentrated. The resulted residue was purified by prep-TLC (CH$_2$Cl$_2$/MeOH=20:1) to give two products: 146B-1 and 146B-2. 146B-1: 70 mg. $^1$H NMR (400 MHz, DMSO-d6) δ 8.22 (s, 1H), 8.13-7.89 (m, 3H), 7.86 (d, J=8.4 Hz, 1H), 7.35-7.10 (m, 6H), 6.74 (dd, J=3.2, 1.6 Hz, 1H), 3.97-3.79 (m, 1H), 2.90-2.79 (m, 2H), 2.76-2.63 (m, 2H), 2.25 (s, 3H), 2.13-1.93 (m, 2H), 1.85-1.66 (m, 2H). MS: M/e 505 (M+1)$^+$. 146B-2: 25 mg. $^1$H NMR (400 MHz, DMSO-d6) δ 8.24 (s, 1H), 8.15-7.82 (m, 3H), 7.69 (d, J=7.6 Hz, 1H), 7.33-7.19 (m, 4H), 7.17-7.06 (m, 2H), 6.74 (dd, J=3.2, 1.6 Hz, 1H), 4.08-3.88 (m, 1H), 3.14-3.01 (m, 2H), 2.73-2.60 (m, 2H), 2.25 (s, 3H), 2.17-1.98 (m, 2H), 1.73-1.53 (m, 2H). MS: M/e 505 (M+1)$^+$.

Example 147: 2-(5-amino-2-(furan-2-yl)-7H-pyrazolo[4,3-e][1,2,4]triazolo[1,5-c]pyrimidin-7-yl)-N-(2-(4-methylpiperazin-1-yl)ethyl)-2-phenylpropanamide A mixture of 2-(5-amino-2-(furan-2-yl)-7H-pyrazolo[4,3-e][1,2,4]triazolo[1,5-c]pyrimidin-7-yl)-2-phenylpropanoic acid (100 mg, 0.257 mmol), 2-(4-methylpiperazin-1-yl)ethan-1-amine (36.8 mg, 0.257 mmol), HATU (117.8 mg, 0.308 mmol) and DIPEA (66.3 mg, 0.514 mmol) in DMF (3 mL) was stirred overnight. The reaction mixture was poured into $H_2O$ (10 mL) and extracted with EtOAc (10 mL×3). The combined organic layer was washed with brine, dried over $Na_2SO_4$, concentrated and purified by prep-HPLC to give the target product (10 mg, 30.3%). $^1$H NMR (400 MHz, DMSO-d6) δ8.29 (s, 1H), 8.03 (s, 2H), 7.96 (s, 1H), 7.71 (s, 1H), 7.34-7.23 (m, 4H), 7.11 (d, J=6.4 Hz, 2H), 6.76-6.74 (m, 1H), 3.62-2.83 (m, 12H), 2.78 (s, 3H), 2.29 (s, 3H) ppm. MS: M/e 515 (M+1)$^+$.

Example 147B: (R)-2-(5-amino-2-(furan-2-yl)-7H-pyrazolo[4,3-e][1,2,4]triazolo[1,5-c]pyrimidin-7-yl)-N-(2-(4-methylpiperazin-1-yl)ethyl)-2-phenylpropanamide A mixture of (R)-2-(5-amino-2-(furan-2-yl)-7H-pyrazolo[4,3-e][1,2,4]triazolo[1,5-c]pyrimidin-7-yl)-2-phenylpropanoic acid (100 mg, 0.257 mmol), 2-(4-methylpiperazin-1-yl)ethan-1-amine (36.8 mg, 0.257 mmol), HATU (117.8 mg, 0.308 mmol) and DIPEA (66.3 mg, 0.514 mmol) in DMF (3 mL) was stirred overnight. The reaction mixture was poured into $H_2O$ (10 mL) and extracted with EtOAc (10 mL×3). The combined organic layer was washed with brine, dried over $Na_2SO_4$, concentrated and purified by prep-HPLC to give the target product (35 mg, 26.5%). $^1$H NMR (400 MHz, DMSO-d6) $^1$H NMR (400 MHz, DMSO-d6) δ 8.29 (s, 1H), 8.03 (s, 2H), 7.96 (s, 1H), 7.71 (s, 1H), 7.34-7.23 (m, 4H), 7.11 (d, J=6.4 Hz, 2H), 6.76-6.74 (m, 1H), 3.62-2.83 (m, 12H), 2.78 (s, 3H), 2.29 (s, 3H) ppm. MS: M/e 515 (M+1)$^+$.

Example 148B: (R)-2-(5-amino-2-(furan-2-yl)-7H-pyrazolo[4,3-e][1,2,4]triazolo[1,5-c]pyrimidin-7-yl)-N-(2-(4-hydroxypiperidin-1-yl)ethyl)-2-phenylpropanamide To a mixture of (R)-2-(5-amino-2-(furan-2-yl)-7H-pyrazolo[4,3-e][1,2,4]triazolo[1,5-c]pyrimidin-7-yl)-2-phenylpropanoic acid (50 mg, 0.13 mmol), 1-(2-aminoethyl)piperidin-4-ol (20 mg, 0.14 mmol), DIPEA (70 mg, 0.54 mmol) in THF (2 mL) was added HATU (53 mg, 0.14 mmol) at rt and the mixture was stirred at rt for 16 hrs. The mixture was diluted with 10 mL of EtOAc, washed with brine (5 mL×3), dried over $Na_2SO_4$, and concentrated. The resulted residue was purified by prep-TLC (DCM/MeOH=10:1) and the resulted solid was lyophilized to give the title product (15 mg, yield: 23%). $^1$H NMR (400 MHz, DMSO-d6+D2O) δ 8.29 (s, 1H), 7.94 (s, 1H), 7.39-7.24 (m, 4H), 7.20-7.02 (m, 2H), 6.76 (dd, J=3.2, 1.6 Hz, 1H), 3.58-3.33 (m, 3H), 3.32-2.80 (m, 6H), 2.29 (s, 3H), 1.95-1.76 (m, 2H), 1.74-1.42 (m, 2H). MS: M/e 516 (M+1)$^+$.

Example 149B: (R)-2-(5-amino-2-(furan-2-yl)-7H-pyrazolo[4,3-e][1,2,4]triazolo[1,5-c]pyrimidin-7-yl)-N-(2-(4-hydroxycyclohexyl)ethyl)-2-phenylpropanamide To a mixture of (R)-2-(5-amino-2-(furan-2-yl)-7H-pyrazolo[4,3-e][1,2,4]triazolo[1,5-c]pyrimidin-7-yl)-2-phenylpropanoic acid (75 mg, 0.19 mmol), 4-(2-aminoethyl)cyclohexan-1-ol (30 mg, 0.21 mmol), DIPEA (100 mg, 0.77 mmol) in DMF (2 mL) was added HATU (86 mg, 0.22 mmol) at rt and the mixture was stirred at rt for 16 hrs. The mixture was diluted with 20 mL of EtOAc, washed with brine (10 mL×3), dried over $Na_2SO_4$, and concentrated. The resulted residue was purified by prep-TLC (EtOAc, 100%) and the resulted solid was lyophilized to give the title product (62 mg, yield: 63%). $^1$H NMR (400 MHz, DMSO-d6) δ 8.23 (s, 1H), 8.15-7.81 (m, 3H), 7.53 (dt, J=17.6, 5.6 Hz, 1H), 7.35-7.21 (m, 4H), 7.18-7.11 (m, 2H), 6.74 (dd, J=3.2, 1.6 Hz, 1H), 3.63 (s, 1H), 3.27-3.07 (m, 3H), 2.29 (s, 3H), 1.78-1.65 (m, 1H), 1.65-1.51 (m, 1H), 1.50-1.42 (m, 1H), 1.34-1.21 (m, 5H), 1.10-0.72 (m, 3H). MS: M/e 515 (M+1)$^+$.

Example 150B: (R)-2-(5-amino-2-(furan-2-yl)-7H-pyrazolo[4,3-e][1,2,4]triazolo[1,5-c]pyrimidin-7-yl)-N-(2-(6-methylpyridin-2-yl)ethyl)-2-phenylpropanamide To a mixture of (R)-2-(5-amino-2-(furan-2-yl)-7H-pyrazolo[4,3-e][1,2,4]triazolo[1,5-c]pyrimidin-7-yl)-2-phenylpropanoic acid (75 mg, 0.19 mmol), 2-(6-methylpyridin-2-yl)ethan-1-amine (35 mg, 0.26 mmol), DIPEA (100 mg, 0.77 mmol) in DMF (2 mL) was added HATU (86 mg, 0.22 mmol) at rt and the mixture was stirred at rt for 16 hrs. The mixture was diluted with 20 mL of EtOAc, washed with brine (10 mL×3), dried over $Na_2SO_4$, and concentrated. The resulted residue was purified by prep-TLC (EtOAc, 100%) and the resulted solid was lyophilized to give the title product (48 mg, yield: 50%). $^1$H NMR (400 MHz, DMSO-d6) δ 8.22 (s, 1H), 8.10-7.85 (m, 3H), 7.61 (s, 1H), 7.51-7.34 (m, 1H), 7.33-7.21 (m, 4H), 7.16-7.07 (m, 2H), 7.05-6.78 (m, 2H), 6.75 (dd, J=3.2, 1.6 Hz, 1H), 3.57-3.43 (m, 2H), 3.01-2.80 (m, 2H), 2.29 (s, 3H), 2.25 (s, 3H). MS: M/e 508 (M+1)$^+$.

Example 151B: (cis)-4-((R)-2-(5-amino-2-(furan-2-yl)-7H-pyrazolo[4,3-e][1,2,4]triazolo[1,5-c]pyrimidin-7-yl)-2-phenylpropanamido)cyclohexyl acetate A solution of (R)-2-(5-amino-2-(furan-2-yl)-7H-pyrazolo[4,3-e][1,2,4]triazolo[1,5-c]pyrimidin-7-yl)-N-((cis)-4-hydroxycyclohexyl)-2-phenylpropanamide (50 mg, 0.1 mmol) in $Ac_2O$ (2 mL) was heated at 70° C. for 4 hrs. The solution was concentrated, diluted with 10 mL of EtOAc, washed with aq. $NaHCO_3$ (5 mL), brine (5 mL×2), dried over $Na_2SO_4$ and concentrated, purified by prep-HPLC to give the title product (35 mg, yield: 66%). $^1$H NMR (400 MHz, DMSO-d6) δ 8.24 (s, 1H), 8.11-7.86 (m, 3H), 7.57 (d, J=7.8 Hz, 1H), 7.34-7.22 (m, 4H), 7.21-7.12 (m, 2H), 6.74 (dd, J=3.2, 1.6 Hz, 1H), 4.86-4.67 (m, 1H), 3.85-3.67 (m, 1H), 2.28 (s, 3H), 1.92 (s, 3H), 1.70-1.44 (m, 8H). MS: M/e 529 (M+1)+.

Cell Culture and Transfection

HEK293 cells were maintained in Dulbecco's modified Eagle's medium (DMEM, Gibco) supplemented with 10% fetal bovine serum (FBS, Thermo Scientific), 100 units/mL penicillin (Gibco), and 0.1 mg/mL streptomycin (Gibco) in a humidified 37° C. environment with 5% CO2. Plasmid encoding wild-type human A2A receptor (A2AR) (in pcDNA3.1) was synthesized by Genscript (Nanjing, China). Transfection of the plasmids was performed in 6-well plates with 4×105 cells using Lipofectamin 2000 (ThermoFisher Scientific) according to the instruction of the manufacturer. Cell clones that stably express A2AR were established and maintained in the same complete medium as the HEK293 cells in addition of G-418 (Gibico). Expression level of A2AR in each single cell clone was determined using immunoblotting and FACS method. HEK293-A2AR stable cells were then transfected with pGL4.29[luc2P/CRE/Hygro] (Promega) luciferase reporter plasmid for establishing the HEK293-A2AR-luc2p/CRE/Hygro stable cell line.

Luciferase Reporter Assay

HEK293-A2AR-luc2p/CRE/Hygro cells were seeded at a density of 5,000 cells/well in DMEM with 1% FBS and 1 U/mL adenosine deaminase (ADA) (Sigma). After 18 h, the cells were treated with 3 nM CGS21680 plus a series dilution of A2AR antagonist, the compounds disclosed herein at the concentration of 0.1~10000 nM, prepared in DMEM with 1% FBS. After 5 h incubation, the luciferase activity in cells were measured using the Bright-Glo Luciferase Assay System (Promega) according to manufacturer's instructions. The luminescence signal was measured using a PHERAstar FS plate reader (BMG Labtech). Luminescence intensity from 10 μM preladenant treatment was set as 0%. Maximal luminescence intensity was determined in the presence of 3 nM CGS21680 and was set as 100%. The IC50 value was calculated from a dose dependent inhibition curve across the range of compound concentrations.

Adenosine Receptor Binding Assay

Binding affinity of test compounds to four human adenosine receptors, A1, A2A, A2B and A3 was determined in radioligand competitive binding assay (conducted by Cerep, France) using following protocols. For A1 receptor (A1R), membrane homogenates from CHO cells transfected with A1R were incubated for 60 min at 22° C. with 1 nM [3H]DPCPX in the absence or presence of the test compound in a buffer containing 50 mM Tris-HCl (pH 7.4), 5 mM MgCl2, 1 mM EDTA/Tris and 2 UI/mL ADA. For A2AR, membrane homogenates from HEK293 cells transfected with A2AR were incubated for 120 min at 22° C. with 6 nM [3H]CGS21680 in the absence or presence of the test compound in a buffer containing 50 mM Tris-HCl (pH 7.4), 10 mM MgCl2, and 2 UI/mL ADA. For A2B receptor (A2BR), membrane homogenates from HEK293 cells transfected with A2BR were incubated for 60 min at 22° C. with 5 nM [3H]CPX in the absence or presence of the test compound in a buffer containing 10 mM Hepes/Tris (pH 7), 1 mM $MgCl_2$, and 1 mM EDTA. For A3 receptor (A3R), membrane homogenates from HEK293 cells transfected with A3R were incubated for 120 min at 22° C. with 0.15 nM [125I] AB-MECA in the absence or presence of the test compound in a buffer containing 50 mM Tris-HCl (pH 7.4), 5 mM $MgCl_2$, 1 mM EDTA and 2 UI/mL ADA. Nonspecific binding was determined in the presence of unlabeled 1 μM DPCPX, 10 μM NECA, 100 μM NECA, and 1 μM IB-MECA in A1R, A2AR, A2BR, A3R binding assays, respectively. Following incubation, the samples are rapidly filtered and washed with ice-cold 50 mM Tris-HCl. Then filters are dried and counted for radioactivity in a scintillation counter (Topcount, Packard) using a scintillation cocktail (Microscint 0, Packard). Duplicate experiments were performed for each assay. The results are expressed as a percent inhibition of control radioligand specific binding.

Mouse BBB Assay

Mice were acclimated for 1 week prior to use at 18-30 g body weight. Fasted mice were dosed orally at 10 mg/kg dose. At 1, 2 and 4 hours postdose, plasma samples from cardiac blood collected in tubes containing K2EDTA as the anticoagulant, and excised cerebral hemispheres were immediately frozen and stored at −80° C. until bioanalysis. Total concentrations of the compound were determined by LC-MS/MS. Brain homogenate concentrations were converted to brain concentrations for the calculations of brain-to-plasma ratios.

TABLE 1

Results of Luciferase reporter assay

| Example | $IC_{50}$ (nM) |
|---|---|
| 1 | 1.4 |
| 1A | 13.0 |
| 1B | 0.7 |
| 2 | 11.9 |
| 3 | 5.2 |
| 4 | 3.8 |
| 4A | 50.0 |
| 4B | 2.2 |
| 5 | 7.0 |
| 6 | 0.9 |
| 7 | 1.5 |
| 8 | 2.0 |
| 9 | 31.9 |
| 10 | 16.5 |
| 11 | 36.0 |
| 12 | 10.2 |
| 13 | 8.3 |
| 14 | 6.1 |
| 15 | 7.9 |
| 16 | 44.6 |
| 17 | 3.0 |
| 17A | 17.8 |
| 17B | 0.6 |
| 18 | 0.9 |
| 18A | 6.4 |
| 18B | 0.4 |
| 19 | 4.5 |
| 20 | 14.6 |
| 21 | 15.3 |
| 22 | 1.4 |
| 23 | 1.9 |
| 24 | 5.6 |
| 25 | 1.5 |
| 26 | 2.6 |
| 27 | 16.1 |
| 28 | 1.6 |
| 29 | 1.3 |
| 30 | 10.8 |
| 31 | 5.8 |
| 31A | 28.0 |
| 31B | 2.3 |
| 32 | 25.0 |
| 33 | 8.4 |
| 33A | 13.2 |

TABLE 1-continued

Results of Luciferase reporter assay

| Example | IC$_{50}$ (nM) |
|---|---|
| 33B | 2.3 |
| 34 | 9.5 |
| 35 | 10.7 |
| 36 | 12.9 |
| 37 | 500.3 |
| 38 | 22.6 |
| 39 | 7.6 |
| 40 | 14.9 |
| 41 | 9.3 |
| 42 | 3.9 |
| 43 | 4.1 |
| 44 | 22.5 |
| 45 | 22.4 |
| 46 | 10.9 |
| 47 | 12.8 |
| 48 | 2.9 |
| 48A | 12.6 |
| 48B | 1.6 |
| 49 | 3.7 |
| 50 | 5.3 |
| 51 | 2.7 |
| 52 | 6.7 |
| 52B | 5.0 |
| 53 | 12.5 |
| 54 | 8.1 |
| 55 | 13.8 |
| 56 | 10.9 |
| 57 | 29.0 |
| 58 | 1.8 |
| 58A | 14.2 |
| 58B | 1.3 |
| 59 | 11.1 |
| 60 | 8.2 |
| 61 | 12.4 |
| 62 | 91.1 |
| 63 | 4.3 |
| 64 | 35.1 |
| 65 | 25.5 |
| 66 | 6.2 |
| 66B | 2.4 |
| 67 | 75.5 |
| 68 | 72.1 |
| 69 | 10.5 |
| 69A | 41.6 |
| 69B | 3.9 |
| 70 | 1.7 |
| 71 | 3.8 |
| 72 | 7.8 |
| 73 | 9.3 |
| 74 | 11.1 |
| 75 | 16.9 |
| 76 | 5.2 |
| 76A | 40.4 |
| 76B | 2.2 |
| 77 | 15.3 |
| 78 | 83.3 |
| 79 | 31 |
| 80 | 9.4 |
| 81 | 119.9 |
| 82 | 4.5 |
| 82A | 7.9 |
| 82B | 3.8 |
| 83 | 11.2 |
| 84 | 17 |
| 85 | 7.3 |
| 86 | 85.9 |
| 87 | 4.9 |
| 88 | 437.0 |
| 89 | 767.5 |
| 90 | 6.9 |
| 91 | 15.1 |
| 92 | 12.4 |
| 92A | |
| 92B | |
| 93 | 3.8 |
| 94 | 11.2 |
| 95 | 9.5 |
| 96 | 7.5 |
| 97 | 10.4 |
| 98 | 19.2 |
| 99 | 12.0 |
| 100 | 11.8 |
| 101 | 35.1 |
| 102 | 13.3 |
| 102B | 10.7 |
| 103 | 6.1 |
| 104 | 18.2 |
| 104B | 9.1 |
| 105 | 10.7 |
| 105B | 5.0 |
| 106 | 50.9 |
| 106B | 41.7 |
| 107 | 76.3 |
| 107B | 32.2 |
| Intermediate-Ia | 194.1 |
| Intermediate-Ib | 566.9 |
| 108 | 3 |
| 108B | 2.5 |
| 109 | 1.0 |
| 109B | 0.7 |
| 110 | 2.4 |
| 110B | 2.9 |
| 111 | 0.6 |
| 111B | 0.5 |
| 112 | 4.1 |
| 112B | 1.2 |
| 113B | 0.9 |
| 114 | 3.3 |
| 114B | 4.6 |
| 115 | 1.9 |
| 115B | 3.3 |
| 116 | 2.2 |
| 117 | 3.4 |
| 117B | 3.2 |
| 118 | 7.2 |
| 118B | 6.0 |
| 119 | 3.2 |
| 119B | 2.0 |
| 123 | 8.5 |
| 128 | 12.8 |
| 128B | 7.6 |
| 130 | 6.9 |
| 132 | 15.7 |
| 133 | 15 |
| 135 | 11.2 |
| 136 | 7.9 |
| 137 | 13.0 |
| 138 | 33.2 |
| 139 | 1.9 |
| 140 | 1.2 |
| 141B | 1.1 |
| 142B | 1.0 |
| 143B | 5.8 |
| 144B | 2.1 |
| 145B | 9.0 |
| 146B-1 | 39.3 |
| 146B-2 | 43.9 |
| 147 | 24.7 |
| 147B | 18.9 |
| 148B | 19.3 |
| 149B | 1.7 |
| 150B | 26.5 |
| 151B | 2.0 |
| | 8.5 |

TABLE 2

Results of binding assay

| Example | Structure | A1 | A2A |
|---|---|---|---|
| 31B | 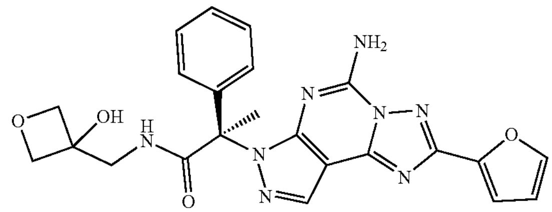 [SMILES: C[C@](C(=O)NCC1(O)COC1)(c1ccccc1)n1ncc2c1nc(N)n1nc(-c3ccco3)nc21] | Ki = 180 nM | Ki = 1.2 nM |
| 48B | 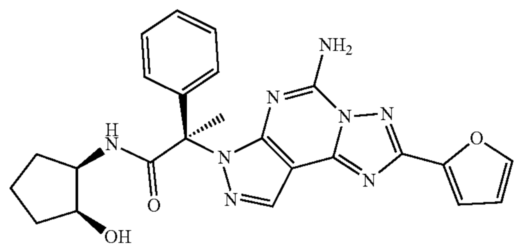 [SMILES: C[C@](C(=O)N[C@@H]1CCC[C@@H]1O)(c1ccccc1)n1ncc2c1nc(N)n1nc(-c3ccco3)nc21] | Ki = 12 nM | Ki = 2.2 nM |
| 82B | (two structures shown, connected by "or") | Ki = 7.2 nM | Ki = 1.7 nM |
| 69B | 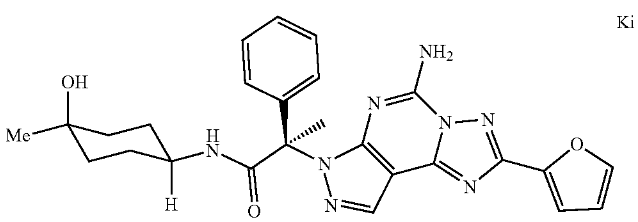 | Ki = 540 nM | Ki = 1.6 nM |
| 76B | 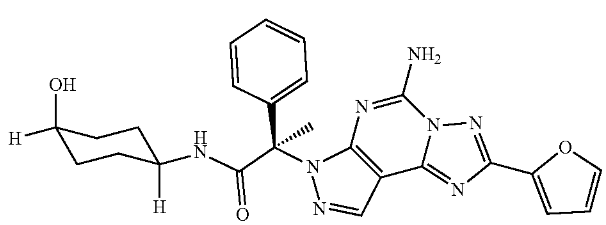 [SMILES: C[C@](C(=O)NC1CCC(O)CC1)(c1ccccc1)n1ncc2c1nc(N)n1nc(-c3ccco3)nc21] | Ki = 150 nM | Ki = 1.6 nM |
| Preladenant | | Ki = 337 nM | Ki = 1.3 nM |

TABLE 3

Results of Mouse BBB assay at 1 h

| Example | Structure | Plasma (ng · mL⁻¹) | Brain (ng · g⁻¹) |
|---|---|---|---|
| 31B | 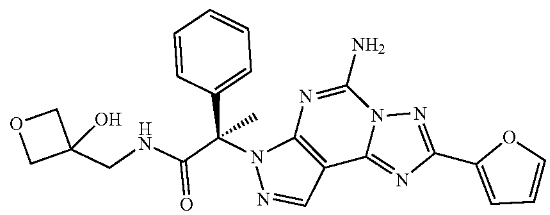 [SMILES: C[C@](C(=O)NCC1(O)COC1)(c1ccccc1)n1ncc2c1nc(N)n1nc(-c3ccco3)nc21] | 177 | BLOQ |
| 48B | 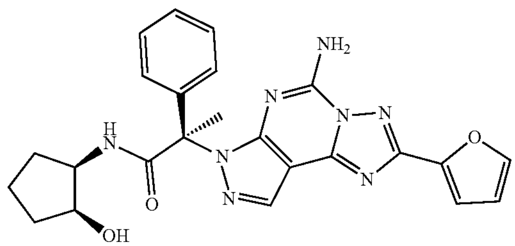 [SMILES: C[C@](C(=O)N[C@@H]1CCC[C@@H]1O)(c1ccccc1)n1ncc2c1nc(N)n1nc(-c3ccco3)nc21] | 56.3 | 8.69 |
| 69B | 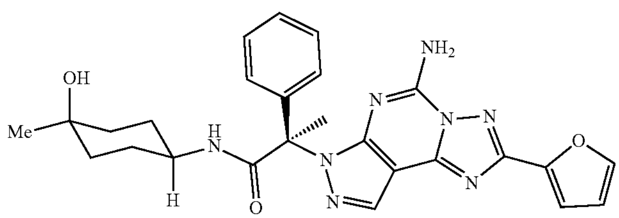 [SMILES: CC1(O)CCC(NC(=O)[C@@](C)(c2ccccc2)n2ncc3c2nc(N)n2nc(-c4ccco4)nc32)CC1] | 29.4 | BLOQ |
| 76B | 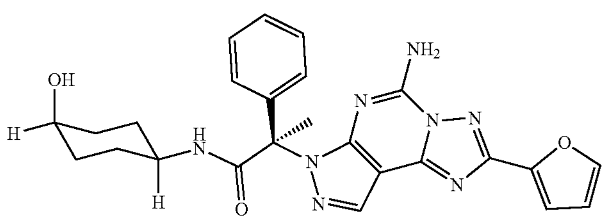 [SMILES: C[C@](C(=O)NC1CCC(O)CC1)(c1ccccc1)n1ncc2c1nc(N)n1nc(-c3ccco3)nc21] | 39.1 | BLOQ |
| Preladenant | | 197 | 258 |

BLOQ: below limit of quantitation
Plasma is 1 1 ng/ml and Brain is 5 ng/g.

What is claimed is:
1. A compound of formula (I)

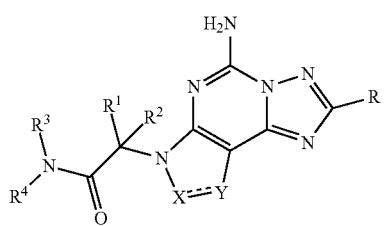

or a stereoisomer thereof, or a pharmaceutically acceptable salt thereof,
wherein:
X is N, C(=O), or $CR^a$;
Y is $CR^a$ or $NR^a$;

╌╌╌ is a single or double bond;

$R^a$ is independently selected from hydrogen, —$C_{1-6}$alkyl, —$C_{3-8}$cycloalkyl, heterocyclyl, aryl, or heteroaryl;

R is an aryl group or a 5 or 6-membered heteroaryl group containing 1 or 2 heteroatoms independently selected from —N=, =N—, —NH—, —O—, —S—, —SO— or —$SO_2$—, and said aryl or heteroaryl group is optionally substituted with at least one substituent $R^{15}$;

$R^1$ and $R^2$, which may be the same or different, are each independently selected from hydrogen, —$C_{1-6}$alkyl, —$C_{2-6}$alkenyl, —$C_{2-6}$alkynyl, cycloalkyl, heterocyclyl, aryl, or heteroaryl, wherein said $C_{1-6}$alkyl, —$C_{2-6}$alkenyl, —$C_{2-6}$alkynyl, cycloalkyl, heterocyclyl, aryl, or heteroaryl are each independently optionally substituted with at least one substituent $R^{15}$, provided that $R^1$ and $R^2$ are not both hydrogen; or $R^1$ and $R^2$, together with the carbon atom to which they are attached, form a 3- to 12-membered saturated, partially or fully unsaturated ring comprising 0, 1 or 2 heteroatoms independently selected from —N=, =N—, —NH—, —O—, —S—, —SO— or —SO$_2$—, and said ring is optionally substituted with at least one substituent $R^{15}$;

$R^3$ is hydrogen;

$R^4$ is hydrogen, $C_{1-6}$alkyl, $C_{3-8}$cycloalkyl, aryl, heteroaryl, or heterocyclyl, wherein each of said $C_{1-6}$alkyl, $C_{3-8}$cycloalkyl, aryl, heteroaryl, or heterocyclyl is independently and optionally substituted with one or two substituents $R^5$; or two adjacent substituents $R^5$ on the $C_{3-8}$cycloalkyl, aryl, heteroaryl, or heterocyclyl ring together with the atoms they are attached form a fused ring;

$R^5$ is independently hydrogen, halogen, —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, $C_{3-8}$cycloalkyl, heterocyclyl, aryl, heteroaryl, —CN, —NO$_2$, oxo, —OR$^b$, —SO$_2$R$^b$, —COR$^b$, —CO$_2$R$^b$, —CONR$^b$R$^c$, —C(=NR$^b$)NR$^c$R$^d$, —NR$^b$R$^c$, —NR$^b$COR$^c$, —NR$^b$CONR$^c$R$^d$, —NR$^b$CO$_2$R$^c$, —NR$^b$SONR$^c$R$^d$, —NR$^b$SO$_2$NR$^c$R$^d$, or —NR$^b$SO$_2$R$^c$, wherein, each of said —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, $C_{3-8}$cycloalkyl, heterocyclyl, aryl, or heteroaryl is independently and optionally substituted with one or two substituents $R^6$;

$R^6$ is independently hydrogen, halogen, —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, $C_{3-8}$cycloalkyl, heterocyclyl, aryl, heteroaryl, —CN, —NO$_2$, oxo, or —OR$^c$, wherein, said —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, cycloalkyl, heterocyclyl, aryl, or heteroaryl is each independently and optionally substituted with one or two substituents $R^7$;

$R^7$ for each occurrence is independently hydrogen, halogen, —$C_{1-6}$alkyl, —$C_{2-6}$alkenyl, —$C_{2-6}$alkynyl, cycloalkyl, heterocyclyl, aryl, heteroaryl, —CN, —NO$_2$, oxo, —$C_{1-6}$alkoxy, —$C_{1-6}$alkoxy-$C_{1-6}$alkoxy or hydroxyl;

$R^b$, $R^c$, $R^d$, $R^e$, which may be the same or different, are each independently hydrogen, —$C_{1-6}$alkyl, $C_{1-6}$alkoxy-$C_{1-6}$alkyl-, —$C_{2-6}$alkenyl, —$C_{2-6}$alkynyl, cycloalkyl, heterocyclyl, aryl, or heteroaryl, wherein said $C_{1-6}$alkyl, —$C_{2-6}$alkenyl, —$C_{2-6}$alkynyl, cycloalkyl, heterocyclyl, aryl, or heteroaryl are each independently optionally substituted with at least one substituent $R^{15}$; and $R^{15}$ is independently hydrogen, halogen, cyano, —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, —$C_{1-6}$alkoxy, $C_{3-8}$cycloalkyloxy, cycloalkyl, heterocyclyl, aryl, or heteroaryl.

2. The compound of claim 1, wherein X is N and Y is CR$^a$ so that X and Y form a —N=CR$^a$— moiety.

3. The compound of claim 1, wherein R is furanyl, pyrazinyl or thiazolyl.

4. The compound of claim 1, wherein $R^1$ is hydrogen and $R^2$ is phenyl; or $R^1$ is hydrogen and $R^2$ is $C_{1-6}$alkyl; or $R^1$ is $C_{1-6}$alkyl and $R^2$ is phenyl; or $R^1$ is $C_{1-6}$alkyl and $R^2$ is pyridinyl; or $R^1$ is $C_{1-6}$alkyl and $R^2$ is $C_{1-6}$alkyl substituted with heterocyclyl, aryl, or heteroaryl, or $R^1$ and $R^2$, together with the carbon atom to which they are attached, form a 3- to 12-membered saturated ring comprising 0 heteroatom.

5. The compound of claim 1, wherein $R^4$ is $C_{1-6}$alkyl optionally substituted with one or two substituents $R^5$, wherein each $R^5$ is independently selected from aryl, heteroaryl, heterocyclyl, cycloalkyl, —OR$^b$ or —NR$^b$R$^c$ as defined with formula (I).

6. The compound of claim 1, wherein $R^4$ is $C_{1-6}$alkyl, wherein $R^4$ is optionally substituted with a $R^5$ substituent selected from the group consisting of:
   i) an aryl group, wherein said aryl group is optionally substituted with halogen, —$C_{1-6}$alkyl, halo$C_{1-6}$alkyl, or —OR$^e$, wherein R$^e$ is $C_{1-6}$alkyl optionally substituted with halogen,
   ii) a heterocyclyl group, wherein said heterocyclyl group is optionally substituted with aryl and —OR$^e$, wherein said aryl is optionally substituted with $R^7$, and R$^e$ and $R^7$,
   iii) a $C_{3-8}$cycloalkyl group, wherein said $C_{3-8}$cycloalkyl group is optionally substituted with hydroxyl, and
   iv) a heteroaryl group, wherein said heteroaryl group is optionally substituted with halogen, $C_{1-6}$alkyl, $C_{3-8}$cycloalkyl, or —OR$^e$, wherein said $C_{1-6}$alkyl and $C_{3-8}$cycloalkyl is optionally substituted with hydroxy.

7. The compound of claim 6, wherein $R^5$ is a phenyl group optionally substituted with $C_{1-6}$alkyl, $C_{1-6}$alkyoxy, halo$C_{1-6}$alkyl, halo$C_{1-6}$alkoxy, F, Cl, or Br.

8. The compound of claim 6, wherein $R^5$ is a 3- to 12-membered heterocyclyl, either monocyclic or bicyclic, comprising 1 or 2 or 3 heteroatoms independently selected from —N= or =N—, —NH—, —O—, —S—, —SO— or —SO$_2$—.

9. The compound of claim 6, wherein $R^5$ is a heterocyclyl ring selected from the group consisting of oxetanyl, piperazinyl, tetrahydrofuranyl, pyranyl, and morpholino, each of which is optionally substituted with hydroxyl.

10. The compound of claim 6, wherein $R^5$ is a $C_{3-8}$cycloalkyl selected from the group consisting of cyclopropyl, cyclobutyl, cyclopentyl, cyclohexyl, cycloheptyl, and cyclooctyl.

11. The compound of claim 6, wherein $R^5$ is a heteroaryl group selected from the group consisting of pyridinyl including pyridin-2-yl, pyridin-3-yl and pyridin-4-yl, optionally substituted with hydroxycyclobutyl, methyl, methoxy, or halogen.

12. The compound of claim 1, wherein $R^4$ is $C_{1-6}$alkyl optionally substituted with —OR$^b$ or —NR$^b$R$^c$, wherein R$^b$ and R$^c$ are independently hydrogen, $C_{1-6}$alkyl, or $C_{1-6}$alkoxy$C_{1-6}$alkyl-.

13. The compound of claim 12, wherein $R^4$ is 2-methoxyethyl, 2-(dimethylamino)ethyl, 2-(2-methoxyethoxy)ethyl, 2-(methylamino)ethyl, 2-hydroxypropyl, (R)-2-hydroxypropyl, or 2-hydroxyethyl.

14. The compound of claim 1, wherein $R^4$ is $C_{3-8}$cycloalkyl optionally substituted with $C_{1-6}$alkyl, $C_{1-6}$alkoxy, or hydroxyl, said $C_{3-8}$cycloalkyl is selected from the group consisting of cyclopropyl, cyclobutyl, cyclopentyl, cyclohexyl, cycloheptyl, and cyclooctyl.

15. The compound of claim 14, wherein:

R⁴ is 4-substituted cyclohexyl wherein the substituent at position 4 and the amino group attached to position 1 are in (cis) or (trans) configurations; or R⁴ is 3-substituted cyclobutyl wherein the substituent at position 3 and the amino group attached to position 1 are in (cis) or (trans) configurations.

16. The compound of claim 1, wherein R⁴ is a phenyl group.

17. The compound of claim 1, wherein R⁴ is pyridin-3-yl, pyridin-4-yl, or pyridin-2-yl.

18. The compound of claim 1, wherein R⁴ is a heterocyclyl selected from pyranyl, piperidinyl, pyrrolidinyl, tetrahydrofuranyl, chroman-4-yl, or dihydrobenzofuran-3-yl, each of which is independently optionally substituted with one or two R⁵ substituents; or two adjacent R⁵ substituents on the heterocyclyl ring together with the atoms they are attached form a fused ring.

19. The compound of claim 18, wherein the heterocyclyl is optionally substituted with aryl, oxo, or hydroxy, wherein aryl is further optionally substituted with —C₁₋₆alkoxy-C₁₋₆alkoxy.

20. The compound of claim 1, wherein R⁴ is:
phenylmethyl;
2-methoxyphenylmethyl;
3-methoxyphenylmethyl;
4-methoxyphenylmethyl;
2-fluorophenylmethyl;
2-(trifluoromethoxy)phenylmethyl;
4-(trifluoromethoxy)phenylmethyl;
1-phenylethyl;
(S)-1-phenylethyl;
(R)-1-phenylethyl;
2-phenylethyl;
3-(trifluoromethyl)phenylmethyl;
4-(trifluoromethyl)phenylmethyl;
3-methylphenylmethyl;
4-methylphenylmethyl;
4-fluorophenylmethyl;
(benzo[d][1,3]dioxol-5-ylmethyl;
(3-hydroxyoxetan-3-yl)methyl;
oxetan-3-ylmethyl;
2-(4-(4-(2-methoxyethoxy)phenyl)piperazin-1-yl)ethyl;
2-(piperazin-1-yl)ethyl;
(tetrahydrofuran-2-yl)methyl;
((S)-tetrahydrofuran-3-yl)methyl;
((R)-tetrahydrofuran-2-yl)methyl;
((S)-tetrahydrofuran-2-yl)methyl;
((R)-tetrahydrofuran-3-yl)methyl;
2-(tetrahydrofuran-3-yl)ethyl;
(tetrahydro-2H-pyran-3-yl)methyl;
2-(tetrahydro-2H-pyran-4-yl)ethyl;
(4-hydroxytetrahydro-2H-pyran-4-yl)methyl;
(tetrahydro-2H-pyran-4-yl)methyl;
2-morpholinoethyl;
(1-hydroxycyclopropyl)methyl;
(1-hydroxycyclobutyl)methyl;
(1-hydroxycyclohexyl)methyl;
pyridin-2-ylmethyl;
pyridin-4-ylmethyl;
pyridin-3-ylmethyl;
(6-(1-hydroxycyclobutyl)pyridin-2-yl)methyl;
(6-methylpyridin-2-yl)methyl;
(5-methylpyridin-2-yl)methyl;
(4-methylpyridin-2-yl)methyl;
(3-methylpyridin-2-yl)methyl;
(6-methoxypyridin-2-yl)methyl;
(5-methoxypyridin-2-yl)methyl;
(4-methoxypyridin-2-yl)methyl;
(3-methoxypyridin-2-yl)methyl;
(6-fluoropyridin-2-yl)methyl;
(5-fluoropyridin-2-yl)methyl;
(4-fluoropyridin-2-yl)methyl;
(3-fluoropyridin-2-yl)methyl;
2-hydroxycycloheptyl;
3-hydroxycycloheptyl;
4-hydroxycycloheptyl;
5-hydroxycycloheptyl;
cyclohexyl;
4-hydroxy-4-methylcyclohexyl;
(trans)-4-hydroxycyclohexyl;
(cis)-4-hydroxy-4-methylcyclohexyl;
(cis)-4-hydroxycyclohexyl;
(1s,4s)-4-hydroxy-4-methylcyclohexyl;
(1s,4s)-4-hydroxycyclohexyl;
(1S,2R)-2-hydroxycyclohexyl;
(1s,4s)-4-hydroxy-4-methylcyclohexyl;
(1S,2S)-2-hydroxycyclohexyl;
(1R,2S)-2-hydroxycyclohexyl;
(trans)-4-hydroxy-4-methylcyclohexyl;
3-hydroxycyclohexyl;
(1R,3R)-3-hydroxycyclohexyl;
(1S,3R)-3-hydroxycyclohexyl;
(1R,3S)-3-hydroxycyclohexyl;
(1S,3S)-3-hydroxycyclohexyl;
4-oxocyclohexyl;
cyclopentyl;
2-hydroxycyclopentyl;
3-hydroxycyclopentyl;
(1S,2R)-2-hydroxycyclopentyl;
(1S,2S)-2-hydroxycyclopentyl;
(1R,2S)-2-hydroxycyclopentyl;
(1R,3R)-3-hydroxycyclopentyl;
(1S,3S)-3-hydroxycyclopentyl;
(1S,3R)-3-hydroxycyclopentyl;
(1R,3S)-3-hydroxycyclopentyl;
(trans)-3-hydroxycyclobutyl;
(cis)-3-hydroxycyclobutyl;
(cis)-3-hydroxy-3-methylcyclobutyl;
1-(hydroxymethyl)cyclopropyl;
cyclopropyl;
1,2,3,4-tetrahydronaphthalen-1-yl;
2,3-dihydro-1H-inden-1-yl;
tetrahydro-2H-pyran-4-yl;
(S)-tetrahydro-2H-pyran-3-yl;
(R)-tetrahydro-2H-pyran-3-yl;
tetrahydro-2H-pyran-4-yl;
(R)-chroman-4-yl;
(S)-chroman-4-yl;
2,3-dihydrobenzofuran-3-yl;
1-(4-(2-methoxyethoxy)phenyl)piperidin-4-yl;
(R)-piperidin-3-yl(E652);

(S)-piperidin-3-yl;
4-hydroxypiperidin-1-yl;
piperidin-4-yl;
(S)-5-oxopyrrolidin-3-yl;
(S)-2-oxopyrrolidin-3-yl;
(R)-2-oxopyrrolidin-3-yl;
4-oxocyclohexan-1-yl;
(3S,4R)-4-hydroxytetrahydrofuran-3-yl;
(3S,4S)-4-hydroxytetrahydrofuran-3-yl;
(3S,4S)-4-hydroxytetrahydrofuran-3-yl; or
(3R,4R)-4-hydroxytetrahydrofuran-3-yl.

21. The compound of claim 1, which is selected from

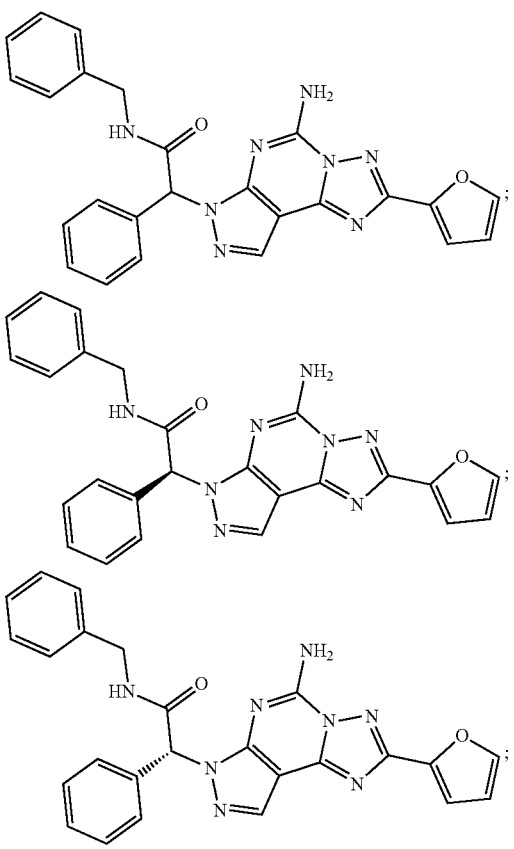

2-(5-amino-2-(furan-2-yl)-7H-pyrazolo[4,3-e][1,2,4]triazolo[1,5-c]pyrimidin-7-yl)-N-cyclohexyl-2-phenylacetamide;
2-(5-amino-2-(furan-2-yl)-7H-pyrazolo[4,3-e][1,2,4]triazolo[1,5-c]pyrimidin-7-yl)-N,2-diphenylacetamide;
2-(5-amino-2-(furan-2-yl)-7H-pyrazolo[4,3-e][1,2,4]triazolo[1,5-c]pyrimidin-7-yl)-N-methyl-2-phenylacetamide;

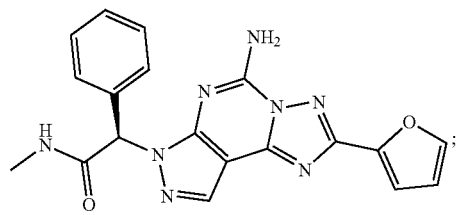

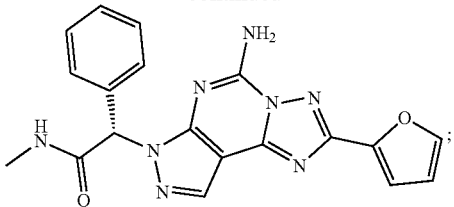

2-(5-amino-2-(furan-2-yl)-7H-pyrazolo[4,3-e][1,2,4]triazolo[1,5-c]pyrimidin-7-yl)-N-ethyl-2-phenylacetamide;
2-(5-amino-2-(furan-2-yl)-7H-pyrazolo[4,3-e][1,2,4]triazolo[1,5-c]pyrimidin-7-yl)-N-(2-methoxybenzyl)-2-phenylacetamide;
2-(5-amino-2-(furan-2-yl)-7H-pyrazolo[4,3-e][1,2,4]triazolo[1,5-c]pyrimidin-7-yl)-N-(2-fluorobenzyl)-2-phenylacetamide;
2-(5-amino-2-(furan-2-yl)-7H-pyrazolo[4,3-e][1,2,4]triazolo[1,5-c]pyrimidin-7-yl)-2-phenyl-N-(2-(trifluoromethoxy)benzyl)acetamide;
2-(5-amino-2-(furan-2-yl)-7H-pyrazolo[4,3-e][1,2,4]triazolo[1,5-c]pyrimidin-7-yl)-2-phenyl-N—((S)-1-phenylethyl)acetamide;
2-(5-amino-2-(furan-2-yl)-7H-pyrazolo[4,3-e][1,2,4]triazolo[1,5-c]pyrimidin-7-yl)-2-phenyl-N—((R)-1-phenylethyl)acetamide;
2-(5-amino-2-(furan-2-yl)-7H-pyrazolo[4,3-e][1,2,4]triazolo[1,5-c]pyrimidin-7-yl)-2-phenyl-N-(tetrahydro-2H-pyran-4-yl)acetamide;
2-(5-amino-2-(furan-2-yl)-7H-pyrazolo[4,3-e][1,2,4]triazolo[1,5-c]pyrimidin-7-yl)-N-cyclopentyl-2-phenylacetamide;
2-(5-amino-2-(furan-2-yl)-7H-pyrazolo[4,3-e][1,2,4]triazolo[1,5-c]pyrimidin-7-yl)-2-phenyl-N-(1,2,3,4-tetrahydronaphthalen-1-yl)acetamide;
2-(5-amino-2-(furan-2-yl)-7H-pyrazolo[4,3-e][1,2,4]triazolo[1,5-c]pyrimidin-7-yl)-N-(2,3-dihydro-1H-inden-1-yl)-2-phenylacetamide;
2-(5-amino-2-(furan-2-yl)-7H-pyrazolo[4,3-e][1,2,4]triazolo[1,5-c]pyrimidin-7-yl)-N—((R)-chroman-4-yl)-2-phenylacetamide;
2-(5-amino-2-(furan-2-yl)-7H-pyrazolo[4,3-e][1,2,4]triazolo[1,5-c]pyrimidin-7-yl)-N—((S)-chroman-4-yl)-2-phenylacetamide;
2-(5-amino-2-(furan-2-yl)-7H-pyrazolo[4,3-e][1,2,4]triazolo[1,5-c]pyrimidin-7-yl)-N-phenethyl-2-phenylacetamide;

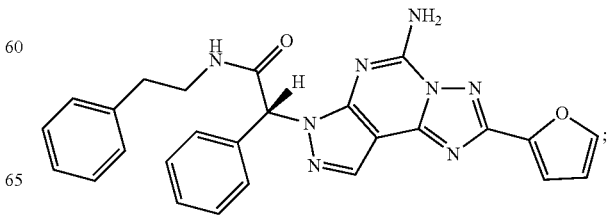

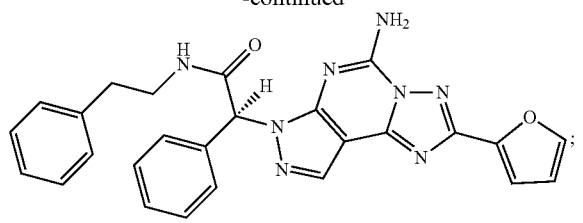

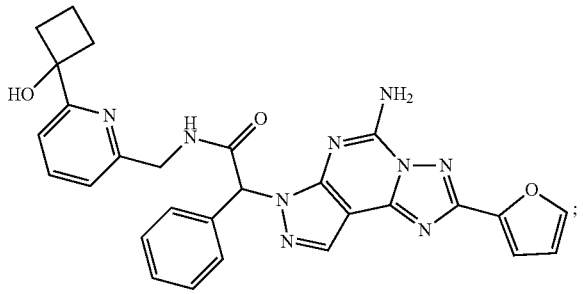

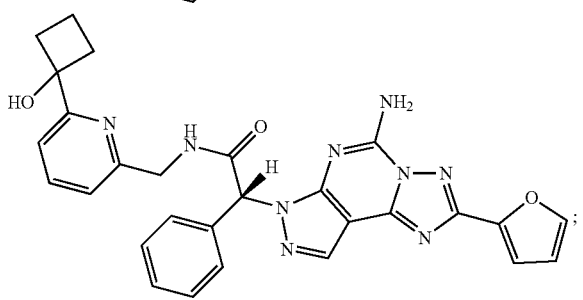

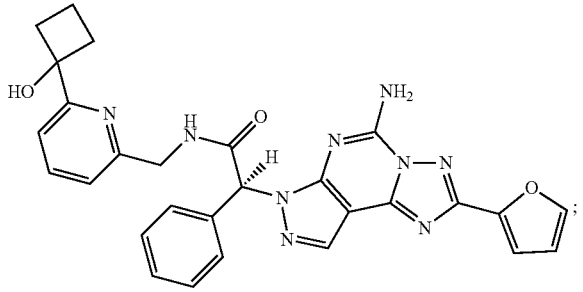

2-(5-amino-2-(furan-2-yl)-7H-pyrazolo[4,3-e][1,2,4]triazolo[1,5-c]pyrimidin-7-yl)-2-phenylacetamide;

2-(5-amino-2-(furan-2-yl)-7H-pyrazolo[4,3-e][1,2,4]triazolo[1,5-c]pyrimidin-7-yl)-N-(2,3-dihydrobenzofuran-3-yl)-2-phenylacetamide;

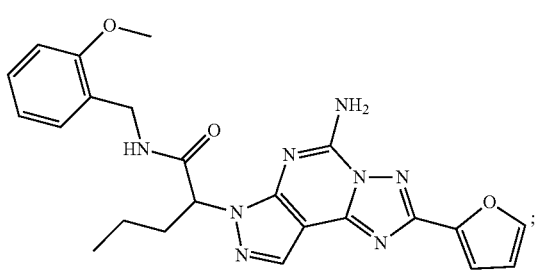 [SMILES: CCCC(C(=O)NCc1ccccc1OC)n1ncc2c1nc(N)n1nc(-c3ccco3)nc21]

2-(5-amino-2-(furan-2-yl)-7H-pyrazolo[4,3-e][1,2,4]triazolo[1,5-c]pyrimidin-7-yl)-2-phenyl-N-(3-(trifluoromethyl)benzyl)acetamide;

2-(5-amino-2-(furan-2-yl)-7H-pyrazolo[4,3-e][1,2,4]triazolo[1,5-c]pyrimidin-7-yl)-N-(3-methylbenzyl)-2-phenylacetamide;

2-(5-amino-2-(furan-2-yl)-7H-pyrazolo[4,3-e][1,2,4]triazolo[1,5-c]pyrimidin-7-yl)-2-phenyl-N-(4-(trifluoromethoxy)benzyl)acetamide;

2-(5-amino-2-(furan-2-yl)-7H-pyrazolo[4,3-e][1,2,4]triazolo[1,5-c]pyrimidin-7-yl)-N-(4-methylbenzyl)-2-phenylacetamide;

2-(5-amino-2-(furan-2-yl)-7H-pyrazolo[4,3-e][1,2,4]triazolo[1,5-c]pyrimidin-7-yl)-N-(4-fluorobenzyl)-2-phenylacetamide;

2-(5-amino-2-(furan-2-yl)-7H-pyrazolo[4,3-e][1,2,4]triazolo[1,5-c]pyrimidin-7-yl)-N-(2-methoxybenzyl)-4-methylpentanamide;

2-(5-amino-2-(furan-2-yl)-7H-pyrazolo[4,3-e][1,2,4]triazolo[1,5-c]pyrimidin-7-yl)-N-(4-methoxybenzyl)-2-phenylacetamide;

2-(5-amino-2-(furan-2-yl)-7H-pyrazolo[4,3-e][1,2,4]triazolo[1,5-c]pyrimidin-7-yl)-2-phenyl-N-(4-(trifluoromethyl)benzyl)acetamide;

2-(5-amino-2-(furan-2-yl)-7H-pyrazolo[4,3-e][1,2,4]triazolo[1,5-c]pyrimidin-7-yl)-N-phenethyl-2-phenylpropanamide;

2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-phenylpropanamide;

(S)-2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-phenylpropanamide;

(R)-2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-phenylpropanamide;

2-(5-amino-2-(furan-2-yl)-7H-pyrazolo[4,3-e][1,2,4]triazolo[1,5-c]pyrimidin-7-yl)-N-methyl-2-phenylpropanamide;

2-(5-amino-2-(furan-2-yl)-7H-pyrazolo[4,3-e][1,2,4]triazolo[1,5-c]pyrimidin-7-yl)-(trans)-N-(4-hydroxy-4-methylcyclohexyl)-2-phenylpropanamide;

(S)-2-(5-amino-2-(furan-2-yl)-7H-pyrazolo[4,3-e][1,2,4]triazolo[1,5-c]pyrimidin-7-yl)-(trans)-N-(4-hydroxy-4-methylcyclohexyl)-2-phenylpropanamide;

(R)-2-(5-amino-2-(furan-2-yl)-7H-pyrazolo[4,3-e][1,2,4]triazolo[1,5-c]pyrimidin-7-yl)-(trans)-N-(4-hydroxy-4-methylcyclohexyl)-2-phenylpropanamide;

2-(5-amino-2-(furan-2-yl)-7H-pyrazolo[4,3-e][1,2,4]triazolo[1,5-c]pyrimidin-7-yl)-N,2-diphenylpropanamide;

2-(5-amino-2-(furan-2-yl)-7H-pyrazolo[4,3-e][1,2,4]triazolo[1,5-c]pyrimidin-7-yl)-N-benzyl-2-phenylpropanamide;

2-(5-amino-2-(furan-2-yl)-7H-pyrazolo[4,3-e][1,2,4]triazolo[1,5-c]pyrimidin-7-yl)-N-(3-hydroxycyclopentyl)-2-phenylpropanamide;

2-(5-amino-2-(furan-2-yl)-7H-pyrazolo[4,3-e][1,2,4]triazolo[1,5-c]pyrimidin-7-yl)-N-(1-(hydroxymethyl)cyclopropyl)-2-phenylpropanamide;

2-(5-amino-2-(furan-2-yl)-7H-pyrazolo[4,3-e][1,2,4]triazolo[1,5-c]pyrimidin-7-yl)-N—((R)-2-hydroxypropyl)-2-phenylpropanamide;

2-(5-amino-2-(furan-2-yl)-7H-pyrazolo[4,3-e][1,2,4]tri-
azolo[1,5-c]pyrimidin-7-yl)-N-(2-methoxyethyl)-2-
phenylpropanamide;

2-(5-amino-2-(furan-2-yl)-7H-pyrazolo[4,3-e][1,2,4]tri-
azolo[1,5-c]pyrimidin-7-yl)-N-cyclopropyl-2-phenyl-
propanamide;

2-(5-amino-2-(furan-2-yl)-7H-pyrazolo[4,3-e][1,2,4]tri-
azolo[1,5-c]pyrimidin-7-yl)-N-(2-morpholinoethyl)-2-
phenylpropanamide;

2-(5-amino-2-(furan-2-yl)-7H-pyrazolo[4,3-e][1,2,4]tri-
azolo[1,5-c]pyrimidin-7-yl)-N-(benzo[d][1,3]dioxol-5-
ylmethyl)-2-phenylpropanamide;

2-(5-amino-2-(furan-2-yl)-7H-pyrazolo[4,3-e][1,2,4]tri-
azolo[1,5-c]pyrimidin-7-yl)-N-cyclohexyl-2-phenyl-
propanamide;

(R)-2-(5-amino-2-(furan-2-yl)-7H-pyrazolo[4,3-e][1,2,4]
triazolo[1,5-c]pyrimidin-7-yl)-N-((1R,2S)-2-hydroxy-
cyclopentyl)-2-phenylpropanamide;

2-(5-amino-2-(furan-2-yl)-7H-pyrazolo[4,3-e][1,2,4]t
riazolo[1,5-c]pyrimidin-7-yl)-2-phenyl-N-((tetrahy-
drofuran-2-yl)methyl)propenamide;

2-(5-amino-2-(furan-2-yl)-7H-pyrazolo[4,3-e][1,2,4]tri-
azolo[1,5-c]pyrimidin-7-yl)-2-phenyl-N—(((R)-tetra-
hydrofuran-2-yl)methyl)propenamide;

2-(5-amino-2-(furan-2-yl)-7H-pyrazolo[4,3-e][1,2,4]tri-
azolo[1,5-c]pyrimidin-7-yl)-2-phenyl-N—(((S)-tetra-
hydrofuran-2-yl)methyl)propenamide;

2-(5-amino-2-(furan-2-yl)-7H-pyrazolo[4,3-e][1,2,4]tri-
azolo[1,5-c]pyrimidin-7-yl)-(trans)-N-(4-hydroxycy-
clohexyl)-2-phenylpropanamide;

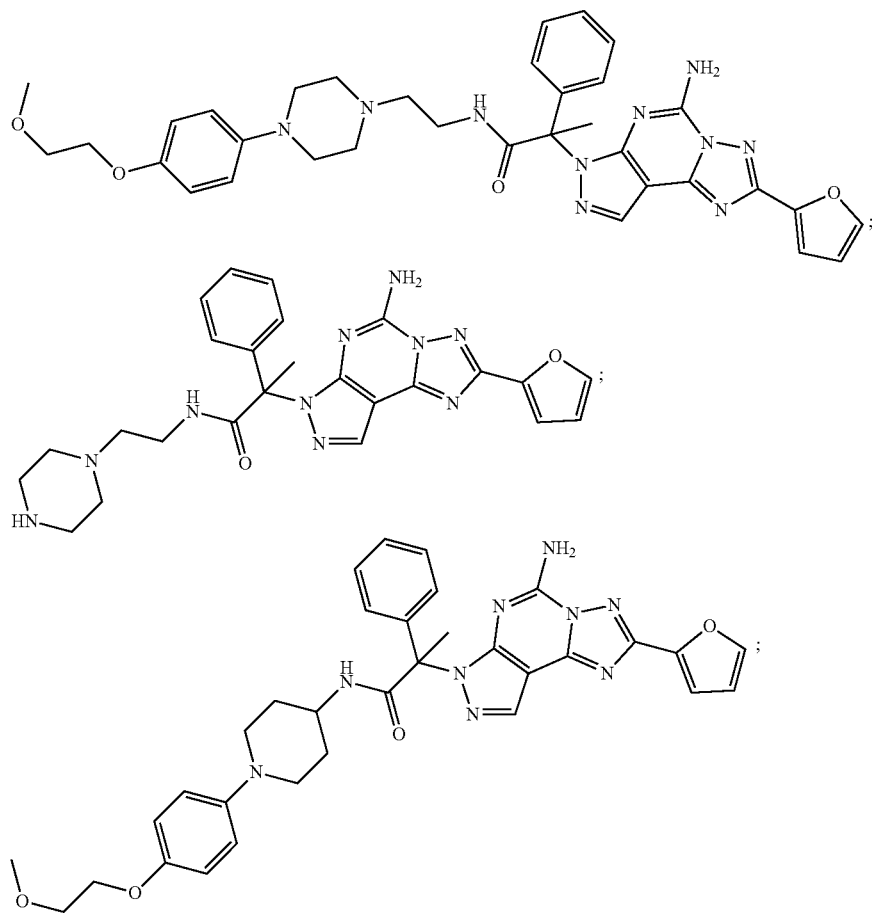

2-(5-amino-2-(furan-2-yl)-7H-pyrazolo[4,3-e][1,2,4]tri-
azolo[1,5-c]pyrimidin-7-yl)-N-((1S,2R)-2-hydroxycy-
clopentyl)-2-phenylpropanamide;

2-(5-amino-2-(furan-2-yl)-7H-pyrazolo[4,3-e][1,2,4]tri-
azolo[1,5-c]pyrimidin-7-yl)-N-((1R,2S)-2-hydroxycy-
clopentyl)-2-phenylpropanamide;

(S)-2-(5-amino-2-(furan-2-yl)-7H-pyrazolo[4,3-e][1,2,4]
triazolo[1,5-c]pyrimidin-7-yl)-N-((1R,2S)-2-hydroxy-
cyclopentyl)-2-phenylpropanamide;

(R)-2-(5-amino-2-(furan-2-yl)-7H-pyrazolo[4,3-e][1,2,4]
triazolo[1,5-c]pyrimidin-7-yl)-N-((trans)-4-hydroxy-
cyclohexyl)-2-phenylpropanamide;

2-(5-amino-2-(furan-2-yl)-7H-pyrazolo[4,3-e][1,2,4]tri-
azolo[1,5-c]pyrimidin-7-yl)-2-phenyl-N—(((S)-tetra-
hydrofuran-3-yl)methyl)propenamide;

2-(5-amino-2-(furan-2-yl)-7H-pyrazolo[4,3-e][1,2,4]tri-
azolo[1,5-c]pyrimidin-7-yl)-2-phenyl-N—(((R)-tetra-
hydrofuran-3-yl)methyl)propenamide;

2-(5-amino-2-(furan-2-yl)-7H-pyrazolo[4,3-e][1,2,4]triazolo[1,5-c]pyrimidin-7-yl)-N-(2-hydroxyethyl)-2-phenylpropanamide;

2-(5-amino-2-(furan-2-yl)-7H-pyrazolo[4,3-e][1,2,4]triazolo[1,5-c]pyrimidin-7-yl)-N-((1S,2R)-2-hydroxycyclohexyl)-2-phenylpropanamide;

2-(5-amino-2-(furan-2-yl)-7H-pyrazolo[4,3-e][1,2,4]triazolo[1,5-c]pyrimidin-7-yl)-N-((1S,2S)-2-hydroxycyclohexyl)-2-phenylpropanamide;

2-(5-amino-2-(furan-2-yl)-7H-pyrazolo[4,3-e][1,2,4]triazolo[1,5-c]pyrimidin-7-yl)-N-((1R,2S)-2-hydroxycyclohexyl)-2-phenylpropanamide;

2-(5-amino-2-(furan-2-yl)-7H-pyrazolo[4,3-e][1,2,4]triazolo[1,5-c]pyrimidin-7-yl)-N-((1S,2R)-2-hydroxycyclohexyl)-2-phenylpropanamide;

(R)-2-(5-amino-2-(furan-2-yl)-7H-pyrazolo[4,3-e][1,2,4]triazolo[1,5-c]pyrimidin-7-yl)-N-((1R,2S)-2-hydroxycyclohexyl)-2-phenylpropanamide;

2-(5-amino-2-(furan-2-yl)-7H-pyrazolo[4,3-e][1,2,4]triazolo[1,5-c]pyrimidin-7-yl)-2-phenyl-N—((S)-tetrahydro-2H-pyran-3-yl)propenamide;

2-(5-amino-2-(furan-2-yl)-7H-pyrazolo[4,3-e][1,2,4]triazolo[1,5-c]pyrimidin-7-yl)-2-phenyl-N—((R)-tetrahydro-2H-pyran-3-yl)propenamide;

2-(5-amino-2-(furan-2-yl)-7H-pyrazolo[4,3-e][1,2,4]triazolo[1,5-c]pyrimidin-7-yl)-2-phenyl-N-((tetrahydro-2H-pyran-3-yl)methyl)propenamide;

2-(5-amino-2-(furan-2-yl)-7H-pyrazolo[4,3-e][1,2,4]triazolo[1,5-c]pyrimidin-7-yl)-N-(2-(dimethylamino)ethyl)-2-phenylpropanamide;

2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-(o-tolyl)propenamide;

2-(5-amino-2-(furan-2-yl)-7H-pyrazolo[4,3-e][1,2,4]triazolo[1,5-c]pyrimidin-7-yl)-2-phenyl-N-(pyridin-3-yl)propenamide;

2-(5-amino-2-(furan-2-yl)-7H-pyrazolo[4,3-e][1,2,4]triazolo[1,5-c]pyrimidin-7-yl)-2-phenyl-N-(pyridin-4-yl)propenamide;

2-(5-amino-2-(furan-2-yl)-7H-pyrazolo[4,3-e][1,2,4]triazolo[1,5-c]pyrimidin-7-yl)-2-phenyl-N-(pyridin-2-ylmethyl)propenamide;

(R)-2-(5-amino-2-(furan-2-yl)-7H-pyrazolo[4,3-e][1,2,4]triazolo[1,5-c]pyrimidin-7-yl)-2-phenyl-N-(pyridin-2-ylmethyl)propenamide;

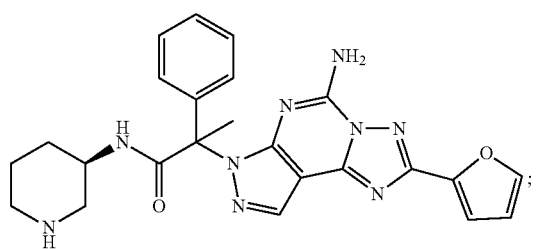

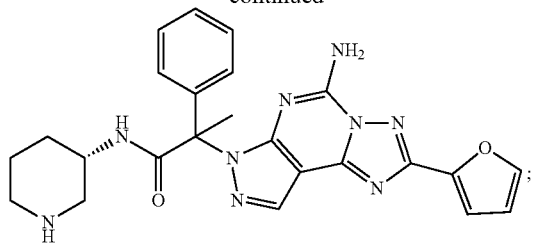

2-(5-amino-2-(furan-2-yl)-7H-pyrazolo[4,3-e][1,2,4]triazolo[1,5-c]pyrimidin-7-yl)-(cis)-N-(4-hydroxy-4-methylcyclohexyl)-2-phenylpropanamide;

(S)-2-(5-amino-2-(furan-2-yl)-7H-pyrazolo[4,3-e][1,2,4]triazolo[1,5-c]pyrimidin-7-yl)-(cis)-N-(4-hydroxy-4-methylcyclohexyl)-2-phenylpropanamide;

(R)-2-(5-amino-2-(furan-2-yl)-7H-pyrazolo[4,3-e][1,2,4]triazolo[1,5-c]pyrimidin-7-yl)-(cis)-N-(4-hydroxy-4-methylcyclohexyl)-2-phenylpropanamide;

2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-(2-methoxyphenyl)propenamide;

2-(5-amino-2-(furan-2-yl)-7H-pyrazolo[4,3-e][1,2,4]triazolo[1,5-c]pyrimidin-7-yl)-N-((1-hydroxycyclobutyl)methyl)-2-phenylpropanamide;

2-(5-amino-2-(furan-2-yl)-7H-pyrazolo[4,3-e][1,2,4]triazolo[1,5-c]pyrimidin-7-yl)-N-((1-hydroxycyclohexyl)methyl)-2-phenylpropanamide;

2-(5-amino-2-(furan-2-yl)-7H-pyrazolo[4,3-e][1,2,4]triazolo[1,5-c]pyrimidin-7-yl)-2-phenyl-N-(2-(tetrahydro-2H-pyran-4-yl)ethyl)propenamide;

2-(5-amino-2-(furan-2-yl)-7H-pyrazolo[4,3-e][1,2,4]triazolo[1,5-c]pyrimidin-7-yl)-2-phenyl-N-(2-(tetrahydrofuran-3-yl)ethyl)propenamide;

2-(5-amino-2-(furan-2-yl)-7H-pyrazolo[4,3-e][1,2,4]triazolo[1,5-c]pyrimidin-7-yl)-N-(2-(2-methoxyethoxy)ethyl)-2-phenylpropanamide;

2-(5-amino-2-(furan-2-yl)-7H-pyrazolo[4,3-e][1,2,4]triazolo[1,5-c]pyrimidin-7-yl)-(cis)-N-(4-hydroxycyclohexyl)-2-phenylpropanamide;

(S)-2-(5-amino-2-(furan-2-yl)-7H-pyrazolo[4,3-e][1,2,4]triazolo[1,5-c]pyrimidin-7-yl)-(cis)-N-(4-hydroxycyclohexyl)-2-phenylpropanamide;

(R)-2-(5-amino-2-(furan-2-yl)-7H-pyrazolo[4,3-e][1,2,4]triazolo[1,5-c]pyrimidin-7-yl)-(cis)-N-(4-hydroxycyclohexyl)-2-phenylpropanamide;

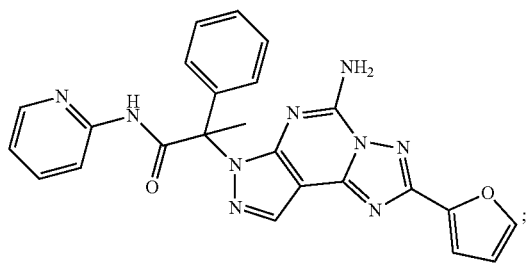

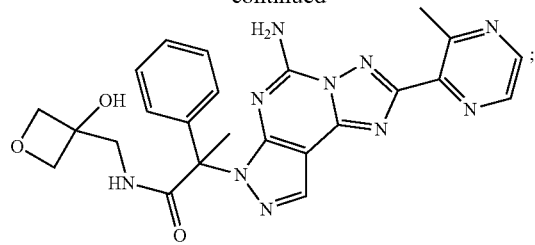

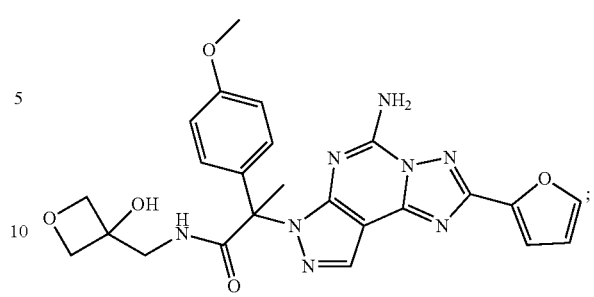

2-(5-amino-2-(furan-2-yl)-7H-pyrazolo[4,3-e][1,2,4]tri-
azolo[1,5-c]pyrimidin-7-yl)-N-(oxetan-3-ylmethyl)-2-
phenylpropanamide;

2-(5-amino-2-(furan-2-yl)-7H-pyrazolo[4,3-e][1,2,4]tri-
azolo[1,5-c]pyrimidin-7-yl)-N-((4-hydroxytetrahydro-
2H-pyran-4-yl)methyl)-2-phenylpropanamide;

2-(5-amino-2-(furan-2-yl)-7H-pyrazolo[4,3-e][1,2,4]tri-
azolo[1,5-c]pyrimidin-7-yl)-N-(2-(methylamino)
ethyl)-2-phenylpropanamide;

2-(5-amino-2-(furan-2-yl)-7H-pyrazolo[4,3-e][1,2,4]tri-
azolo[1,5-c]pyrimidin-7-yl)-N-((3-hydroxyoxetan-3-
yl)methyl)-2-phenylacetamide;

2-(5-amino-2-(furan-2-yl)-7H-pyrazolo[4,3-e][1,2,4]tri-
azolo[1,5-c]pyrimidin-7-yl)-2-(2-fluorophenyl)-N-((3-
hydroxyoxetan-3-yl)methyl)propenamide;

2-(5-amino-2-(furan-2-yl)-7H-pyrazolo[4,3-e][1,2,4]tri-
azolo[1,5-c]pyrimidin-7-yl)-N-((1-hydroxycyclopro-
pyl)methyl)-2-phenylpropanamide;

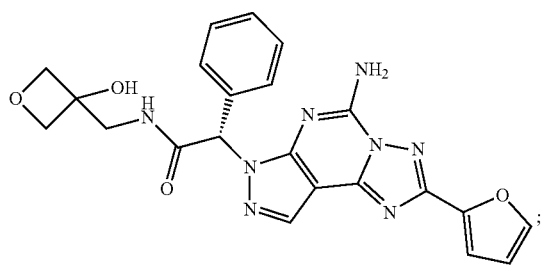

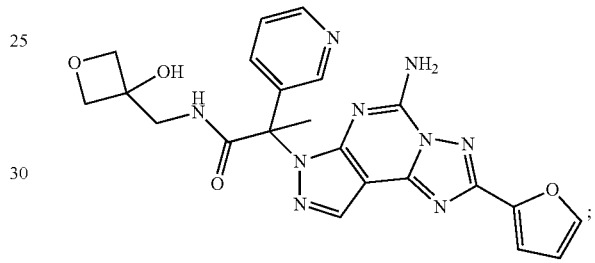

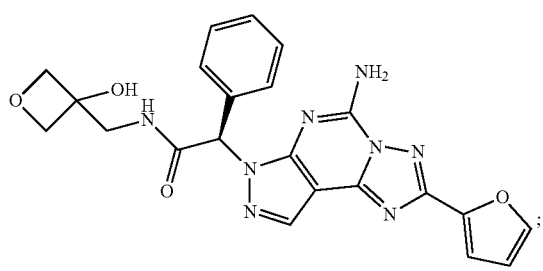

2-(5-amino-2-(furan-2-yl)-7H-pyrazolo[4,3-e][1,2,4]tri-
azolo[1,5-c]pyrimidin-7-yl)-N-((1R,2S)-2-hydroxycy-
clopentyl)-2-phenylacetamide;

2-(5-amino-2-(furan-2-yl)-7H-pyrazolo[4,3-e][1,2,4]tri-
azolo[1,5-c]pyrimidin-7-yl)-N-((1S,2R)-2-hydroxycy-
clohexyl)-2-phenylacetamide;

2-(5-amino-2-(furan-2-yl)-7H-pyrazolo[4,3-e][1,2,4]tri-
azolo[1,5-c]pyrimidin-7-yl)-(cis)-N-(4-hydroxycyclo-
hexyl)-2-phenylacetamide;

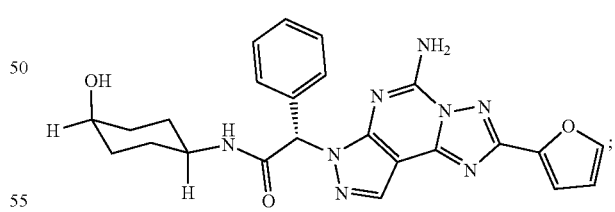

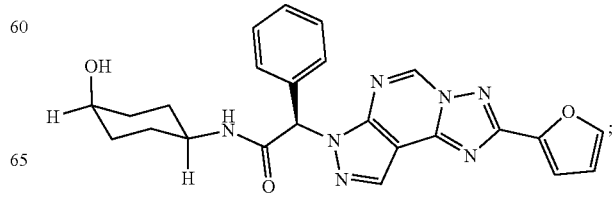

2-(5-amino-2-(furan-2-yl)-7H-pyrazolo[4,3-e][1,2,4]tri-
azolo[1,5-c]pyrimidin-7-yl)-2-phenyl-N-(pyridin-4-yl-
methyl)propenamide;

2-(5-amino-2-(furan-2-yl)-7H-pyrazolo[4,3-e][1,2,4]tri-
azolo[1,5-c]pyrimidin-7-yl)-2-phenyl-N-(pyridin-3-yl-
methyl)propenamide;

2-(5-amino-2-(furan-2-yl)-7H-pyrazolo[4,3-e][1,2,4]tri-
azolo[1,5-c]pyrimidin-7-yl)-N-((3-hydroxyoxetan-3-
yl)methyl)-2-(m-tolyl)propenamide;

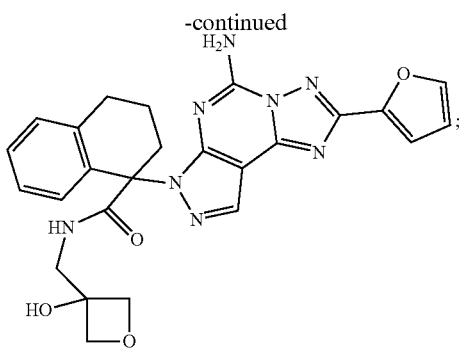

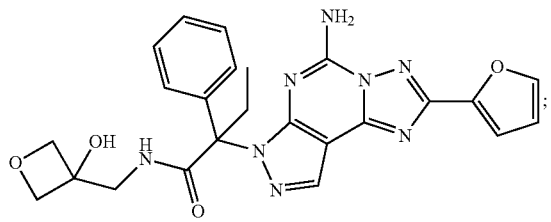

2-(5-amino-2-(furan-2-yl)-7H-pyrazolo[4,3-e][1,2,4]triazolo[1,5-c]pyrimidin-7-yl)-N-((1R,3R)-3-hydroxycyclopentyl)-2-phenylpropanamide;

2-(5-amino-2-(furan-2-yl)-7H-pyrazolo[4,3-e][1,2,4]triazolo[1,5-c]pyrimidin-7-yl)-N-((1S,3S)-3-hydroxycyclopentyl)-2-phenylpropanamide;

2-(5-amino-2-(furan-2-yl)-7H-pyrazolo[4,3-e][1,2,4]triazolo[1,5-c]pyrimidin-7-yl)-(cis)-N-(4-hydroxy-4-methylcyclohexyl)-2-phenylacetamide;

2-(5-amino-2-(furan-2-yl)-7H-pyrazolo[4,3-e][1,2,4]triazolo[1,5-c]pyrimidin-7-yl)-2-phenyl-N-((tetrahydro-2H-pyran-4-yl)methyl)propenamide;

2-(5-amino-2-(furan-2-yl)-7H-pyrazolo[4,3-e][1,2,4]triazolo[1,5-c]pyrimidin-7-yl)-2-phenyl-N-(tetrahydro-2H-pyran-4-yl)propenamide;

2-(5-amino-2-(furan-2-yl)-7H-pyrazolo[4,3-e][1,2,4]triazolo[1,5-c]pyrimidin-7-yl)-N-(3-hydroxycyclohexyl)-2-phenylpropanamide;

2-(5-amino-2-(furan-2-yl)-7H-pyrazolo[4,3-e][1,2,4]triazolo[1,5-c]pyrimidin-7-yl)-N—((S)-5-oxopyrrolidin-3-yl)-2-phenylpropanamide;

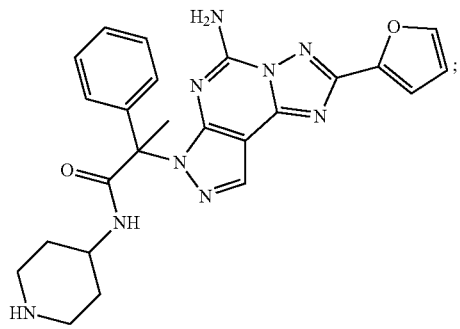 [SMILES: CC(C(=O)NC1CCNCC1)(c1ccccc1)n1ncc2c1nc(N)n1nc(-c3ccco3)nc21]

2-(5-amino-2-(furan-2-yl)-7H-pyrazolo[4,3-e][1,2,4]triazolo[1,5-c]pyrimidin-7-yl)-(trans)-N-(3-hydroxycyclobutyl)-2-phenylpropanamide;

(R)-2-(5-amino-2-(furan-2-yl)-7H-pyrazolo[4,3-e][1,2,4]triazolo[1,5-c]pyrimidin-7-yl)-(trans)-N-(3-hydroxycyclobutyl)-2-phenylpropanamide;

2-(5-amino-2-(furan-2-yl)-7H-pyrazolo[4,3-e][1,2,4]triazolo[1,5-c]pyrimidin-7-yl)-N-((1s,3s)-3-hydroxycyclobutyl)-2-phenylpropanamide;

(R)-2-(5-amino-2-(furan-2-yl)-7H-pyrazolo[4,3-e][1,2,4]triazolo[1,5-c]pyrimidin-7-yl)-(cis)-N-(3-hydroxycyclobutyl)-2-phenylpropanamide;

2-(5-amino-2-(furan-2-yl)-7H-pyrazolo[4,3-e][1,2,4]triazolo[1,5-c]pyrimidin-7-yl)-N-((1S,3S)-3-hydroxy-3-methylcyclobutyl)-2-phenylpropanamide;

(R)-2-(5-amino-2-(furan-2-yl)-7H-pyrazolo[4,3-e][1,2,4]triazolo[1,5-c]pyrimidin-7-yl)-(cis)-N-(3-hydroxy-3-methylcyclobutyl)-2-phenylpropanamide;

2-(5-amino-2-(furan-2-yl)-7H-pyrazolo[4,3-e][1,2,4]triazolo[1,5-c]pyrimidin-7-yl)-N-((3S,4R)-4-hydroxytetrahydrofuran-3-yl)-2-phenylpropanamide;

(R)-2-(5-amino-2-(furan-2-yl)-7H-pyrazolo[4,3-e][1,2,4]triazolo[1,5-c]pyrimidin-7-yl)-N-((3S,4R)-4-hydroxytetrahydrofuran-3-yl)-2-phenylpropanamide;

2-(5-amino-2-(furan-2-yl)-7H-pyrazolo[4,3-e][1,2,4]triazolo[1,5-c]pyrimidin-7-yl)-N-((3S,4S)-4-hydroxytetrahydrofuran-3-yl)-2-phenylpropanamide;

(R)-2-(5-amino-2-(furan-2-yl)-7H-pyrazolo[4,3-e][1,2,4]triazolo[1,5-c]pyrimidin-7-yl)-N-((3S,4S)-4-hydroxytetrahydrofuran-3-yl)-2-phenylpropanamide;

2-(5-amino-2-(furan-2-yl)-7H-pyrazolo[4,3-e][1,2,4]triazolo[1,5-c]pyrimidin-7-yl)-N-((6-methylpyridin-2-yl)methyl)-2-phenylpropanamide;

(R)-2-(5-amino-2-(furan-2-yl)-7H-pyrazolo[4,3-e][1,2,4]triazolo[1,5-c]pyrimidin-7-yl)-N-((6-methylpyridin-2-yl)methyl)-2-phenylpropanamide;

2-(5-amino-2-(furan-2-yl)-7H-pyrazolo[4,3-e][1,2,4]triazolo[1,5-c]pyrimidin-7-yl)-N-((5-methylpyridin-2-yl)methyl)-2-phenylpropanamide;

(R)-2-(5-amino-2-(furan-2-yl)-7H-pyrazolo[4,3-e][1,2,4]triazolo[1,5-c]pyrimidin-7-yl)-N-((5-methylpyridin-2-yl)methyl)-2-phenylpropanamide;

2-(5-amino-2-(furan-2-yl)-7H-pyrazolo[4,3-e][1,2,4]triazolo[1,5-c]pyrimidin-7-yl)-N-((4-methylpyridin-2-yl)methyl)-2-phenylpropanamide;

(R)-2-(5-amino-2-(furan-2-yl)-7H-pyrazolo[4,3-e][1,2,4]triazolo[1,5-c]pyrimidin-7-yl)-N-((4-methylpyridin-2-yl)methyl)-2-phenylpropanamide;

2-(5-amino-2-(furan-2-yl)-7H-pyrazolo[4,3-e][1,2,4]triazolo[1,5-c]pyrimidin-7-yl)-N-((3-methylpyridin-2-yl)methyl)-2-phenylpropanamide;

(R)-2-(5-amino-2-(furan-2-yl)-7H-pyrazolo[4,3-e][1,2,4]triazolo[1,5-c]pyrimidin-7-yl)-N-((3-methylpyridin-2-yl)methyl)-2-phenylpropanamide;

2-(5-amino-2-(furan-2-yl)-7H-pyrazolo[4,3-e][1,2,4]triazolo[1,5-c]pyrimidin-7-yl)-N-((6-methoxypyridin-2-yl)methyl)-2-phenylpropanamide;

(R)-2-(5-amino-2-(furan-2-yl)-7H-pyrazolo[4,3-e][1,2,4]triazolo[1,5-c]pyrimidin-7-yl)-N-((6-methoxypyridin-2-yl)methyl)-2-phenylpropanamide;
(R)-2-(5-amino-2-(furan-2-yl)-7H-pyrazolo[4,3-e][1,2,4]triazolo[1,5-c]pyrimidin-7-yl)-N-((5-methoxypyridin-2-yl)methyl)-2-phenylpropanamide;
2-(5-amino-2-(furan-2-yl)-7H-pyrazolo[4,3-e][1,2,4]triazolo[1,5-c]pyrimidin-7-yl)-N-((4-methoxypyridin-2-yl)methyl)-2-phenylpropanamide;
(R)-2-(5-amino-2-(furan-2-yl)-7H-pyrazolo[4,3-e][1,2,4]triazolo[1,5-c]pyrimidin-7-yl)-N-((4-methoxypyridin-2-yl)methyl)-2-phenylpropanamide;
2-(5-amino-2-(furan-2-yl)-7H-pyrazolo[4,3-e][1,2,4]triazolo[1,5-c]pyrimidin-7-yl)-N-((3-methoxypyridin-2-yl)methyl)-2-phenylpropanamide;
(R)-2-(5-amino-2-(furan-2-yl)-7H-pyrazolo[4,3-e][1,2,4]triazolo[1,5-c]pyrimidin-7-yl)-N-((3-methoxypyridin-2-yl)methyl)-2-phenylpropanamide;
2-(5-amino-2-(furan-2-yl)-7H-pyrazolo[4,3-e][1,2,4]triazolo[1,5-c]pyrimidin-7-yl)-N-((6-fluoropyridin-2-yl)methyl)-2-phenylpropanamide;
2-(5-amino-2-(furan-2-yl)-7H-pyrazolo[4,3-e][1,2,4]triazolo[1,5-c]pyrimidin-7-yl)-N-((5-fluoropyridin-2-yl)methyl)-2-phenylpropanamide;
(R)-2-(5-amino-2-(furan-2-yl)-7H-pyrazolo[4,3-e][1,2,4]triazolo[1,5-c]pyrimidin-7-yl)-N-((5-fluoropyridin-2-yl)methyl)-2-phenylpropanamide;
2-(5-amino-2-(furan-2-yl)-7H-pyrazolo[4,3-e][1,2,4]triazolo[1,5-c]pyrimidin-7-yl)-N-((4-fluoropyridin-2-yl)methyl)-2-phenylpropanamide;
(R)-2-(5-amino-2-(furan-2-yl)-7H-pyrazolo[4,3-e][1,2,4]triazolo[1,5-c]pyrimidin-7-yl)-N-((4-fluoropyridin-2-yl)methyl)-2-phenylpropanamide;
2-(5-amino-2-(furan-2-yl)-7H-pyrazolo[4,3-e][1,2,4]triazolo[1,5-c]pyrimidin-7-yl)-N-((3-fluoropyridin-2-yl)methyl)-2-phenylpropanamide;
(R)-2-(5-amino-2-(furan-2-yl)-7H-pyrazolo[4,3-e][1,2,4]triazolo[1,5-c]pyrimidin-7-yl)-N-((3-fluoropyridin-2-yl)methyl)-2-phenylpropanamide;
2-(5-amino-2-(furan-2-yl)-7H-pyrazolo[4,3-e][1,2,4]triazolo[1,5-c]pyrimidin-7-yl)-N-((1S,3R)-3-hydroxycyclohexyl)-2-phenylpropanamide;
2-(5-amino-2-(furan-2-yl)-7H-pyrazolo[4,3-e][1,2,4]triazolo[1,5-c]pyrimidin-7-yl)-N-(4-oxocyclohexyl)-2-phenylpropanamide;
(R)-2-(5-amino-2-(furan-2-yl)-7H-pyrazolo[4,3-e][1,2,4]triazolo[1,5-c]pyrimidin-7-yl)-N-(4-oxocyclohexyl)-2-phenylpropanamide;
2-(5-amino-2-(furan-2-yl)-7H-pyrazolo[4,3-e][1,2,4]triazolo[1,5-c]pyrimidin-7-yl)-N-((6-(1-hydroxycyclobutyl)pyridin-2-yl)methyl)-2-phenylpropanamide;
2-(5-amino-2-(furan-2-yl)-7H-pyrazolo[4,3-e][1,2,4]triazolo[1,5-c]pyrimidin-7-yl)-N-((3-hydroxyoxetan-3-yl)methyl)-2-methyl-3-phenylpropanamide;
2-(5-amino-2-(thiazol-2-yl)-7H-pyrazolo[4,3-e][1,2,4]triazolo[1,5-c]pyrimidin-7-yl)-N-((3-hydroxyoxetan-3-yl)methyl)-2-phenylpropanamide;
2-(5-amino-2-(furan-2-yl)-7H-pyrazolo[4,3-e][1,2,4]triazolo[1,5-c]pyrimidin-7-yl)-N-((1R,3S)-3-hydroxycyclopentyl)-2-phenylpropanamide;
2-(5-amino-2-(furan-2-yl)-7H-pyrazolo[4,3-e][1,2,4]triazolo[1,5-c]pyrimidin-7-yl)-N-((1S,3R)-3-hydroxycyclopentyl)-2-phenylpropanamide;

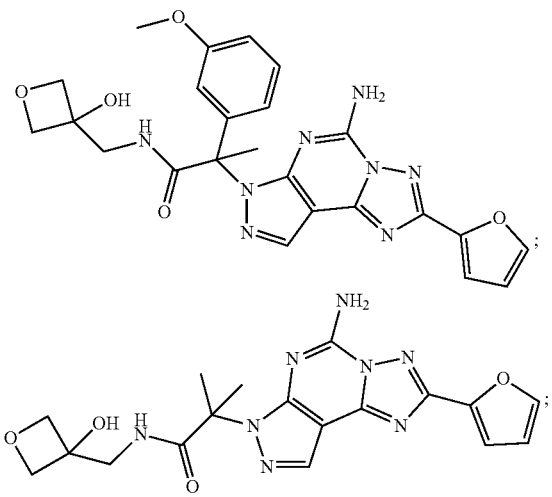

2-(5-amino-2-(furan-2-yl)-7H-pyrazolo[4,3-e][1,2,4]triazolo[1,5-c]pyrimidin-7-yl)-N-((cis)-4-hydroxycyclohexyl)-2-(2-methoxyphenyl)propenamide;
2-(5-amino-2-(furan-2-yl)-7H-pyrazolo[4,3-e][1,2,4]triazolo[1,5-c]pyrimidin-7-yl)-N-((cis)-4-hydroxy-4-methylcyclohexyl)-2-(2-methoxyphenyl)propenamide;
(R)-2-(5-amino-2-(furan-2-yl)-7H-pyrazolo[4,3-e][1,2,4]triazolo[1,5-c]pyrimidin-7-yl)-2-phenyl-N-((3-(trifluoromethyl)pyridin-2-yl)methyl)propenamide;
(R)-2-(5-amino-2-(furan-2-yl)-7H-pyrazolo[4,3-e][1,2,4]triazolo[1,5-c]pyrimidin-7-yl)-2-phenyl-N-((3-(trifluoromethyl)pyridin-2-yl)methyl)propenamide;
(R)-2-(5-amino-2-(furan-2-yl)-7H-pyrazolo[4,3-e][1,2,4]triazolo[1,5-c]pyrimidin-7-yl)-2-phenyl-N-((4-(trifluoromethyl)pyridin-2-yl)methyl)propenamide;
(R)-2-(5-amino-2-(furan-2-yl)-7H-pyrazolo[4,3-e][1,2,4]triazolo[1,5-c]pyrimidin-7-yl)-2-phenyl-N-((6-(trifluoromethyl)pyridin-2-yl)methyl)propenamide;
(R)-2-(5-amino-2-(furan-2-yl)-7H-pyrazolo[4,3-e][1,2,4]triazolo[1,5-c]pyrimidin-7-yl)-2-phenyl-N-(tetrahydro-2H-thiopyran-4-yl)propenamide;
(R)-2-(5-amino-2-(furan-2-yl)-7H-pyrazolo[4,3-e][1,2,4]triazolo[1,5-c]pyrimidin-7-yl)-N-((1S,4s)-1-oxidotetrahydro-2H-thiopyran-4-yl)-2-phenylpropanamide;
(R)-2-(5-amino-2-(furan-2-yl)-7H-pyrazolo[4,3-e][1,2,4]triazolo[1,5-c]pyrimidin-7-yl)-N-((1R,4r)-1-oxidotetrahydro-2H-thiopyran-4-yl)-2-phenylpropanamide;
(R)-2-(5-amino-2-(furan-2-yl)-7H-pyrazolo[4,3-e][1,2,4]triazolo[1,5-c]pyrimidin-7-yl)-N-((1R,4r)-1-oxidotetrahydro-2H-thiopyran-4-yl)-2-phenylpropanamide;
(R)-2-(5-amino-2-(furan-2-yl)-7H-pyrazolo[4,3-e][1,2,4]triazolo[1,5-c]pyrimidin-7-yl)-N-(2-(4-methylpiperazin-1-yl)ethyl)-2-phenylpropanamide;
(R)-2-(5-amino-2-(furan-2-yl)-7H-pyrazolo[4,3-e][1,2,4]triazolo[1,5-c]pyrimidin-7-yl)-N-(2-(4-hydroxypiperidin-1-yl)ethyl)-2-phenylpropanamide;
(R)-2-(5-amino-2-(furan-2-yl)-7H-pyrazolo[4,3-e][1,2,4]triazolo[1,5-c]pyrimidin-7-yl)-N-(2-(4-hydroxycyclohexyl)ethyl)-2-phenylpropanamide;

(R)-2-(5-amino-2-(furan-2-yl)-7H-pyrazolo[4,3-e][1,2,4]triazolo[1,5-c]pyrimidin-7-yl)-N-(2-(6-methylpyridin-2-yl)ethyl)-2-phenylpropanamide; or (cis)-4-((R)-2-(5-amino-2-(furan-2-yl)-7H-pyrazolo[4,3-e] [1,2,4]triazolo[1,5-c]pyrimidin-7-yl)-2-phenylpropanamido)cyclohexyl acetate;

or a pharmaceutically acceptable salt thereof.

22. A pharmaceutical composition comprising the compound of claim 1 or a stereoisomer thereof, or a pharmaceutically acceptable salt thereof and a pharmaceutically acceptable excipient.

23. A method of inhibiting A2A receptor activity in a subject, comprising administering to the subject the compound of claim 1 or a stereoisomer thereof, or a pharmaceutically acceptable salt thereof.

24. The compound of claim 1, wherein X is N and Y is $CR^a$ so that X and Y form a —N=$CR^a$— moiety, wherein $R^a$ is hydrogen or $C_{1-3}$alkyl; and/or wherein $R^1$ is hydrogen and $R^2$ is $C_{1-4}$alkyl; $R^1$ is $C_{1-4}$alkyl and $R^2$ is phenyl; $R^1$ is $C_{1-4}$alkyl and $R^2$ is pyridinyl; or $R^1$ is $C_{1-4}$alkyl and $R^2$ is a $C_{1-4}$alkyl substituted with a phenyl group.

25. The compound of claim 1, wherein X is N and Y is $CR^a$ so that X and Y form a —N=$CR^a$— moiety, wherein $R^a$ is hydrogen; and/or wherein $R^1$ is hydrogen and $R^2$ is propyl or but-2-yl; $R^1$ is methyl, or ethyl and $R^2$ is phenyl; $R^1$ is methyl and $R^2$ is pyridinyl; or $R^1$ is methyl and $R^2$ is benzyl.

26. The compound of claim 6, wherein:
i) $R^5$ is a phenyl group optionally substituted with methoxy, fluoro, trifluoromethoxy, trifluoromethyl, or methyl, or
ii) $R^5$ is a 4-, 5-, 6-, 7-, or 8-membered monocyclic heterocyclyl ring comprising 1 or 2 or 3 heteroatoms independently selected from —N=  or  =N—, —NH—, —O—, —S—, —SO— or —$SO_2$—, or
iii) $R^5$ is cyclopropyl, cyclobutyl, or cyclohexyl.

27. The compound of claim 1, wherein $R^4$ is $C_{1-6}$alkyl optionally substituted with a benzo[d][1,3]dioxol-5-yl, cyclopropyl, cyclobutyl, cyclopentyl, cyclohexyl or cycloheptyl.

28. The compound of claim 27, wherein $R^4$ is:
i) 4-substituted cyclohexyl wherein the substituent at position 4 and the amino group attached to position 1 are in (cis) configurations; or
ii) a 3-substituted cyclobutyl wherein the substituent at position 3 and the amino group attached to position 1 are in (cis) configurations.

29. The compound of claim 1, wherein R is furan-2-yl, 3-methylpyrazin-2-yl or thiazol-2-yl.

\* \* \* \* \*

UNITED STATES PATENT AND TRADEMARK OFFICE
CERTIFICATE OF CORRECTION

PATENT NO. : 11,472,811 B2
APPLICATION NO. : 16/982681
DATED : October 18, 2022
INVENTOR(S) : Guoliang Zhang et al.

It is certified that error appears in the above-identified patent and that said Letters Patent is hereby corrected as shown below:

In the Claims

In Claim 1, Column 135, Line 35, please replace:
"–OR$^c$,"
With:
-- –OR$^e$,--

In Claim 20, Column 138, Line 25, please replace:
"(1 s,4s)-4-hydroxy-4-methylcyclohexyl;"
With:
"(1s,4s)-4-hydroxy-4-methylcyclohexyl;--

In Claim 20, Column 138, Line 26, please replace:
"(1 s,4s)-4-hydroxycyclohexyl;"
With:
--(1s,4s)-4-hydroxycyclohexyl;--

In Claim 20, Column 138, Line 27, please replace:
"(1 S,2R)-2-hydroxycyclohexyl;"
With:
--(1S,2R)-2-hydroxycyclohexyl;--

In Claim 20, Column 138, Line 28, please replace:
"(1 s,4s)-4-hydroxy-4-methylcyclohexyl;"
With:
--(1s,4s)-4-hydroxy-4-methylcyclohexyl;--

In Claim 20, Column 138, Line 29, please replace:
"(1 S,2S)-2-hydroxycyclohexyl;"

Signed and Sealed this
Twenty-fifth Day of April, 2023

Katherine Kelly Vidal
*Director of the United States Patent and Trademark Office*

With:
--(1S,2S)-2-hydroxycyclohexyl;--

In Claim 20, Column 138, Line 36, please replace:
"(1R,3 S)-3-hydroxycyclohexyl;"
With:
--(1R,3S)-3-hydroxycyclohexyl;--

In Claim 20, Column 138, Line 49, please replace:
"(1R,3 S)-3-hydroxycyclopentyl;"
With:
--(1R,3S)-3-hydroxycyclopentyl;--